United States Patent
Ritter et al.

(10) Patent No.: US 9,024,093 B2
(45) Date of Patent: May 5, 2015

(54) FLUORINATION OF ORGANIC COMPOUNDS

(75) Inventors: Tobias Ritter, Cambridge, MA (US); Takeru Furuya, Cambridge, MA (US); Pingping Tang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 546 days.

(21) Appl. No.: 13/130,033

(22) PCT Filed: Nov. 20, 2009

(86) PCT No.: PCT/US2009/065339
§ 371 (c)(1),
(2), (4) Date: Aug. 3, 2011

(87) PCT Pub. No.: WO2010/059943
PCT Pub. Date: May 27, 2010

(65) Prior Publication Data
US 2011/0312903 A1    Dec. 22, 2011

Related U.S. Application Data

(60) Provisional application No. 61/116,345, filed on Nov. 20, 2008, provisional application No. 61/143,441, filed on Jan. 9, 2009, provisional application No. 61/167,018, filed on Apr. 6, 2009, provisional application No. 61/177,907, filed on May 13, 2009.

(51) Int. Cl.
| | |
|---|---|
| *C07C 25/13* | (2006.01) |
| *C07B 39/00* | (2006.01) |
| *C07C 17/093* | (2006.01) |
| *C07C 37/62* | (2006.01) |
| *C07C 41/22* | (2006.01) |
| *C07C 45/63* | (2006.01) |
| *C07C 67/287* | (2006.01) |
| *C07C 67/307* | (2006.01) |
| *C07C 209/74* | (2006.01) |
| *C07C 231/12* | (2006.01) |
| *C07C 253/30* | (2006.01) |
| *C07C 269/06* | (2006.01) |
| *C07C 291/04* | (2006.01) |
| *C07D 311/72* | (2006.01) |
| *C07D 493/06* | (2006.01) |
| *C07D 498/08* | (2006.01) |
| *C07J 17/00* | (2006.01) |
| *C07J 51/00* | (2006.01) |
| *C07K 1/13* | (2006.01) |
| *C07C 201/12* | (2006.01) |

(52) U.S. Cl.
CPC ............. *C07B 39/00* (2013.01); *C07B 2200/07* (2013.01); *C07C 17/093* (2013.01); *C07C 37/62* (2013.01); *C07C 41/22* (2013.01); *C07C 45/63* (2013.01); *C07C 67/287* (2013.01); *C07C 67/307* (2013.01); *C07C 209/74* (2013.01); *C07C 231/12* (2013.01); *C07C 253/30* (2013.01); *C07C 269/06* (2013.01); *C07C 291/04* (2013.01); *C07C 2101/16* (2013.01); *C07C 2102/10* (2013.01); *C07D 311/72* (2013.01); *C07D 493/06* (2013.01); *C07D 498/08* (2013.01); *C07J 17/005* (2013.01); *C07J 51/00* (2013.01); *C07K 1/13* (2013.01); *C07C 201/12* (2013.01)

(58) Field of Classification Search
USPC .......................................... 570/123, 126, 168
See application file for complete search history.

(56) References Cited

U.S. PATENT DOCUMENTS

| | | | |
|---|---|---|---|
| 3,137,701 | A | 6/1964 | Ayer |
| 3,641,153 | A | 2/1972 | Kyburz et al. |
| 3,972,936 | A | 8/1976 | Christy |
| 3,991,103 | A | 11/1976 | Barton et al. |
| 4,236,008 | A | 11/1980 | Henderson |
| 4,402,956 | A | 9/1983 | Silvestrini et al. |
| 4,487,773 | A | 12/1984 | Temple, Jr. et al. |
| 6,069,110 | A | 5/2000 | Klaui et al. |
| 6,127,583 | A | 10/2000 | Sonoda et al. |
| 7,108,846 | B1 | 9/2006 | Marchand et al. |
| 7,115,249 | B2 | 10/2006 | Luthra et al. |
| 2005/0085474 | A1 | 4/2005 | Ebenbeck et al. |
| 2005/0137421 | A1 | 6/2005 | Walsh et al. |
| 2006/0083677 | A1 | 4/2006 | Brady et al. |
| 2007/0092441 | A1 | 4/2007 | Wadsworth et al. |
| 2009/0247517 | A1 | 10/2009 | Liu et al. |
| 2011/0054175 | A1 | 3/2011 | Ritter et al. |
| 2011/0212936 | A1 | 9/2011 | Furuya et al. |
| 2012/0095217 | A1 | 4/2012 | Ritter et al. |
| 2012/0149900 | A1 | 6/2012 | Ritter et al. |

(Continued)

FOREIGN PATENT DOCUMENTS

| | | |
|---|---|---|
| DE | 23 60 940 A1 | 4/1975 |
| EP | 0 915 094 A1 | 5/1999 |

(Continued)

OTHER PUBLICATIONS

Tius; Tetrahedron, 1995, vol. 51, 4, 3997-4010.*
Tredwell ( organic and biomolecular Chemistry, 2006, 4, 26-32).*
Alvarez-Corral (Chemical Reviews, Jul. 17, 2008, 108, 3174-3198).*
Jung; Angewandte Chemie International Edition in English, 1996, 35, 17-42.*
Wong; Angewandte Chemie international Edition; 2005, 44, 192-212.*

(Continued)

*Primary Examiner* — Sudhakar Katakam
*Assistant Examiner* — Pancham Bakshi
(74) *Attorney, Agent, or Firm* — Wolf, Greenfield & Sacks, P.C.; C. Hunter Baker; Gitrada A. Harmon

(57) ABSTRACT

Methods for fluorinating organic compounds are described herein.

16 Claims, No Drawings

(56) References Cited

U.S. PATENT DOCUMENTS

2012/0316120 A1 12/2012 Ritter
2012/0316341 A1 12/2012 Ritter et al.

FOREIGN PATENT DOCUMENTS

| GB | 1 177 525 A | 1/1970 |
|---|---|---|
| JP | 63-166159 A | 7/1988 |
| WO | WO 03/020732 A2 | 3/2003 |
| WO | WO 2005/063254 A2 | 7/2005 |
| WO | WO 2005/117872 A2 | 12/2005 |
| WO | WO 2006/078752 A2 | 7/2006 |
| WO | WO 2008/081477 A1 | 7/2008 |
| WO | WO 2008/091818 A1 | 7/2008 |
| WO | WO 2009/033751 A2 | 3/2009 |
| WO | WO 2009/100014 A1 | 8/2009 |
| WO | WO 2009/141053 A1 | 11/2009 |
| WO | WO 2009/149347 A1 | 12/2009 |
| WO | WO 2010/059943 A2 | 5/2010 |
| WO | WO 2010/081034 A2 | 7/2010 |
| WO | WO 2010/081036 A2 | 7/2010 |
| WO | WO 2011/006088 A2 | 1/2011 |
| WO | WO 2012/024604 A2 | 2/2012 |
| WO | WO 2012/054782 A2 | 4/2012 |
| WO | WO 2012/142162 A2 | 10/2012 |

OTHER PUBLICATIONS

Extended European Search Report for EP 09759505.2, mailed Jan. 20, 2012.
International Search Report and Written Opinion for PCT/US2009/046401, mailed Sep. 22, 2009.
International Preliminary Report on Patentability for PCT/US2009/046401, mailed Dec. 16, 2010.
International Search Report and Written Opinion for PCT/US2009/032855, mailed Jun. 8, 2009.
International Preliminary Report on Patentability for PCT/US2009/032855, mailed Aug. 12, 2010.
Invitation to Pay Additional Fees for PCT/US2010/041561, mailed Sep. 28, 2010.
International Search Report and Written Opinion for PCT/US2010/041561, mailed Jun. 15, 2011.
International Preliminary Report on Patentability for PCT/US2010/041561, mailed Jan. 19, 2012.
Extended European Search Report for EP 10729595.8, mailed May 22, 2013.
International Search Report and Written Opinion for PCT/US2010/020544, mailed Oct. 7, 2010.
International Preliminary Report on Patentability for PCT/US2010/020544, mailed Jul. 21, 2011.
Extended European Search Report for EP 09828291.6, mailed May 18, 2012.
International Search Report and Written Opinion for PCT/US2009/065339, mailed Jul. 12, 2010.
International Preliminary Report on Patentability for PCT/US2009/065339, mailed Jun. 3, 2011.
International Search Report and Written Opinion for PCT/US2011/048451, mailed Mar. 22, 2012.
International Preliminary Report on Patentability for PCT/US2011/048451, mailed Mar. 7, 2013.
International Search Report and Written Opinion for PCT/US2012/033125, mailed Nov. 9, 2012.
International Preliminary Report on Patentability for PCT/US2012/033125, mailed Oct. 24, 2013.
Extended European Search Report for EP 10729593.3, mailed May 3, 2012.
International Search Report and Written Opinion for PCT/US2010/020540, mailed Oct. 6, 2010.
International Preliminary Report on Patentability for PCT/US2010/020540, mailed Jul. 21, 2011.
International Search Report and Written Opinion for PCT/US2011/057176, mailed May 3, 2012.
International Preliminary Report on Patentability for PCT/US2011/057176, mailed May 2, 2013.
Office Communication, mailed Feb. 25, 2013, for U.S. Appl. No. 12/996,274.
Notice of Allowance, mailed Aug. 21, 2013, for U.S. Appl. No. 12/996,274.
Office Communication, mailed Sep. 18, 2012, for U.S. Appl. No. 12/865,703.
Office Communication, mailed Jan. 28, 2013, for U.S. Appl. No. 12/865,703.
[No Author Listed] PubChem Compound Summary titled "Dadle" (Jul. 28, 2006) [Retrieved from the Internet Sep. 14, 2010: <http://pubchem.ncbi.nim.nih.gov/summary/summary.cgi?cid=6917707&loc=ec_rcs]. 4 pages.
[No Author Listed] PubChem Compound Summary titled "Enkephalin, Leucine" (Mar. 25, 2005) [Retrieved from the Internet Sep. 14, 2010: <http://pubchem.ncbi.nim.nih.gov/summary/summary.cgi?cid=3903&loc=ec_rcs Sep. 14, 2010>]. 5 pages.
[No Author Listed] Wired Chemist. Common Bond Energies (D) and Bond Lengths (r). 2013. Available at http://www.wiredchemist.com/chemistry/data/bond_energies_lengths.html. Last accessed Nov. 18, 2013. 10 pages.
Adams et al., Nucleophilic routes to selectively fluorinated aromatics. Chem Soc Rev. 1999;28:225-31.
Ahmed et al., Boronic acids as inhibitors of steroid sulfatase. Bioorg Med Chem. Dec. 15, 2006;14(24):8564-73. Epub Sep. 14, 2006.
Andrae et al., Energy-adjustedab initio pseudopotentials for the second and third row transition elements. Theor Chem Acta. 1990;77(2):123-41.
Andrae et al., Energy-adjustedab initio pseudopotentials for the second and third row transition elements: Molecular test for M2 (M=Ag, Au) and MH (M=Ru, Os). Theor Chim Acta. 1991;78(4):247-66.
Avdeef et al., Octanol-, chloroform-, and propylene glycol dipelargonat-water partitioning of morphine-6-glucuronide and other related opiates. J Med Chem. Oct. 25, 1996;39(22):4377-81.
Becke, Density-functional thermochemistry. III. The role of exact exchange. J Chem Phys. 1993;98(7): 5648-52.
Berge et al., Pharmaceutical Salts. J. Pharmaceutical Sciences 1977;66:1-19.
Bergman et al., Fluorine-18-labeled fluorine gas for synthesis of tracer molecules. Nucl Med Biol. Oct. 1997;24(7):677-83.
Berry et al., An octahedral coordination complex of iron(VI). Science. Jun. 30, 2006;312(5782):1937-41. Epub Jun. 1, 2006.
Billingsley et al., Palladium-catalyzed borylation of aryl chlorides: scope, applications, and computational studies. Angew Chem. 2007;119(28):5455-59.
Black et al., Observations on the mechanism of halogen-bridge cleavage by unidentate ligands in square planar palladium and platinum complexes. Australian Journal of Chemistry. 1994;47(2):217-227.
Bohm et al., Fluorine in medicinal chemistry. Chembiochem. May 3, 2004;5(5):637-43.
Brown et al., Transition-metal-mediated reactions for C(sp2)-F bond construction: the state of play. Angew Chem Int Ed Engl. 2009;48(46):8610-4. doi: 10.1002/anie.200902121.
Buzzi et al., The antimigraine drug, sumatriptan (GR43175), selectively blocks neurogenic plasma extravasation from blood vessels in dura mater. Br J Pharmacol. Jan. 1990;99(1):202-6.
Campbell et al., Synthesis and structure of solution-stable one-dimensional palladium wires. Nat Chem. Nov. 13, 2011;3(12):949-53. doi: 10.1038/nchem.1197.
Cámpora et al., Redox Behavior of an Organometallic Palladium(II)/Palladium(IV) System. A New Method for the Synthesis of Cationic Palladium(IV) Complexes. Organometallics. 2005;24(15):3624-3628.
Canty et al., Carbon—Oxygen Bond Formation at Metal(IV) Centers: Reactivity of Palladium(II) and Platinum(II) Complexes of the [2,6-(Dimethylaminomethyl)phenyl-N,C,N]—(Pincer) Ligand toward Iodomethane and Dibenzoyl Peroxide; Structural Studies of M(II) and M(IV) Complexes. Organometallics. 2004;23(23):5432-5439.
Canty et al., Synthesis and Characterization of Ambient Temperature Stable Organopalladium(IV) Complexes, Including Aryl-, .eta.1-Allyl-, Ethylpalladium(IV), and Pallada(IV)cyclopentane Complexes.

(56) References Cited

OTHER PUBLICATIONS

Structures of the Poly(pyrazol-1-yl)borate Complexes PdMe3{(pz)3BH} and PdMe3{(pz)4B } and Three Polymorphs of PdMe2Et{(pz)3BH}. Organometallics. 1995;14(1):199-206.
Canty et al., Synthesis of halogeno, pseudohalogeno, and carboxylatopalladium(IV) complexes by halogen exchange. Crystal structure of azido(2,2'-bipyridyl)-benzylpalladium(II), formed on reductive elimination of ethane from Pd(N3)Me2(CH2Ph)(bpy). J Organometallic Chem. 1992;433(1-2):213-22.
Chan et al., Palladium(II)-catalyzed selective monofluorination of benzoic acids using a practical auxiliary: a weak-coordination approach. Angew Chem Int Ed Engl. Sep. 19, 2011;50(39):9081-4. doi: 10.1002/anie.201102985. Epub Jul. 11, 2011.
Chuang et al., A dinuclear palladium catalyst for α-hydroxylation of carbonyls with O2. J Am Chem Soc. Feb. 16, 2011;133(6):1760-2. doi: 10.1021/ja108396k. Epub Jan. 19, 2011.
Chung et al., Segmental spinal nerve ligation model of neuropathic pain. Methods Mol Med. 2004;99:35-45.
Constaninou et al., Xenon difluoride exchanges fluoride under mild conditions: a simple preparation of [(18)F]xenon difluoride for PET and mechanistic studies. J Am Chem Soc. Feb. 28, 2001;123(8):1780-1.
Cope et al., Electrophilic aromatttic substitution reactions by platinum(II) and palladium(II) chlorides on N,N-dimethylbenzylamines J Am Chem Soc. 1968;90(4):909-913.
Couturier et al., Fluorinated tracers for imaging cancer with positron emission tomography. Eur J Nucl Med Mol Imaging. Aug. 2004;31(8):1182-206. Epub Jul. 6, 2004.
Czarnik, Encoding methods for combinatorial chemistry. Curr Opin Chem Biol. Jun. 1997;1(1):60-6.
Danielson et al., Use of 19F NMR to probe protein structure and conformational changes. Annu Rev Biophys Biomol Struct. 1996;25:163-95.
Dick et al., A highly selective catalytic method for the oxidative functionalization of C-H bonds. J Am Chem Soc. Mar. 3, 2004;126(8):2300-1.
Dick et al., Carbon—Nitrogen Bond-Forming Reactions of Palladacycles with Hypervalent Iodine Reagents. Organometallics. 2007;26(6):1365-1370.
Dick et al., Unusually stable palladium(IV) complexes: detailed mechanistic investigation of C-O bond-forming reductive elimination. J Am Chem Soc. Sep. 21, 2005;127(37):12790-1.
Edwards et al., In vitro and in vivo studies of neutral cyclometallated complexes against murine leukemias. Canadian Journal of Chemistry. 2005;83(6-7):980-989.
Ehlers et al., A set of f-polarization functions for pseudo-potential basis sets of the transition metals Sc Cu, Y Ag and La Au. Chem Phys Lett. 1993;208(1-2):111-14.
Ernst et al., Presynaptic dopaminergic deficits in Lesch-Nyhan disease. N Engl J Med. Jun. 13, 1996;334(24):1568-72.
Espinet et al., (CN)-chelate, N,N'-bridged dimeric palladium complexes derived from hydrazones PhC(R):NN'HPh. X-ray structure of [Pd(o-C6H4C(R):NNPh)L]2 [R = Me, L = P(OMe)3]. Inorg Chem., 1989;28(23):4207-4211.
Evans, The determination of the paramagnetic susceptibility of substances in solution by nuclear magnetic resonance. J Chem Soc. 1959;2003-2005.
Fier et al., Copper-mediated fluorination of aryl iodides. J Am Chem Soc. Jul. 4, 2012;134(26):10795-8. doi: 10.1021/ja304410x. Epub Jun. 22, 2012.
Fier et al., Copper-mediated fluorination of arylboronate esters. Identification of a copper(III) fluoride complex. J Am Chem Soc. Feb. 20, 2013;135(7):2552-9. doi: 10.1021/ja310909q. Epub Feb. 5, 2013.
Folgado et al., Fluxionality in hexacoordinated copper(II) complexes with 2,2':6',2"-terpyridine (terpy) and related ligands: structural and spectroscopic investigations. Inorg Chem. 1990;29(11):2035-2042.
Ford et al., Regioselectivity in metallation reactions of 2-(2'-naphthyl)pyridine: l'-versus 3'-reactivity in mercuration and pallada-tion reactions. Crystal structure of chloro(pyridine) [2-(2—pyridiny)naphthyl-C3,N]palladium. J Organometallic Chem. 1995;493(1-2):215-20.
Fraser et al., Molecular Fluoro Palladium Complexes. J Am Chem Soc. 1997;119(20):4769-70.
Fulmer et al., NMR Chemical Shifts of Trace Impurities: Common Laboratory Solvents, Organics, and Gases in Deuterated Solvents Relevant to the Organometallic Chemist. Organometallics. 2010;29(9):2176-2179.
Furuya et al., Carbon-Fluorine Bond Formation for the Synthesis of Aryl Fluorides. Synthesis. 2010;11:1804-1821.
Furuya et al., Carbon-fluorine bond formation. Curr Opin Drug Discov Devel. Nov. 2008;11(6):803-19.
Furuya et al., Carbon-fluorine reductive elimination from a high-valent palladium fluoride. J Am Chem Soc. Aug. 6, 2008;130(31):10060-1. doi: 10.1021/ja803187x. Epub Jul. 11, 2008.
Furuya et al., Catalysis for fluorination and trifluoromethylation. Nature. May 26, 2011;473(7348):470-7. doi: 10.1038/nature10108.
Furuya et al., Fluorination of boronic acids mediated by silver(I) triflate. Org Lett. Jul. 2, 2009;11(13):2860-3. doi: 10.1021/ol901113t.
Furuya et al., Mechanism of C-F reductive elimination from palladium(IV) fluorides. J Am Chem Soc. Mar. 24, 2010;132(11):3793-807. doi: 10.1021/ja909371t.
Furuya et al., Palladium-mediated fluorination of arylboronic acids. Angew Chem Int Ed Engl. 2008;47(32):5993-6. doi: 10.1002/anie.200802164.
Furuya et al., Silver-mediated fluorination of functionalized aryl stannanes. J Am Chem Soc. Feb. 11, 2009;131(5):1662-3. doi: 10.1021/ja8086664.
Gay et al., Lithiations of .alpha.- and .beta.-(dimethylaminomethyl)naphthalenes with n-butyllithium and condensations with benzophenone. Some related results. J Am Chem Soc. 1967;89(10):2297-2303.
Gilicinski et al., On the relative power of electrophilic fluorinating reagents of the N F class. J Fluor Chem. 1992;59(1):157-162.
Grushin et al., Ar—F Reductive Elimination from Palladium(II) Revisited. Organometallics. 2007;26(20):4997-5002.
Grushin et al., Facile Ar-CF3 bond formation at Pd. Strikingly different outcomes of reductive elimination from [(Ph3P)2Pd(CF3)Ph] and [(Xantphos)Pd(CF3)Ph]. J Am Chem Soc. Oct. 4, 2006;128(39):12644-5.
Grushin et al., Is fluoride bonded to two Pd acceptors still basic? Three CH2Cl2 molecules encapsulating a Pd2(mu-F)2 square and new implications for catalysis. Angew Chem Int Ed Engl. Dec. 2, 2002;41(23):4476-9.
Grushin et al., Palladium Fluoride Complexes: One More Step toward Metal-Mediated C-F Bond Formation. Chemistry—A European Journal. 2002;8(5):1006-14.
Gullick et al., Catalytic asymmetric heterogeneous aziridination of styrene using Cu2+– exchanged zeolite Y: effect of the counter-cation on enantioselectivity and on the reaction profile. New J Chem. 2004;28:1470-1478.
Hariharan et al., The influence of polarization functions on molecular orbital hydrogenation energies. Theor Chim Acta. 1973;28(3):213-22.
Hartwell et al., The formation of palladium(II)- and platinum(II)-carbon bonds by proton abstraction from benzo[h]quinoline and 8-methylquinoline. J Chem Soc D. 1970:912.
Harvey et al., A new general synthesis of polycyclic aromatic compounds based on enamine chemistry. J Org Chem. 1991;56(3):1210-1217.
Henriksen et al., Recent development and potential use of μ- and κ-opioid receptor ligands in positron emission tomography studies. Drug Dev Res. 2006;67(12):890-904.
Henriksen et al., Syntheses, biological evaluation, and molecular modeling of 18F-labeled 4-anilidopiperidines as mu-opioid receptor imaging agents. J Med Chem. Dec. 1, 2005;48(24):7720-32.
Huang et al., Silver-mediated trifluoromethoxylation of aryl stannanes and arylboronic acids. J Am Chem Soc. Aug. 31, 2011;133(34):13308-10. doi: 10.1021/ja204861a. Epub Aug. 9, 2011.

(56) References Cited

OTHER PUBLICATIONS

Hull et al., Palladium-catalyzed fluorination of carbon-hydrogen bonds. J Am Chem Soc. Jun. 7, 2006;128(22):7134-5.
Ishiyama et al., Mild iridium-catalyzed borylation of arenes. High turnover numbers, room temperature reactions, and isolation of a potential intermediate. J Am Chem Soc. Jan. 23, 2002;124(3):390-1.
Jasim et al., Contrasting Reactivity of Fluoropyridines at Palladium and Platinum: C-F Oxidative Addition at Palladium, P-C and C-F Activation at Platinum. Organometallics 2004;23(26):6140-49.
Jeschke, The Unique Role of Fluorine in the Design of Active Ingredients for Modern Crop Protection. ChemBioChem. 2004;5(5):570-589.
Jones et al., Systemic gabapentin and S(+)-3-isobutyl-gamma-aminobutyric acid block secondary hyperalgesia. Brain Res. Nov. 9, 1998;810(1-2):93-9.
Julia et al., Orientation de la palladation du noyau naphtalenique dans les α et β dimethylaminomethyl naphtalenes. J Organometallic Chem. 1975;102(2):239-43.
Jun et al., The effect of intrathecal gabapentin and 3-isobutyl gamma-aminobutyric acid on the hyperalgesia observed after thermal injury in the rat. Anesth Analg. Feb. 1998;86(2):348-54.
Kamlet et al., Application of palladium-mediated (18)F-fluorination to PET radiotracer development: overcoming hurdles to translation. PLoS One. 2013;8(3):e59187. doi:10.1371/journal.pone.0059187. Epub Mar. 12, 2013.
Kaspi et al., Xenon difluoride induced aryl iodide reductive elimination: a simple access to difluoropalladium(II) complexes. Inorg Chem. Jan. 7, 2008;47(1):5-7. Epub Dec. 4, 2007.
Khusnutdinova et al., The aerobic oxidation of a Pd(II) dimethyl complex leads to selective ethane elimination from a Pd(III) intermediate. J Am Chem Soc. Feb. 1, 2012;134(4):2414-22. doi: 10.1021/ja210841f. Epub Jan. 20, 2012.
Kilbourn et al., Fluorine-18 labeling of proteins. J Nucl Med. Apr. 1987;28(4):462-70.
Kim et al., An experimental model for peripheral neuropathy produced by segmental spinal nerve ligation in the rat. Pain. Sep. 1992;50(3):355-63.
Kirk, Fluorination in Medicinal Chemistry: Methods, Strategies, and Recent Developments. Org Process Res Dev. 2008;12(2):305-321.
Laali et al., N-(trifluoromethylsulfonyl)aryloxytrifluoromethylsulfoximines [ArO-SO(CF3)=NTf] and N-aryltriflimides Ar-N(Tf)2 by thermal and photolytic dediazoniation of [ArN2][BF4]in[BMIM][Tf2N] ionic liquid: exploiting the ambident nucleophilic character of a "nonnucleophilic" anion. J Org Chem. Aug. 31, 2007;72(18):6758-62. Epub Aug. 1, 2007.
Lanci et al., Oxidatively induced reductive elimination from ((t)Bu2bpy)Pd(Me)2: palladium(IV) intermediates in a one-electron oxidation reaction. J Am Chem Soc. Nov. 4, 2009;131(43):15618-20. doi: 10.1021/ja905816q.
Lasne et al., Chemistry of beta(+)-emitting compounds based on fluorine-18. In: Contrast Agents II. 2002;222:201-58.
Lee et al., A fluoride-derived electrophilic late-stage fluorination reagent for PET imaging. Science. Nov. 4, 2011;334(6056):639-42. doi: 10.1126/science.1212625.
Lee et al., Nickel-mediated oxidative fluorination for PET with aqueous [18F] fluoride. J Am Chem Soc. Oct. 24, 2012;134(42):17456-8. doi: 10.1021/ja3084797. Epub Oct. 12, 2012.
Li et al., Synthesis and local anesthetic activity of fluoro-substituted imipramine and its analogues. Bioorg Med Chem Lett. Jul. 1, 2007;17(13):3733-5. Epub Apr. 10, 2007.
Liang et al., Introduction of fluorine and fluorine-containing functional groups. Angew Chem Int Ed Engl. Aug. 5, 2013;52(32):8214-64. doi: 10.1002/anie.201206566. Epub Jul. 19, 2013.
Liu et al., Oxidative aliphatic C-H fluorination with fluoride ion catalyzed by a manganese porphyrin. Science. Sep. 14, 2012;337(6100):1322-5. doi: 10.1126/science.1222327.
Liu et al., Synthesis and properties of 12-fluororetinal and 12-fluororhodopsin. Model system for fluorine-19 NMR studies of visual pigments. J Am Chem Soc. 1981;103(24):7195-201.
Lockner et al., Practical Radical Cyclizations with Arylboronic Acids and Trifluoroborates. Org. Lett. 2011;13(20):5628-5631.
Lovey et al., Fluorinated retinoic acids and their analogs. 3. Synthesis and biological activity of aromatic 6-fluoro analogs. J Med Chem. 1982;25(1):71-75.
Mack et al., Effect of Chelate Ring Expansion on Jahn-Teller Distortion and Jahn-Teller Dynamics in Copper(II) Complexes. Inorg Chem. 2012;51(14):7851-7858.
Maeda et al., Amino Acids and Peptides. X. : Leu-Enkephalin Analogues Containing a Fluorinated Aromatic Amino Acid. Chem Pharm Bull. 1989;37(3):826-28.
Maimone et al., Evidence for in situ catalyst modification during the Pd-catalyzed conversion of aryl triflates to aryl fluorides. J Am Chem Soc. Nov. 16, 2011;133(45):18106-9. doi: 10.1021/ja208461k. Epub Oct. 21, 2011.
Makleit et al., Synthesis and chemical transformation of halogen-containing morphine derivatives. Magyar Kemikusok Lapja. 1997;52(6):282-89.
Marshall et al., Single-Crystal X-ray and Solution 13C NMR Study of Fluoro(p-nitrophenyl)bis(triphenylphosphine)palladium(II). Are There Effects of Through-Conjugation? Organometallics. 1998;17(24):5427-30.
Matthews et al., Equilibrium acidities of carbon acids. VI. Establishment of an absolute scale of acidities in dimethyl sulfoxide solution. J Am Chem Soc. 1975;97(24):7006-7014.
Mazzotti et al., Palladium(III)-Catalyzed Fluorination of Arylboronic Acid Derivatives. J Am Chem Soc. Sep. 25, 2013;135(38):14012-5. doi: 10.1021/ja405919z. Epub Sep. 16, 2013.
McGaraughty et al., Effects of A-317491, a novel and selective P2X3/P2X2/3 receptor antagonist, on neuropathic, inflammatory and chemogenic nociception following intrathecal and intraplantar administration. Br J Pharmacol. Dec. 2003;140(8):1381-8. Epub Nov. 17, 2003.
McMurtrey et al., Pd-catalyzed C-H fluorination with nucleophilic fluoride. Pd-catalyzed C-H fluorination with nucleophilic fluoride. Org Lett. Aug. 17, 2012;14(16):4094-7. doi: 10.1021/1301739f. Epub Jul. 30, 2012.
Mendoza-Espinosa et al., Synthesis of 4- and 4,5-Functionalized Imidazol-2-ylidenes from a Single 4,5-Unsubstituted Imidazol-2-ylidene. J Am Chem Soc. 2010;132(21):7264-7265.
Miao et al., PET of EGFR Expression with an [18]F-Labeled Affibody Molecule. J Nucl Med. 2012;53:1110-1118 (10.2967/jnumed.111.100842).
Miller et al., Synthesis of 11C, 18F, 15O, and 13N radiolabels for positron emission tomography. Angew Chem Int Ed Engl. 2008;47(47):8998-9033. doi: 10.1002/anie.200800222.
Mirica et al., Structure and electronic properties of Pd(III) complexes. Coord Chem Rev. 2013;257(2):299-314.
Muller et al., Fluorine in pharmaceuticals: looking beyond intuition. Science. Sep. 28, 2007;317(5846):1881-6.
Muller et al., the rhodium(II)-catalyzed aziridination of olefins with {[(4-nitrophenyl)sulfonyl]imino}phenyl-lambda3-iodane. Canadian J of Chem. 1998;76(6):738-750.
Murphy et al., One-pot synthesis of arylboronic acids and aryl trifluoroborates by Ir-catalyzed borylation of arenes. Org Lett. Mar. 1, 2007;9(5):757-60. Epub Feb. 3, 2007.
Murphy et al., Organometallic Fluorides: Compounds Containing Carbonminus signMetalminus signFluorine Fragments of d-Block Metals. Chem Rev. Dec. 18, 1997;97(8):3425-3468.
Nagakura et al., Allodynia and hyperalgesia in adjuvant-induced arthritic rats: time course of progression and efficacy of analgesics. J Pharmacol Exp Ther. Aug. 2003;306(2):490-7. Epub May 1, 2003.
Nesterenko et al., Quantum-Chemical Study of the Mechanism and Regioselectivity of Transannular Cyclization of Dienes of the Bicyclo[3.3.1]nonane Series Treated with Bromosuccinimide and F-TEDA-BF. Theor Exp Chem. 2002;38:156-61.
Niedenzu et al., Boron-nitrogen compounds. 99. Studies on B-(pyrazol-1-yl)pyrazaboles. Inorg Chem. 1984;23(23):3713-3716.
Noel et al., Accelerating palladium-catalyzed C-F bond formation: use of a microflow packed-bed reactor. Angew Chem Int Ed Engl. Sep. 12, 2011;50(38):8900-3. doi: 10.1002/anie.201104652. Epub Aug. 11, 2011.

(56) References Cited

OTHER PUBLICATIONS

Nozaki-Taguchi et al., A novel model of primary and secondary hyperalgesia after mild thermal injury in the rat. Neurosci Lett. Sep. 18, 1998;254(1):25-8.

Onishi et al., Palladium Polypyrazolylborate Complexes Containing A Pd—C Bond. Chem Lett. 1976:955-58.

Ortiz et al., A Convenient Synthesis of Methyl- and Isopropyl-Benzyl Ethers Using Silver(II) Oxide as Reagent. Synth Commun. 1993;23(6):749-56.

Pangborn et al., Safe and Convenient Procedure for Solvent Purification. Organometallics. 1996;15(5):1518-1520.

Park et al., Metabolism of fluorine-containing drugs. Annu Rev Pharmacol Toxicol. 2001;41:443-70.

Pawlikowski et al., Alkyl carbon-nitrogen reductive elimination from platinum(IV)-sulfonamide complexes. J Am Chem Soc. Aug. 29, 2007;129(34):10382-93. Epub Aug. 2, 2007.

Perdew et al., Accurate and simple analytic representation of the electron-gas correlation energy. Phys Rev B Condens Matter. Jun. 15, 1992;45(23):13244-13249.

Perez et al., Thermal Study of [Pd(2-Phpy)Cl(L)] Complexes (L=pyridines and amines). Journal of Thermal Analysis and Calorimetry. 2001;66(2):361-370.

Phelps, Positron emission tomography provides molecular imaging of biological processes. Proc Natl Acad Sci U S A. Aug. 1, 2000;97(16):9226-33.

Powers et al., Bimetallic palladium catalysis: direct observation of Pd(III)-Pd(III) intermediates. J Am Chem Soc. Dec. 2, 2009;131(47):17050-1. doi: 10.1021/ja906935c.

Powers et al., Bimetallic Pd(III) complexes in palladium-catalysed carbon-heteroatom bond formation. Nat Chem. Jul. 2009;1(4):302-9.

Powers et al., Bimetallic redox synergy in oxidative palladium catalysis. Acc Chem Res. Jun. 19, 2012;45(6):840-50. doi: 10.1021/ar2001974. Epub Oct. 27, 2011.

Powers et al., Bimetallic reductive elimination from dinuclear Pd(III) complexes. J Am Chem Soc. Oct. 13, 2010;132(40):14092-103. doi: 10.1021/ja1036644.

Powers et al., Connecting binuclear Pd(III) and mononuclear Pd(IV) chemistry by Pd-Pd bond cleavage. J Am Chem Soc. Jul. 25, 2012;134(29):12002-9. doi: 10.1021/ja304401u. Epub Jul. 17, 2012.

Powers et al., On the mechanism of palladium-catalyzed aromatic C-H oxidation. J Am Chem Soc. Oct. 20, 2010;132(41):14530-6. doi: 10.1021/ja1054274.

Powers et al., Palladium(III) in Synthesis and Catalysis. Top Organomet Chem. Jan. 1, 2011;503:129-156.

Privalov et al., Theoretical Studies of the Mechanism of Aerobic Alcohol Oxidation with Palladium Catalyst Systems. Organometallics.2005;24(5):885-893.

Rebstock et al., Synthesis and deprotonation of 2-(pyridyl)phenols and 2-(pyridyl)anilines. Org Biomol Chem. Sep. 7, 2003;1(17):3064-8.

Reed et al., Intermolecular interactions from a natural bond orbital, donor-acceptor viewpoint. Chem Rev. 1988;88(6):899-926.

Roe et al., Structure and Solution Dynamics of [(Ph3P)2Pd(Ph)(FHF)]. Organometallics. 2000;19(22):4575-82.

Ryabov et al., Synthesis by ligand exchange, structural characterization, and aqueous chemistry of ortho-palladated oximes. Inorg Chem. 1992;31(14):3083-3090.

Sandford, Elemental fluorine in organic chemistry (1997-2006). J Fluorine Chem. 2007;128:90-104.

Sasaki et al., Solid phase synthesis and opioid receptor binding activities of [D-Ala2, D-Leu5]enkephalin analogs containing a fluorinated aromatic amino acid. Chem Pharm Bull (Tokyo). Nov. 1990;38(11):3162-3.

Serguchev et al., Transannular additions of selectfluor and xenon difluoride: regioselectivity and mechanism. J Phys Org Chem. 2011;24(5):407-13.

Sheldrick, A short history of SHELX. Acta Cryst Sect A. 2008;A64:112-122.

Singh et al., Recent highlights in electrophilic fluorination with 1-chloromethyl-4-fluoro- 1,4- diazoniabicyclo[2.2.2]octane bis(tetrafluoroborate). Acc Chem Res. Jan. 2004;37(1):31-44.

Sladojevich et al., Late-stage deoxyfluorination of alcohols with PhenoFluor. J Am Chem Soc. Feb, 20, 2013;135(7):2470-3. doi: 10.1021/ja3125405. Epub Feb. 11, 2013.

Still et al., Rapid chromatographic technique for preparative separations with moderate resolution. J Org Chem. 1978;43(14):2923-2925.

Strassman et al., Sensitization of meningeal sensory neurons and the origin of headaches. Nature. Dec. 12, 1996;384(6609):560-4.

Sun et al., Room-temperature nucleophilic aromatic fluorination: experimental and theoretical studies. Angew Chem Int Ed Engl. Apr. 21, 2006;45(17):2720-5.

Szostak et al., Electron transfer reduction of carboxylic acids using SmI2-H2O-Et3N. Org Lett. Feb. 3, 2012;14(3):840-3. doi: 10.1021/ol203361k. Epub Jan. 24, 2012.

Tang et al., Deoxyfluorination of phenols. J Am Chem Soc. Aug. 3, 2011;133(30):11482-4. doi: 10.1021/ja2048072. Epub Jul. 12, 2011.

Tang et al., Silver-catalyzed late-stage fluorination. J Am Chem Soc. Sep. 1, 2010;132(34):12150-4. doi: 10.1021/ja105834t.

Tang et al., Silver-mediated fluorination of aryl silanes. Tetrahedron. Jun. 17, 2011;67(24):4449-4454.

Taylor et al., Catalytic asymmetric heterogeneous aziridination of styrene using CuHY: effect of nitrene donor on enantioselectivity. J Chem Soc Perkin Trans 2. 2001:1714-1723.

Teare et al., Synthesis and reactivity of [18F]N-fluorobenzenesulfonimide. Chem Commun (Camb). Jun. 21, 2007;2007(23):2330-2.

Thordarson, Determining association constants from titration experiments in supramolecular chemistry. Chem Soc Rev. Mar. 2011;40(3):1305-23. doi: 10.1039/cOcs00062k. Epub Dec. 1, 2010.

Ting et al., Arylfluoroborates and alkylfluorosilicates as potential PET imaging agents: high-yielding aqueous biomolecular 18F-labeling. J Am Chem Soc. Sep. 28, 2005;127(38):13094-5.

Trofimenko, Recent advances in poly(pyrazolyl)borate (scorpionate) chemistry. Chem Rev. 1993;93(3):943-980.

Trofimenko, Boron-pyrazole chemistry. II. Poly(1-pyrazolyl)-borates. J Am Chem Soc. 1967;89(13):3170-3177.

Trofimenko, Polypyrazolylborates, a new class of ligands. Acc Chem Res. 1971;4(1):17-22.

Valenzano et al., Pharmacological and pharmacokinetic characterization of the cannabinoid receptor 2 agonist, GW405833, utilizing rodent models of acute and chronic pain, anxiety, ataxia and catalepsy. Neuropharmacology. Apr. 2005;48(5):658-72.

Vasdev et al., On the preparation of fluorine-18 labelled XeF(2) and chemical exchange between fluoride ion and XeF(2). J Am Chem Soc. Oct. 30, 2002;124(43):12863-8.

Vincente et al., Synthesis of Tris- and Tetrakis(pyrazol-l-yl)borate Gold(III) Complexes. Crystal Structures of [Au {κ2-N,N'-BH(Pz)3}C12] (pz = Pyrazol-1-y1) and [Au {κ2-N,N'-B(Pz)4}(κ2-C,N- C6H4CH2NMe2-2)]C1O4·CHCl3. Inorg Chem. 2002;41(7):1870-1875.

Walker et al., The VR1 antagonist capsazepine reverses mechanical hyperalgesia in models of inflammatory and neuropathic pain. J Pharmacol Exp Ther. Jan. 2003;304(1):56-62.

Wang et al., Versatile Pd(OTf)2 × 2 H2O-catalyzed ortho-fluorination using NMP as a promoter. J Am Chem Soc. Jun. 10, 2009;131(22):7520-1. doi: 10.1021/ja901352k.

Watson et al., Formation of ArF from LPdAr(F): catalytic conversion of aryl triflates to aryl fluorides. Science. Sep. 25, 2009;325(5948):1661-4. doi: 10.1126/science.1178239. Epub Aug. 13, 2009.

Weiss et al., Electrostatic Activation of Hypervalent Organo-Iodine Compounds: Bis(onio)-Substituted Aryliodine(III) Salts. Angew Chem Int Ed. 1994;33(8):891-93.

Wilen et al., Strategies in Optical Resolution. Tetrahedron. 1977;33:2725-36.

Wilen, Tables of Resolving Agents and Optical Resolutions. E.L. Eliel, ed. Universtify of Notre Dame Press, Notre Dame, IN. 1972:268-98.

(56) References Cited

OTHER PUBLICATIONS

Woo et al., Direct conversion of pyranose anomeric OH→F→R in the artemisinin family of antimalarial trioxanes. Tetrahedron Lett. 1998;39(12):1533-36.

Xanthos et al., Animal Models of Chronic Pain: Chronic post-ischemia pain: a novel animal model of Complex Regional Pain Syndrome Type I produced by prolonged hindpaw ischemia and reperfusion in the rat. J Pain. 2004;5:S1. Abstract B01.

Yahav et al., Synthesis of the Elusive (R3P)2MF2 (M = Pd, Pt) Complexes. J Am Chem Soc 2003;125(45):13634-35.

Yahav-Levi et al., Competitive aryl-iodide vs aryl-aryl reductive elimination reactions in Pt(IV) complexes: experimental and theoretical studies. J Am Chem Soc. Jan. 16, 2008;130(2):724-31.

Yaksh et al., An automated flinch detecting system for use in the formalin nociceptive bioassay. J Appl Physiol (1985). Jun. 2001;90(6):2386-402.

Yamada et al., Synthesis and Reaction of New Type I-N Ylide, N-Tosyliminoiodinane. Chem Lett. 1975;4(4):361-62.

Yandulov et al., Aryl-fluoride reductive elimination from Pd(II): feasibility assessment from theory and experiment. J Am Chem Soc. Feb. 7, 2007;129(5):1342-58.

Ye et al., Mild copper-mediated fluorination of aryl stannanes and aryl trifluoroborates. J Am Chem Soc. Mar. 27, 2013;135(12):4648-51. doi: 10.1021/ja400300g. Epub Mar. 13, 2013.

Zhang et al., Interception of the radicals produced in electrophilic fluorination with radical traps (Tempo, Dmpo) studied by electrospray ionization mass spectrometry. Rapid Commun Mass Spectrom. 2006;20(12):1877-82.

Zhang et al., Investigation of radical cation in electrophilic fluorination by ESI-MS. Org Lett. Sep. 1, 2005;7(18):3877-80.

\* cited by examiner

FLUORINATION OF ORGANIC COMPOUNDS

This application is a national stage application under 35 U.S.C. §371 of International Application No.: PCT/US2009/065339, filed Nov. 20, 2009, published as International Publication No. WO 2010/059943 on May 27, 2010, claims priority under 35 U.S.C. §119(e) to U.S. provisional applications: U.S. Ser. No. 61/116,345, filed Nov. 20, 2008; U.S. Ser. No. 61/143,441, filed Jan. 9, 2009; U.S. Ser. No. 61/167,018, filed Apr. 6, 2009; and U.S. Ser. No. 61/177,907, filed May 13, 2009; each of which is incorporated herein by reference.

FIELD OF THE INVENTION

The invention relates to methods of fluorinating an organic compound using a silver-containing compound and a fluorinating agent.

BACKGROUND OF INVENTION

Functionalized aryl fluorides are used as pharmaceuticals and agrochemicals, in part due to their favorable pharmacological properties such as increased metabolic stability (see, for example, Müller et al., Science 2007, 317, 1881-1886; Kirk et al., Org. Process Res. Dev. 2001, 41, 443-470; and Jeschke, P. ChemBioChem 2004, 5, 570-589). Aryl fluorides also find applications as tracers in positron emission tomography using the [$^{18}$F] isotope (Lasne, et al. In Contrast Agents II, 2002; Vol. 222, pp 201-258). Fluorine has the highest electronegativity, the highest oxidation potential, and the smallest anionic radius of all elements, each of which complicates carbon-fluorine bond formation when compared to other carbon-heteroatom bond formations (see, for example, Chambers, R. D., Fluorine in organic chemistry. Oxford: N.Y., 2004; and Furuya et al. Curr. Opin. Drug Discov. Devel. 2008, 11, 803-819).

SUMMARY OF INVENTION

Described herein are novel methods for fluorinating organic compounds.

In one aspect, the invention features a method of fluorinating an organic compound, the method comprising providing an organic compound comprising an organostannane, a boron substituent or a silane substituent, a silver-containing compound, and a fluorinating agent, under conditions sufficient to fluorinate the organic compound, thereby providing a fluorinated organic compound.

In some embodiments, the organic compound is fluorinated regiospecifically. In some embodiments, the organic compound comprises an aryl group. In some embodiments, the aryl group may be an electron-poor aryl group, an electron-rich aryl group, an electron-neutral aryl group or an ortho,ortho-disubstituted aryl group. In some embodiments, the aryl group is a heteroaryl group (e.g., a fused bicyclic group). In some embodiments, the heteroaryl group is an indole or quinoline. In some embodiments, the organic compound comprises a vinyl group (e.g., a substituted or unsubstituted vinyl group), wherein the organostannane, boron substituent or silane substituent is attached to the vinyl group.

In some embodiments, the organic compound comprises an organostannane. In some embodiments, the organostannane comprises a trialkyltin moiety (e.g., a tributyltin or trimethyltin moiety).

In some embodiments, the organic compound comprises a boron substituent, e.g., a group of the formulae:

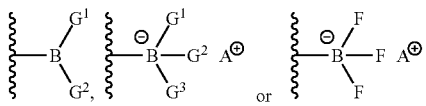

wherein $G^1$, $G^2$ and $G^3$ are, independently, —OH, —OR, or —R;

each R is, independently, optionally substituted aliphatic, optionally substituted heteroaliphatic, optionally substituted aryl, or optionally substituted heteroaryl, or $G^1$ and $G^2$ are joined to form an optionally substituted 5- to 8-membered ring having at least one O atom directly attached to B, wherein the ring is comprised of carbon atoms and optionally one or more additional heteroatoms independently selected from the group consisting of N, S, and O; and wherein $A^\oplus$ is a metal cation or ammonium.

In some embodiments, $G^1$ and $G^2$ are both —OH.

In some embodiments, $G^1$, $G^2$ and $G^3$ are all —OH.

In some embodiments, the organic compound comprises a silane substituent. In some embodiments, the silane substituent is a trialkoxysilane (e.g., trimethoxysilane or triethoxysilane). In some embodiments, the silane substituent is trihydroxysilane.

In some embodiments, organic compound comprises one or more functional groups (e.g., an alcohol, aldehyde, ester, ketone, alkoxy group, cyano group, amine, amide, or N-oxide.) In some embodiments, the functional group is unprotected. In some embodiments, the organic compound comprises one or more chiral centers.

In some embodiments, the organic compound is 3-deoxy-3-(tributylstannyl)estrone, 6-deoxy-6-(tributylstannyl)-δ-tocopherol, 10-(tributylstannyl)camptothecin, 6-demethoxy-6-(tributylstannyl)quinine, 4'-(tributylstannyl)flavanone, 4-(tributylstannyl)maculosin, 3-(tributylstannyl)-β-estradiol-β-hepta-benzoyl-lactose, N-Boc-4-(tributylstannyl)-L-phenylalanyl-L-phenylalanine Methyl Ester, (tributylstannyl)ezetimibe, (tributylstannyl)DOPA or a tributylstannyl Rifamycin S derivative.

In some embodiments, the fluorinated organic compound is 3-deoxy-3-fluoroestrone, 6-deoxy-6-fluoro-δ-tocopherol, 10-fluorocamptothecin, 6-demethoxy-6-fluoroquinine, 4'-(fluoro)flavanone, 4-(fluoro)maculosin, 3-(fluoro)-β-estradiol-β-hepta-benzoyl-lactose, N-Boc-4-(Fluoro)-L-phenylalanyl-L-phenylalanine Methyl Ester, 4-(fluoro)-leuenkephalin, (14-fluoro)ezetimibe, (5-fluoro)DOPA, and a fluorinated rifamycin S derivative.

In some embodiments, e.g., wherein the organic compound is an organostannane, the method further comprises reacting a precursor of the organostannane with a tin-containing reagent to provide the organostannane. In some embodiments, the precursor of the organostannane comprises a halogen substituent (e.g., bromine or iodine), a Grignard substituent, a triflate substituent, a nonaflate substituent or a diazonium substituent.

In some embodiments, e.g., wherein the organic compound comprises a boron substituent, the method further comprises reacting a precursor of the organic compound with a boron-containing reagent to provide the organic compound comprising a boron substituent. In some embodiments, the precursor comprises a halogen substituent. In some embodiments, the precursor is borylated at an unactivated C—H bond, e.g., an aromatic, alkenyl or alkynyl C—H bond.

In some embodiments, e.g., wherein the organic compound comprises a silane substituent, the method further comprises reacting a precursor of the organic compound with a silicon-containing reagent to provide the compound comprising a silane substituent. In some embodiments, the precursor comprises a Grignard substituent (—Mg—X, wherein X is a halogen). In some embodiments, the precursor comprises a halogen substituent. In some embodiments, the precursor comprises a triflyl substituent.

In some embodiments, the organic compound is a precursor to a pharmaceutically acceptable compound.

In some embodiments, the silver-containing compound is a silver complex. In some embodiments, silver-containing compound is a silver salt, e.g., a silver(I) salt. In some embodiments, the silver(I) salt is selected from the group consisting of silver(I) fluoride, silver(I) acetate, silver(I) tetrafluoroborate, silver(I) perchlorate, silver(I) nitrate, silver(I) carbonate, silver(I) cyanide, silver(I) benzoate, silver(I) triflate, silver(I) hexafluorophosphate, silver(I) hexafluoroantimonate, silver(I) oxide, silver(I) nitrite and silver(I) phosphate. In some embodiments, the silver(I) salt is silver(I) triflate. In some embodiments, the silver(I) salt is silver(I) oxide.

In some embodiments, the reaction includes from about 5 to about 0.01 molar equivalents of silver-containing compound relative to the organic compound (e.g., about 3 equivalents of the silver-containing compound, about 2 equivalents of the silver-containing compound or about 1 equivalent of the silver-containing compound). In some embodiments, the reaction includes a catalytic amount silver-containing compound relative to the organic compound. In some embodiments, the reaction includes less than about 1 equivalent of the silver-containing compound, e.g., about 90%, about 80%, about 70%, about 60%, about 50 mol %, about 40 mol %, about 30 mol %, about 20 mol % or about 10 mol % of the silver-containing compound. In some embodiments, the reaction includes less than about 10 mol % of the silver-containing compound (e.g., about 9%, about 8%, about 7%, about 6%, about 5%, about 4%, about 3%, about 2%, about 1%, or less).

In some embodiments, the fluorinating agent comprises $^{18}F$ or $^{19}F$. In some embodiments, the fluorinating agent is an electrophilic fluorinating agent. In some embodiments, the fluorinating agent is selected from the group consisting of N-fluoropyridinium triflate, N-fluoro-2,4,6-trimethylpyridinium triflate, N-fluoro-2,4,6-trimethylpyridinium tetrafluoroborate, N-fluoro-2,6-dichloropyridinium tetrafluoroborate, N-fluoro-2,6-dichloropyridinium triflate, N-fluoropyridinium pyridine heptafluorodiborate, N-fluoropyridinium tetrafluoroborate, N-fluoropyridinium triflate, an N-fluoroarylsulfonimide, N-chloromethyl-N'-fluorotriethylenediammonium bis(tetrafluoroborate) (Selectfluor®), N-chloromethyl-N'-fluorotriethylenediammonium bis(hexafluorophosphate), and $XeF_2$. In some embodiments, the fluorinating agent is N-chloromethyl-N'-fluorotriethylenediammonium bis(tetrafluoroborate) (Selectfluor®). In some embodiments, the fluorinating agent is N-chloromethyl-N'-fluorotriethylenediammonium bis(hexafluorophosphate).

In some embodiments, the reaction further comprises a solvent. In some embodiments, the solvent is a polar aprotic solvent (e.g., acetone). In some embodiments, the solvent is a polar protic solvent (e.g., methanol). In some embodiments, the reaction further comprises a reagent. In some embodiments, the reagent is an acid. In some embodiments, the reagent is a base. In some embodiments, the reagent is an inorganic base (e.g., NaOH, KOH, BaO, MgO, $NaHCO_3$, $KHCO_3$, $Na_2CO_3$ or $Ba(OH)_2$). In some embodiments, the inorganic base is $NaHCO_3$. In some embodiments, the reagent is an organic base (e.g., 2,6-lutidine). In some embodiments, the reaction includes about 5 to about 0.01 molar equivalents of a base relative to the organic compound (e.g., about 2.0 equivalents, about 1.5 equivalents, about 1.2 equivalents, about 1.0 equivalents, or about 0.5 equivalents). In some embodiments, the reaction includes a second reagent. In some embodiments, the second reagent is a salt (e.g., sodium triflate). In some embodiments, the second reagent is present in an amount from about a 1:1 molar ratio with the silver-Ar compound. In some embodiments, the second reagent is present in an amount from about a 1:2 molar ratio with the silver-Ar compound.

In some embodiments, the reaction proceeds in one step. In some embodiments, the reaction proceeds in two steps. In some embodiments, the reaction proceeds via an intermediate. In some embodiments, the intermediate is isolated.

In some embodiments, the reaction further comprises an inert atmosphere. In some embodiments, the reaction is performed under anhydrous conditions. In some embodiments, the reaction is performed at ambient temperature. In some embodiments, the reaction is heated. In some embodiments, the reaction is cooled. In some embodiments, the organic compound is immobilized on a solid support. In some embodiments, the fluorination takes place at a late stage in the synthesis of the fluorinated organic compound. In some embodiments, the fluorination is the last step in the synthesis of the fluorinated organic compound (e.g., wherein the organic compound is made using a multi step synthesis).

In some embodiments, the method further comprises purification (e.g., removing one or more impurities from the fluorinated organic compound such as a tin containing product, a boron containing product or a silicon containing product) of the fluorinated organic compound from the reaction mixture, e.g., by column chromatography on silica gel or preparative thin-layer chromatography.

In some embodiments, the silver-containing compound and the fluorinating agent are added to the organic compound comprising an organostannane, a boron substituent or a silane substituent.

In some embodiments, the silver-containing compound and an additional reagent (e.g., a base) are added to the organic compound comprising an organostannane, a boron substituent or a silane substituent, resulting in an intermediate product. In some embodiments, the intermediate is isolated and a fluorinating agent and a silver-containing compound are added thereto, resulting in formation of a fluorinated organic compound.

In some embodiments, the reaction is catalytic, e.g., the reaction includes a catalytic amount silver-containing compound relative to the organic compound.

In some embodiments, the yield of the fluorinated organic compound from the organic compound is at least about 60% (e.g., at least about 65%, 70%, 75%, 80%, 85%, 90% or 95%). In some embodiments, the fluorinated organic compound comprises $^{19}F$. In some embodiments, the fluorinated organic compound comprises $^{18}F$. In some embodiments, the fluorinated organic compound is an imaging agent, e.g., a PET imaging agent. In some embodiments, the fluorinated organic compound is a pharmaceutically acceptable compound. In some embodiments, the fluorinated organic compound is 3-deoxy-3-fluoroestrone, 6-deoxy-6-fluoro-δ-tocopherol, 10-fluorocamptothecin or 6-demethoxy-6-fluoroquinine.

In one aspect, the invention features a method of fluorinating an organic compound, the method comprising combining silver(I) triflate, an arylstannane and N-chloromethyl-N'-fluorotriethylenediammonium bis(hexafluorophosphate), under conditions sufficient to fluorinate the arylstannane, thereby providing a fluorinated organic compound.

In one aspect, the invention features a method of fluorinating an organic compound, the method comprising combining silver(I) triflate, an organic compound comprising a boron substituent, a base and N-chloromethyl-N'-fluorotriethylenediammonium bis(tetrafluoroborate), under conditions sufficient to fluorinate the organic compound, thereby providing a fluorinated organic compound.

In one aspect, the invention features a method of fluorinating an organic compound, the method comprising combining silver(I) oxide, an organic compound comprising a silane substituent, a base and N-chloromethyl-N'-fluorotriethylenediammonium bis(tetrafluoroborate), under conditions sufficient to fluorinate the organic compound, thereby providing a fluorinated organic compound.

In one aspect, the invention features a reaction mixture comprising a silver-containing compound, an organic compound comprising an organostannane, a boron substituent or a silane substituent, and a fluorinating agent.

In one aspect, the invention features a compound selected from the group consisting of 3-deoxy-3-(tributylstannyl)estrone, 6-deoxy-6-(tributylstannyl)-δ-tocopherol, 10-(tributylstannyl)camptothecin, 6-demethoxy-6-(tributylstannyl)quinine, 4'-(tributylstannyl)flavanone, 4-(tributylstannyl)maculosin, 3-(tributylstannyl)-β-estradiol-β-hepta-benzoyl-lactose, N-Boc-4-(tributylstannyl)-L-phenylalanyl-L-phenylalanine Methyl Ester, (tributylstannyl)ezetimibe, (tributylstannyl)DOPA and a tributylstannyl Rifamycin S derivative.

In one aspect, the invention features a compound selected from the group consisting of 3-deoxy-3-fluoroestrone, 6-deoxy-6-fluoro-δ-tocopherol, 10-fluorocamptothecin, 6-demethoxy-6-fluoroquinine, 4'-(fluoro)flavanone, 4-(fluoro)maculosin, 3-(fluoro)-β-estradiol-β-hepta-benzoyl-lactose, N-Boc-4-(Fluoro)-L-phenylalanyl-L-phenylalanine Methyl Ester, 4-(fluoro)-leu-enkephalin, (14-fluoro) ezetimibe, (5-fluoro)DOPA, and a fluorinated rifamycin S derivative.

In one aspect, the invention features a pharmaceutical composition, comprising 3-deoxy-3-fluoroestrone and a pharmaceutically acceptable carrier.

In one aspect, the invention features a pharmaceutical composition, comprising 6-deoxy-6-fluoro-δ-tocopherol and a pharmaceutically acceptable carrier.

In one aspect, the invention features a pharmaceutical composition, comprising 10-fluorocamptothecin and a pharmaceutically acceptable carrier.

In one aspect, the invention features a pharmaceutical composition, comprising 6-demethoxy-6-fluoroquinine and a pharmaceutically acceptable carrier.

In one aspect, the invention features a pharmaceutical composition, comprising 4'-(fluoro)flavanone and a pharmaceutically acceptable carrier.

In one aspect, the invention features a pharmaceutical composition, comprising 4-(fluoro)maculosin and a pharmaceutically acceptable carrier.

In one aspect, the invention features a pharmaceutical composition, comprising 3-(fluoro)-β-estradiol-δ-hepta-benzoyl-lactose and a pharmaceutically acceptable carrier.

In one aspect, the invention features a pharmaceutical composition, comprising 4-(fluoro)-leu-enkephalin and a pharmaceutically acceptable carrier.

In one aspect, the invention features a pharmaceutical composition, comprising (14-fluoro)ezetimibe and a pharmaceutically acceptable carrier.

In one aspect, the invention features a pharmaceutical composition, comprising (5-fluoro)DOPA and a pharmaceutically acceptable carrier.

In one aspect, the invention features a pharmaceutical composition, comprising fluorinated rifamycin S derivative and a pharmaceutically acceptable carrier.

In one aspect, the invention features a kit comprising a silver-containing compound, an organic compound comprising an organostannane, a boron substituent or a silane substituent, and a fluorinating agent.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively. The term "aralkylamino" refers to a —NH(aralkyl) radical. The term alkylaminoalkyl refers to a (alkyl)NH-alkyl-radical; the term dialkylaminoalkyl refers to a (alkyl)$_2$N-alkyl-radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl. An aryl moiety may also be a "heteroaryl" moiety. Heteroaryl refers to an aromatic monocyclic, bicyclic, or tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted (e.g., by one or more substituents). The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any ring atom can be substituted (e.g., by one or more substituents). The cycloalkenyl groups can contain fused rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom may optionally be the point of attachment of the heterocycloalkenyl substituent. Any ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-10 carbon atoms. In some embodiments, aliphatic groups contain 1-8 carbon atoms, 1-7 carbon atoms, 1-6 carbon atoms, 1-5 carbon atoms, 1-4 carbon atoms, 1-3 carbon atoms, or 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkylamino, dialkylamino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The details of one or more embodiments of the invention are set forth in the accompa-nying drawings and the description below. Other features, objects, and advantages of the invention will be apparent from the description and drawings, and from the claims.

All references cited herein, whether in print, electronic, computer readable storage media or other form, are expressly incorporated by reference in their entirety, including but not limited to, abstracts, articles, journals, publications, texts, treatises, internet web sites, databases, patents, patent applications and patent publications.

DETAILED DESCRIPTION

Described herein are methods of making fluorinated organic compounds. Upon reaction of an organic compound comprising an organostannane, a boron substituent or a silane substituent, with a silver-containing compound and a fluorinating agent, the method provides a fluorinated organic compound in which the organostannane, boron substituent or silane substituent is replaced with a fluorine substituent (for example, see Schemes 1-5). In some embodiments, the organic compound is fluorinated regiospecifically.

Scheme 1.

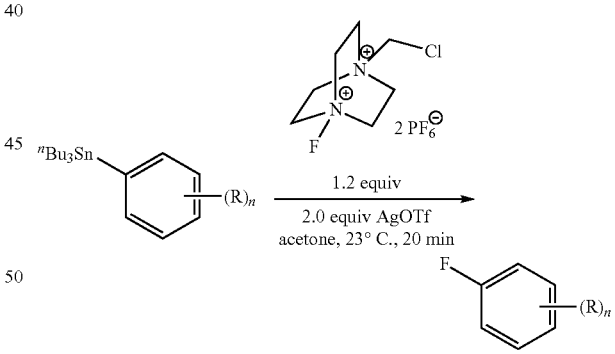

Scheme 2.

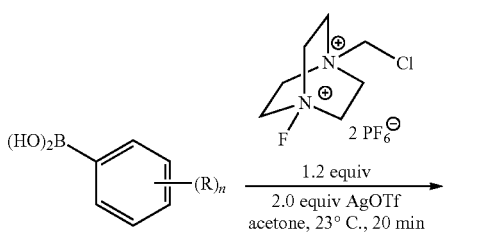

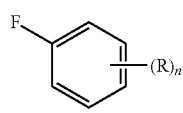

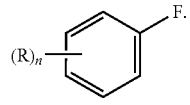

Scheme 3.

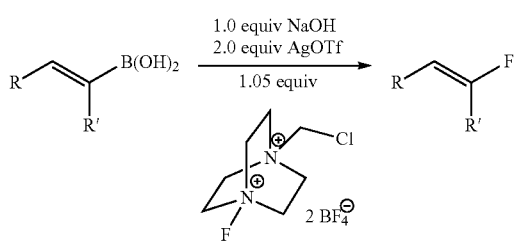

Scheme 4.

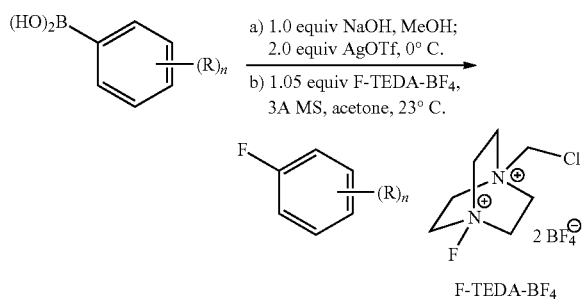

F-TEDA-BF$_4$

Scheme 5.

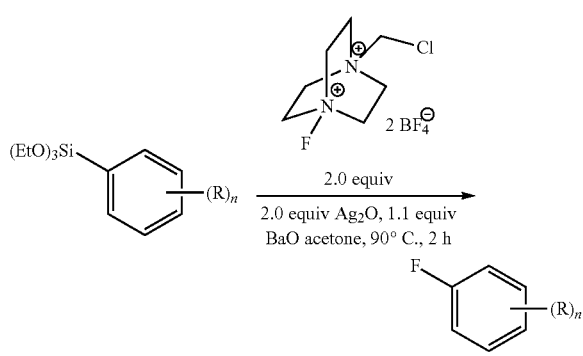

Scheme 6

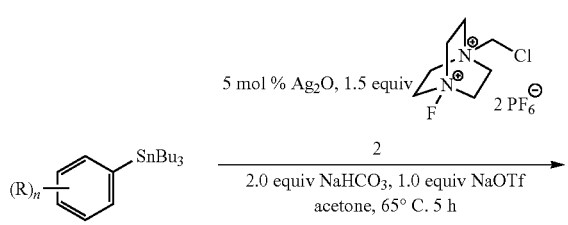

In the above Schemes 1-6, R and R' are substituents and n may be 0, 1, 2, 3, 4 or 5. Exemplary substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as CF$_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as OCF$_3$), halo, hydroxy, carboxy, carboxylate, cyano, nitro, amino, alkylamino, dialkylamino, SO$_3$H, sulfate, phosphate, methylenedioxy (—O—CH$_2$—O— wherein oxygens are attached to vicinal atoms), ethylenedioxy, oxo, thioxo (e.g., C=S), imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). The substituents are independently any one single, or any subset of the aforementioned substituents. A substituent may itself be substituted with any one of the above substituents. In some embodiments, two R groups may be taken together to form a ring, e.g., an aryl, heteroaryl, cyclyl or heterocyclyl ring, which may itself be further substituted with any one of the above substituents.

Organic Compounds

Methods of fluorinating an organic compound are described herein. The organic compound may be a small organic molecule or a large organic molecule. A small organic molecule includes any molecule having a molecular weight of less than 1000 g/mol, of less than 900 g/mol, of less than 800 g/mol, of less than 700 g/mol, of less than 600 g/mol, of less than 500 g/mol, of less than 400 g/mol, of less than 300 g/mol, of less than 200 g/mol or of less than 100 g/mol. A large organic molecule include any molecule of between 1000 g/mol to 5000 g/mol, of between 1000 g/mol to 4000 g/mol, of between 1000 g/mol to 3000 g/mol, of between 1000 g/mol to 2000 g/mol, or of between 1000 g/mol to 1500 g/mol. Organic compounds include aryl compounds, heteroaryl compounds, carbocyclic compounds, heterocyclic compounds, aliphatic compounds, heteroaliphatic compounds. In some embodiments, the organic compound is an aryl compound (e.g., a phenyl compound), or a heteroaryl compound (e.g. a quinolyl or indolyl compound). In some embodiments, the organic compound comprises a vinyl group. In some embodiments, the organic compound comprises a substituted vinyl group.

In some embodiments, the organic compound contains a chiral center. In some embodiments, the organic compound is further substituted with one or more functional groups (e.g., alcohols, aldehydes, ketones, esters, alkenes, alkoxy groups, cyano groups, amines, amides and N-oxides). In some embodiments, the functional groups are unprotected. In some embodiments, the organic compound is a precursor of a pharmaceutically acceptable compound.

Organostannanes

Methods of fluorinating an organic compound are described herein. In some embodiments, the organic compound comprises an organostannane. The organostannane may be a trialkylstannane, e.g., trimethylstannane or tributylstannane.

Exemplary organostannanes include 3-deoxy-3-(tributylstannyl)estrone, 6-deoxy-6-(tributylstannyl)-δ-tocopherol, 10-(tributylstannyl)camptothecin, and 6-demethoxy-6-(tributylstannyl)quinine.

Boron Substituents

Methods of fluorinating an organic compound are described herein. In some embodiments, the organic compound comprises a boron substituent. The boron substituent may be of the formula:

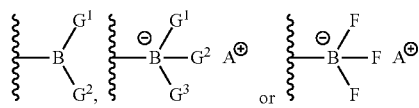

wherein $G^1$, $G^2$ and $G^3$ are, independently, —OH, —OR, or —R, wherein each R is, independently, optionally substituted aliphatic, optionally substituted heteroaliphatic, optionally substituted aryl, or optionally substituted heteroaryl, or $G^1$ and $G^2$ are joined to form an optionally substituted 5- to 8-membered ring having at least one O atom directly attached to B, wherein the ring is comprised of carbon atoms and optionally one or more additional heteroatoms independently selected from the group consisting of N, S, and O. $A^+$ may be a metal cation or ammonium.

As used herein, a boron substituent is intended to encompass free boronic acid substituents (i.e., wherein $G^1$ and $G^2$ are both —OH) and oligomeric anhydrides thereof (including dimers, trimers, and tetramers, and mixtures thereof), boronic ester substituents (i.e., wherein $G^1$ is —OH or —OR and $G^2$ is —OR), borinic acid substituents (i.e., wherein $G^1$ is —OH and $G^2$ is —R), borinic ester substituents (i.e., wherein $G^1$ is —OR and $G^2$ is —R), trihydroxoborates (i.e., wherein $G^1$, $G^2$ and $G^3$ are all —OH), and trialkoxyborates (i.e., wherein $G^1$, $G^2$ and $G^3$ are all —OR, e.g., —OCH$_3$).

In some embodiments, $G^1$ and $G^2$ are joined to form a 5-membered ring. Exemplary 5-membered rings include:

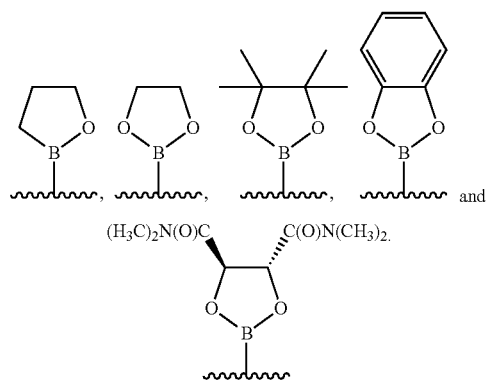

In some embodiments, $G^1$ and $G^2$ are joined to form a 6-membered ring. Exemplary 6-membered rings include:

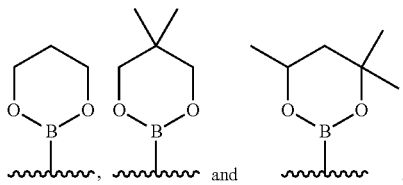

In some embodiments, $G^1$ and $G^2$ are joined to form an 8-membered ring. Exemplary 8-membered rings include:

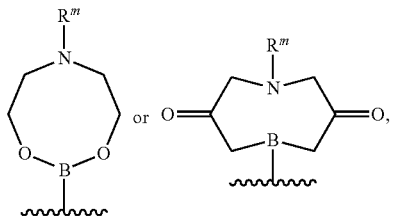

wherein $R^m$ is hydrogen, a suitable amino protecting group, or an optionally substituted aliphatic, optionally substituted heteroaliphatic, optionally substituted aryl, or optionally substituted heteroaryl group.

Furthermore, as used herein, a boron substituent is also intended to encompass a trifluoroborate substituent. For example, in some embodiments, a boron substituent is a group of the formula:

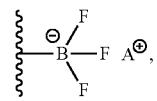

wherein $A^\oplus$ is a metal cation or ammonium.

Furthermore, as used herein, a boron substituent is also intended to encompass trihydroxy- and trialkoxy borates. For example, in some embodiments, a boron substituent is a group of the formulae:

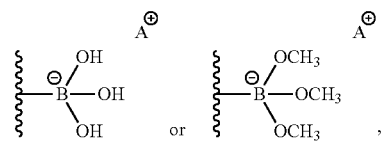

wherein $A^\oplus$ is a metal cation or ammonium.

Exemplary metal cations include lithium, sodium, potassium, magnesium, and calcium cations. In some embodiments, the metal cation is a potassium cation.

An organic compound comprising a boron substituent may be obtained via a variety of known methods. For example, a halogen-containing precursor may be reacted with a boron-containing compound to generate the organic compound comprising a boron substituent. An unactivated C—H bond may also be borylated, for example, using a suitable catalyst.

Silane Substituents

Methods of fluorinating an organic compound are described herein. In some embodiments, the organic compound comprises a silane substituent. The silane substituent may be a trialkoxysilane, e.g., trimethoxysilane or triethoxysilane. The silane substituent may be a trihydroxysilane.

An organic compound comprising a silane substituent may be obtained via a variety of known methods. For example, a Grignard-containing precursor may be reacted with a silicon-containing compound (e.g., a tetraalkoxysilane) to generate the organic compound comprising a silane substituent. In another example, a halogen-containing precursor or a triflyl-containing precursor may be reacted with a silicon-containing compound (e.g., a tetraalkoxysilane) in the presence of a suitable catalyst (e.g., a $Pd^0$ or $Rh^I$ catalyst) to generate the organic compound comprising a silane substituent.

Silver-Containing Compounds

The methods described herein generally include a silver-containing compound. The silver-containing compound may be a silver complex or a silver salt, e.g., a silver(I) salt. Exemplary silver salts include silver(I) salts such as silver(I) fluoride, silver(I) acetate, silver(I) tetrafluoroborate, silver(I) perchlorate, silver(I) nitrate, silver(I) carbonate, silver(I) cyanide, silver(I) benzoate, silver(I) triflate, silver(I) hexafluorophosphate, silver(I) hexafluoroantimonate, silver(I) oxide, silver(I) nitrite and silver(I) phosphate. In preferred embodiments, the silver salt is silver(I) triflate or silver(I) oxide.

Fluorinating Agents

The methods described herein generally include a fluorinating agent. In some embodiments, the fluorinating agent is an electrophilic fluorinating agent. In some embodiments, the fluorinating agent is commercially available. In some embodiments, the electrophilic fluorinating agent is also an inorganic fluorinating agent. Exemplary electrophilic fluorinating agents include N-fluoropyridinium triflate, N-fluoro-2,4,6-trimethylpyridinium triflate, N-fluoro-2,4,6-trimethylpyridinium tetrafluoroborate, N-fluoro-2,6-dichloropyridinium tetrafluoroborate, N-fluoro-2,6-dichloropyridinium triflate, N-fluoropyridinium pyridine heptafluorodiborate, N-fluoropyridinium tetrafluoroborate, N-fluoropyridinium triflate, an N-fluoroarylsulfonimide, N-chloromethyl-N'-fluorotriethylenediammonium bis(tetrafluoroborate)) (Selectfluor®, N-chloromethyl-N'-fluorotriethylenediammonium bis(hexafluorophosphate), N-chloromethyl-N'-fluorotriethylenediammonium bis(triflate) and $XeF_2$. In some embodiments, the fluorinating agent is Selectfluor®. In some embodiments, the fluorinating agent is N'-fluorotriethylenediammonium bis(hexafluorophosphate).

The fluorinating agent may be enriched with a particular isotope of fluorine. In some embodiments, the fluorinating agent is labeled with $^{19}F$ (i.e., transfers a $^{19}F$ fluorine substituent to the organic compound). In some embodiments, reaction of the $^{19}F$-labeled fluorinating agent with the organic compound and silver-containing compound provides a fluorinated $^{19}F$-labeled organic compound.

In some embodiments, the fluorinating agent is labeled with $^{18}F$ (i.e., transfers an $^{18}F$ fluorine substituent to the organic compound). In some embodiments, reaction of the $^{18}F$-labeled fluorinating agent with the organic compound and silver-containing compound provides a fluorinated $^{18}F$-labeled organic compound.

However, in some embodiments, the fluorinating agent is labeled with a mixture of $^{18}F$ and $^{19}F$. In some embodiments, reaction of the mixture of $^{19}F$ and $^{18}F$ fluorinating agent with the organic compound and silver-containing compound provides a mixture of fluorinated $^{19}F$-labeled organic compound and fluorinated $^{18}F$-labeled organic compound.

Reaction Conditions

Described herein are methods of fluorinating organic compounds using silver-containing compounds and a fluorinating agent (e.g., an electrophilic fluorinating agent). In some embodiments, the reaction further comprises a solvent. The solvent may be a polar aprotic solvent. Exemplary polar aprotic solvents include acetone, acetonitrile, tetrahydrofuran, 1,4-dioxane, dimethylformamide and dimethylsulfoxide. In some embodiments, the solvent is acetone. The solvent may be a polar protic solvent. Exemplary polar protic solvents include methanol, ethanol, isopropanol and n-butanol. In some embodiments, the solvent is methanol.

In some embodiments, the reaction is performed under ambient temperature, pressure and atmosphere. In some embodiments, the reaction is performed in an inert atmosphere (e.g., an atmosphere that is substantially free of dioxygen). In some embodiments, the reaction is performed under anhydrous conditions (e.g., in a solvent that is substantially free of water). In some embodiments, the reaction is heated. In some embodiments, the reaction is cooled. In some embodiments, the reaction is performed at room temperature (e.g., about 20-25° C.).

In some embodiments, the reaction proceeds in a single step. In a one-step procedure, an organic compound comprising an organostannane, a boron substituent or a silane substituent may be combined with a silver-containing compound and a fluorinating agent, and optionally an additional reagent such as a base (e.g., NaOH, KOH, BaO, MgO, $NaHCO_3$, $KHCO_3$, $Na_2CO_3$, $Ba(OH)_2$ or 2,6-lutidine) or a salt (e.g., sodium triflate), to yield a fluorinated organic compound.

In some embodiments, the reaction takes place in one pot with two consecutive additions of reagents. For example, an organic compound comprising an organostannane, a boron substituent or a silane substituent may be first reacted with a silver-containing compound in the presence of an optional additional reagent such as a base (e.g., NaOH, KOH, BaO, MgO, $NaHCO_3$, $KHCO_3$, $Na_2CO_3$, $Ba(OH)_2$ or 2,6-lutidine), in a solvent such as acetone. Following an initial reaction period, a fluorinating agent and optionally additional silver-containing compound are added, to yield a fluorinated organic compound.

In some embodiments, the reaction proceeds in two steps. In a two-step procedure, the organic compound comprising an organostannane, a boron substituent or a silane substituent may be first reacted with a silver-containing compound in the presence of an optional additional reagent, such as a base (e.g., NaOH, KOH, BaO, MgO, $NaHCO_3$, $KHCO_3$, $Na_2CO_3$, $Ba(OH)_2$ or 2,6-lutidine). In some embodiments, an intermediate product is isolated from the first reaction. An intermediate product may be further reacted with a fluorinating agent, and in some embodiments, a silver-containing compound may also be added in the second step. In some embodiments, each step further comprises a solvent, and the solvents may be the same or may be different. For example, the first step may take place in methanol, while the second step may take place in acetone. In some embodiments, each step may be performed at a different temperature. For example, the first step may further comprise cooling (e.g., to 0° C.), while the second step may proceed at ambient temperature.

In some embodiments, the reaction is catalytic. For example, in some embodiments, the reaction includes less than about 1 equivalent of the silver-containing compound, e.g., about 90%, about 80%, about 70%, about 60%, about 50 mol %, about 40 mol %, about 30 mol %, about 20 mol % or about 10 mol % of the silver-containing compound. In some embodiments, the reaction includes less than about 10 mol % of the silver-containing compound (e.g., about 9%, about 8%, about 7%, about 6%, about 5%, about 4%, about 3%, about 2%, about 1%, or less).

In some embodiments, the fluorination reaction is performed on an organic compound that is immobilized on a solid support. The term "solid support" refers a material to which a compound is attached to facilitate identification, isolation, purification, or chemical reaction selectivity of the compound. Such materials are known in the art and include, for example, beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, and material having a rigid or semi-rigid surface. The solid supports optionally have functional groups such as amino, hydroxy, carboxy, or halo groups, (see, Obrecht, D. and Villalgrodo, J. M., *Solid-Supported Combinatorial and Parallel Synthesis of Small-Molecular-Weight Compound Libraries*, Pergamon-Elsevier Science Limited (1998)), and include those useful in techniques such as the "split and pool" or "parallel" synthesis techniques, solid-phase and solution-phase techniques, and encoding techniques (see, for example, Czarnik, A. W., *Curr. Opin. Chem. Bio.*, (1997) 1, 60).

In some embodiments, the fluorination of the compound comprising an organostannane, a boron substituent or a silane substituent takes place at a late stage in the synthesis of the fluorinated organic compound. In some embodiments, the fluorination is the last step in the synthesis of the fluorinated organic compound.

In some embodiments, subsequent to the reaction, one or more components of the reaction mixture (e.g., a fluorinated organic compound) are purified from the reaction mixture. In some embodiments, the fluorinated organic compound is purified by column chromatography on silica gel. In some embodiments, the fluorinated organic compound is purified by preparative thin-layer chromatography.

Reaction Products

Described herein are methods of making fluorinated organic compounds. In some embodiments, the fluorinated organic compounds are generated from their corresponding precursors in yields of at least about 60% (e.g., at least about 65%, 70%, 75%, 80%, 85%, 90% or 95%).

The reaction conditions described herein are tolerant of many functional groups as well as chiral centers. In some embodiments, the fluorinated organic compound is further substituted by one or more functional groups, such as alcohols, aldehydes, ketones, esters, alkenes, alkoxy groups, cyano groups, amines, amides and N-oxides. In some embodiments, the fluorinated organic compound contains a chiral center that is derived from the starting material. The stereochemistry at the chiral center may remain substantially unchanged (e.g., little to no racemization of the chiral center occurs during the reaction).

In some embodiments, the fluorinated organic compound comprises $^{19}F$. In some embodiments, the $^{19}F$-containing fluorinated organic compound is an imaging agent, such as an MRI imaging agents. In some embodiments, the $^{19}F$-containing fluorinated organic compound may be used as a probe, such as a biological NMR probes for use in in vivo NMR spectroscopy.

In some embodiments, the fluorinated organic compound comprises $^{18}F$. In some embodiments, the $^{18}F$-containing fluorinated organic compound is an imaging agent, such as a PET imaging agent.

In some embodiments, the fluorinated organic compound is a pharmaceutically acceptable compound. In some embodiments, the fluorinated organic compound is a pharmaceutical agent approved by the United States Food and Drug Administration (FDA) for administration to a human (see, for example, http://www.accessdata.fda.gov/scripts/cder/drugsatfda/).

In some embodiments, the fluorinated organic compound is a compound having pharmaceutical activity. Exemplary fluorinated organic compounds include 3-deoxy-3-fluoroestrone, 6-deoxy-6-fluoro-δ-tocopherol, 10-fluorocamptothecin, or 6-demethoxy-6-fluoroquinine.

Methods of Treatment

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Described herein are compounds and compositions useful in the treatment of a disorder. In general, the compounds described herein are fluorinated derivatives of a pharmaceutical agent (e.g., a fluorinated estrone). Also envisioned herein are other compounds, wherein one or more fluorine moieties have been added to the pharmaceutical agent, e.g., replacing a hydrogen or functional group such as an —OH with a fluorine.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Kits

The compounds used in the methods described herein (e.g., an organic compound comprising an organostannane, a boron substituent or a silane substituent, a silver-containing compound and a fluorinating agent) may be provided in a kit. The kit includes (a) a compound used in a method described herein, and, optionally (b) informational material. The informational material can be descriptive, instructional, marketing or other material that relates to the methods described herein and/or the use of the compounds for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to administer a compound described herein in a suitable manner to perform the methods described herein, e.g., in a suitable dose, dosage form, or mode of administration (e.g., a dose, dosage form, or mode of administration described herein). In another embodiment, the informational material can include instructions to administer a compound described herein to a suitable subject, e.g., a human, e.g., a human having or at risk for a disorder described herein.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, a flavoring agent (e.g., a bitter antagonist or a sweetener), a fragrance, a dye or coloring agent, for example, to tint or color one or more components in the kit, or other cosmetic ingredient, and/or a second agent for treating a condition or disorder described herein. Alternatively, the other ingredients can be included in the kit, but in different compositions or containers than a compound described herein. In such embodiments, the kit can include instructions for admixing a compound described herein and the other ingredients, or for using a compound described herein together with the other ingredients.

In some embodiments, the components of the kit are stored under inert conditions (e.g., under Nitrogen or another inert gas such as Argon). In some embodiments, the components of the kit are stored under anhydrous conditions (e.g., with a desiccant). In some embodiments, the components are stored in a light blocking container such as an amber vial.

A compound described herein can be provided in any form, e.g., liquid, dried or lyophilized form. It is preferred that a compound described herein be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

EXAMPLES

Materials and Methods

Solvents other than methanol were dried by passage through alumina. Except as indicated otherwise, reactions were magnetically stirred and monitored by thin layer chromatography (TLC) using EMD TLC plates pre-coated with 250 μm thickness silica gel 60 F254 plates and visualized by fluorescence quenching under UV light. In addition, TLC plates were stained using ceric ammonium molybdate or potassium permanganate stain. Flash chromatography was performed on Dynamic Adsorbents Silica Gel 40-63 μm particle size or Whatman Silica Gel 60 μm particle size using a forced flow of eluent at 0.3-0.5 bar pressure. Concentration under reduced pressure was performed by rotary evaporation at 25-30° C. at appropriate pressure. Purified compounds were further dried under high vacuum (0.01-0.05 Torr). NMR spectra were recorded on a Varian Mercury 400 (400 MHz for $^1$H, 100 MHz for $^{13}$C, 375 MHz for $^{19}$F, and 126 MHz for $^{31}$P acquisitions), Unity/Inova 500 (500 MHz for $^1$H, 125 MHz for $^{13}$C acquisitions), or Unity/Inova 600 (600 MHz for $^1$H acquisitions) spectrometer. $^{13}$C NMR spectra are recorded $^1$H decoupled. $^{19}$F NMR spectra are recorded $^1$H coupled. Chemical shifts are reported in ppm with the solvent resonance as the internal standard. Data is reported as follows: s=singlet, d=doublet, t=triplet, q=quartet, h=heptet, m=multiplet, br=broad; coupling constants in Hz; integration. High-resolution mass spectra were obtained on Jeol AX-505 or SX-102 spectrometers at the Harvard University Mass Spectrometry Facilities. Sodium hydroxide was purchased from Mallinckrodt chemicals, Molecular sieves 3 Å were purchased from EMD chemicals and finely grinded and dried at 130° C. overnight prior to use. Dichloro[1,1'-bis(diphenylphosphino)-ferrocene]palladium(II) dichloromethane adduct and silver oxide were purchased from Strem. 1-Chloromethyl-4-fluoro-1,4-diazoniabicyclo[2.2.2]octane bis(tetrafluoro-borate), bis(pinacolato)diboron, (1,5-Cyclooctadiene)(methoxy)iridium(I) dimer, 5-bromoindazole, 4-(dimethylamino)pyridine, di-tert-butyl dicarbonate, N-Boc-5-bromoindole, 6-bromoquinoxaline, n-Butyllithium, tert-butyllithium, isopropylmagnesium chloride, tetrakis(triphenylphosphine)palladium, lithium chloride, 4-(dimethylamino)pyridine, di-tert-butyl dicarbonate, trifluoromethanesulfonic anhydride, pyridine, bis(tributyltin), sodium hydride, ethanethiol, 2,4,6-colidine, N-phenylbis(trifluoromethanesulfonimide), tetraethyl orthosilicate, triethoxysilane, bis(acetonitrile)(1,5-cyclooctadiene)rhodium(I) tetrafluoroborate and acetone (CHROMASOLV® Plus, for HPLC, >99.9%) were purchased from Aldrich. m-Toluic acid methyl ester was purchased from Alfa Aesar. Bis(neopentylglycolato)diborone was purchased from Frontier Scientific. Boronic acids were purchased from either Aldrich, Alfar, Frontier Scientific, Beta Pharma, Matrix Scientific, Boron Molecular, or CombiPhos Catalysts and used as received. NMR spectroscopic data of known compounds correspond to the data given in the appropriate references. Pyridine and triethylamine were distilled over calcium hydride. Silver triflate was purchased from Aldrich or Strem. 1-Chloromethyl-4-fluoro-1,4-diazoniabicyclo[2.2.2]octane bis(tetrafluoroborate) was purchased from Aldrich or Alfa Aesar and used as received. Ammonium hexafluorophosphate and tributyltin chloride were purchased from Alfa Aesar and used as received. Commercially available aryl silanes (phenyltriethoxysilane, p-tolyltriethoxysilane, 4-chlorophenyltriethoxysilane, p-methoxyphenyltriethoxysilane, 4-trifluomethylphenyltriethoxysilane, ethyl 4-triethoxysilylbenzoate, 2-(3-triethoxysilylphenyl)-1,3-dioxolane, 1-naphthyltriethoxysilane) were purified by distillation prior to use. NMR spectroscopic data of known compounds correspond to the data given in the appropriate references. Freshly prepared arylstannanes and 1-chloromethyl-4-fluoro-1,4-diazoniabicyclo[2.2.2]octane bis(hexafluorophosphate) were used for fluorination reactions.

Example 1

Identification of optimal silver(I) Salt in stannane reactions

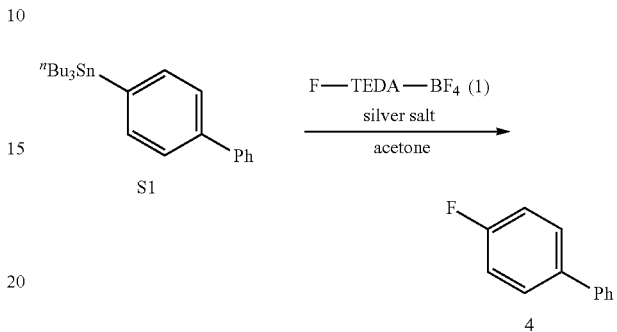

Under ambient atmosphere, to 4-(biphenyl)tributylstannane (S1) (8.9 mg, 0.020 mmol, 1.0 equiv) in acetone (0.4 mL) at 23° C. was added silver salt (0.040 mmol, 2.0 equiv) and 1-chloromethyl-4-fluoro-1,4-diazoniabicyclo[2.2.2]octane bis(trifluoroborate) (1) (8.5 mg, 0.024 mmol, 1.2 equiv). The reaction mixture was stirred at 23° C. for 20 min. To the reaction mixture was added 3-nitrofluorobenzene (2.00 μL, 0.0188 mmol). The yields were determined by comparing integration of the $^{19}$F NMR (375 MHz, acetone, 23° C.) resonance of 4-fluorobiphenyl (−118.1 ppm) and that of 3-nitrofluorobenzene (−112.0 ppm). Yields are reported in Table 1.

TABLE 1

| Identification of optimal silver(I) salt | | | |
|---|---|---|---|
| Silver salt | Yield [%] ($^{19}$F NMR) | Silver salt | Yield [%] ($^{19}$F NMR) |
| AgF | 51 | AgCl | 0 |
| AgOAc | 20 | AgOBz | 1 |
| Ag(TFA) | 0 | AgOTf | 63 |
| AgBF$_4$ | 40 | AgPF$_6$ | 55 |
| AgClO$_4$ | 49 | AgSbF$_6$ | 5 |
| AgNO$_3$ | 11 | AgNO$_2$ | 29 |
| Ag$_2$CO$_3$ | 9 | Ag$_3$PO$_4$ | 27 |
| AgCN | 4 | none | 0 |

Example 2

Synthesis of 1-Chloromethyl-4-fluoro-1,4-diazoniabicyclo[2.2.2]octane bis(hexafluorophosphate) (2)

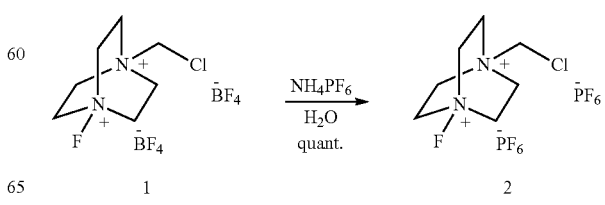

To 1-chloromethyl-4-fluoro-1,4-diazoniabicyclo[2.2.2]octane bis(tetrafluoroborate) (1) (1.06 g, 3.00 mmol, 1.00 equiv) in H$_2$O (9.0 mL) at 23° C. was added ammonium hexafluorophosphate (2.93 g, 18.0 mmol, 6.00 equiv). After stirring for 1 h, the suspension was filtered off and washed with H$_2$O (5×5 mL) and Et$_2$O (10 mL) to afford 1.43 g of the title compound as a colorless solid (quantitative yield).

NMR Spectroscopy: $^1$H NMR (400 MHz, acetonitrile-d3, 23° C., δ): 5.27 (s, 2H), 4.70 (dt, J=7.6 Hz, 7.2 Hz, 6H), 4.24 (t, J=7.2, 6H). $^{13}$C NMR (125 MHz, acetonitrile-d6, 23° C., δ): 70.08, 58.18 (d, J$_{CF}$=15.3 Hz), 54.67. $^{19}$F NMR (375 MHz, acetonitrile-d3, 23° C., δ): 47.61 (s, 1F), −72.89 (d, J$_{FP}$=710 Hz, 6F). $^{31}$P NMR (162 MHz, acetonitrile-d3, 23° C., δ): −143.5 (h, J$_{FP}$=710 Hz). Mass Spectrometry: HRMS-FIA (m/z): Calcd for [M-PF$_6$]$^+$, 325.04659. Found, 325.04664.

Example 3

Synthesis of (4-Biphenyl)tributylstannane (S1)

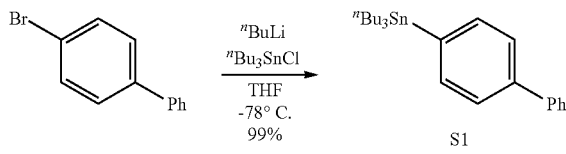

To 4-bromobiphenyl (2.00 g, 8.58 mmol, 1.00 equiv) in THF (20 mL) at −78° C. was added $^n$BuLi (2.5 M in hexane, 3.43 mL, 8.6 mmol, 1.0 equiv). The reaction mixture was stirred at −78° C. for 30 min before the addition of $^n$Bu$_3$SnCl (2.79 g, 8.58 mmol, 1.00 equiv). After stirring for 1.0 hr at −78° C., the reaction mixture was warmed to 23° C. and the solvent was removed in vacuo. The residue was dissolved in 20 mL of Et$_2$O and filtered through a plug of neutral alumina. The filtrate was concentrated in vacuo to afford 3.76 g of the title compound as a colorless oil (99% yield).

R$_f$=0.58 (hexanes). NMR Spectroscopy: $^1$H NMR (600 MHz, CDCl$_3$, 23° C., δ): 7.61 (d, J=8.4 Hz, 2H), 7.58–7.51 (m, 4H), 7.44 (dd, J=7.8 Hz, 7.8 Hz, 2H), 7.34 (t, J=8.4 Hz, 1H), 1.62–1.54 (m, 6H), 1.38–1.32 (m, 6H), 1.15–1.03 (m, 6H), 0.91 (t, J=6.0 Hz, 9H). $^{13}$C NMR (100 MHz, CDCl$_3$, 23° C., δ): 141.31, 140.76, 136.89, 128.71, 127.14, 127.08, 126.96, 126.63, 29.16, 27.44, 13.71, 9.62.

Example 4

Synthesis of tributyl(4-hydroxyphenyl)stannane (S2)

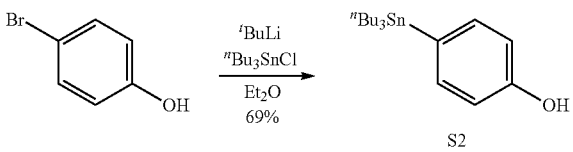

To 4-bromophenol (346 mg, 2.00 mmol, 1.00 equiv) in Et$_2$O (10 mL) at −78° C. was added $^t$BuLi (1.7 M in pentane, 3.65 mL, 6.2 mmol, 3.1 equiv). The reaction mixture was stirred at −78° C. for 2.0 hr before the addition of $^n$Bu$_3$SnCl (780 mg, 2.40 mmol, 1.20 equiv). After stirring for 2.0 hr at −78° C., the reaction mixture was warmed to 23° C. and quenched with saturated aqueous NH$_4$Cl (10 mL). The phases were separated and the aqueous phase was extracted with Et$_2$O (3×10 mL). The combined organic phases were washed with brine (30 mL) and dried (Na$_2$SO$_4$). The filtrate was concentrated in vacuo and the residue was purified by chromatography on silica gel eluting with hexanes/EtOAc 19:1 (v/v) to afford 530 mg of the title compound as a colorless oil (69% yield).

R$_f$=0.68 (hexanes/EtOAc 3:1 (v/v)). NMR Spectroscopy: $^1$H NMR (600 MHz, CDCl$_3$, 23° C., δ): 7.32 (d, J=7.8 Hz, 2H), 6.83 (d, J=7.8 Hz, 2H), 4.62 (s, 1H), 1.56–1.46 (m, 6H), 1.36–1.28 (m, 6H), 1.08–0.96 (m, 6H), 0.88 (t, J=6.0 Hz, 9H). $^{13}$C NMR (125 MHz, CDCl$_3$, 23° C., δ): 155.67, 137.65, 132.06, 115.29, 29.07, 27.35, 13.57, 9.58.

Example 5

Synthesis of (4-methoxyphenyl)trimethylstannane (S3)

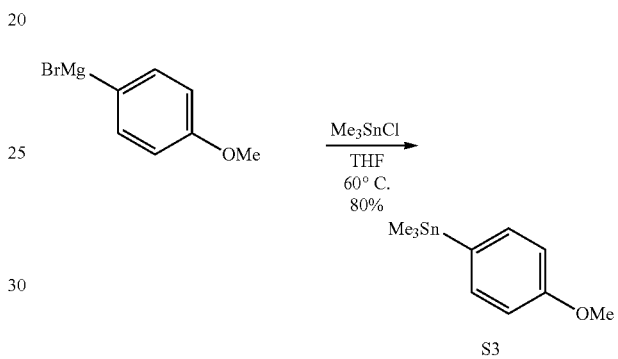

To trimethyltin chloride (1.71 g, 8.58 mmol, 1.00 equiv) in THF (50 mL) at 23° C. was added 4-methoxyphenylmagnesium bromide (0.50 M in THF, 34.3 mL, 17 mmol, 2.0 equiv). After stirring for 1.0 hr at 60° C., the reaction mixture was cooled to 0° C. and quenched with saturated aqueous NH$_4$Cl (50 mL), and Et$_2$O (50 mL) was added. The phases were separated and the aqueous phase was extracted with Et$_2$O (2×50 mL). The combined organic phases were washed with brine (100 mL) and dried (Na$_2$SO$_4$). The filtrate was concentrated in vacuo and the residue was purified by fractional distillation to afford 1.86 g of the title compound as a colorless oil (80% yield).

R$_f$=0.14 (hexanes). NMR Spectroscopy: $^1$H NMR (600 MHz, CDCl$_3$, 23° C., δ): 7.47 (d, J=8.4 Hz, 2H), 6.98 (d, J=8.4 Hz, 2H), 3.85 (s, 3H), 0.38–0.29 (m, 9H). $^{13}$C NMR (100 MHz, CDCl$_3$, 23° C., δ): 159.86, 136.85, 132.34, 113.97, 55.00, −9.54.

Example 6

Synthesis of tributyl(2,4,6-trimethylphenyl)stannane (S4)

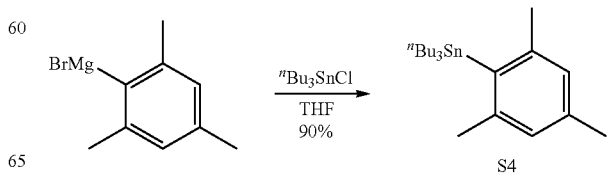

To 2,4,6-trimethylphenylmagnesium bromide (1.0 M in THF, 10.0 mL, 10 mmol, 1.0 equiv) in THF (30 mL) at −78° C. was added "Bu₃SnCl (3.25 g, 10.0 mmol, 1.00 equiv). After stirring for 1.0 hr at 23° C., the solvent was removed in vacuo and the residue was purified by fractional distillation to afford 3.68 g of the title compound as a colorless oil (90% yield).

$R_f$=0.76 (hexanes). NMR Spectroscopy: $^1$H NMR (500 MHz, CDCl₃, 23° C., δ): 6.88 (s, 2H), 2.37 (s, 6H), 2.31 (s, 3H), 1.55–1.46 (m, 6H), 1.39–1.30 (m, 6H), 1.11–1.07 (m, 6H), 0.92 (t, J=6.0 Hz, 9H). $^{13}$C NMR (125 MHz, CDCl₃, 23° C., δ): 145.18, 138.32, 137.83, 127.59, 29.18, 27.44, 25.54, 20.91, 13.62, 12.49.

Example 7

Synthesis of tributyl(4-fluorophenyl)stannane (S5)

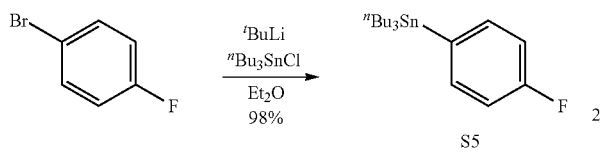

To 1-bromo-4-fluorobenzene (1.75 g, 10.0 mmol, 1.00 equiv) in Et₂O (25 mL) at −78° C. was added $^t$BuLi (1.7 M in pentane, 11.8 mL, 20 mmol, 2.0 equiv). The reaction mixture was stirred at −78° C. for 30 min before the addition of "Bu₃SnCl (3.26 g, 10.0 mmol, 1.00 equiv). The reaction mixture was warmed to 23° C. and stirred for 1.0 hr before being filtered through a plug of neutral alumina. The filtrate was concentrated in vacuo to afford 3.76 g of the title compound as a colorless oil (98% yield).

$R_f$=0.63 (hexanes). NMR Spectroscopy: $^1$H NMR (600 MHz, CDCl₃, 23° C., δ): 7.41 (dd, J=8.4 Hz, 6.6 Hz, 2H), 7.04 (dd, J=9.6 Hz, 8.4 Hz, 2H), 1.59-1.46 (m, 6H), 1.36–1.30 (m, 6H), 1.11–1.09 (m, 6H), 0.89 (t, J=6.0 Hz, 9H). $^{13}$C NMR (100 MHz, CDCl₃, 23° C., δ): 163.24 (d, J=245 Hz), 137.83 (d, J=6.9 Hz), 136.65 (d, J=4.6 Hz), 115.11 (d, J=19.0 Hz), 29.07, 27.38, 13.66, 9.65. $^{19}$F NMR (375 MHz, CDCl₃, 23° C., δ): −114.1.

Example 8

Synthesis of tributyl(4-cyanophenyl)stannane (S6)

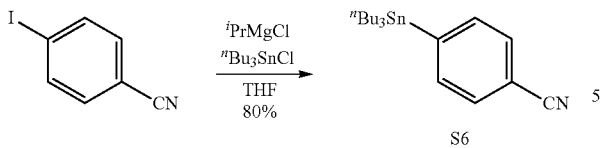

To 4-iodobenzonitrile (2.29 g, 10.0 mmol, 1.00 equiv) in THF (30 mL) at −40° C. was added $^i$PrMgCl (2.0 M in Et₂O, 5.50 mL, 11 mmol, 1.1 equiv). The reaction mixture was stirred for 1.0 hr at −40° C. before the addition of nBu₃SnCl (3.91 g, 12.0 mmol, 1.20 equiv). After stirring for 1.0 hr at −40° C., the reaction mixture was warmed to 23° C. and quenched with saturated aqueous NH₄Cl (30 mL), and Et₂O (20 mL) was added. The phases were separated and the aqueous phase was extracted with Et₂O (2×20 mL). The combined organic phases were washed with brine (50 mL) and dried (Na₂SO₄). The filtrate was concentrated in vacuo and the residue was purified by chromatography on silica gel eluting with hexanes to afford 3.14 g of the title compound as a colorless oil (80% yield).

$R_f$=0.25 (hexanes/EtOAc 50:1 (v/v)). NMR Spectroscopy: $^1$H NMR (500 MHz, CDCl₃, 23° C., δ): 7.56–7.55 (m, 4H), 1.57–1.49 (m, 6H), 1.34–1.30 (m, 6H), 1.11–1.07 (m, 6H), 0.89 (t, J=6.0 Hz, 9H). $^{13}$C NMR (125 MHz, CDCl₃, 23° C., δ): 150.27, 136.83, 130.65, 119.17, 111.51, 28.92, 27.24, 13.58, 9.68.

Example 9

Synthesis of tributyl(4-formylphenyl)stannane (S7)

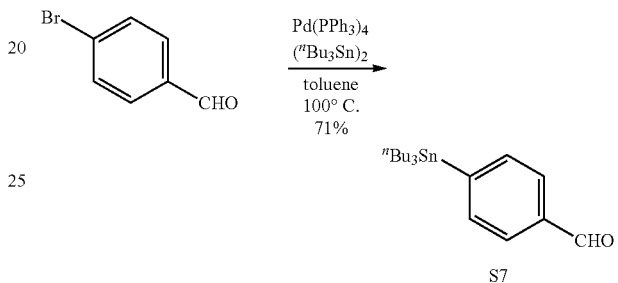

To 4-bromobenzaldehyde (185 mg, 1.00 mmol, 1.00 equiv) in toluene (10 mL) at 23° C. was added tetrakis(triphenylphosphine)palladium (58.0 mg, 0.0500 mmol, 5.00 mol %) and bis(tri-n-butyltin) (1.01 mL, 2.00 mmol, 2.00 equiv). After stirring for 24 hr at 100° C., the reaction mixture was cooled to 23° C. and concentrated in vacuo. The residue was purified by chromatography on silica gel eluting with hexanes to afford 280 mg of the title compound as a colorless oil (71% yield).

$R_f$=0.50 (hexanes/EtOAc 9:1 (v/v)). NMR Spectroscopy: $^1$H NMR (600 MHz, CDCl₃, 23° C., δ): 9.99 (s, 1H), 7.79 (d, J=7.8 Hz, 2H), 7.66 (d, J=7.8 Hz, 2H), 1.58–1.42 (m, 6H), 1.36–1.26 (m, 6H), 1.12–0.98 (m, 6H), 0.88 (t, J=6.0 Hz, 9H). $^{13}$C NMR (100 MHz, CDCl₃, 23° C., δ): 192.89, 152.61, 136.94, 135.87, 128.45, 29.00, 27.30, 13.63, 9.69.

Example 10

Synthesis of tributyl[{(4-dimethylamino)methyl}phenyl]stannane (S8)

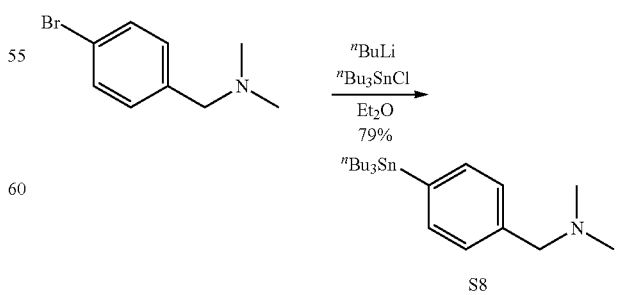

To (4-bromobenzyl)dimethylamine (2.14 g, 10.0 mmol, 1.00 equiv) in Et₂O (25 mL) at 23° C. was added "BuLi (2.4

M in hexane, 4.17 mL, 10 mmol, 1.0 equiv). The reaction mixture was warmed to 23° C. and stirred for 2.0 hr before the addition of $^n$Bu$_3$SnCl (3.25 g, 10.0 mmol, 1.00 equiv) at −78° C. After stirring for 1.0 hr at 23° C., the reaction mixture was concentrated in vacuo. The residue was purified by chromatography on silica gel eluting with hexanes/EtOAc 1:1 (v/v) to afford 3.35 g of the title compound as a colorless oil (79% yield).

$R_f$=0.20 (hexanes/EtOAc 1:1 (v/v)). NMR Spectroscopy: $^1$H NMR (500 MHz, CDCl$_3$, 23° C., δ): 7.42 (d, J=6.5 Hz, 2H), 7.27 (d, J=6.5 Hz, 2H), 3.41 (s, 2H), 2.26 (s, 6H), 1.64–1.48 (m, 6H), 1.40–1.30 (m, 6H), 1.15–0.99 (m, 6H), 0.90 (t, J=6.0 Hz, 9H). $^{13}$C NMR (100 MHz, CDCl$_3$, 23° C., δ): 140.30, 138.40, 136.36, 128.72, 64.40, 45.36, 29.07, 27.35, 13.64, 9.52. Mass Spectrometry: HRMS-FIA (m/z): Calcd for [M+H]$^+$, 426.21772. Found, 426.21651.

Example 11

Synthesis of tributyl[{(4-dimethylamino)methyl}phenyl]stannane N-oxide (S9)

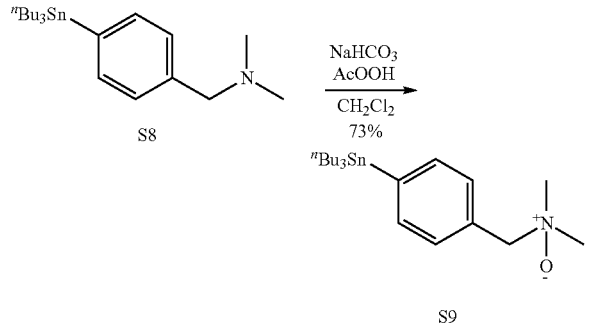

To tributyl[{4-dimethylamino}methyl]phenyl]stannane (S8) (42.4 mg, 0.100 mmol, 1.00 equiv) in CH$_2$Cl$_2$ (1.0 mL) at 0° C. was added sodium bicarbonate (16.8 mg, 0.200 mmol, 2.00 equiv) and peracetic acid (21.0 μL, 32 wt. % in dilute acetic acid, 0.10 mmol, 1.0 equiv). The reaction mixture was warmed to 23° C. and stirred for 10 min before being filtered through a plug of basic alumina. The filtrate was concentrated in vacuo and purified by preparative TLC eluting with CH$_2$Cl$_2$/MeOH 9:1 (v/v) to afford 32.9 mg of the title compound as a light orange solid (73% yield).

$R_f$=0.15 (CH$_2$Cl$_2$/MeOH 9:1 (v/v)). NMR Spectroscopy: $^1$H NMR (500 MHz, CDCl$_3$, 23° C., δ): 7.50 (d, J=7.5 Hz, 2H), 7.39 (d, J=7.5 Hz, 2H), 4.38 (s, 2H), 3.11 (s, 6H), 1.58–1.42 (m, 6H), 1.36–1.27 (m, 6H), 1.12–0.97 (m, 6H), 0.86 (t, J=6.0 Hz, 9H). $^{13}$C NMR (100 MHz, CDCl$_3$, 23° C., δ): 144.77, 136.84, 131.20, 130.06, 76.76, 57.72, 28.97, 27.27, 13.60, 9.56. Mass Spectrometry: HRMS-FIA (m/z): Calcd for [M+H]$^+$, 442.21264. Found, 442.21307.

Example 12

Synthesis of N-Boc-5-bromoindole (S10)

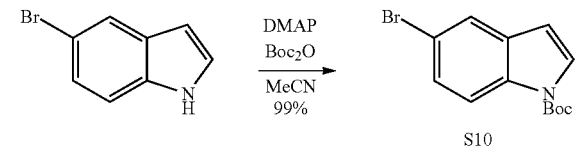 [SMILES: Brc1ccc2[nH]ccc2c1 ; CC(C)(C)OC(=O)n1ccc2cc(Br)ccc21 ; "S10"]

To 5-bromoindole (196 mg, 1.00 mmol, 1.00 equiv) in acetonitrile (2.0 mL) at 23° C. was added di-tert-butyl dicarbonate (276 mL, 1.20 mmol, 1.20 equiv) and 4-dimethylaminopyridine (12.0 mg, 0.100 mmol, 10.0 mol %). After stirring for 30 min at 23° C., the reaction mixture was concentrated in vacuo. The residue was purified by chromatography on silica gel eluting with hexanes/EtOAc 30:1 (v/v) to afford 293 mg of the title compound as a colorless solid (99% yield).

$R_f$=0.35 (hexanes/EtOAc 30:1 (v/v)). NMR Spectroscopy: $^1$H NMR (400 MHz, CDCl$_3$, 23° C., δ): 8.02 (d, J=8.8 Hz, 1H), 7.69 (d, J=2.0 Hz, 1H), 7.58 (d, J=3.6 Hz, 1H), 7.39 (dd, J=8.8 Hz, 2.0 Hz, 1H), 6.50 (d, J=3.6 Hz, 1H), 1.67 (s, 9H). $^{13}$C NMR (100 MHz, CDCl$_3$, 23° C., δ): 149.40, 133.90, 132.22, 127.00, 123.51, 116.54, 115.94, 106.45, 84.12, 28.14. (Note: Only ten peaks were observed probably due to accidental overlap of two peaks)

Example 13

Synthesis of N-Boc-5-(tributylstannyl)indole (S11)

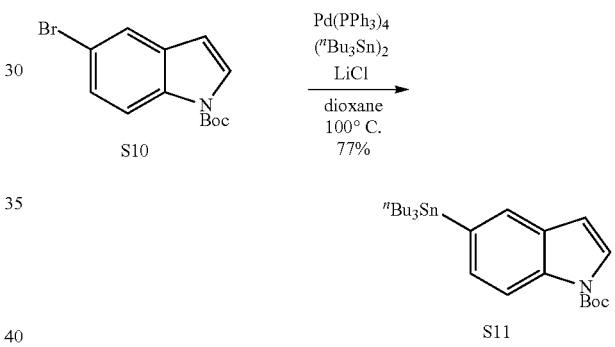

To N-Boc-5-bromoindole (S10) (285 mg, 0.962 mmol, 1.00 equiv) in dioxane (2.5 mL) at 23° C. was added lithium chloride (203 mg, 4.81 mmol, 5.00 equiv), tetrakis(triphenylphosphine)palladium (55.6 mg, 0.0481 mmol, 5.00 mol %) and bis(tri-n-butyltin) (0.972 mL, 1.92 mmol, 2.00 equiv). After stirring for 6.0 hr at 100° C., the reaction mixture was cooled to 23° C. and concentrated in vacuo. The residue was dissolved in 10 mL hexanes and filtered through a plug of Celite. The filtrate was concentrated in vacuo and the residue was purified by chromatography on silica gel eluting with hexanes/EtOAc 50:1 (v/v) to afford 376 mg of the title compound as a colorless oil (77% yield).

$R_f$=0.22 (hexanes/EtOAc 50:1 (v/v)). NMR Spectroscopy: $^1$H NMR (500 MHz, CDCl$_3$, 23° C., δ): 8.15 (d, J=7.0 Hz, 1H), 7.70 (s, 1H), 7.60 (d, J=3.5 Hz, 1H), 7.44 (d, J=8.0 Hz, 1H), 6.59 (d, J=3.5 Hz, 1H), 1.70 (s, 9H), 1.67–1.55 (m, 6H), 1.43–1.35 (m, 6H), 1.20–1.06 (m, 6H) 0.96 (t, J=6.0 Hz, 9H). $^{13}$C NMR (125 MHz, CDCl$_3$, 23° C., δ): 149.84, 135.24, 134.56, 131.88, 130.68, 129.00, 125.38, 114.77, 107.09, 83.48, 29.12, 28.18, 27.38, 13.67, 9.66. Mass Spectrometry: HRMS-FIA (m/z): Calcd for [M+H]$^+$, 508.22320. Found, 508.22257.

Example 14

Synthesis of 5-(tributylstannyl)isatin (S12)

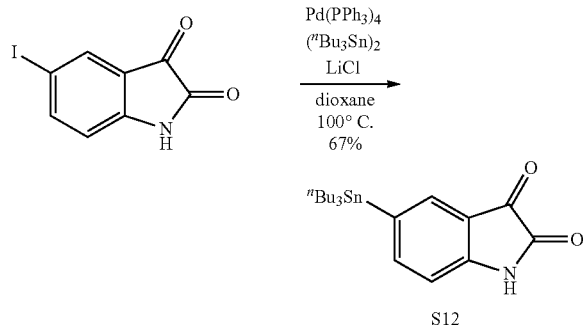

To 5-iodoisatin (273 mg, 1.00 mmol, 1.00 equiv) in dioxane (10 mL) at 23° C. was added lithium chloride (212 mg, 5.00 mmol, 5.00 equiv), tetrakis(triphenylphosphine)palladium (58.0 mg, 0.0500 mmol, 5.00 mol %) and bis(tri-n-butyltin) (1.01 mL, 2.00 mmol, 2.00 equiv). After stirring for 5 hr at 100° C., the reaction mixture was cooled to 23° C. and concentrated in vacuo. The residue was purified by chromatography on silica gel eluting with hexanes/EtOAc 4:1 (v/v) to afford 289 mg of the title compound as a colorless oil (67% yield).

$R_f$=0.73 (hexanes/EtOAc 1:1 (v/v)). NMR Spectroscopy: $^1$H NMR (500 MHz, CDCl$_3$, 23° C., δ): 9.10 (s br, 1H), 7.67 (s, 1H), 7.63 (d, J=7.5 Hz, 1H), 6.97 (d, J=7.5 Hz, 1H), 1.58–1.42 (m, 6H), 1.36–1.26 (m, 6H), 1.12–0.98 (m, 6H), 0.88 (t, J=6.0 Hz, 9H). $^{13}$C NMR (125 MHz, CDCl$_3$, 23° C., δ): 183.85, 159.82, 149.35, 146.72, 137.41, 133.00, 117.81, 112.48, 29.02, 27.26, 13.60, 9.73. Mass Spectrometry: HRMS-FIA (m/z): Calcd for [M+H]$^+$, 438.14495. Found, 438.14536.

Example 15

Synthesis of 6-(quinolinyl)tributylstannane (S13)

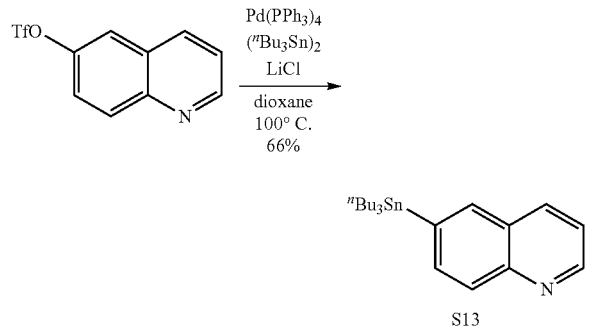

To 6-quinolinyl trifluoromethanesulfonate (277 mg, 1.00 mmol, 1.00 equiv) in dioxane (10 mL) at 23° C. was added lithium chloride (212 mg, 5.00 mmol, 5.00 equiv), tetrakis(triphenylphosphine)palladium (58.0 mg, 0.0500 mmol, 5.00 mol %) and bis(tri-n-butyltin) (1.01 mL, 2.00 mmol, 2.00 equiv). After stirring for 5 hr at 100° C., the reaction mixture was cooled to 23° C. and concentrated in vacuo. The residue was purified by chromatography on silica gel eluting with hexanes/EtOAc 9:1 (v/v) to afford 275 mg of the title compound as colorless oil (66% yield).

$R_f$=0.61 (hexanes/EtOAc 1:1 (v/v)). NMR Spectroscopy: $^1$H NMR (500 MHz, CDCl$_3$, 23° C., δ): 8.89 (d, J=4.0 Hz, 1H), 8.12 (d, J=8.0 Hz, 1H), 8.06 (d, J=8.0 Hz, 1H), 7.91 (s, 1H), 7.81 (d, J=8.0 Hz, 1H), 7.38 (dd, J=8.0 Hz, 4.0 Hz, 1H), 1.66–1.50 (m, 6H), 1.42–1.28 (m, 6H), 1.22–1.06 (m, 6H), 0.90 (t, J=6.0 Hz, 9H). $^{13}$C NMR (125 MHz, CDCl$_3$, 23° C., δ): 150.46, 148.51, 141.45, 137.06, 136.52, 135.91, 128.45, 128.34, 121.18, 29.38, 27.60, 13.91, 10.00. Mass Spectrometry: HRMS-FIA (m/z): Calcd for [M+H]$^+$, 420.17077. Found, 420.17191.

Example 16

Synthesis of 3-(trifluoromethanesulfonyl)estrone (S14)

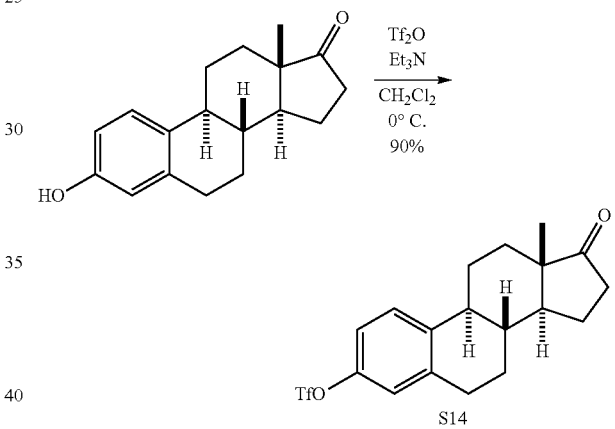

To estrone (1.00 g, 3.70 mmol, 1.00 equiv) in CH$_2$Cl$_2$ (19 mL) at 0° C. was added triethylamine (1.03 mL, 7.40 mmol, 2.00 equiv) and trifluoromethanesulfonic anhydride (684 μL, 4.07 mmol, 1.10 equiv). The reaction mixture was stirred at 0° C. for 20 min before the addition of saturated aqueous NaHCO$_3$ (20 mL). The phases were separated and the aqueous phase was extracted with CH$_2$Cl$_2$ (2×20 mL). The combined organic phases are washed with brine (40 mL) and dried (Na$_2$SO$_4$). The filtrate was concentrated in vacuo and the residue was purified by chromatography on silica gel eluting with hexanes/EtOAc 4:1 (v/v) to afford 1.34 g of the title compound as a colorless oil (90% yield).

$R_f$=0.60 (hexanes/EtOAc 7:3 (v/v)). NMR Spectroscopy: $^1$H NMR (500 MHz, CDCl$_3$, 23° C., δ): 7.34 (d, J=9.0 Hz, 1H), 7.03 (dd, J=9.0 Hz, 2.5 Hz, 1H), 6.99 (d, J=2.5 Hz, 1H), 2.97–2.92 (m, 2H), 2.51 (dd, J=19.0 Hz, 8.5 Hz, 1H), 2.43–2.37 (m, 1H), 2.33–2.26 (m, 1H), 2.20–1.95 (m, 4H), 1.68–1.42 (m, 6H), 0.92 (s, 3H). $^{13}$C NMR (125 MHz, CDCl$_3$, 23° C., δ): 220.59, 147.83, 140.53, 139.55, 127.43, 121.47, 118.99 (q, J=320 Hz), 118.53, 50.63, 48.09, 44.34, 38.00, 36.03, 31.73, 29.62, 26.33, 25.92, 21.80, 14.03. $^{19}$F NMR (375 MHz, CDCl$_3$, δ): −73.36.

Example 17

Synthesis of 3-deoxy-3-(tributystannyl)estrone (S15)

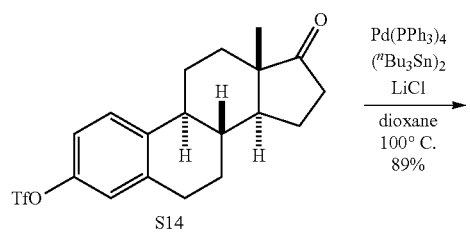

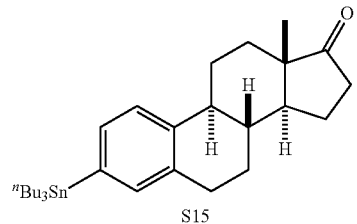

To 3-(trifluoromethanesulfonyl)estrone (S14) (402 mg, 1.00 mmol, 1.00 equiv) in dioxane (10 mL) at 23° C. was added lithium chloride (212 mg, 5.00 mmol, 5.00 equiv), tetrakis(triphenylphosphine)palladium (58.0 mg, 0.0500 mmol, 5.00 mol %) and bis(tri-n-butyltin) (1.01 mL, 2.00 mmol, 2.00 equiv). After stirring for 14 hr at 100° C., the reaction mixture was cooled to 23° C. and concentrated in vacuo. The residue was purified by chromatography on silica gel eluting with hexanes/EtOAc 19:1 (v/v) to afford 484 mg of the title compound as a colorless oil (89% yield).

$R_f$=0.48 (hexanes/EtOAc 19:1 (v/v)). NMR Spectroscopy: $^1$H NMR (600 MHz, CDCl$_3$, 23° C., δ): 7.30–7.12 (m, 3H), 2.94–2.90 (m, 2H), 2.52 (dd, J=19.0 Hz, 8.5 Hz, 1H), 2.45–2.40 (m, 1H), 2.36–2.30 (m, 1H), 2.18–1.95 (m, 4H), 1.68–1.42 (m, 12H), 1.38–1.28 (m, 6H), 1.06–0.96 (m, 6H), 0.95–0.87 (m, 12H). $^{13}$C NMR (125 MHz, CDCl$_3$, 23° C., δ): 220.84, 139.47, 138.70, 137.30, 135.88, 133.95, 124.82, 50.56, 47.98, 44.47, 38.07, 35.82, 31.61, 29.35, 29.08, 27.38, 26.55, 25.50, 21.55, 13.82, 13.65, 9.48. Mass Spectrometry: HRMS-FIA (m/z): Calcd for [M+H]$^+$, 545.27999. Found, 545.28035.

Example 18

Synthesis of 6-(trifluoromethanesulfonyl)-δ-tocopherol (S16)

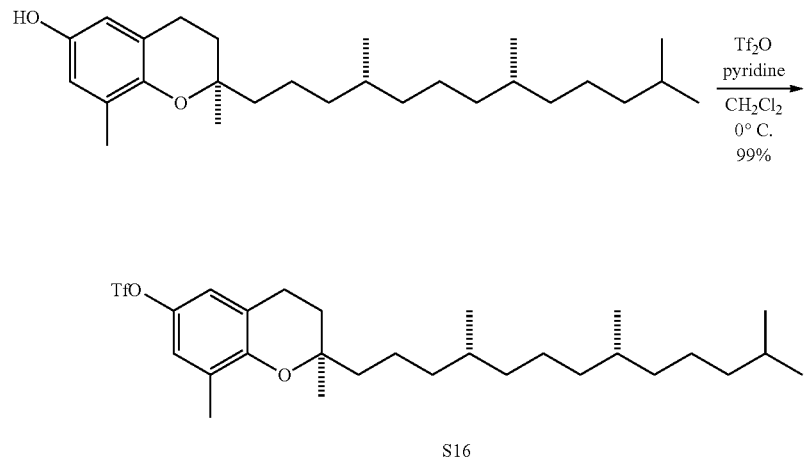 [SMILES: Cc1cc(O)cc2c1O[C@](C)(CCC[C@H](C)CCC[C@H](C)CCCC(C)C)CC2 ; Cc1cc(OS(=O)(=O)C(F)(F)F)cc2c1O[C@](C)(CCC[C@H](C)CCC[C@H](C)CCCC(C)C)CC2 ; "S16"]

To δ-tocopherol (805 mg, 2.00 mmol, 1.00 equiv) in CH$_2$Cl$_2$ (10 mL) at 0° C. was added pyridine (484 µL, 6.00 mmol, 3.00 equiv) and trifluoromethanesulfonic anhydride (404 µL, 2.40 mmol, 1.20 equiv). The reaction mixture was stirred at 0° C. for 15 min before the addition of saturated aqueous NaHCO$_3$ (10 mL). The phases were separated and the aqueous phase was extracted with CH$_2$Cl$_2$ (2×10 mL). The combined organic phases are washed with brine (20 mL) and dried (Na$_2$SO$_4$). The filtrate was concentrated in vacuo and the residue was purified by chromatography on silica gel eluting with hexanes to afford 1.06 g of the title compound as a colorless oil (99% yield).

$R_f$=0.75 (hexanes/EtOAc 9:1 (v/v)). NMR Spectroscopy: $^1$H NMR (600 MHz, CDCl$_3$, 23° C., δ): 6.85 (d, J=3.0 Hz, 1H), 6.81 (d, J=3.0 Hz, 1H), 2.80–2.70 (m, 2H), 2.16 (s, 3H), 1.84–1.72 (m, 2H), 1.60–0.80 (m, 36H). $^{13}$C NMR (100 MHz, CDCl$_3$, 23° C., δ): 151.68, 141.46, 128.36, 121.67, 120.72, 119.06, 118.77 (q, J=319 Hz), 76.82, 40.12, 39.38, 37.44, 37.39, 37.37, 37.28, 32.80, 32.66, 30.63, 27.98, 24.81, 24.44, 24.12, 22.70, 22.61, 22.41, 20.91, 19.73, 19.62, 16.16. $^{19}$F NMR (375 MHz, CDCl$_3$, 23° C., δ): −73.45. Mass Spectrometry: HRMS-FIA (m/z): Calcd for [M+Na]$^+$, 557.28829. Found, 557.28842.

Example 19

Synthesis of 6-deoxy-6-(tributylstannyl)-δ-tocopherol (S17)

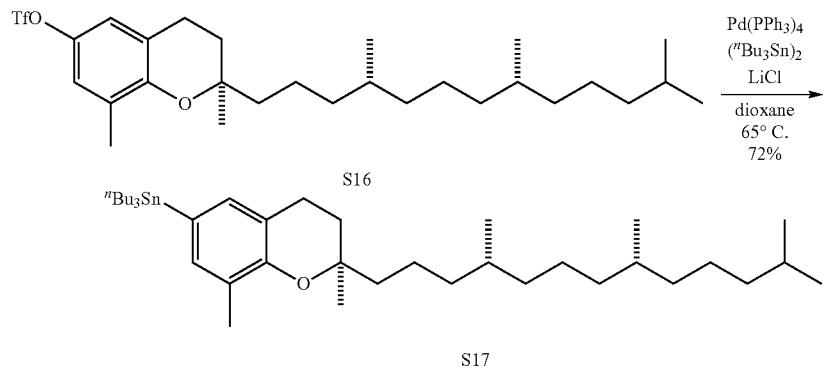

To trifluoromethanesulfonyl-δ-tocopherol (S16) (230 mg, 0.430 mmol, 1.00 equiv) in THF (4.3 mL) at 23° C. was added lithium chloride (91.1 mg, 2.15 mmol, 5.00 equiv), tetrakis (triphenylphosphine)palladium (24.9 mg, 0.0215 mmol, 5.00 mol %) and bis(tri-n-butyltin) (434 μL, 0.860 mmol, 2.00 equiv). After stirring for 21 hr at 65° C., the reaction mixture was cooled to 23° C. and concentrated in vacuo. The residue was dissolved in MeCN (3 mL) and was extracted with hexanes (3×3 mL). The combined hexanes phase were concentrated in vacuo and the excess bis(tri-n-butyltin) was removed by distillation (50 Torr, 170° C.). The residue was dissolved in hexanes/Et$_3$N 19:1 (v/v) and passed through a plug of basic alumina. The filtrate was concentrated in vacuo to afford 210 mg of the title compound as a colorless oil (72% yield).

No R$_f$ value available due to the instability of the title compound on silica gel. NMR Spectroscopy: $^1$H NMR (600 MHz, CDCl$_3$, 23° C., δ): 7.00 (s, 1H), 6.94 (s, 1H), 2.80–2.70 (m, 2H), 2.17 (s, 3H), 1.87–1.81 (m, 1H), 1.79–1.73 (m, 1H), 1.60–0.84 (m, 36H). $^{13}$C NMR (100 MHz, CDCl$_3$, 23° C., δ): 152.49, 136.20, 135.13, 129.52, 125.91, 120.31, 75.91, 40.45, 39.37, 37.44, 37.27, 32.79, 32.70, 31.18, 30.63, 29.13, 27.97, 27.44, 24.80, 24.44, 24.37, 22.72, 22.63, 22.22, 21.00, 19.74, 19.65, 16.05, 13.69, 9.53.

Mass Spectrometry: HRMS-FIA (m/z): Calcd for [M+Na]$^+$, 699.44973. Found, 699.44992.

Example 20

Synthesis of 10-(trifluoromethanesulfonyloxy)camptothecin (S18)

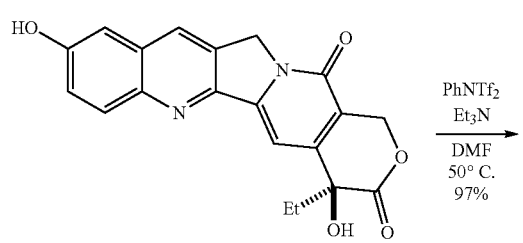

To 10-hydroxycamptothecin (200 mg, 0.549 mmol, 1.00 equiv) in DMF (5.0 mL) at 23° C. was added triethylamine (153 μL, 1.10 mmol, 2.00 equiv) and N-phenylbis(trifluoromethanesulfonimide) (294 mg, 0.824 mmol, 1.50 equiv) and the reaction mixture was stirred for 3 hr at 50° C. The reaction mixture was cooled to 23° C. and concentrated in vacuo. The residue was purified by chromatography on silica gel eluting with hexanes/EtOAc 3:7 (v/v) to afford 265 mg of the title compound as a colorless solid (97% yield).

R$_f$=0.25 (hexanes/EtOAc 3:7 (v/v)). NMR Spectroscopy: $^1$H NMR (400 MHz, CDCl$_3$, 23° C., δ): 8.44 (s, 1H), 8.33 (d, J=9.6 Hz, 1H), 7.86 (d, J=2.4 Hz, 1H), 7.71 (s, 1H), 7.70 (dd, J=9.6 Hz, 2.4 Hz, 1H), 5.74 (d, J=16.8 Hz, 1H), 5.33 (s, 2H), 5.31 (d, J=16.8 Hz, 1H), 3.94 (s, 1H), 2.00–1.81 (m, 2H), 1.04 (t, J=7.6 Hz, 3H). $^{13}$C NMR (125 MHz, CDCl$_3$, 23° C., δ): 173.72, 157.48, 153.96, 150.10, 147.79, 147.59, 145.54, 132.63, 131.17, 129.99, 128.12, 124.25, 119.58, 119.56, 118.73 (q, J=319 Hz), 98.70, 72.69, 66.25, 49.97, 31.61, 7.79. $^{19}$F NMR (375 MHz, CDCl$_3$, 23° C., δ): −72.99.

Example 21

Synthesis of 10-(tributylstannyl)camptothecin (S19)

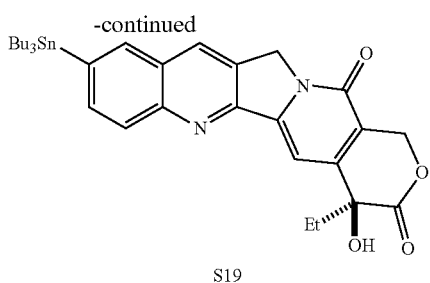

S19

To 10-(trifluoromethanesulfonyloxy)camptothecin (S18) (170 mg, 0.342 mmol, 1.00 equiv) in dioxane (6.8 mL) at 23° C. was added lithium chloride (72.0 mg, 1.71 mmol, 5.00 equiv), tetrakis(triphenylphosphine)palladium (20.0 mg, 0.0171 mmol, 5.00 mol %) and bis(tri-n-butyltin) (346 µL, 0.685 mmol, 2.00 equiv). After stiffing for 24 hr at 100° C., the reaction mixture was cooled to 23° C. and concentrated in vacuo. The residue was purified by chromatography on silica gel eluting with EtOAc/hexanes 1:1 (v/v) to afford 115 mg of the title compound as a light yellow solid (53% yield).

$R_f$=0.77 (EtOAc). NMR Spectroscopy: $^1$H NMR (500 MHz, CDCl$_3$, 23° C., δ): 8.34 (s, 1H), 8.18 (d, J=8.5 Hz, 1H), 8.00 (s, 1H), 7.90 (d, J=8.5 Hz, 1H), 7.73 (s, 1H), 5.73 (d, J=16.0 Hz, 1H), 5.30 (d, J=16.0 Hz, 1H), 5.29 (s, 2H), 4.05 (s, 1H), 1.97–1.82 (m, 2H), 1.66–1.50 (m, 6H), 1.40–1.09 (m, 12H), 1.03 (t, J=7.0 Hz, 3H), 0.90 (t, J=7.0 Hz, 9H). $^{13}$C NMR (100 MHz, CDCl$_3$, 23° C., δ): 173.83, 157.64, 151.97, 150.16, 148.83, 146.41, 143.91, 137.88, 136.37, 130.59, 128.36, 128.28, 127.63, 118.53, 98.26, 72.84, 66.21, 50.06, 31.55, 29.03, 27.29, 13.62, 9.79, 7.77. Mass Spectrometry: HRMS-FIA (m/z): Calcd for [M+H]$^+$, 639.22393. Found, 639.22374.

Example 22

Synthesis of cupreine (S20)

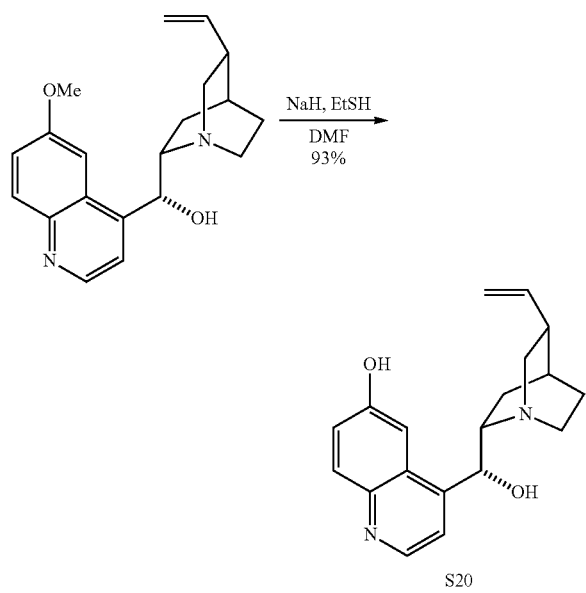

NaH (60% in mineral oil, 800 mg, 20.0 mmol, 10.0 equiv) was washed with hexane, dried, and suspended in DMF (20 mL). To this suspension at 0° C. was added ethanethiol (2.96 mL, 40.0 mmol, 20.0 equiv) dropwise over 5 min. The reaction mixture was stirred at 23° C. for 10 min before the addition of quinine (649 mg, 2.00 mmol, 1.00 equiv) in DMF (10 mL) and further stirred for 13 hr at 100° C. The reaction mixture was cooled to 23° C. and neutralized with aqueous 1N HCl. The phases were separated and the aqueous phase was extracted with CH$_2$Cl$_2$ (3×30 mL). The combined organic phases were washed with brine (50 mL) and dried (K$_2$CO$_3$). The filtrate was concentrated in vacuo and the residue was triturated with Et$_2$O to afford 580 mg of the title compound as a colorless solid (93% yield).

$R_f$=0.25 (CH$_2$Cl$_2$/MeOH 9:1 (v/v)). NMR Spectroscopy: $^1$H NMR (500 MHz, CD$_3$OD, 23° C., δ): 8.56 (d, J=4.5 Hz, 1H), 7.88 (d, J=9.0 Hz, 1H), 7.60 (d, J=5.0 Hz, 1H), 7.32 (d, J=9.0 Hz, 1H), 7.28 (s, 1H), 5.72–5.67 (m, 1H), 5.53 (d, J=2.5 Hz, 1H), 4.95 (d, J=17.0 Hz, 1H), 4.86 (d, J=10.0 Hz, 1H), 3.70 (s br, 1H), 3.09–3.02 (m, 2H), 2.73–2.61 (m, 2H), 2.31 (s br, 1H), 1.90–1.80 (m, 2H), 1.75 (s br, 1H), 1.55 (s br, 1H), 1.46–1.37 (m, 1H). $^{13}$C NMR (125 MHz, CD$_3$OD, 23° C., δ): 158.10, 149.70, 147.33, 143.88, 142.52, 131.42, 128.37, 123.43, 119.78, 115.01, 105.13, 72.05, 60.90, 57.47, 44.20, 40.78, 29.16, 28.04, 21.62.

Example 23

Synthesis of 6-(trifluoromethanesulfonyl)cupreine (S21)

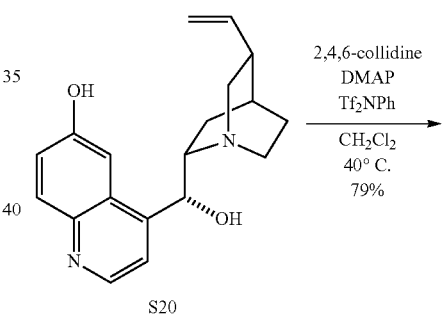

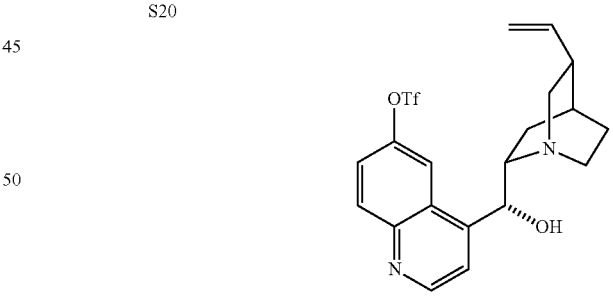

To cupreine (S20) (310 mg, 1.00 mmol, 1.00 equiv) in CH$_2$Cl$_2$ (5 mL) at 23° C. was added 2,4,6-collidine (132 µL, 1.00 mmol, 1.00 equiv), 4-(dimethylamino)pyridine (14.6 mg, 0.120 mmol, 0.120 equiv) and N-phenylbis(trifluoromethanesulfonimide) (357 mg, 1.00 mmol, 1.00 equiv) and the reaction mixture was stirred for 24 hr at 40° C. The reaction mixture was concentrated in vacuo and the residue was purified by chromatography on silica gel eluting with CH$_2$Cl$_2$/MeOH 47:3 (v/v) to afford 350 mg of the title compound as a colorless solid (79% yield).

$R_f$=0.25 (EtOAc/MeOH 9:1 (v/v)). NMR Spectroscopy: $^1$H NMR (500 MHz, CD$_3$OD, 23° C., δ): 8.90 (d, J=4.5 Hz, 1H), 8.36 (d, J=3.0 Hz, 1H), 8.19 (d, J=9.5 Hz, 1H), 7.77 (d, J=4.5 Hz, 1H), 7.74 (dd, J=9.5 Hz, 3.0 Hz, 1H), 5.82-5.74 (m, 1H), 5.45 (d, J=5.0 Hz, 1H), 4.96 (d, J=17.0 Hz, 1H), 4.91 (d, J=10.0 Hz, 1H), 3.51 (s br, 1H), 3.13 (s br, 1H), 3.03 (dd, J=14.0 Hz, 11.0 Hz, 1H), 2.67-2.59 (m, 2H), 2.32 (s br, 1H), 1.87-1.77 (m, 3H), 1.63-1.53 (m, 2H). $^{13}$C NMR (125 MHz, CD$_3$OD, 23° C., δ): 152.54, 148.54, 148.00, 142.66, 133.19, 127.47, 124.14, 121.66, 120.26 (q, J=319 Hz), 117.86, 114.90, 73.27, 61.88, 57.32, 43.63, 40.82, 29.11, 28.22, 23.15. (Note: only nineteen peaks were observed probably due to accidental overlap of two peaks.) $^{19}$F NMR (375 MHz, CD$_3$OD, 23° C., δ): -74.90. Mass Spectrometry: HRMS-FIA (m/z): Calcd for [M+H]$^+$, 443.12469. Found, 443.12970.

Example 24

Synthesis of 6-demethoxy-6-(tributylstannyl)quinine (S22)

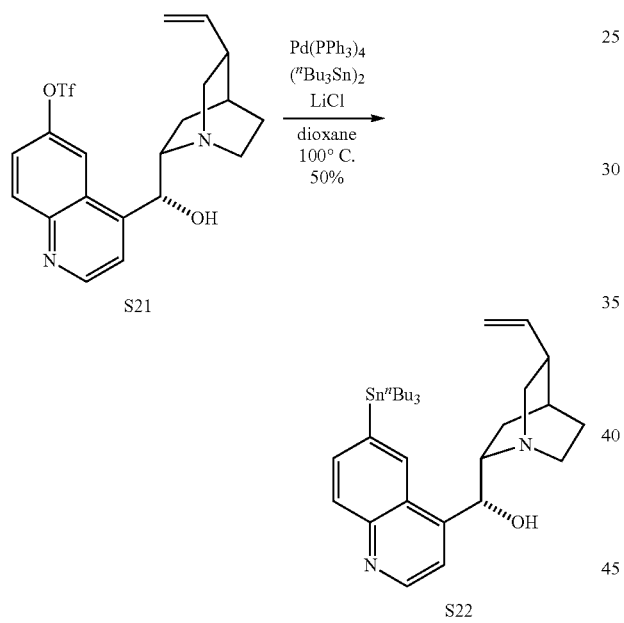

To 6-(trifluoromethanesulfonyl)cupreine (S21) (221 mg, 0.500 mmol, 1.00 equiv) in dioxane (5.0 mL) at 23° C. was added lithium chloride (106 mg, 2.50 mmol, 5.00 equiv), tetrakis(triphenylphosphine)-palladium (29.0 mg, 0.0250 mmol, 5.00 mol %) and bis(tri-n-butyltin) (504 μL, 1.00 mmol, 2.00 equiv). After stirring for 24 hr at 100° C., the reaction mixture was cooled to 23° C. and concentrated in vacuo. The residue was purified by chromatography on silica gel eluting with EtOAc/MeOH 19:1 (v/v) to afford 146 mg of the title compound as colorless oil (50% yield).

$R_f$=0.25 (EtOAc/MeOH 9:1 (v/v)). NMR Spectroscopy: $^1$H NMR (500 MHz, CDCl$_3$, 23° C., δ): 8.86 (d, J=4.5 Hz, 1H), 8.07 (s, 1H), 8.05 (d, J=8.0 Hz, 1H), 7.83 (d, J=8.0 Hz, 1H), 7.66 (d, J=4.5 Hz, 1H), 6.26 (s br, 1H), 5.62–5.53 (m, 1H), 5.03 (d, J=17.0 Hz, 1H), 5.01 (d, J=10.0 Hz, 1H), 4.27 (s br, 1H), 3.54–3.45 (m, 2H), 3.20 (dd, J=10.0 Hz, 10.0 Hz, 1H), 3.10 (d, J=13 Hz, 1H), 2.65 (s br, 1H), 2.10–1.97 (m, 3H), 1.80 (s br, 1H), 1.66–1.47 (m, 6H), 1.44–1.12 (m, 13H), 0.87 (t, J=6.0 Hz, 9H). $^{13}$C NMR (125 MHz, CDCl$_3$, 23° C., δ): 149.87, 148.03, 144.62, 143.43, 137.94, 136.88, 130.22, 129.02, 124.47, 118.43, 117.01, 68.14, 60.84, 55.61, 44.72, 37.69, 29.09, 27.28, 26.83, 25.01, 19.67, 13.65, 9.86. Mass Spectrometry: HRMS-FIA (m/z): Calcd for [M+H]$^+$, 585.28669. Found, 585.28610.

Example 25

Ethyl 4-(tributylstannane)benzoate (S61)

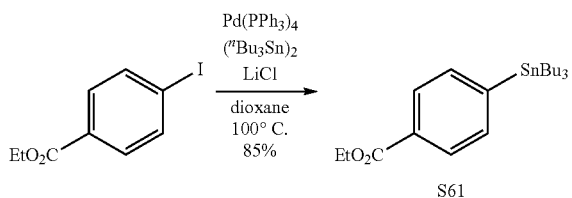

To Ethyl 4-iodobenzoate (275 mg, 1.00 mmol, 1.00 equiv) in dioxane (10 mL) at 23° C. was added lithium chloride (210 mg, 5.00 mmol, 5.00 equiv), tetrakis(triphenylphosphine) palladium (57.8 mg, 0.0500 mmol, 5.00 mol %) and bis(tri-n-butyltin) (1.01 mL, 2.00 mmol, 2.00 equiv). After stirring for 21 hr at 100° C., the reaction mixture was cooled to 23° C. and concentrated in vacuo. The residue was purified by chromatography on silica gel eluting with hexanes/EtOAc 20:1 (v/v) to afford 374 mg of the title compound as a colorless oil (85% yield).

$R_f$=0.20 (hexanes). NMR Spectroscopy: $^1$H NMR (500 MHz, CDCl$_3$, 23° C., δ): 7.96 (d, J=8.0 Hz, 2H), 7.54 (d, J=8.0 Hz, 2H), 4.37 (q, J=6.0 Hz, 2H), 1.58–1.50 (m, 6H), 1.40–1.30 (m, 9H), 1.10–1.06 (m, 6H), 0.88 (t, J=7.3 Hz, 9H). $^{13}$C NMR (125 MHz, CDCl$_3$, 23° C., δ): 167.06, 149.45, 136.36, 129.92, 128.33, 60.79, 29.02, 27.31, 14.34, 13.64, 9.64.

Example 26

(4-Methoxyphenyl)tributylstannane (S62)

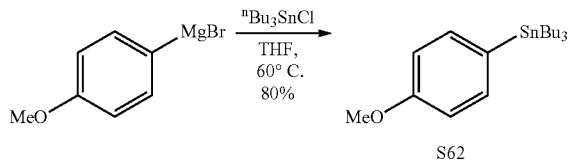

To tributyltin chloride (652 mg, 2.00 mmol, 1.00 equiv) in THF (2 mL) at 23° C. was added 4-methoxyphenylmagnesium bromide (0.50 M in THF, 8.0 mL, 4.0 mmol, 2.0 equiv). After stirring for 1.0 hr at 60° C., the reaction mixture was cooled to 0° C. and quenched with saturated aqueous NH$_4$Cl (10 mL), and Et$_2$O (10 mL) was added. The phases were separated and the aqueous phase was extracted with Et$_2$O (2×10 mL). The combined organic phases were washed with brine (10 mL) and dried (Na$_2$SO$_4$). The filtrate was concentrated in vacuo and the residue was purified by fractional distillation to afford 637 mg of the title compound as a colorless oil (80% yield).

$R_f$=0.20 (hexanes). NMR Spectroscopy: $^1$H NMR (500 MHz, CDCl$_3$, 23° C., δ): 7.37 (d, J=7.0 Hz, 2H), 6.90 (d, J=7.0 Hz, 2H), 3.80 (s, 3H), 1.56–1.50 (m, 6H), 1.35–1.31

(m, 6H), 1.04–1.00 (m, 6H), 0.89 (t, J=6.0 Hz, 9H). $^{13}$C NMR (100 MHz, CDCl$_3$, 23° C., δ): 159.67, 137.47, 132.00, 113.89, 54.94. 29.09, 27.37, 13.67, 9.58.

Example 27

(4-Bromophenyl)tributylstannane (S63)

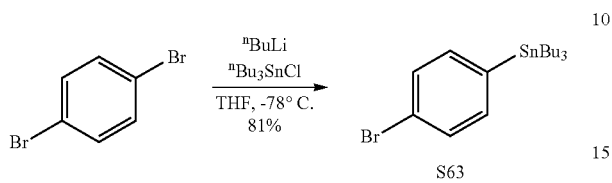

To p-dibromobenzene (932 mg, 4.00 mmol, 1.00 equiv) in THF (10 mL) at −78° C. was added $^n$BuLi (2.5 M in hexane, 1.6 mL, 4.0 mmol, 1.0 equiv). The reaction mixture was stirred at −78° C. for 30 min before the addition of $^n$Bu$_3$SnCl (1.30 g, 4.00 mmol, 1.00 equiv). After stirring for 1.0 hr at −78° C., the reaction mixture was warmed to 23° C. and the solvent was removed in vacuo. the residue was purified by fractional distillation to afford 1.45 g of the title compound as a colorless oil (81% yield).

R$_f$=0.50 (hexanes). NMR Spectroscopy: $^1$H NMR (500 MHz, CDCl$_3$, 23° C., δ): 7.46 (d, J=7.0 Hz, 2H), 7.32 (d, J=7.0 Hz, 2H), 1.56–1.50 (m, 6H), 1.35–1.31 (m, 6H), 1.08–1.04 (m, 6H), 0.89 (t, J=7.5 Hz, 9H). $^{13}$C NMR (125 MHz, CDCl$_3$, 23° C., δ): 140.62, 137.89, 130.97, 122.75, 29.01, 27.32. 13.65, 9.62.

Example 28

N-Boc-4-(Trifluoromethanesulfonyl)-L-phenylalanine Methyl Ester (S64)

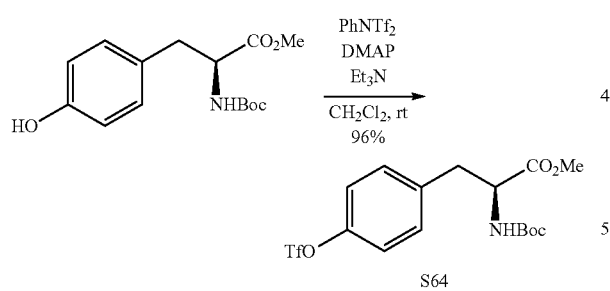

To N-Boc-L-tyrosine methyl ester (295 mg, 1.00 mmol, 1.00 equiv) in CH$_2$Cl$_2$ (2.0 mL) at 23° C. was added triethylamine (418 □L, 3.00 mmol, 3.00 equiv), DMAP (12 mg, 0.10 mmol, 0.10 equiv) and N-phenylbis(trifluoromethanesulfonimide) (535 mg, 1.50 mmol, 1.50 equiv) and the reaction mixture was stirred for 3 hr at 23° C. The reaction mixture was concentrated in vacuo. The residue was purified by chromatography on silica gel eluting with hexanes/EtOAc 3:1 (v/v) to afford 410 mg of the title compound as a colorless solid (96% yield).

R$_f$=0.25 (hexane/EtOAc 3:1 (v/v)). NMR Spectroscopy: $^1$H NMR (500 MHz, CDCl$_3$, 23° C., δ): 7.23–7.20 (m, 4H), 5.08–5.05 (m, 1H), 4.60 (m, 1H), 3.72 (s, 3H), 3.20–3.01 (m, 2H), 1.40 (s, 9H). $^{13}$C NMR (125 MHz, CDCl$_3$, 23° C., δ): 171.88, 154.93, 148.57, 136.92, 131.09, 121.29, 80.16, 54.18, 52.33, 37.85, 28.19. $^{19}$F NMR (375 MHz, CDCl$_3$, 23° C., δ): −74.90. Mass Spectrometry: HRMS-FIA (m/z): Calcd for [M+Na]$^+$, 450.0805. Found, 450.0806.

Example 29

N-Boc-4-(Tributylstannyl)-L-phenylalanine Methyl Ester (S65)

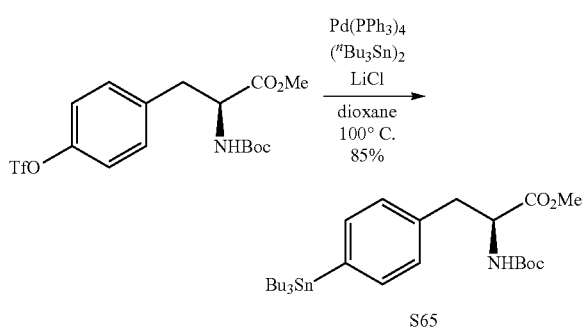

To N-Boc-4-(Trifluoromethanesulfonyl)-L-phenylalanine methyl ester (214 mg, 0.500 mmol, 1.00 equiv) in dioxane (5 mL) at 23° C. was added lithium chloride (105 mg, 2.50 mmol, 5.00 equiv), tetrakis(triphenylphosphine)palladium (29 mg, 0.025 mmol, 5.00 mol %) and bis(tri-n-butyltin) (0.51 mL, 0.10 mmol, 2.0 equiv). After stiffing for 5 hr at 100° C., the reaction mixture was cooled to 23° C. and concentrated in vacuo. The residue was purified by chromatography on silica gel eluting with hexanes/EtOAc 4:1 (v/v) to afford 242 mg of the title compound as a colorless oil (85% yield).

R$_f$=0.50 (hexane/EtOAc 3:1 (v/v)). NMR Spectroscopy: $^1$H NMR (500 MHz, CDCl$_3$, 23° C., δ): 7.38 (d, J=7.5 Hz, 2H), 7.08 (d, J=7.5 Hz, 2H), 4.97 (d, J=8.0 Hz, 1H), 4.60-5.57 (m, 1H), 3.71 (s, 3H), 3.09-3.02 (m, 2H), 1.56–1.50 (m, 6H), 1.41 (s, 9H), 1.36–1.29 (m, 6H), 1.05-0.98 (m, 6H), 0.89 (t, J=7.3 Hz, 9H). $^{13}$C NMR (125 MHz, CDCl$_3$, 23° C., δ): 172.42, 155.07, 140.30, 136.62, 135.54, 128.86, 79.83, 54.34, 52.13, 38.31, 29.04, 28.26, 27.33, 13.63, 9.51.

Example 30

4'-(Trifluoromethanesulfonyl)flavanone (S66)

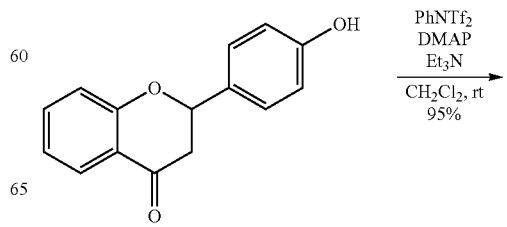

-continued

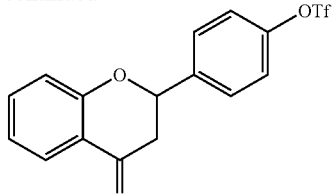

S66

To 4'-hydroxyflavanone (240 mg, 1.00 mmol, 1.00 equiv) in CH$_2$Cl$_2$ (2.0 mL) at 23° C. was added triethylamine (418 μL, 3.00 mmol, 3.00 equiv), DMAP (12 mg, 0.10 mmol, 0.10 equiv) and N-phenylbis(trifluoromethanesulfonimide) (535 mg, 1.50 mmol, 1.50 equiv) and the reaction mixture was stirred for 3 hr at 23° C. The reaction mixture was concentrated in vacuo. The residue was purified by chromatography on silica gel eluting with hexanes/EtOAc 10:1 (v/v) to afford 353 mg of the title compound as a colorless solid (95% yield).

R$_f$=0.5 (hexane/EtOAc 10:1 (v/v)). NMR Spectroscopy: $^1$H NMR (500 MHz, CDCl$_3$, 23° C., δ): 7.94 (dd, J=8.0 Hz, 1.5 Hz, 1H), 7.60 (dd, J=7.0 Hz, 2.5 Hz, 2H), 7.56–7.52 (m, 1H), 7.36 (dd, J=7.0 Hz, 2.0 Hz, 2H), 7.11–7.06 (m, 2H), 5.52 (dd, J=13.0 Hz, 3.0 Hz, 1H), 3.04 (dd, J=17.0 Hz, 3.5 Hz, 1H), 2.92 (dd, J=17.0 Hz, 3.5 Hz, 1H). $^{13}$C NMR (125 MHz, CDCl$_3$, 23° C., δ): 191.07, 161.09, 149.42, 139.34, 136.40, 127.99, 127.15, 122.02, 121.86, 120.87, 118.04, 78.44, 44.68. $^{19}$F NMR (375 MHz, CDCl$_3$, 23° C., δ): −75.05. Mass Spectrometry: HRMS-FIA (m/z): Calcd for [M+H]$^+$, 373.0352. Found, 373.0354.

Example 31

4'-(Tributylstannyl)flavanone (S67)

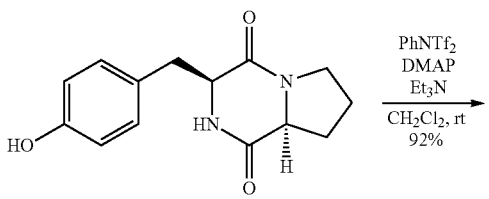

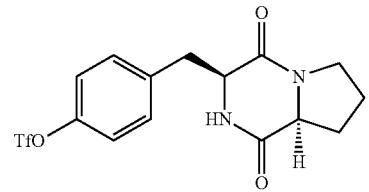

S67

To 4-(Trifluoromethanesulfonyl)flavanone (200 mg, 0.538 mmol, 1.00 equiv) in dioxane (5 mL) at 23° C. was added lithium chloride (113 mg, 2.69 mmol, 5.00 equiv), tetrakis(triphenylphosphine)palladium (31 mg, 0.027 mmol, 5.00 mol %) and bis(tri-n-butyltin) (0.55 mL, 0.11 mmol, 2.0 equiv). After stirring for 3 hr at 100° C., the reaction mixture was cooled to 23° C. and concentrated in vacuo. The residue was purified by chromatography on silica gel eluting with hexanes/EtOAc 20:1 (v/v) to afford 222 mg of the title compound as a colorless oil (80% yield).

R$_f$=0.3 (hexane/EtOAc 10:1 (v/v)). NMR Spectroscopy: $^1$H NMR (500 MHz, CDCl$_3$, 23° C., δ): 7.94 (dd, J=8.5 Hz, 1.5 Hz, 1H), 7.56–7.50 (m, 3H), 7.45 (dd, J=7.5 Hz, 3.5 Hz, 2H), 7.08–7.05 (m, 2H), 5.47 (dd, J=13.5 Hz, 3.0 Hz, 1H), 3.13 (dd, J=17.0 Hz, 3.0 Hz, 1H), 2.91 (dd, J=17.0 Hz, 3.0 Hz, 1H), 1.59–1.53 (m, 6H), 1.39–1.32 (m, 6H), 1.10–1.03 (m, 6H), 0.91 (d, J=7.3 Hz, 9H). $^{13}$C NMR (125 MHz, CDCl$_3$, 23° C., δ): 192.11, 161.64, 143.19, 138.18, 136.89, 136.15, 127.03, 125.61, 121.54, 120.94, 118.13, 79.75, 44.53, 29.05, 27.36, 13.65, 9.59. Mass Spectrometry: HRMS-FIA (m/z): Calcd for [M+H]$^+$, 515.1966. Found, 515.1978.

Example 32

4-(Trifluoromethanesulfonyl)maculosin (S68)

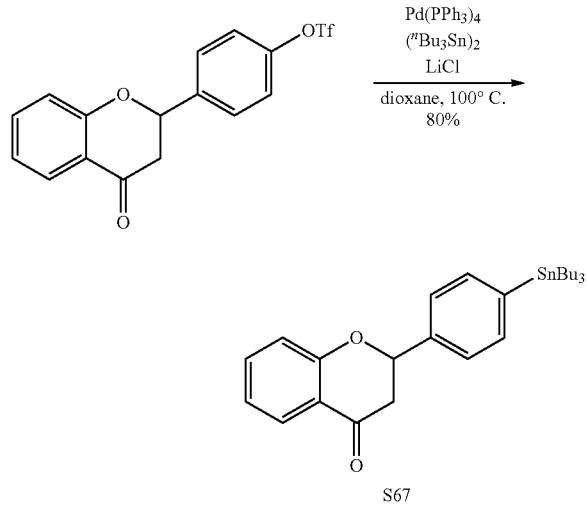

S68

To maculosin (100 mg, 0.384 mmol, 1.00 equiv) in CH$_2$Cl$_2$ (1.0 mL) at 23° C. was added triethylamine (0.16 mL, 1.2 mmol, 3.0 equiv), DMAP (4.7 mg, 0.038 mmol, 0.10 equiv) and N-phenylbis(trifluoromethanesulfonimide) (206 mg, 0.576 mmol, 1.50 equiv) and the reaction mixture was stirred for 3 hr at 23° C. The reaction mixture was concentrated in vacuo. The residue was purified by chromatography on silica gel eluting with EtOAc/MeOH 10:1 (v/v) to afford 138 mg of the title compound as a colorless solid (92% yield).

R$_f$=0.5 (EtOAc/MeOH 10:1 (v/v)). NMR Spectroscopy: $^1$H NMR (500 MHz, CDCl$_3$, 23° C., δ): 7.38–7.36 (m, 2H), 7.28–7.24 (m, 2H), 6.29 (br s, 1H), 4.32 (dd, J=8.0 Hz, 3.0 Hz, 1H), 4.07 (t, J=8.0 Hz, 1H), 2.34–2.31 (m, 1H), 2.02–1.99 (m, 1H), 1.94–1.88 (m, 2H). $^{13}$C NMR (125 MHz, CDCl$_3$, 23° C., δ): 169.52, 164.45, 148.74, 136.75, 131.28, 121.81, 59.06, 56.15, 45.39, 36.15, 28.34, 22.38. $^{19}$F NMR (375 MHz, CDCl$_3$, 23° C., δ): −76.44. Mass Spectrometry: HRMS-FIA (m/z): Calcd for [M+H]$^+$, 393.0727. Found, 393.0738.

Example 33

4-(Tributylstannyl)maculosin (S69)

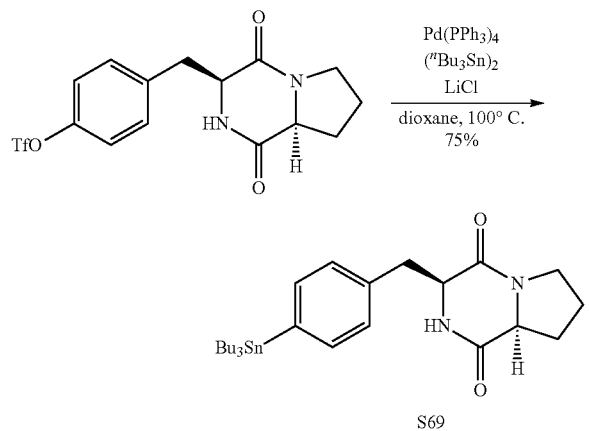

To 4-(Trifluoromethanesulfonyl)maculosin (100 mg, 0.255 mmol, 1.00 equiv) in dioxane (2 mL) at 23° C. was added lithium chloride (53.5 mg, 1.28 mmol, 5.00 equiv), tetrakis(triphenylphosphine)palladium (14.7 mg, 0.0127 mmol, 5.00 mol %) and bis(tri-n-butyltin) (0.26 mL, 0.51 mmol, 2.0 equiv). After stiffing for 24 hr at 100° C., the reaction mixture was cooled to 23° C. and concentrated in vacuo. The residue was purified by chromatography on silica gel eluting with EtOAc/CHCl$_3$ 3:1 (v/v) to afford 102 mg of the title compound as a colorless oil (80% yield).

$R_f$=0.3 (EtOAc/CHCl$_3$ 3:1 (v/v)). NMR Spectroscopy: $^1$H NMR (500 MHz, CDCl$_3$, 23° C., δ): 7.39–7.38 (m, 2H), 7.17–7.15 (m, 2H), 6.51 (dd, J=10.0 Hz, 3.5 Hz, 1H), 4.23–4.20 (m, 1H), 3.64–3.58 (m, 1H), 3.41–3.36 (m, 1H), 3.11 (dd, J=14.0 Hz, 7.0 Hz, 1H), 3.03 (dd, J=14.0 Hz, 4.0 Hz, 1H), 2.86 (dd, J=10.5 Hz, 6.5 Hz, 1H), 2.15–2.11 (m, 1H), 1.94–1.91 (m, 1H), 1.83–1.75 (m, 1H), 1.66–1.61 (m, 1H), 1.56–1.44 (m, 6H), 1.35–1.25 (m, 6H), 1.10–0.97 (m, 6H), 0.88 (d, J=7.3 Hz, 9H). $^{13}$C NMR (125 MHz, CDCl$_3$, 23° C., δ): 169.29, 164.84, 140.98, 136.77, 134.75, 129.47, 59.06, 57.69, 45.06, 40.44, 29.01, 28.85, 27.27, 21.68, 13.61, 9.52. Mass Spectrometry: HRMS-FIA (m/z): Calcd for [M+H]$^+$, 535.2341. Found, 535.2347.

Example 34

3-(Trifluoromethanesulfonyl)-β-estradiol (S70)

To 3-(Trifluoromethanesulfonyl)estrone (402 mg, 1.00 mmol, 1.00 equiv) in MeOH/THF (2.0 mL, v/v 1/1) at 0° C. was added sodium borohydride (76 mg, 2.0 mmol, 2.0 equiv) and the reaction mixture was stirred for 0.5 hr at 0° C. The reaction mixture was quenched with saturated aqueous NH$_4$Cl (10 mL), and EtOAc (10 mL) was added. The phases were separated and the aqueous phase was extracted with EtOAc (2×10 mL). The combined organic phases were washed with brine (10 mL) and dried (Na$_2$SO$_4$). concentrated in vacuo. The residue was purified by chromatography on silica gel eluting with hexane/EtOAc 3:1 (v/v) to afford 384 mg of the title compound as a colorless solid (95% yield).

$R_f$=0.25 (hexane/EtOAc 3:1 (v/v)). NMR Spectroscopy: $^1$H NMR (500 MHz, CDCl$_3$, 23° C., δ): 7.33 (d, J=8.5 Hz, 1H), 7.02 (dd, J=8.5 Hz, 2.5 Hz, 1H), 6.96 (d, J=3.0 Hz, 1H), 3.74 (t, J=8.5 Hz, 1H), 2.89 (dd, J=9.0 Hz, 4.0 Hz, 2H), 2.35–2.30 (m, 1H), 2.25–2.20 (m, 1H), 2.15–2.11 (m, 1H), 1.99–1.89 (m, 2H), 1.74–1.69 (m, 1H), 1.54–1.17 (m, 8H), 0.79 (s, 3H). $^{13}$C NMR (125 MHz, CDCl$_3$, 23° C., δ): 147.43, 140.85, 139.49, 127.12, 121.09, 118.07, 81.71, 50.00, 44.05, 43.13, 38.19, 36.55, 30.51, 29.47, 26.74, 26.05, 23.06. $^{19}$F NMR (375 MHz, CDCl$_3$, 23° C., δ): −73.39.

Example 35

3-(Trifluoromethanesulfonyl)-β-estradiol-β-hepta-benzoyl-lactose (S71)

A mixture of acceptor 3-(Trifluoromethanesulfonyl)-β-estradiol (202 mg, 0.500 mmol, 1.00 equiv), donor 4 (909 mg, 0.750 mmol, 1.50 equiv), and powered 4 Å molecular sieves in anhyd CH$_2$Cl$_2$ (5 mL) was stirred for 1 h at r.t. under Ar. TMSOTf (4.5 µL, 0.025 mmol, 0.050 equiv) was added. The mixture was stirred for 1 h. Et$_3$N was added, and the mixture was filtered and concentrated in vacuo. The residue was purified by chromatography on silica gel eluting with hexane/EtOAc 3:1 (v/v) to afford 655 mg of the title compound as a white foam (90% yield).

R$_f$=0.3 (hexane/EtOAc 3:1 (v/v)). NMR Spectroscopy: $^1$H NMR (500 MHz, CDCl$_3$, 23° C., δ): 8.02–7.96 (m, 10H), 7.91 (dd, J=8.5 Hz, 1.0 Hz, 2H), 7.73 (dd, J=8.5 Hz, 1.0 Hz, 2H), 7.63–7.30 (m, 18H), 7.22 (dd, J=8.5 Hz, 7.5 Hz, 2H), 7.17 (dd, J=8.5 Hz, 7.5 Hz, 2H), 6.97 (dd, J=8.5 Hz, 2.5 Hz, 1H), 6.92–6.91 (m, 1H), 5.81 (dd, J=9.5 Hz, 9.5 Hz, 1H), 5.74–5.71 (m, 2H), 5.47 (dd, J=9.5 Hz, 8.0 Hz, 1H), 5.38 (dd, J=10.5 Hz, 3.5 Hz, 1H), 4.89 (d, J=8.0 Hz, 1H), 4.75 (d, J=8.5 Hz, 1H), 4.63–4.60 (m, 1H), 4.49 (dd, J=12.0 Hz, 5.0 Hz, 1H), 4.23 (dd, J=9.5 Hz, 9.5 Hz, 1H), 3.91 (dd, J=7.0 Hz, 6.5 Hz, 1H), 3.84–3.82 (m, 1H), 3.75 (dd, J=11.0 Hz, 6.5 Hz, 1H), 3.69 (dd, J=11.0 Hz, 6.5 Hz, 1H), 3.58 (dd, J=9.0 Hz, 8.0 Hz, 1H), 2.83–2.81 (m, 2H), 2.11–2.01 (m, 2H), 1.98–1.88 (m, 1H), 1.82–1.78 (m, 1H), 1.68–1.51 (m, 3H), 1.31–1.21 (m, 4H), 1.18–1.10 (m, 2H), 0.58 (s, 3H). $^{13}$C NMR (125 MHz, CDCl$_3$, 23° C., □): 165.81, 165.57, 165.41, 165.39, 165.20, 165.11, 164.78, 147.40, 140.65, 139.40, 133.52, 133.38, 133.34, 133.30, 133.24, 133.15, 133.12, 129.99, 129.74, 129.71, 129.67, 129.63, 129.59, 129.49, 129.41, 128.86, 128.71, 128.62, 128.56, 128.49, 128.31, 128.23, 127.09, 121.06, 118.03, 101.83, 100.99, 89.95, 76.32, 73.00, 72.94, 71.94, 71.74, 71.40, 69.93, 67.53, 62.55, 61.12, 49.61, 43.91, 43.07, 37.78, 37.05, 29.42, 28.67, 26.62, 25.77, 22.96, 11.32. $^{19}$F NMR (375 MHz, CDCl$_3$, 23° C., δ): −73.38. Mass Spectrometry: HRMS-FIA (m/z): Calcd for [M+NH$_4$]$^+$, 1474.4498. Found, 1474.4486.

Example 36

3-(Tributylstannyl)-β-estradiol-β-hepta-benzoyl-lactose (S72)

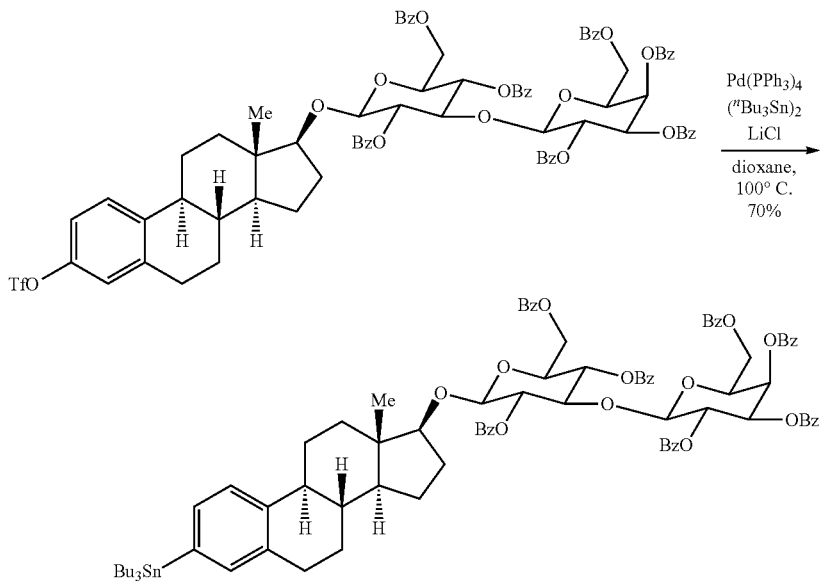

To 3-(Trifluoromethanesulfonyl)-δ-estradiol-β-hepta-benzoyl-lactose (200 mg, 0.137 mmol, 1.00 equiv) in dioxane (2 mL) at 23° C. was added lithium chloride (28.7 mg, 0.683 mmol, 5.00 equiv), tetrakis(triphenylphosphine)palladium (7.9 mg, 0.069 mmol, 5.00 mol %) and bis(tri-n-butyltin) (0.14 mL, 0.27 mmol, 2.0 equiv). After stiffing for 21 hr at 100° C., the reaction mixture was cooled to 23° C. and concentrated in vacuo. The residue was purified by chromatography on silica gel eluting with hexane/EtOAc 4:1 (v/v) to afford 154 mg of the title compound as a colorless oil (70% yield).

R$_f$=0.3 (hexane/EtOAc 4:1 (v/v)). NMR Spectroscopy: $^1$H NMR (500 MHz, CDCl$_3$, 23° C., δ): 8.04–7.97 (m, 10H), 7.93 (dd, J=8.0 Hz, 1.0 Hz, 2H), 7.74 (dd, J=8.0 Hz, 1.0 Hz, 2H), 7.66–7.31 (m, 18H), 7.22 (dd, J=8.5 Hz, 8.5 Hz, 2H), 7.18–7.14 (m, 4H), 5.82 (dd, J=10.0 Hz, 9.0 Hz, 1H), 5.77–5.73 (m, 2H), 5.49 (dd, J=10.0 Hz, 8.0 Hz, 1H), 5.40 (dd, J=10.0 Hz, 3.0 Hz, 1H), 4.90 (d, J=8.0 Hz, 1H), 4.78 (d, J=8.0 Hz, 1H), 4.64–4.61 (m, 1H), 4.51 (dd, J=12.0 Hz, 5.0 Hz, 1H), 4.24 (dd, J=9.5 Hz, 9.5 Hz, 1H), 3.93 (dd, J=7.0 Hz, 6.5 Hz, 1H), 3.86–3.84 (m, 1H), 3.78 (dd, J=11.5 Hz, 6.5 Hz, 1H), 3.71 (dd, J=11.5 Hz, 6.5 Hz, 1H), 3.60 (dd, J=9.0 Hz, 8.0 Hz, 1H), 2.83–2.80 (m, 2H), 2.13–2.01 (m, 2H), 1.98–1.92 (m, 1H), 1.83–1.84 (m, 1H), 1.75–1.49 (m, 9H), 1.37–1.24 (m, 10H), 1.18–0.97 (m, 8H), 0.91 (t, J=7.3 Hz, 9H), 0.57 (s, 3H). $^{13}$C NMR (125 MHz, CDCl$_3$, 23° C., δ): 165.81, 165.55, 165.42, 165.37, 165.19, 165.11, 164.77, 139.88, 138.31, 137.25, 136.04, 133.71, 133.50, 133.36, 133.28, 133.21, 133.11, 133.08, 129.98, 129.71, 129.65, 129.61, 129.58, 129.48, 129.39, 128.83, 128.68, 128.61, 128.54, 128.47, 128.27, 128.21, 124.79, 101.78, 100.95, 90.04, 76.33, 72.97, 71.92, 71.74, 71.39, 69.91, 67.54, 62.59, 61.14, 49.78, 44.29, 43.16, 38.11, 37.29, 29.41, 29.05, 28.65, 27.37, 27.0, 25.62, 22.94, 13.63, 11.32, 9.45.

Example 37

N-Boc-4-(Tributylstannyl)-L-phenylalanyl-L-phenylalanine Methyl Ester (S73)

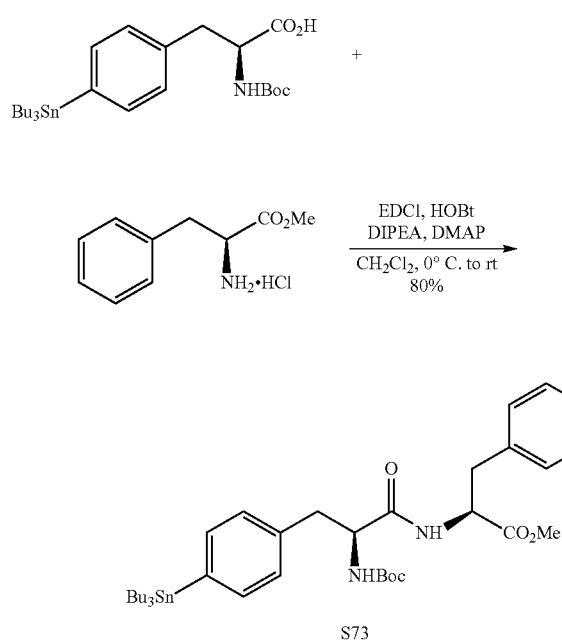

To N-Boc-4-(tributylstannyl)-L-phenylalanine (1.67 g, 3.00 mmol, 1.00 equiv) and L-phenylalanine methyl ester hydrochloride (647 mg, 3.00 mmol, 1.00 equiv) in CH$_2$Cl$_2$ (30 mL) at 0° C. was added EDCI (1.15 g, 6.00 mmol, 2.00 equiv), HOBt (810 mg, 6.00 mmol, 2.00 equiv), n,n-diisopropylethyl amine (1.56 mL, 9.00 mmol, 3.00 equiv) and 4-(Dimethylamino)pyridine (36 mg, 0.30 mmol, 0.10 equiv). After stirring for 1 hr at 0° C., the reaction mixture was allowed to stirred at room temperature for 12 hr. The reaction mixture was quenched with water (20 mL), and CH$_2$Cl$_2$ (10 mL) was added. The phases were separated and the aqueous phase was extracted with CH$_2$Cl$_2$ (2×10 mL). The combined organic phases were washed with brine (10 mL) and dried (Na$_2$SO$_4$). concentrated in vacuo. The residue was purified by chromatography on silica gel eluting with hexane/EtOAc 3:1 (v/v) to afford 1.72 g of the title compound as a white foam (80% yield).

R$_f$=0.30 (hexane/EtOAc 3:1 (v/v)). NMR Spectroscopy: $^1$H NMR (500 MHz, CDCl$_3$, 23° C., δ): 7.39 (d, J=8.0 Hz, 2H), 7.23–7.21 (m, 3H), 7.15 (d, J=7.5 Hz, 2H), 6.97 (dd, J=7.5 Hz, 2.0 Hz, 2H), 6.38 (d, J=7.5 Hz, 1H), 4.90 (br s, 1H), 4.80 (br s, 1H), 4.35 (br s, 1H), 3.68 (s, 3H), 3.09–2.99 (m, 4H), 1.55–1.50 (m, 6H), 1.38 (s, 9H), 1.36–1.29 (m, 6H), 1.05–1.01 (m, 6H), 0.87 (t, J=7.3 Hz, 9H). $^{13}$C NMR (125 MHz, CDCl$_3$, 23° C., δ): 171.38, 170.83, 155.27, 140.29, 136.74, 136.06, 135.64, 129.19, 128.99, 128.49, 127.06, 80.12, 55.47, 53.21, 52.20, 37.92, 29.03, 28.18, 27.33, 13.61, 9.50. Mass Spectrometry: HRMS-FIA (m/z): Calcd for [M+Na]$^+$, 739.3103. Found, 739.3069.

Example 38

N-Boc-glycylglycyl-L-phenylalanine Methyl Ester (S74)

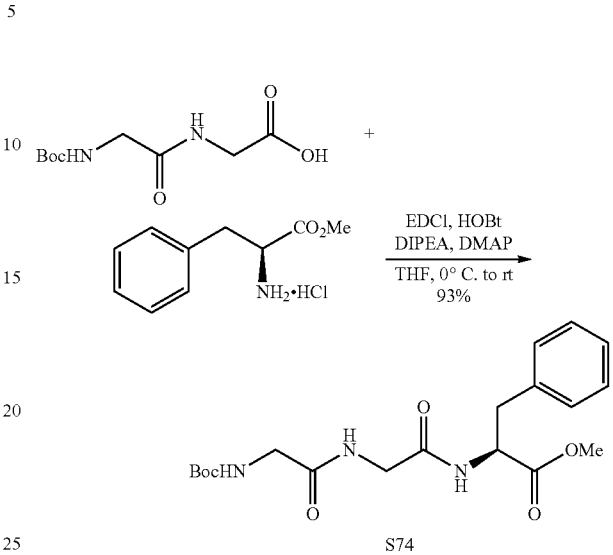

To N-Boc-glycylglycine (696 mg, 3.00 mmol, 1.00 equiv) in THF (10.0 mL) at 0° C. was added EDCI (1.15 g, 6.00 mmol, 2.00 equiv), HOBt (810 mg, 6.00 mmol, 2.00 equiv), n,n-diisopropylethyl amine (1.56 mL, 9.00 mmol, 3.00 equiv) and 4-(Dimethylamino)pyridine (36 mg, 0.030 mmol, 0.10 equiv) and L-phenylalanine methyl ester (647 mg, 3.00 mmol, 1.00 equiv). The reaction mixture was stirred for 1 hr at 0° C. and stirred for 12 h at room temperature. The reaction mixture was diluted with ethyl acetate and washed with water and dried (Na$_2$SO$_4$). The filtrate is concentrated in vacuo and the residue is purified by chromatography on silica gel eluting with DCM/MeOH 10:1 (v/v) to afford 1.10 g of the title compound as a colorless oil (93% yield).

R$_f$=0.50 (DCM/MeOH 10:1 (v/v)). NMR Spectroscopy: $^1$H NMR (500 MHz, CDCl$_3$, 23° C., δ): 7.29–7.21 (m, 2H), 7.13–7.11 (m, 2H), 7.02 (d, J=8.0 Hz, 1H), 5.46 (br s, 1H), 4.82 (dd, J=14.0 Hz, 6.5 Hz, 1H), 3.94 (dd, J=16.5 Hz, 5.5 Hz, 1H), 3.88 (dd, J=16.5 Hz, 6.0 Hz, 1H), 3.80 (d, J=5.0 Hz, 2H), 3.69 (s, 3H), 3.13 (dd, J=14.0 Hz, 6.0 Hz, 1H), 3.04 (dd, J=14.0 Hz, 7.0 Hz, 1H), 1.45 (s, 9H). $^{13}$C NMR (125 MHz, CDCl$_3$, 23° C., δ): 171.79, 170.07, 168.53, 156.07, 135.78, 129.15, 128.49, 127.05, 80.16, 53.36, 52.30, 44.01, 42.75, 37.71, 28.24.

Example 39

N-Boc-glycylglycyl-L-phenylalanyl-L-leucine Methyl Ester (S75)

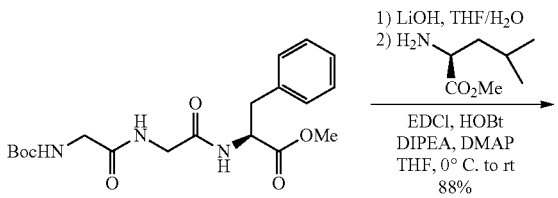

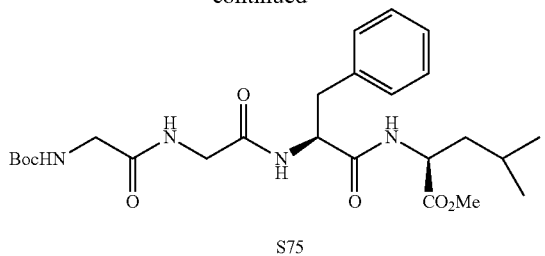

S75

To N-Boc-glycylglycyl-L-phenylalanine Methyl Ester (786 mg, 2.00 mmol, 1.00 equiv) in THF (4.0 mL) and water (2 mL) at 0° C. was added LiOH (96 mg, 4.00 mmol, 2.00 equiv). The reaction mixture was stirred for 2 hr at 0° C. The reaction mixture was diluted with ethyl acetate and the pH was adjusted to pH 2-3 by using HCl (1N). The layers were separated and the aqueous layer was extracted with ethyl acetate, dried (Na$_2$SO$_4$). The filtrate is concentrated in vacuo to give the crude product.

To this crude product in THF (10.0 mL) at 0° C. was added EDCI (764 g, 4.00 mmol, 2.00 equiv), HOBt (540 mg, 4.00 mmol, 2.00 equiv), n,n-diisopropylethyl amine (1.00 mL, 6.00 mmol, 3.00 equiv) and 4-(Dimethylamino)pyridine (24 mg, 0.020 mmol, 0.10 equiv) and L-leucine methyl ester (544 mg, 3.00 mmol, 1.50 equiv). The reaction mixture was stirred for 1 hr at 0° C. and stirred for 12 h at room temperature. The reaction mixture was diluted with ethyl acetate and washed with water and dried (Na$_2$SO$_4$). The filtrate is concentrated in vacuo and the residue is purified by chromatography on silica gel eluting with DCM/MeOH 10:1 (v/v) to afford 880 mg of the title compound as a white solid (88% yield).

R$_f$=0.50 (DCM/MeOH 10:1 (v/v)). NMR Spectroscopy: $^1$H NMR (500 MHz, CDCl$_3$, 23° C., δ): 7.40 (br s, 1H), 7.27–7.12 (m, 7H), 5.57 (br s, 1H), 4.95–4.93 (m, 1H), 4.59–4.54 (m, 1H), 3.96–3.85 (m, 4H), 3.70 (s, 3H), 3.11 (dd, J=13.5 Hz, 5.5 Hz, 1H), 2.98 (dd, J=13.5 Hz, 7.0 Hz, 1H), 1.63–1.51 (m, 3H), 1.45 (s, 9H), 0.89 (d, J=6.0 Hz, 6H). $^{13}$C NMR (125 MHz, CDCl$_3$, 23° C., δ): 172.95, 170.78, 169.74, 168.41, 156.13, 136.36, 129.37, 128.42, 126.87, 80.05, 54.15, 52.21, 50.83, 43.89, 42.99, 41.05, 38.71, 28.34, 24.77, 22.69, 21.86. Mass Spectrometry: HRMS-FIA (m/z): Calcd for [M+Na]$^+$, 529.2633. Found, 529.2630.

Example 40

N-Boc-4-(tributylstannyl)-L-phenylalanyl-glycylglycyl-L-phenylalanyl-L-leucine Methyl Ester (S76)

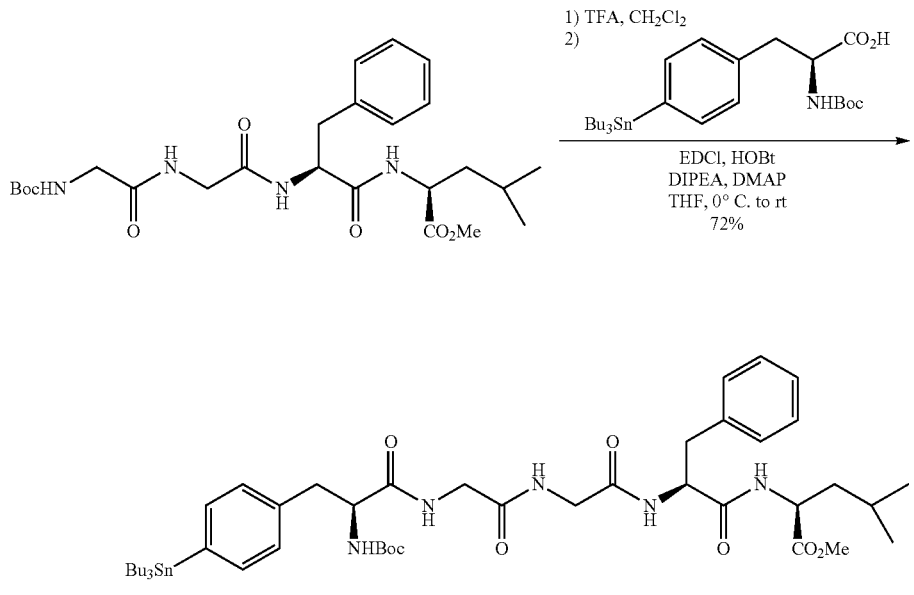

S76

To N-Boc-glycylglycyl-L-phenylalanyl-L-leucine Methyl Ester (101 mg, 0.200 mmol, 1.00 equiv) in CH$_2$Cl$_2$ (2.0 mL) at 0° C. was added trifluoroacetic acid (0.2 mL). The reaction mixture was stirred for 2 hr at 0° C. The reaction mixture was concentrated in vacuo to give the crude product.

To the crude product in THF (10.0 mL) at 0° C. was added EDCI (76.7 mg, 0.400 mmol, 2.00 equiv), HOBt (54 mg, 0.40 mmol, 2.0 equiv), n,n-diisopropylethyl amine (0.20 mL, 0.60 mmol, 3.0 equiv) and 4-(Dimethylamino)pyridine (2.4 mg, 0.020 mmol, 0.10 equiv) and N-Boc-4-(tributylstannyl)-L-phenylalanine (111 mg, 0.200 mmol, 1.00 equiv). The reaction mixture was stirred for 1 hr at 0° C. and stirred for 12 h at room temperature. The reaction mixture was diluted with ethyl acetate and washed with water and dried (Na$_2$SO$_4$). The filtrate is concentrated in vacuo and the residue is purified by chromatography on silica gel eluting with DCM/MeOH 10:1 (v/v) to afford 135 mg of the title compound as a white solid (72% yield).

$R_f$=0.50 (DCM/MeOH 10:1 (v/v)). NMR Spectroscopy: $^1$H NMR (500 MHz, CDCl$_3$, 23° C., δ): 7.52 (br s, 1H), 7.38 (d, J=8.0 Hz, 2H), 7.24–7.13 (m, 8H), 7.01 (br s, 1H), 5.29 (br s, 1H), 4.91–4.89 (m, 1H), 4.58–4.54 (m, 1H), 4.37–4.35 (m, 1H), 3.98–3.85 (m, 4H), 3.69 (s, 3H), 3.18–3.03 (m, 3H), 2.95–2.90 (m, 1H), 1.62–1.48 (m, 9H), 1.40 (s, 9H), 1.39–1.28 (m, 6H), 1.05–1.01 (m, 6H), 0.89–0.86 (m, 15H). $^{13}$C NMR (125 MHz, CDCl$_3$, 23° C., δ): 173.03, 172.37, 170.76, 168.89, 168.24, 155.68, 139.90, 136.52, 136.42, 129.56, 128.96, 128.21, 126.62, 79.73, 55.38, 53.98, 52.15, 50.81, 43.06, 41.11, 39.23, 38.74, 29.01, 28.27, 27.32, 24.74, 22.74, 22.05, 13.61, 9.47. Mass Spectrometry: HRMS-FIA (m/z): Calcd for [M+Na]$^+$, 966.4373. Found, 966.4386.

Example 41

(Trifluoromethanesulfonyl)ezetimibe (S77)

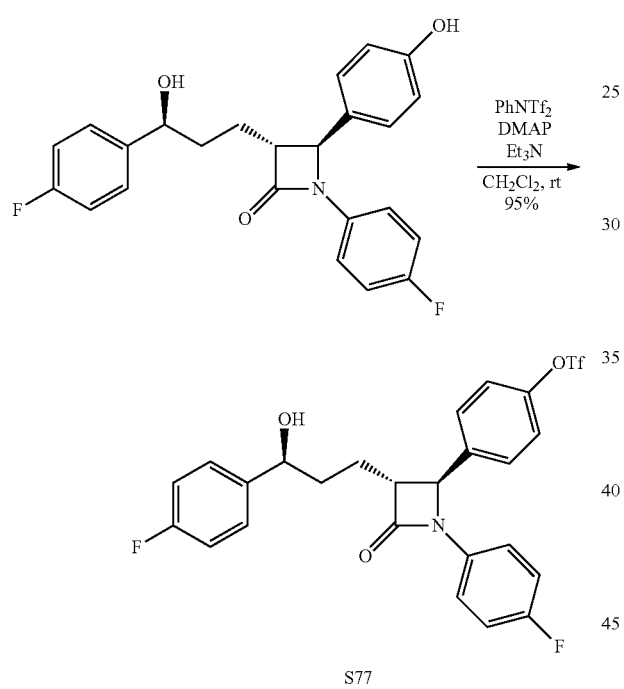

To ezetimibe (205 mg, 0.500 mmol, 1.00 equiv) in CH$_2$Cl$_2$ (2.0 mL) at 23° C. was added triethylamine (209 μL, 1.50 mmol, 3.00 equiv), DMAP (6.0 mg, 0.05 mmol, 0.10 equiv) and N-phenylbis(trifluoromethanesulfonimide) (196 mg, 0.550 mmol, 1.10 equiv) and the reaction mixture was stirred for 3 hr at 23° C. The reaction mixture was concentrated in vacuo. The residue was purified by chromatography on silica gel eluting with hexanes/EtOAc 2:1 (v/v) to afford 258 mg of the title compound as a colorless solid (95% yield).

$R_f$=0.2 (hexane/EtOAc 2:1 (v/v)). NMR Spectroscopy: $^1$H NMR (500 MHz, CDCl$_3$, 23° C., δ): 7.43–7.40 (m, 2H), 7.31–7.28 (m, 4H), 7.21–7.19 (m, 2H), 7.03–6.94 (m, 4H), 4.72 (dd, J=6.5 Hz, 6.0 Hz, 1H), 4.68 (d, J=2.5 Hz, 1H), 3.07 (dt, J=7.5 Hz, 2.0 Hz, 1H), 2.63 (br s, 1H), 2.04–1.89 (m, 4H). $^{13}$C NMR (125 MHz, CDCl$_3$, 23° C., δ): 166.89, 162.15 (d, J=244 Hz), 159.12 (d, J=243 Hz), 149.31, 139.92, 138.18, 133.36, 127.65, 127.31 (d, J=8.3 Hz), 122.31, 118.25 (d, J=8.3 Hz), 115.99 (d, J=22.8 Hz), 115.31 (d, J=21.0 Hz), 72.99, 60.45, 60.29, 36.44, 24.99. $^{19}$F NMR (375 MHz, CDCl$_3$, 23° C., δ): −73.25, −115.14, −117.72.

Example 42

(Tributylstannyl)ezetimibe (S78)

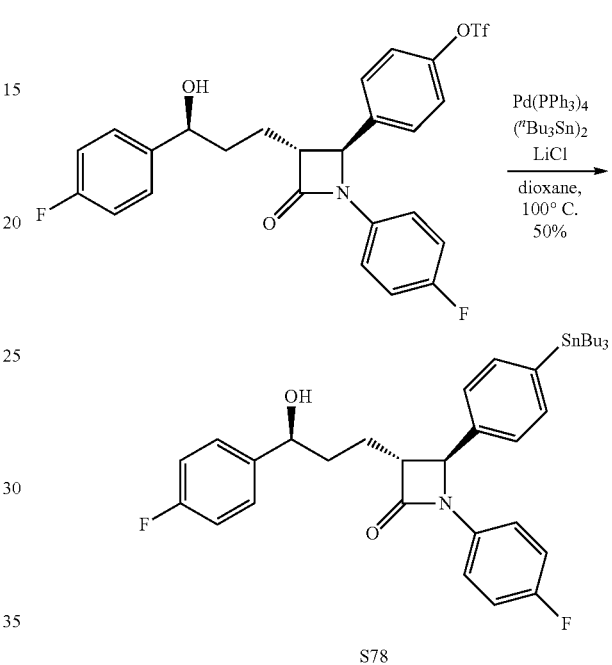

To (Trifluoromethanesulfonyl)ezetimibe (54.1 mg, 0.100 mmol, 1.00 equiv) in dioxane (1 mL) at 23° C. was added lithium chloride (21.0 mg, 0.500 mmol, 5.00 equiv), tetrakis(triphenylphosphine)palladium (5.8 mg, 0.0050 mmol, 5.0 mol %) and bis(tri-n-butyltin) (0.10 mL, 0.20 mmol, 2.0 equiv). After stirring for 12 hr at 100° C., the reaction mixture was cooled to 23° C. and concentrated in vacuo. The residue was purified by chromatography on silica gel eluting with hexanes/EtOAc 3:1 (v/v) to afford 34 mg of the title compound as a colorless oil (50% yield).

$R_f$=0.3 (hexane/EtOAc 3:1 (v/v)). NMR Spectroscopy: $^1$H NMR (500 MHz, CDCl$_3$, 23° C., δ): 7.47 (d, J=8.0 Hz, 2H), 7.32–7.24 (m, 6H), 7.03 (dt, J=9.0 Hz, 2.0 Hz, 2H), 6.94 (dt, J=9.0 Hz, 2.0 Hz, 2H), 4.74 (dd, J=6.5 Hz, 6.0 Hz, 1H), 4.60 (d, J=2.5 Hz, 1H), 3.12 (dt, J=7.5 Hz, 2.0 Hz, 1H), 2.36 (br s, 1H), 2.04–1.91 (m, 4H), 1.59–1.53 (m, 6H), 1.39–1.30 (m, 6H), 1.13–1.03 (m, 6H), 0.89 (d, J=7.5 Hz, 9H). $^{13}$C NMR (125 MHz, CDCl$_3$, 23° C., δ): 167.61, 162.17 (d, J=244 Hz), 158.97 (d, J=241 Hz), 142.99, 140.05 (d, J=2.8 Hz), 137.21, 136.98, 133.91 (d, J=2.6 Hz), 127.37 (d, J=8.1 Hz), 125.25, 118.39 (d, J=8.1 Hz), 115.79 (d, J=22.8 Hz), 115.32 (d, J=21.9 Hz), 73.05, 61.48, 60.18, 36.59, 29.03, 27.32, 25.04, 13.63, 9.59. $^{19}$F NMR (375 MHz, CDCl$_3$, 23° C., δ): −115.32, −118.50. Mass Spectrometry: HRMS-FIA (m/z): Calcd for [M+K]$^+$, 722.2228. Found, 722.2204.

Example 43

(Tributylstannyl)DOPA (S79)

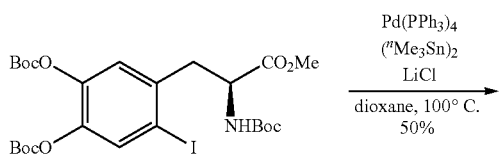

$R_f$=0.5 (hexane/EtOAc 3:1 (v/v)). NMR Spectroscopy: $^1$H NMR (500 MHz, CDCl$_3$, 23° C., δ): 7.27 (br s, 1H), 7.09 (br s, 1H), 4.90 (d, J=8.0 Hz, 1H), 4.52–4.51 (m, 1H), 3.71 (s, 3H), 3.11–3.04 (m, 2H), 1.55 (s, 9H), 1.54 (s, 9H), 1.40 (s, 9H), 0.36 (s, 9H). $^{13}$C NMR (125 MHz, CDCl$_3$, 23° C., δ): 172.50, 155.06, 150.78, 150.60, 142.57, 141.54, 141.36, 140.81, 130.21, 123.25, 83.59, 80.67, 54.31, 52.29, 40.26, 28.18, 27.58, 27.59, −7.91. Mass Spectrometry: HRMS-FIA (m/z): Calcd for [M+H]$^+$, 676.2138. Found, 676.2139.

Example 44

Rifamycin S derivative (S80)

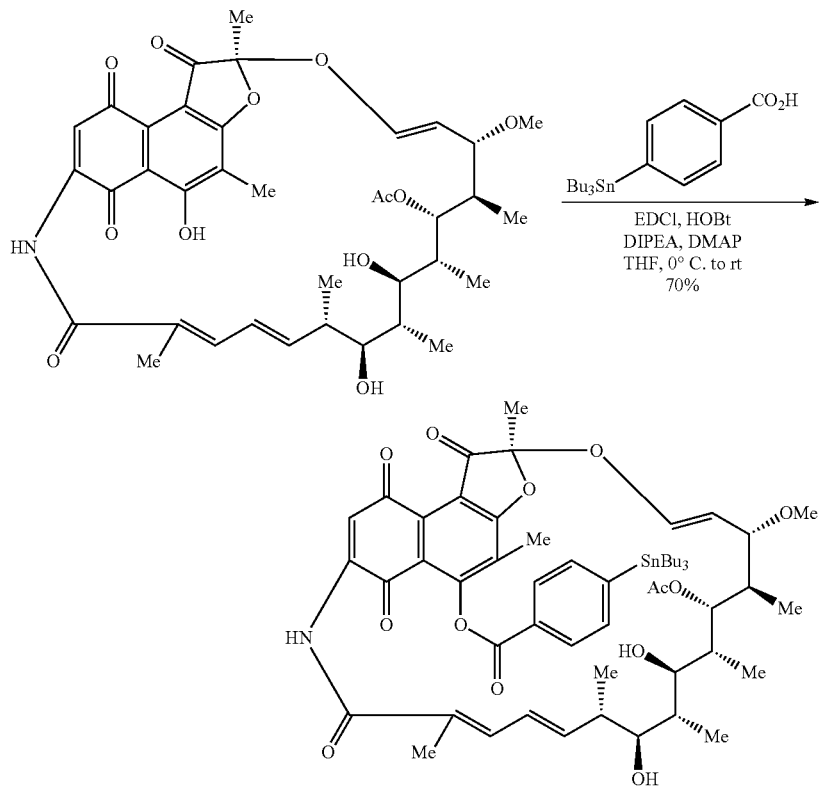

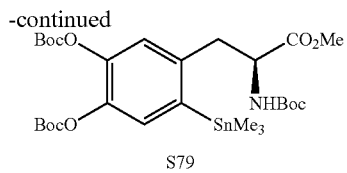

To iodo-DOPA (319 mg, 0.500 mmol, 1.00 equiv) in dioxane (5 mL) at 23° C. was added lithium chloride (105 mg, 2.50 mmol, 5.00 equiv), tetrakis(triphenylphosphine)palladium (17.3 mg, 0.150 mmol, 5.00 mol %) and bis(tri-methyltin) (329 mg, 1.00 mmol, 2.00 equiv). After stirring for 24 hr at 100° C., the reaction mixture was cooled to 23° C. and concentrated in vacuo. The residue was purified by chromatography on silica gel eluting with hexanes/EtOAc 3:1 (v/v) to afford 168 mg of the title compound as a colorless oil (50% yield).

To Rifamycin S (139 mg, 0.200 mmol, 1.00 equiv) in THF (1.0 mL) at 0° C. was added EDCI (76.7 mg, 0.400 mmol, 2.00 equiv), n,n-diisopropylethyl amine (0.20 mL, 0.60 mmol, 3.0 equiv) and 4-(Dimethylamino)pyridine (2.4 mg, 0.020 mmol, 0.10 equiv) and 4-(tributylstannyl)benzoic acid (124 mg, 0.300 mmol, 1.50 equiv). The reaction mixture was stirred for 1 hr at 0° C. and stirred for 12 h at room temperature. The reaction mixture was diluted with ethyl acetate and washed with water and dried (Na$_2$SO$_4$). The filtrate is concentrated in vacuo and the residue is purified by chromatography on silica gel eluting with hexane/EtOAc 2:1 (v/v) to afford 153 mg of the title compound as a white solid (70% yield).

$R_f$=0.30 (hexane/EtOAc 2:1 (v/v)). NMR Spectroscopy: $^1$H NMR (500 MHz, CDCl$_3$, 23° C., δ): 8.26 (s, 1H), 8.18–8.16 (m, 2H), 7.80 (s, 1H), 7.67 (d, J=8.0 Hz, 2H), 6.28–6.15 (m, 3H), 5.89 (dd, J=15.5 Hz, 7.0 Hz, 1H), 5.14 (dd, J=12.5 Hz, 7.0 Hz, 1H), 4.70 (d, J=10.5 Hz, 1H), 3.71 (d, J=5.0 Hz, 1H), 3.61 (d, J=10.0 Hz, 1H), 3.40-3.37 (m, 2H), 3.12 (s, 3H), 3.05-3.02 (m, 1H), 2.34 (s, 3H), 2.32-2.29 (m, 1H), 2.04 (s, 3H), 1.95 (s, 3H), 1.81-1.80 (m, 1H), 1.77 (s, 3H), 1.69-1.67 (m, 1H), 1.61-1.53 (m, 6H), 1.39-1.32 (m, 6H), 1.09-1.01 (m, 9H), 0.91 (t, J=7.5 Hz, 9H), 0.84 (d, J=7.0 Hz, 3H), 0.68 (d, J=7.0 Hz, 3H), 0.18 (d, J=7.0 Hz, 3H). $^{13}$C NMR (125 MHz, CDCl$_3$, 23° C., δ): 192.47, 182.12, 177.67, 173.29, 172.95, 169.43, 164.59, 156.01, 151.97, 144.31, 141.81, 139.93, 136.79, 136.68, 133.54, 132.24, 130.66, 129.35, 127.65, 124.06, 118.61, 116.36, 115.86, 114.63, 108.65, 81.12, 73.50, 73.21, 56.98, 38.82, 37.39, 37.34, 32.81, 29.01, 27.33, 21.91, 21.04, 19.94, 16.97, 13.65, 11.44, 11.11, 9.72, 8.84, 8.36. Mass Spectrometry: HRMS-FIA (m/z): Calcd for [M+H]$^+$, 1090.4333. Found, 1090.4289.

Example 45

Fluorination of arylstannanes with F-TEDA-BF$_4$

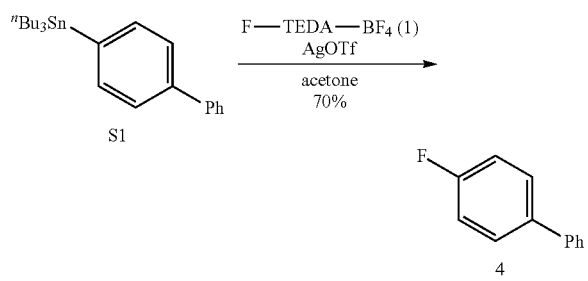

To 4-(biphenyl)tributylstannane (S1) (44.3 mg, 0.100 mmol, 1.00 equiv) in acetone (2.0 mL) at 23° C. was added silver triflate (51.4 mg, 0.0400 mmol, 2.00 equiv) and 1-chloromethyl-4-fluoro-1,4-diazoniabicyclo[2.2.2]octane bis(trifluoroborate) (1) (42.5 mg, 0.120 mmol, 1.20 equiv). The reaction mixture was stirred for 20 min at 23° C. and then concentrated in vacuo. The residue was purified by preparative TLC eluting with hexane to afford 12.0 mg of the title compound as colorless solid (70% yield).

Example 46

Fluorination of Arylstannanes with F-TEDA-PF$_6$ a) With 10.0 mol % of AgOTf

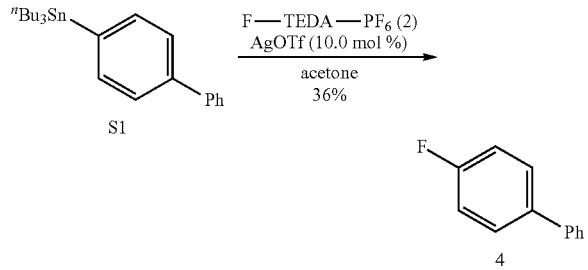

To 4-(biphenyl)tributylstannane (S1) (44.3 mg, 0.100 mmol, 1.00 equiv) in acetone (2.0 mL) at 23° C. was added silver triflate (2.57 mg, 0.0100 mmol, 10.0 mol %) and 1-chloromethyl-4-fluoro-1,4-diazoniabicyclo[2.2.2]octane bis(hexafluorophosphate) (2) (56.5 mg, 0.120 mmol, 1.20 equiv). The reaction mixture was stirred for 24 hr at 23° C. To the reaction mixture was added 3-nitrofluorobenzene (10.0 µL, 0.0939 mmol). The yields were determined to be 36% by comparing the integration of the $^{19}$F NMR (375 MHz, acetone-d6, 23° C.) resonance of 4-fluorobiphenyl (−118.1 ppm) and that of 3-nitrofluorobenzene (−112.0 ppm).

b) With 1.00 equivalent of AgOTf

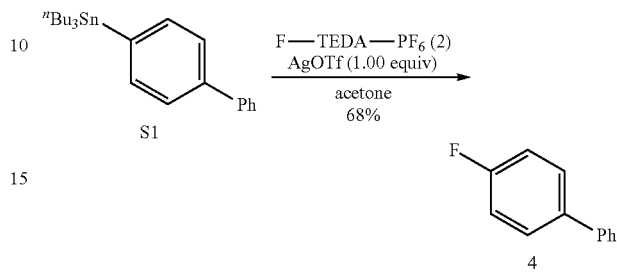

To 4-(biphenyl)tributylstannane (S1) (44.3 mg, 0.100 mmol, 1.00 equiv) in acetone (2.0 mL) at 23° C. was added silver triflate (25.7 mg, 0.100 mmol, 1.00 equiv) and 1-chloromethyl-4-fluoro-1,4-diazoniabicyclo[2.2.2]octane bis (hexafluorophosphate) (2) (56.5 mg, 0.120 mmol, 1.20 equiv). The reaction mixture was stirred for 12 hr at 23° C. To the reaction mixture was added 3-nitrofluorobenzene (10.0 µL, 0.0939 mmol). The yields were determined to be 68% by comparing the integration of the $^{19}$F NMR (375 MHz, acetone-d6, 23° C.) resonance of 4-fluorobiphenyl (−118.1 ppm) and that of 3-nitrofluorobenzene (−112.0 ppm).

c) Effect of NaOTf

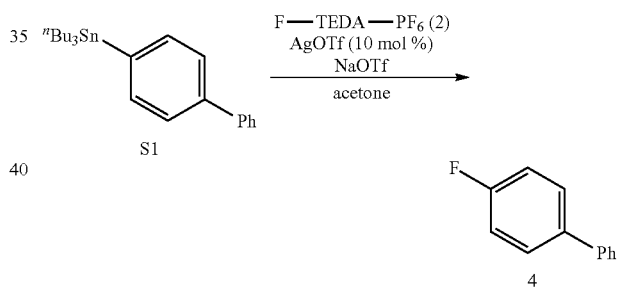

To 4-(biphenyl)tributylstannane (S1) (8.9 mg, 0.020 mmol, 1.0 equiv) in acetone (0.6 mL) at 23° C. was added silver triflate (0.51 mg, 0.0020 mmol, 10 mol %), sodium triflate and 1-chloromethyl-4-fluoro-1,4-diazoniabicyclo [2.2.2]octane bis(hexafluorophosphate) (2) (11 mg, 0.024 mmol, 1.2 equiv). The reaction mixture was stirred for 24 hr at 23° C. To the reaction mixture was added 3-nitrofluorobenzene (2.00 µL, 0.0188 mmol). The yield was determined by comparing the integration of the $^{19}$F NMR (375 MHz, acetone-d6, 23° C.) resonance of 4-fluorobiphenyl (−118.1 ppm) and that of 3-nitrofluorobenzene (−112.0 ppm). Yields are reported in Table 2.

TABLE 2

Effect of NaOTf

| NaOTf | Yield [%] ($^{19}$F NMR) |
|---|---|
| none | 36 |
| 2.0 equiv | 50 |

TABLE 2-continued

Effect of NaOTf

| NaOTf | Yield [%] ($^{19}$F NMR) |
|---|---|
| 5.0 equiv | 49 |
| 10 equiv | 48 | d) Effect of Slow Addition of Arylstannanes

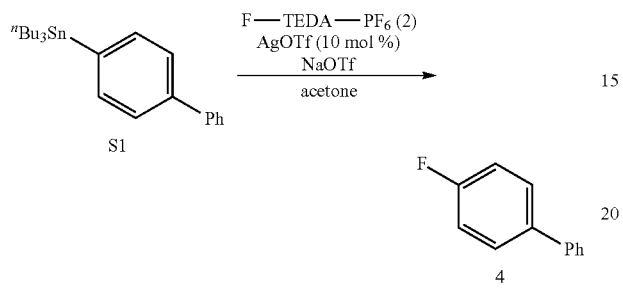

To silver triflate (0.51 mg, 0.0020 mmol, 10 mol %), sodium triflate (6.9 mg, 0.020 mmol, 2.0 equiv) and 1-chloromethyl-4-fluoro-1,4-diazoniabicyclo[2.2.2]octane bis(hexafluorophosphate) (2) (11 mg, 0.024 mmol, 1.2 equiv) in acetone (0.6 mL) at 23° C. was added 4-(biphenyl)tributylstannane (S1) (8.9 mg, 0.020 mmol, 1.0 equiv). The reaction mixture was stirred for 24 hr at 23° C. To the reaction mixture was added 3-nitrofluorobenzene (2.00 µL, 0.0188 mmol). The yield was determined by comparing the integration of the $^{19}$F NMR (375 MHz, acetone-d6, 23° C.) resonance of 4-fluorobiphenyl (−118.1 ppm) and that of 3-nitrofluorobenzene (−112.0 ppm). Yields are reported in Table 3.

TABLE 3

Effect of slow addition

| Manner of addition | Yield [%] ($^{19}$F NMR) |
|---|---|
| One portion | 50 |
| 0.1 equiv every 10 min | 53 | e) Background reaction without AgOTf

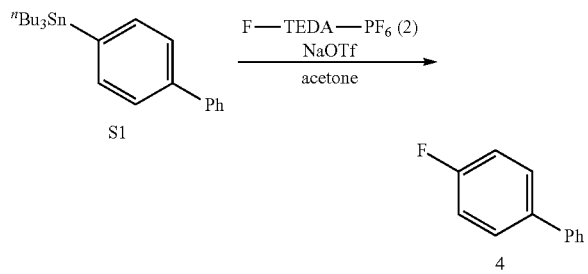

To 4-(biphenyl)tributylstannane (S1) (8.9 mg, 0.020 mmol, 1.0 equiv) in acetone (0.6 mL) at 23° C. was added 1-chloromethyl-4-fluoro-1,4-diazoniabicyclo[2.2.2]octane bis(hexafluorophosphate) (2) (11 mg, 0.024 mmol, 1.2 equiv) and sodium triflate. The reaction mixture was stirred for 24 hr at 23° C. To the reaction mixture was added 3-nitrofluorobenzene (2.00 µL, 0.0188 mmol). The yield was determined by comparing the integration of the $^{19}$F NMR (375 MHz, acetone-d6, 23° C.) resonance of 4-fluorobiphenyl (−118.1 ppm) and that of 3-nitrofluorobenzene (−112.0 ppm). Yields are reported in Table 4.

TABLE 4

Background reaction without AgOTf

| NaOTf | Yield [%] ($^{19}$F NMR) |
|---|---|
| none | 0 |
| 2.0 equiv | 0 |

Example 47

Optimized Conditions for Arylstannanes, General Procedure A: for Volatile Compounds

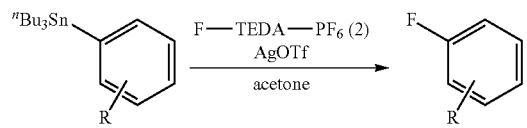

To the arylstannane (0.100 mmol, 1.00 equiv) in acetone (2.0 mL) at 23° C. was added silver triflate (51.4 mg, 0.200 mmol, 2.00 equiv) and 1-chloromethyl-4-fluoro-1,4-diazoniabicyclo[2.2.2]octane bis(hexafluorophosphate) (2) (56.5 mg, 0.120 mmol, 1.20 equiv). The reaction mixture was stirred for 20 min at 23° C. and to the reaction mixture was added 3-nitrofluorobenzene (10.0 µL, 0.0939 mmol). The yields were determined by comparing the integration of the $^{19}$F NMR (375 MHz, acetone-d6, 23° C.) resonance of arylfluoride and that of 3-nitrofluorobenzene (−112.0 ppm). Yields are reported in Table 5.

TABLE 5

Synthesis of volatile arylfluorides

| | $^{19}$F chemical shift | Yield [%] ($^{19}$F NMR) |
|---|---|---|
| H | −115.3 ppm | 82 |
| 4-CN | −105.0 ppm | 76 |
| 4-F | −121.6 ppm | 73 |
| 4-OMe | −126.8 ppm | 76 |
| 2,4,6-Trimethyl | −129.7 ppm | 73 |

Example 48

Optimized Conditions for Arylstannanes, General Procedure B: for Non-Volatile Compounds

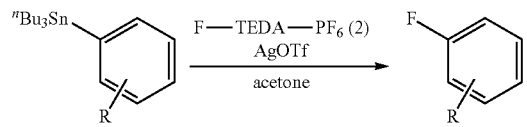

To the arylstannane (0.100 mmol, 1.00 equiv)) in acetone (2.0 mL) at 23° C. was added silver triflate (51.4 mg, 0.0400 mmol, 2.00 equiv) and 1-chloromethyl-4-fluoro-1,4-diazoniabicyclo[2.2.2]octane bis(hexafluorophosphate) (2) (56.5 mg, 0.120 mmol, 1.20 equiv). The reaction mixture was stirred for 20 min at 23° C. and then concentrated in vacuo. The residue was purified by chromatography on silica gel or preparative TLC.

Example 49

Large-Scale Fluorination of 4-(biphenyl)tributylstannane

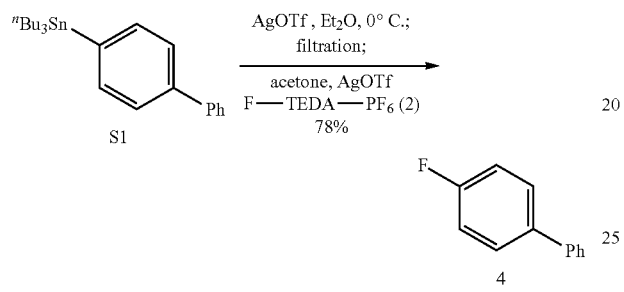

To 4-(biphenyl)tributylstannane (S1) (2.22 g, 5.00 mmol, 1.00 equiv) in Et$_2$O (25 mL) at 0° C. was added silver triflate (2.57 g, 10.0 mmol, 2.00 equiv). The reaction mixture was stirred for 1.0 hr at 0° C. before the addition of cold hexane (100 mL). The precipitate was filtered off and washed with cold hexane (3×30 mL). The red solid was transferred to another flask equipped with silver triflate (643 mg, 2.50 mmol, 0.500 equiv) and 1-chloromethyl-4-fluoro-1,4-diazoniabicyclo[2.2.2]octane bis(hexafluorophosphate) (2) (2.47 g, 5.25 mmol, 1.05 equiv) in acetone (50 mL). After stirring for 30 min at 23° C., the reaction mixture was concentrated in vacuo. The residue was dissolved in hexanes and filtered through a plug of Celite. The filtrate was concentrated in vacuo and the residue was purified by chromatography on silica gel eluting with hexanes to afford 671 mg of 4-fluorobiphenyl as a colorless solid (78% yield).

Example 50

Fluorination of Arylstannanes

4-Fluorobiphenyl (4)

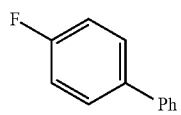

Yield: 14.3 mg (83%). R$_f$=0.60 (hexanes/EtOAc 19:1 (v/v)). NMR Spectroscopy: $^1$H NMR (500 MHz, CDCl$_3$, 23° C., δ): 7.60-7.54 (m, 4H), 7.47 (dd, J=7.5 Hz, 7.0 Hz, 2H), 7.36 (t, J=7.5 Hz, 1H), 7.14 (dd, J=8.0 Hz, 7.5 Hz, 2H). $^{13}$C NMR (125 MHz, CDCl$_3$, 23° C., δ): 162.44 (d, J=244 Hz), 140.24, 137.30, 129.0, 128.75 (d, J=8.5 Hz), 127.24, 127.00, 115.59 (d, J=21 Hz). $^{19}$F NMR (375 MHz, CDCl$_3$, 23° C., δ): −116.2.

4-Fluorophenol (5)

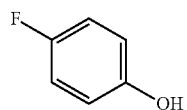

Yield: 8.1 mg (72%). R$_f$=0.60 (hexanes/EtOAc 19:1 (v/v)). NMR Spectroscopy: $^1$H NMR (500 MHz, CDCl$_3$, 23° C., δ): 6.95-6.95 (dd, J=8.0 Hz, 7.5 Hz, 2H), 6.80-6.76 (m, 2H), 5.41 (s, 1H). $^{13}$C NMR (125 MHz, CDCl$_3$, 23° C., δ): 157.32 (d, J=237 Hz), 151.17, 116.25 (d, J=8.0 Hz), 116.01 (d, J=21 Hz). $^{19}$F NMR (375 MHz, CDCl$_3$, 23° C., δ): −124.3.

4-Fluorobenzaldehyde (10)

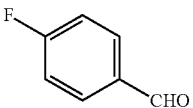

Yield: 9.6 mg (77%). R$_f$=0.77 (hexanes/EtOAc 7:3 (v/v)). NMR Spectroscopy: $^1$H NMR (500 MHz, CDCl$_3$, 23° C., δ): 9.95 (s, 1H), 7.92-7.88 (m, 2H), 7.22-7.18 (dd, J=8.0 Hz, 7.5 Hz, 2H). $^{13}$C NMR (125 MHz, CDCl$_3$, 23° C., δ): 190.43, 166.42 (d, J=255 Hz), 132.89, 132.14 (d, J=9.9 Hz), 116.25 (d, J=22 Hz). $^{19}$F NMR (375 MHz, CDCl$_3$, 23° C., δ): −102.9.

(4-Fluorobenzyl)dimethylamine N-oxide (11)

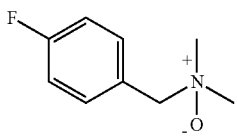

Yield: 10.6 mg (63%). R$_f$=0.05 (CH$_2$Cl$_2$/MeOH 9:1 (v/v)). NMR Spectroscopy: $^1$H NMR (400 MHz, CDCl$_3$, 23° C., δ): 7.50 (dd, J=7.2 Hz, 6.4 Hz, 2H), 7.08 (dd, J=8.4 Hz, 7.2 Hz, 2H), 4.34 (s, 2H), 3.10 (s, 6H). $^{13}$C NMR (125 MHz, CDCl$_3$, 23° C., δ): 163.56 (d, J=249 Hz), 133.94 (d, J=8.1 Hz), 126.49 (d, J=2.9 Hz), 115.74 (d, J=22 Hz), 74.95, 58.03. $^{19}$F NMR (375 MHz, CDCl$_3$, 23° C., δ): −111.5. Mass Spectrometry: HRMS-FIA (m/z): Calcd for [M+Na]$^+$, 192.07951. Found, 192.07923.

N-Boc-5-fluoroindole (12)

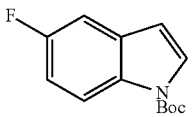

Yield: 17.6 mg (75%). $R_f$=0.75 (hexanes/EtOAc 7:3 (v/v)). NMR Spectroscopy: $^1$H NMR (500 MHz, CDCl$_3$, 23° C., δ): 8.08 (br, 1H), 7.62 (d, J=4.0 Hz, 1H), 7.20 (dd, J=6.5 Hz, 2.0 Hz, 1H), 7.03 (ddd, J=7.0 Hz, 6.5 Hz, 2.0 Hz, 1H), 6.52 (d, J=4.0 Hz, 1H), 1.68 (s, 9H). $^{13}$C NMR (125 MHz, CDCl$_3$, 23° C., δ): 159.27 (d, J=238 Hz), 149.51, 131.60, 131.38 (d, J=10 Hz), 127.51, 116.08 (d, J=9.1 Hz), 112.00 (d, J=24 Hz), 107.01, 106.27 (d, J=24 Hz), 83.9, 28.2. $^{19}$F NMR (375 MHz, CDCl$_3$, 23° C., δ): −121.7.

5-Fluoroisatin (13)

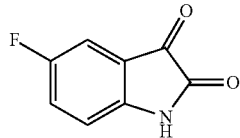 [SMILES: O=C1Nc2ccc(F)cc2C1=O]

Yield: 11.9 mg (72%). $R_f$=0.55 (hexanes/EtOAc 7:3 (v/v)). NMR Spectroscopy: $^1$H NMR (600 MHz, acetone-d6, 23° C., δ): 10.01 (br, 1H), 7.03 (ddd, J=9.0 Hz, 9.0 Hz, 3.0 Hz, 1H), 7.31 (dd, J=6.6 Hz, 2.4 Hz, 1H), 7.20 (dd, J=9.0 Hz, 3.0 Hz, 1H). $^{13}$C NMR (100 MHz, acetone-d6, 23° C., δ): 184.18, 159.68, 159.49 (d, J=241 Hz), 147.66, 125.26 (d, J=24 Hz), 119.41 (d, J=6.8 Hz), 114.33 (d, J=6.8 Hz), 111.74 (d, J=24 Hz). $^{19}$F NMR (375 MHz, acetone-d6, 23° C., δ): −122.1. These spectroscopic data correspond to those of an authentic sample purchased from Alfa Aesar.

6-Fluoroquinoline (14)

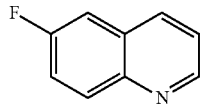

Yield: 11.6 mg (79%). $R_f$=0.47 (EtOAc). NMR Spectroscopy: $^1$H NMR (500 MHz, CDCl$_3$, 23° C., δ): 8.91 (dd, J=4.5 Hz, 1.5 Hz, 1H), 8.18 (d, J=8.0 Hz, 1H), 8.15 (dd, J=9.0 Hz, J=5.5 Hz, 1H), 7.53 (ddd, J=9.0 Hz, 8.5 Hz, 2.0 Hz, 1H), 7.50–7.45 (m, 2H). $^{13}$C NMR (100 MHz, CDCl$_3$, 23° C., δ): 160.43 (d, J=247 Hz), 149.56, 145.11, 135.70 (d, J=5.3 Hz), 131.80 (d, J=9.1 Hz), 128.86, 121.79, 119.94 (d, J=26 Hz), 110.74 (d, J=21 Hz). $^{19}$F NMR (375 MHz, CDCl$_3$, 23° C., δ): −113.0.

3-Deoxy-3-fluoroestrone (15)

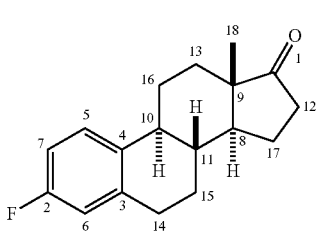

Yield: 23.2 mg (85%). $R_f$=0.33 (hexanes/EtOAc 9:1 (v/v)). NMR Spectroscopy: $^1$H NMR (600 MHz, CDCl$_3$, 23° C., δ): 7.23 (dd, J=8.4 Hz, J=6.0 Hz, 1H, H-5), 6.83 (ddd, J=9.6 Hz, 8.4 Hz, 3.0 Hz, 1H, H-7), 7.03 (dd, J=9.6 Hz, 3.0 Hz, 1H, H-6), 2.92–2.88 (m, 2H, H-14), 2.51 (dd, J=19.2 Hz, 8.4 Hz, 1H, H-12a), 2.42–2.38 (m, 1H, H-16a), 2.29–2.23 (m, 1H, H-10), 2.18–1.94 (m, 4H, H-12b, H-17a, H-15a, H-13b), 1.67–1.41 (m, 6H, H-17b, H-11, H-8, H-16b, H-15b, H-13b), 0.91 (s, 3H, H-18). $^{13}$C NMR (125 MHz, CDCl$_3$, 23° C., δ): 220.67 (C-1), 161.01 (d, J=243 Hz, C-2), 138.65 (d, J=6.4 Hz, C-3), 135.33 (C-4), 126.78 (d, J=8.3 Hz, C-5), 115.11 (d, J=20 Hz, C-6), 112.48 (d, J=20 Hz, C-7), 50.39 (C-8), 47.92 (C-9), 43.99 (C-10), 38.11 (C-11), 35.82 (C-12), 31.53 (C-13), 29.45 (C-14), 26.30 (C-15), 25.89 (C-16), 21.57 (C-17), 13.81 (C-18). $^{19}$F NMR (375 MHz, CDCl$_3$, 23° C., δ): −118.5.

6-Deoxy-6-fluoro-δ-tocopherol (16)

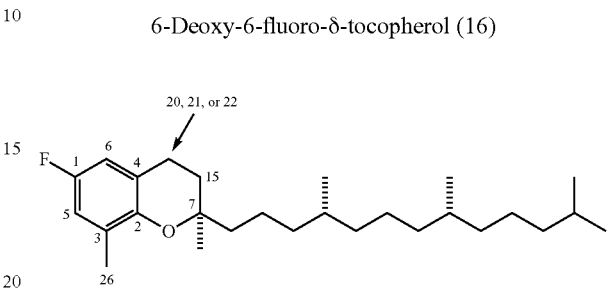

Yield: 27.9 mg (69%). $R_f$=0.46 (hexanes). NMR Spectroscopy: $^1$H NMR (600 MHz, CDCl$_3$, 23° C., δ): 6.67 (dd, J=9.0 Hz, 1.8 Hz, 1H, H-5), 6.59 (dd, J=9.0 Hz, J=1.8 Hz, 1H, H-6), 2.77–2.66 (m, 2H, H-20, 21 or 22), 2.14 (s, 3H, H-26), 1.82–1.70 (m, 2H, H-15), 1.60–0.83 (m, 36H). (Note: due to the overlap of peaks, further assignment has been difficult.) $^{13}$C NMR (100 MHz, CDCl$_3$, 23° C., δ): 155.73 (d, J=235 Hz, C-1), 147.88 (C-2), 127.71 (d, J=8.1 Hz, C-3), 121.32 (d, J=7.2 Hz, C-4), 114.84 (d, J=23 Hz, C-5), 112.21 (d, J=23 Hz, C-6), 75.91 (C-7), 39.90 (C-8), 39.36 (C-9), 37.43 (C-10), 37.40 (C-11), 37.27 (C-12), 32.79 (C-13), 32.65 (C-14), 31.07 (C-15), 27.97 (C-16), 24.79 (C-17), 24.43 (C-18), 24.07 (C-19), 22.71 (C-20), 22.61 (C-21), 22.54 (C-22), 20.92 (C-23), 19.74 (C-24), 19.64 (C-25), 16.11 (C-26). $^{19}$F NMR (375 MHz, CDCl$_3$, 23° C., δ): −126.9. Mass Spectrometry: HRMS-FIA (m/z): Calcd for [M+H]$^+$, 404.34544. Found, 404.34647.

10-Fluorocamptothecin (17)

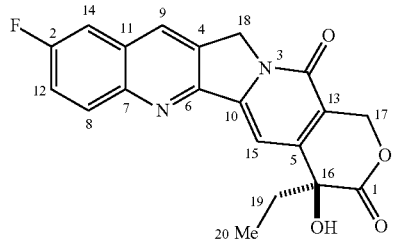

Yield: 25.6 mg (70%). $R_f$=0.35 (EtOAc). NMR Spectroscopy: $^1$H NMR (600 MHz, CDCl$_3$, 23° C., δ): 8.35 (s, 1H, H-9), 8.24 (dd, J=9.0 Hz, 4.8 Hz, 1H, H-8), 7.66 (s, 1H, H-15), 7.61 (ddd, J=7.6 Hz, 6.4 Hz, 3.0 Hz, 1H, H-12), 7.56 (dd, J=9.0 Hz, 3.0 Hz, 1H, H-14), 5.75 (d, J=16.2 Hz, 1H, H-17a), 5.31 (d, J=16.2 Hz, 1H, H-17b), 5.30 (s, 2H, H-18), 3.73 (s, 1H, OH), 1.96-1.84 (m, 2H, H-19), 1.05 (t, J=7.2 Hz, 3H, H-20). $^{13}$C NMR (100 MHz, CDCl$_3$, 23° C., δ): 173.88 (C-1), 161.29 (d, J=240 Hz, C-2), 157.58 (C-3), 152.10 (C-4), 150.11 (C-5), 146.15 (C-6), 146.03 (C-7), 132.34 (d, J=9.1 Hz, C-8), 130.31 (d, J=6.0 Hz, C-9), 129.37 (C-10), 128.85 (d, J=9.9 Hz, C-11), 121.09 (d, J=26 Hz, C-12), 118.77 (C-13), 111.23 (d, J=23 Hz, C-14), 97.98 (C-15), 72.71 (C-16), 66.33 (C-17), 49.99 (C-18), 31.59 (C-19), 7.80 (C-20). $^{19}$F NMR (375 MHz, CDCl$_3$, 23° C., δ): −110.7.

6-Demethoxy-6-fluoroquinine (18)

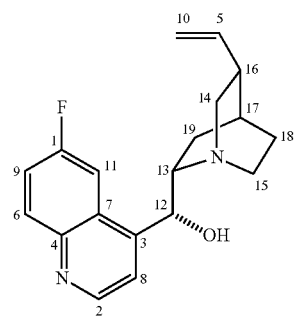

Yield: 22.8 mg (73%). $R_f$=0.40 (CH$_2$Cl$_2$/MeOH 9:1 (v/v)). NMR Spectroscopy: $^1$H NMR (600 MHz, CD$_3$CN, 23° C., δ): 8.85 (d, J=4.2 Hz, 1H, H-2), 8.10 (dd, J=9.0 Hz, 5.4 Hz, 1H, H-6), 7.97 (dd, J=9.0 Hz, 3.0 Hz, 1H, H-11), 7.65 (d, J=4.2 Hz, 1H, H-8), 7.54 (ddd, J=9.0 Hz, 9.0 Hz, 3.0 Hz, 1H, H-9), 5.83 (d, J=3.0 Hz, 1H, H-12), 5.78–5.72 (m, 1H, H-5), 5.06 (d, J=17.4 Hz, 1H, H-10a), 4.99 (d, J=10.2 Hz, 1H, H-10b), 3.92–3.86 (m, 1H, H-15a), 3.48–3.43 (m, 1H, H-13), 3.35 (dd, J=13.2 Hz, 7.2 Hz, 1H, H-14a), 3.06–3.00 (m, 2H, H-14b, H-15b), 2.68 (s br, 1H, H-16), 2.05–1.99 (m, 3H, H-17, H-18a, H-19a), 1.84–1.78 (m, 1H, H-18b), 1.65–1.58 (m, 1H, H-19b). $^{13}$C NMR (100 MHz, CD$_3$CN, 23° C., δ): 161.48 (d, J=244 Hz, C-1), 150.63 (C-2), 146.83 (d, J=6.1 Hz, C-3), 146.45 (C-4), 139.78 (C-5), 133.81 (d, J=9.9 Hz, C-6), 126.76 (d, J=9.9 Hz, C-7), 120.78 (C-8), 120.18 (d, J=26 Hz, C-9), 116.68 (C-10), 108.25 (d, J=24 Hz, C-11), 68.99 (C-12), 61.30 (C-13), 55.61 (C-14), 44.78 (C-15), 38.38 (C-16), 27.87 (C-17), 25.32 (C-18), 20.44 (C-19). $^{19}$F NMR (375 MHz, CD$_3$CN, 23° C., δ): –113.6. Mass Spectrometry: HRMS-FIA (m/z): Calcd for [M+H]$^+$, 313.17162. Found, 313.17160.

Example 51
Synthesis of Deoxy-fluoromarinol (19)

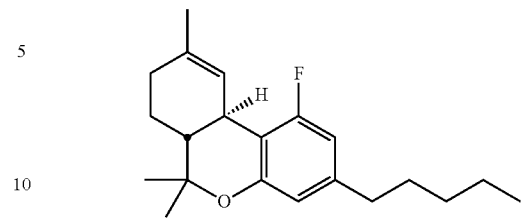

The preparation of Δ$^8$- and Δ$^9$-Tetrahydrocannabinols may be achieved according to literature procedures. Preparation of 4-isopropenyl-1-methylcyclohex-2-enol (S24) can be carried out by treatment of commercial (+)-limonene oxide (S23) with diphenyl diselenide which has previously been reduced to the phenyl selenide in situ. Subsequent oxidation with H$_2$O$_2$ followed by elimination gives the desired product S24 (Scheme 5).

Scheme 5: Preparation of staring material S24.

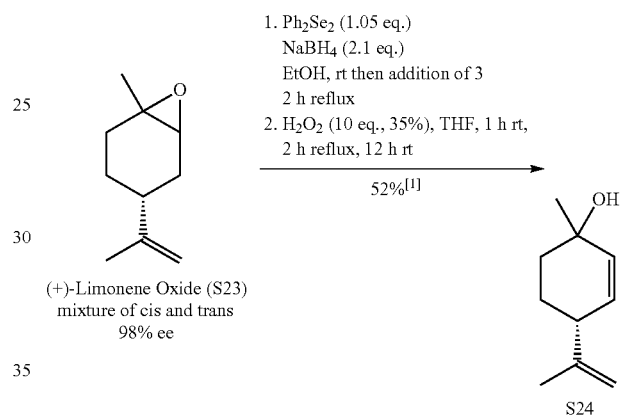

Starting from S24 both isomers of THC may be prepared upon treatment with olivetol (S25). Treatment with a catalytic amount BF$_3$.Et$_2$O in DCM at 0° C. gives the Δ$^9$-tetrahydrocannabinol (S26) selectively in moderate yield. Treating the same staring materials with a catalytic amount p-TsOH under reflux conditions in benzene leads selectively to the Δ$^8$-tetrahydrocannabinol (S25) (Scheme 6).

Scheme 6: Preparation of Δ$^8$- and Δ$^9$-Tetrahydrocannabinol.

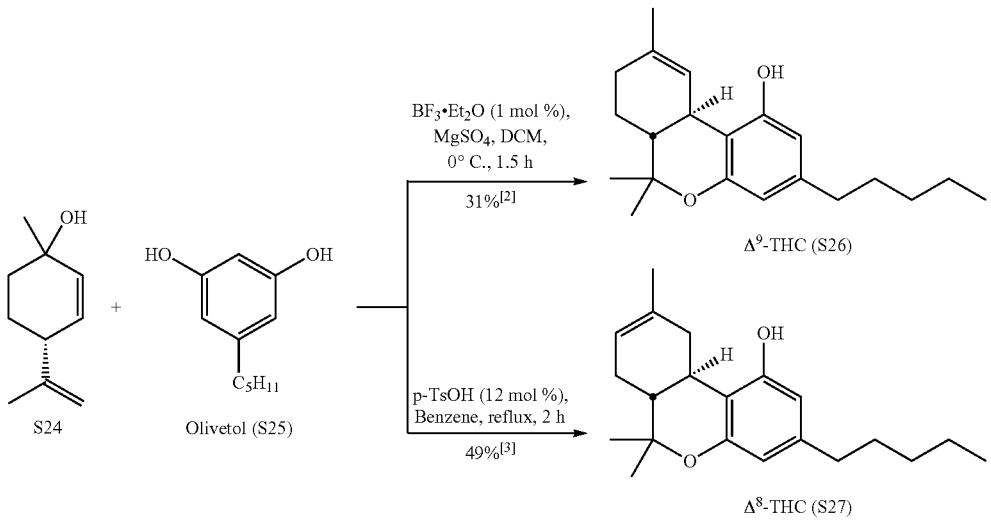

4-Isopropenyl-1-methylcyclohex-2-enol (S24)

A solution of (PhSe)$_2$ (2.15 g, 6.90 mmol, 1.05 eq.) in anhydrous EtOH (7 ml) was cooled to 0° C. under an atmosphere of N$_2$. To the solution was added NaBH$_4$ (521 mg, 13.8 mmol, 2.10 eq.) and the solution stirred at room temperature until the color disappeared. (+)-limonene oxide (S23) (1.10 ml, 6.56 mmol, 1 eq.) was added dropwise as a solution in anhydrous EtOH (2 ml). The mixture was heated to reflux for 2 h. The reaction mixture was quenched with 1 M HCl (15 ml) and the mixture extracted with EtOAc (2×30 ml). The combined organic extracts were washed with a saturated NaHCO$_3$ solution (10 ml), water (10 ml) and brine (10 ml). The organic layer was separated, dried over anhydrous MgSO$_4$, filtered and concentrated in vacuo.

The crude product was dissolved in THF (70 ml) and the solution cooled to 0° C. To the solution was added 35% H$_2$O$_2$ (5.62 ml, 65.6 mmol, 10 eq.) in a dropwise fashion. The mixture was allowed to warm to room temperature and stirred for 1 h and then refluxed for 2 h. The mixture was cooled to room temperature and stirred over night. The reaction was quenched with water (70 ml) and was extracted with EtOAc (3×70 ml). The combined organic extracts were washed with water (50 ml) and brine (50 ml), separated, dried over MgSO$_4$, filtered and concentrated under reduced pressure. The crude product was purified by column chromatography (EtOAc-Hex; 1:10 to 2:3). Product was obtained as a yellow oil (519 mg, 52% yield).

Δ$^9$-Tetrahydrocannabinol (S26)

To a mixture of olivetol (S25) (591 mg, 3.28 mmol, 1 eq.) and 4-isopropenyl-1-methylcyclohex-2-enol (S24) (500 mg, 3.28 mmol, 1 eq.) in anhydrous DCM (20 ml) was added anhydrous MgSO$_4$ (500 mg) under an atmosphere of N$_2$. The suspension was cooled to 0° C. and BF$_3$·Et$_2$O (4 µl, 0.033 mmol, 1 mol %) added. The mixture was stirred at 0° C. (maintained at this temperature at all times) for 1.5 h and subsequently anhydrous NaHCO$_3$ (1 g) added and the reaction mixture stirred until the color faded. The reaction mixture was filtered and the solvent removed under reduced pressure. The crude product was purified by column chromatography (EtOAc-Hex; 0:100 to 2:98) to obtain the product (310 mg, 31% yield).

Δ$^8$-Tetrahydrocannabinol (S27)

To a mixture of olivetol (S25) (591 mg, 3.28 mmol, 1 eq.) and 4-isopropenyl-1-methylcyclohex-2-enol (S24) (500 mg, 3.28 mmol, 1 eq.) in benzene (35 ml) was added p-TsOH·H$_2$O (75 mg, 0.39 mmol, 12 mol %) and the mixture heated to reflux for 2 h. To the reaction mixture was added a saturated NaHCO$_3$ solution (25 ml). The mixture was extracted with EtOAc (3×25 ml). Combined organic extracts were washed with water (20 ml) and brine (20 ml), dried over MgSO$_4$, filtered and concentrated under reduced pressure. The crude product was purified by column chromatography (EtOAc-Hex; 0:100 to 2:98) to obtain the pure product (505 mg, 49% yield isolated).

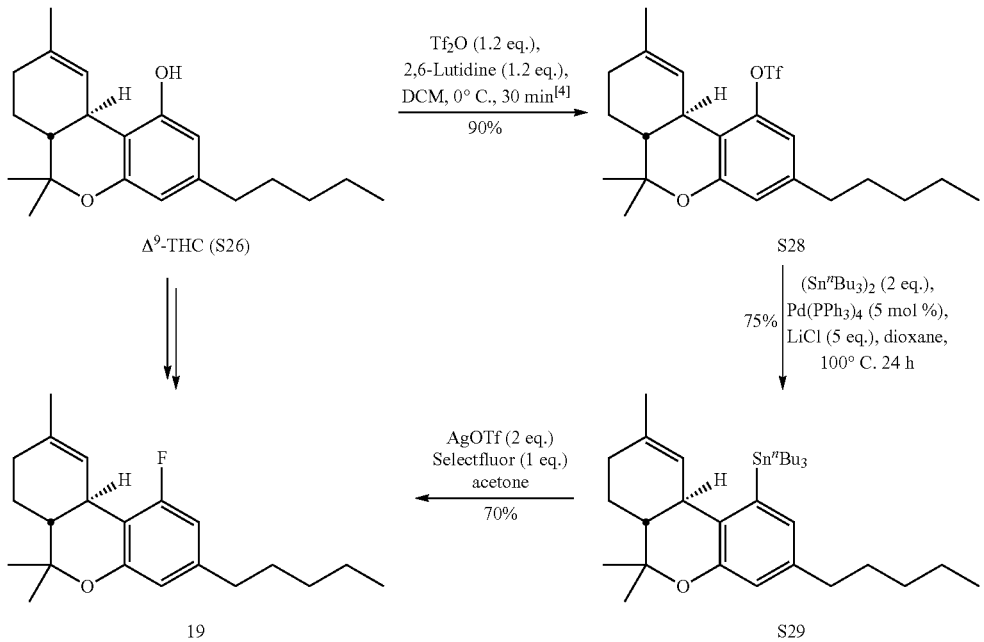

Scheme 7: Synthesis of deoxy-fluoromarinol (19).

(6aR,10aR)-6,6,9-Trimethyl-3-pentyl-6a,7,8,10a-tetrahydro-6H-benzo[c]chromen-1-yl trifluoromethanesulfonate (S28)

Δ$^9$-Tetrahydrocannabinol (S26) (314 mg, 1 mmol, 1 eq.) was dissolved in anhydrous DCM (10 ml) under an atmosphere of N$_2$ and 2,6 lutidine (140 µl, 1.2 mmol, 1.2 eq.) added. The mixture was cooled to 0° C. and Tf$_2$O (202 µl, 1.2 mmol, 1.2 eq.) added dropwise. The mixture was stirred for 30 min. The reaction was quenched with water (10 ml) and was extracted with DCM (2×10 ml). Combined organic extracts were washed with brine (5 ml), dried over MgSO$_4$, filtered and concentrated under reduced pressure. The crude product was purified by column chromatography (EtOAc-Hex; 5:95) to give S28 (402 mg, 90% yield).

Tributyl((6aR,10aR)-6,6,9-trimethyl-3-pentyl-6a,7,8, 10a-tetrahydro-6H-benzo[c]chromen-1-yl)stannane (S29)

(6aR,10aR)-6,6,9-Trimethyl-3-pentyl-6a,7,8,10a-tetrahydro-6H-benzo[c]chromen-1-yl trifluoromethanesulfonate (S28) (250 mg, 0.56 mmol, 1 eq.) will be dissolved in anhydrous dioxane (5 ml) and LiCl (119 mg, 2.8 mmol, 5 eq.), Pd(PPh$_3$)$_4$ (32.4 mg, 0.028 mmol, 5 mol %) and (Sn"Bu$_3$)$_2$ (566 μl, 1.12 mmol, 2 eq.) will be added. The mixture will be heated to 100° C. for 24 h. The reaction mixture will be concentrated under reduced pressure and subjected to column chromatography (EtOAc-Hex; 0:100 to 1:9) to give S29.

(6aR,10aR)-1-Fluoro-6,6,9-trimethyl-3-pentyl-6a,7, 8,10a-tetrahydro-6H-benzo[c]chromene (19)

Tributyl((6aR,10aR)-6,6,9-trimethyl-3-pentyl-6a,7,8,10a-tetrahydro-6H-benzo[c]chromen-1-yl)stannane (S29) (100 mg, 0.17 mmol, 1 eq.) will be dissolved in acetone (3.5 ml), and AgOTf (87.4 mg, 0.34 mmol, 2 eq.) and Selectfluor (71 mg, 0.20 mmol, 1.2 eq.) will be added at room temperature. The mixture will be stirred for 20 min at room temperature and subsequently concentrated under reduced pressure. The concentrate will be subjected to column chromatography (EtOAc-Hex; 0:100 to 5:95) to give 19.

(6aR,10aR)-6,6,9-trimethyl-3-pentyl-6a,7,10,10a-tetrahydro-6H-benzo[c]chromen-1-yl trifluoromethanesulfonate (S30)

To Δ$^8$-THC (960 mg, 3.05 mmol, 1 equiv) in anhydrous CH$_2$Cl$_2$ (100 ml), under an atmosphere of N$_2$ was added 2,6-lutidine (1.1 ml, 9.15 mmol, 3 equiv) in one portion. Tf$_2$O (1.54 ml, 9.15 mmol, 3 equiv) was added dropwise. The mixture was stirred for 1 h at 0° C. H$_2$O (50 ml) was added. The organic layer was separated and the aqueous layer was extracted with CH$_2$Cl$_2$ (100 ml). The combined organic layers were washed with brine (50 ml) and dried (MgSO$_4$). The filtrate was concentrated in vacuo and the residue was purified by chromatography on silica gel eluting with benzene/hexanes 1/9 (v/v) to afford 1.01 g of the title compound as a clear oil (74% yield). R$_f$=0.61 (benzene/hexanes 3:7 (v/v)). $^1$H NMR (400 MHz, CDCl$_3$, 22° C., δ): 6.68 (d, J=2 Hz, 1H) 6.61 (d, J=2 Hz, 1H) 5.45 (brd, J=4 Hz, 1H) 2.93 (brdd, J=4 Hz, J=16 Hz, 1H) 2.84 (dt, J=5 Hz, J=11 Hz, 1H) 2.53 (t, J=8 Hz, 2H) 2.17 (brd, J=14 Hz, 1H) 1.84–1.94 (m, 2H) 1.78 (dt, J=4 Hz, J=11 Hz, 1H) 1.71 (s, 3H) 1.59 (p, J=8 Hz, 2H) 1.40 (s, 3H) 1.26–1.36 (m, 4H) 1.12 (s, 3H) 0.90 (t, J=7 Hz, 3H). $^{13}$C NMR (100 MHz, CDCl$_3$, 22° C., δ): 155.1, 148.5, 143.5, 133.9, 119.4, 118.6 (q, J=321 Hz), 117.6, 116.9, 113.5, 77.5, 44.6, 35.7, 35.3, 31.8, 31.3, 30.4, 27.6, 27.3, 23.3, 22.5, 18.3, 14.0. $^{19}$F NMR (282 MHz, CDCl$_3$, 22° C., δ) −74.2. Mass Spectrometry: HRMS-FIA (m/z): Calcd for [C$_{22}$H$_{29}$F$_3$O$_4$S+H], 447.18114. Found, 447.18084.

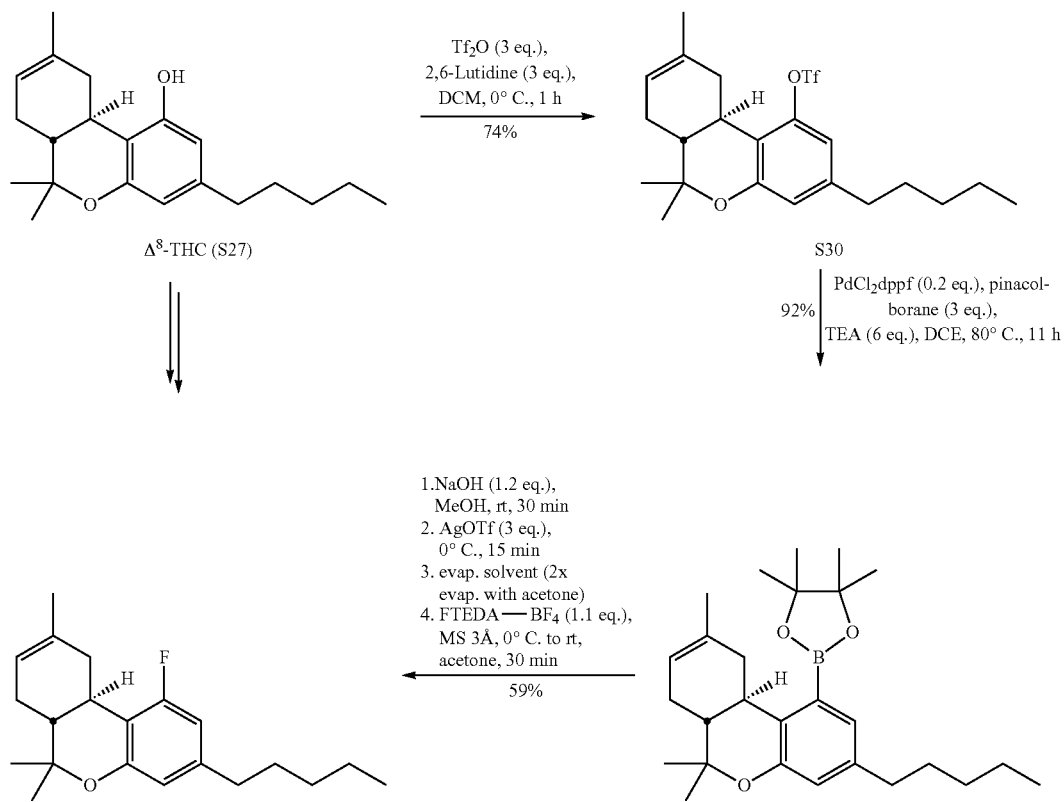

Scheme 8. Synthesis of 1-deoxy-1-fluoro-Δ$^8$-tetrahydrocannabinol (20).

4,4,5,5-tetramethyl-2-((6aR,10aR)-6,6,9-trimethyl-3-pentyl-6a,7,10,10a-tetrahydro-6H-benzo[c]chromen-1-yl)-1,3,2-dioxaborolane (S31)

A solution of (6aR,10aR)-6,6,9-trimethyl-3-pentyl-6a,7,10,10a-tetrahydro-6H-benzo[c]chromen-1-yl trifluoromethanesulfonate (S30) (410 mg, 0.92 mmol, 1 equiv) in anhydrous dichloroethane (20 ml) was degassed with a steady stream on N₂ for 20 min. To the solution was added PdCl$_2$dppf.CH$_2$Cl$_2$ (113 mg, 0.19 mmol, 0.2 equiv), 4,4,5,5-Tetramethyl-1,3,2-dioxaborolane (400 µl, 2.76 mmol, 3 equiv) and triethylamine (770 µl, 5.52 mmol, 6 equiv). The mixture was heated to 80° C. under an atmosphere of N$_2$ for 11 h. The reaction mixture was cooled to room temperature and concentrated in vacuo. The residue was purified by chromatography on silica gel eluting with benzene/hexanes 4/6 (v/v) to afford 373 mg of the title compound as white semi solid (92% yield). R$_f$=0.32 (benzene/hexanes 1:1 (v/v)). $^1$H NMR (600 MHz, CDCl$_3$, 20° C., δ): 7.09 (d, J=2 Hz, 1H) 6.71 (d, J=2 Hz, 1H) 5.44 (bd, J=4 Hz, 1H) 2.99 (dt, J=5 Hz, J=11 Hz, 1H) 2.60 (bdd, J=5 Hz, J=15 Hz, 1H) 2.49–2.52 (m, 2H) 2.10–2.17 (m, 1H) 1.83–1.90 (m, 2H) 1.74 (dt, J=5 Hz, J=12 Hz, 1H), 1.68 (s, 3H) 1.59 (p, J=8 Hz, 2H) 1.38 (s, 3H) 1.36 (s, 6H) 1.34 (s, 6H) 1.28–1.33 (m, 4H) 1.14 (s, 3H) 0.88 (t, J=7 Hz, 3H) $^{13}$C NMR (100 MHz, CDCl$_3$, 22° C., δ): 152.9, 141.4, 134.5, 128.5, 128.1, 120.0, 119.9, 83.5, 76.1, 45.5, 40.4, 35.4, 33.5, 31.7, 30.9, 28.2, 27.5, 25.1, 24.6, 23.2, 22.6, 18.5, 14.0 (C-B not observed). $^{11}$B NMR (96 MHz, CDCl$_3$, 22° C., δ): 29.9. Mass Spectrometry: HRMS-FIA (m/z): Calcd for [C$_{27}$H$_{41}$BO$_3$+H], 425.32215. Found, 425.32224.

(6aR,10aR)-1-fluoro-6,6,9-trimethyl-3-pentyl-6a,7,10,10a-tetrahydro-6H-benzo[c]chromene (20)

To 4,4,5,5-tetramethyl-2-((6aR,10aR)-6,6,9-trimethyl-3-pentyl-6a,7,10,10a-tetrahydro-6H-benzo[c]chromen-1-yl)-1,3,2-dioxaborolane (S31) (50.0 mg, 0.118 mmol, 1 equiv) was added MeOH (1.18 ml) and a solution of NaOH (0.12 M in MeOH, 0.142 mmol, 1.2 equiv). The mixture was stirred at room temperature for 30 min and subsequently cooled to 0° C. At 0° C. AgOTf (91 mg, 0.354 mmol, 3 equiv) was added in one portion and the mixture stirred for 15 min (clear yellow solution). The solvent was removed in vacuo at 0° C. and anhydrous acetone (1.2 ml) added and removed in vacuo (2×). To the residue was added molecular sieves 3 Å (60 mg) and anhydrous acetone (1.2 ml) at 0° C. FTEDA-BF$_4$ (46 mg, 0.130 mmol, 1.1 equiv) was added in one portion and the mixture stirred for 30 min while slowly reaching room temperature. The reaction mixture was filtered through a pad of Celite® and washed with acetone (2×2 ml). The filtrated was concentrated in vacuo and the residue was purified by chromatography on silica gel eluting with benzene/hexanes 1/9 (v/v) to afford 22 mg of the title compound as a clear oil (59% yield). R$_f$=0.45 (benzene/hexanes 1:9 (v/v)). NMR Spectroscopy: $^1$H NMR (600 MHz, CDCl$_3$, 20° C., δ): 6.44 (brs, 1H) 6.41 (dd, J=2 Hz, J=12 Hz, 1H) 5.43 (brs, 1H) 2.93 (brd, J=17 Hz, 1H) 2.76 (dt, J=5 Hz, J=11 Hz, 1H) 2.49 (dt, J=3 Hz, J=8 Hz, 2H) 2.15 (brd, J=15 Hz, 1H) 1.94 (brt, J=15 Hz, 1H) 1.78–1.86 (m, 1H) 1.76 (dt, J=11 Hz, 1H) 1.71 (s, 3H) 1.58 (p, J=8 Hz, 2H) 1.38 (s, 3H) 1.27–1.35 (m, 4H) 1.12 (s, 3H) 0.89 (t, J=7 Hz, 3H). $^{13}$C NMR (100 MHz, CDCl$_3$, 22° C., δ): 162.2 (d, J=245 Hz, C) 154.6 (d, J=9 Hz, C) 143.2 (d, J=10 Hz, C) 134.3 (C) 119.3 (CH) 112.8 (d, J=3 Hz, CH) 111.0 (d, J=19 Hz, C) 107.2 (d, J=23 Hz, CH) 77.1 (C) 43.9 (CH) 36.1 (d, J=9 Hz, CH$_2$) 35.4 (d, J=2 Hz, CH$_2$) 31.5 (CH2) 30.9 (CH) 30.5 (CH2) 27.5 (2x, CH$_2$ and CH$_3$) 23.4 (CH$_3$) 22.5 (CH$_2$) 18.5 (CH$_3$) 14.0 (CH$_3$). $^{19}$F NMR (282 MHz, CDCl$_3$, 22° C., δ) –113.1. Mass Spectrometry: HRMS-FIA (m/z): Calcd for [C$_{21}$H$_{29}$FO+H], 317.22752. Found, 317.22768.

Example 52

Synthesis of dechloro-fluorosertraline (21 and 22)

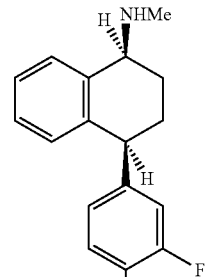

21

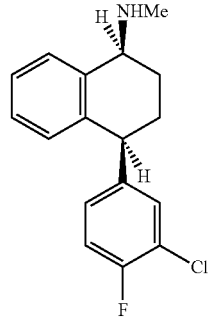

22

(E)-Methyl 4-phenylbut-3-enoate (S32)

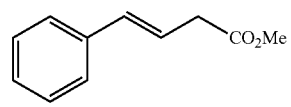 [SMILES: COC(=O)C/C=C/c1ccccc1]

4-Phenylbut-3-enoic acid was dissolved in acetone and added to Cs$_2$CO$_3$, then MeI was added. The suspension was refluxed overnight. Et$_2$O and brine were added and the phases separated. Aqueous layer was washed three times with Et$_2$O. Combined organic layers were dried over MgSO$_4$ and the solvent was evaporated in vacuum. (E)-methyl 4-phenylbut-3-enoate (S32) was obtained as a yellow oil (quantitative). R$_f$ (hexane/EtOAc 8:1)=0.28.

Methyl (E)-2-diazo-4-phenyl-3-butenoate (S33)

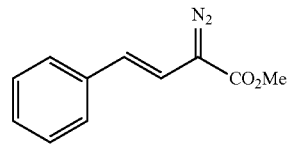

To a stirred solution of (E)-methyl 4-phenylbut-3-enoate (S32) and p-ABSA (see reference above for preparation of p-ABSA) in CH₃CN cooled to 0° C., was added DBU. The reaction mixture was allowed to warm to room temperature over 7 h then quenched with saturated ammonium chloride (NH₄Cl). The aqueous layer was extracted with diethyl ether three times and the combined organic layers were washed with brine and dried over Na₂SO₄. The solvent was removed under reduced pressure and the residue was triturated with a solution of pentane:diethyl ether (1:1). The solid was filtered off and the solvent was removed under reduced pressure. The residue was purified by flash chromatography (SiO₂, pentane:diethyl ether (15:1)) to give the title compound (S33) in 68% yield as a dark red solid, which was stored neat at −10° C. until ready for use.

(1S,2S)-(E)-1-Methoxycarbonyl-2-phenyl-1-(trans-styryl)cyclopropane (S34)

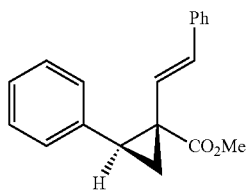 [SMILES: COC(=O)[C@]1(/C=C/c2ccccc2)C[C@H]1c1ccccc1]

A 0° C. solution of rhodium catalyst and styrene in pentane was treated dropwise with a solution of methyl (E)-2-diazo-4-phenyl-3-butenoate (S33) in pentane over 2 h via syringe pump. The mixture was stirred overnight, concentrated, and purified by flash chromatography (SiO₂, hexanes/ethyl acetate (20:1)) to afford the desired product (S34) as a white solid in 73% yield.

(1R,2S)-(E)-1-Carboxyl-1-methoxycarbonyl-2-phenylcyclopropane (S35)

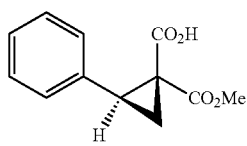 [SMILES: COC(=O)[C@]1(C(=O)O)C[C@H]1c1ccccc1]

A mixture of NaIO₄ in water was treated with KMnO₄ and stirred 0.5 h at ambient temperature. The purple suspension was treated sequentially with K₂CO₃, t-BuOH, and a solution of alkene (S34) in t-BuOH. After stirring an additional 3 h, ethylene glycol was added and stirred 1 h to destroy excess oxidant. The brown suspension was acidified to pH 4 with 1 N HCl and extracted with EtOAc. Drying over MgSO₄, concentration, and purification via radial chromatography (4 mm plate) using hexanes:ethyl acetate:acetic acid (100:10:1) gave the desired product (S35) as a white solid in 83% yield.

(S)-1,1-Bis-(methoxycarbonyl)-2-phenylcyclopropane (S36)

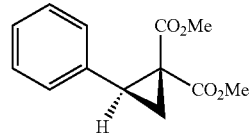

A suspension of K₂CO₃ and carboxylic acid S35 in acetone (freshly distilled from B₂O₃) was treated with Me₂SO₄ (freshly distilled) and stirred 3 h. The mixture was poured into Et₂O and water, the organic layer separated, dried over MgSO₄ and concentrated. Purification via radial chromatography (4 mm plate) using hexanes:ethyl acetate (10:1) as eluent afforded the desired product (S36) as a white solid in 97% yield.

Synthesis of Precursors for Cuprate Reagent

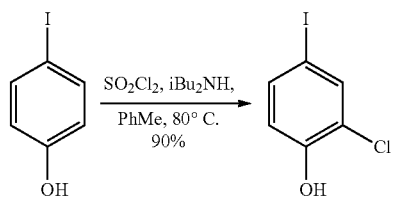 [SMILES: Oc1ccc(I)cc1 ; Oc1ccc(I)cc1Cl]

A round-bottom flask was charged with 4-iodophenol. Toluene, followed by di-iso-butylamine were added under argon, and the solution was warmed up to 70° C. SO₂Cl₂ was slowly syringed in and the mixture was stirred at 70° C. for 1 h. It was then cooled, diluted with Et₂O and washed once with aqueous NaHCO₃ (sat), once with aqueous NaCl (sat) and once with H₂O. After drying the organic phase over MgSO₄, the solvent was removed under vacuum. The crude product was redissolved in 4:1 (v/v) hexanes:ethyl ether, applied to a silica column and eluted using the same solvent. Purification afforded the desired product as a white solid in 90% yield.

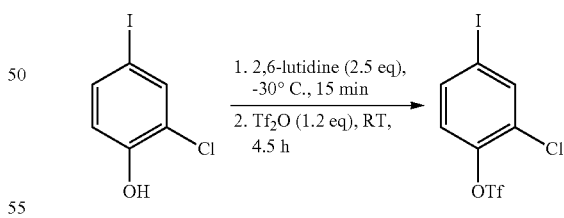

To a flask, starting phenol was dissolved in CH₂Cl₂. The solution was cooled to −30° C., 2,6-lutidine was added, and stirred for 15 min at same temperature. Then, Tf₂O was added to the solution, warmed to room temperature, and stirred for 4.5 h. The reaction mixture was quenched with H₂O at 0° C., and extracted twice with CH₂Cl₂. Combined organic layers were washed with 2 N HCl, 2 N NaOH, brine, dried over MgSO₄, filtered, and concentrated in vacuo. Purification by SiO₂ column chromatography afforded the desired product in 90% yield.

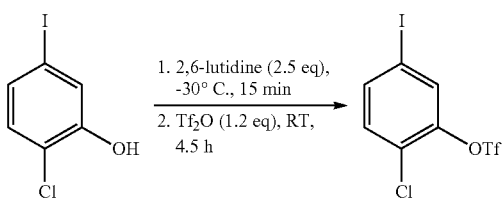 [SMILES: Oc1cc(I)ccc1Cl ; O=S(=O)(Oc1cc(I)ccc1Cl)C(F)(F)F]

The above compound will be synthesized according to the previous procedure.

Synthesis of S37 or S38

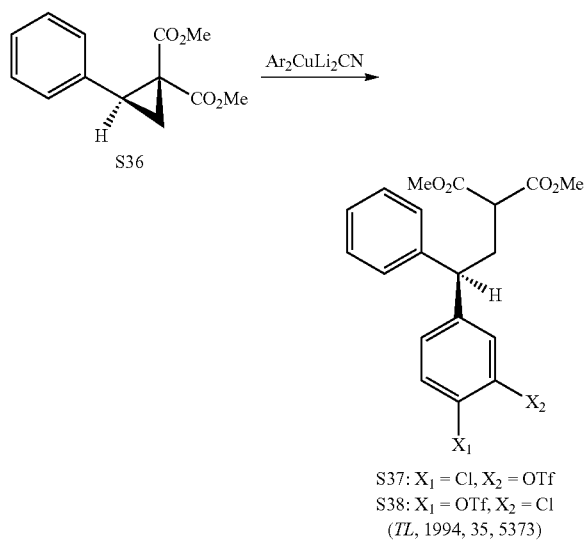

A solution of either aryl iodide substrate in Et$_2$O will be cooled to −78° C., treated with t-BuLi (1.77 M solution in pentane) and stirred 1 h. The freshly generated aryllithium will be cannulated into a suspension of rapidly stirring cuprous cyanide in Et$_2$O, warmed quickly to ambient temperature and stirred 15 min to form the cuprate reagent. The mixture will be treated with a solution of S36 in Et$_2$O and stirred 45 min at ambient temperature. The reaction will then be quenched with NH$_4$Cl (sat aq soln), stirred 1 h, and partitioned between Et$_2$O and water. The organic layer will be dried over MgSO$_4$, filtered, concentrated, and purified via radial chromatography (4 mm plate).

Synthesis of S39 or S40

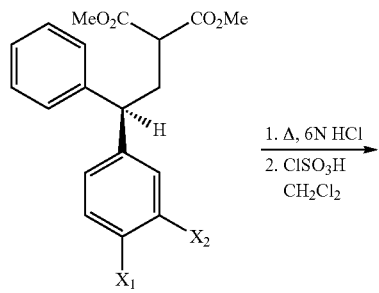

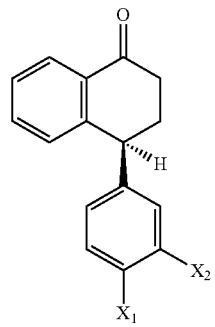

S39: X$_1$ = Cl, X$_2$ = OTf
S40: X$_1$ = OTf, X$_2$ = Cl

Step 1:
Starting material S37 or S38 will be treated with 6 N HCl and heated at reflux for 20 h. The mixture will be cooled and added to ether and 1 N NaOH. The aqueous layer will be washed (ether) and acidified (6 N HCl). Extraction with CH$_2$Cl$_2$, drying over MgSO$_4$, and concentration will afford the desired product.

Step 2:
The acid from Step 1 will be dissolved in CH$_2$Cl$_2$ and treated dropwise with ClSO$_3$H. After 30 min stirring, the cloudy mixture will be added to ether and dilute aqueous NaHCO$_3$. The organic layer will be dried over MgSO$_4$, concentrated, and purified via radial chromatography (4 mm plate) using hexanes:ethyl acetate (20:1 to 10:1) as eluent to afford a white solid. Enantiomeric purity of the tetralone will be determined by HPLC analysis.

Synthesis of S41 or S42

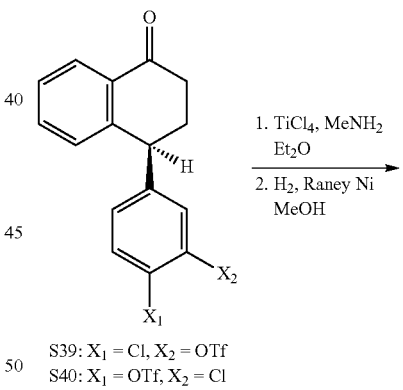

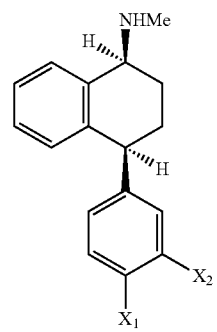

S41: X$_1$ = Cl, X$_2$ = OTf
S42: X$_1$ = OTf, X$_2$ = Cl

Step 1:

Compound S39 or S40 will be placed in a dry Schlenk flask under argon. Anhydrous ether will be added, and the reaction flask cooled to −78° C. Condensed methylamine will be introduced via cannula, followed by the addition of TiCl$_4$. The reaction mixture will be allowed to warm to room temperature slowly and stirred overnight. The reaction mixture will be filtered through a pad of Celite and washed with ether. The combined filtrates will be concentrated to afford the desired product.

Step 2:

The imine from Step 1 will be dissolved in methanol and hydrogenated over Raney-Ni. When the imine disappears (detected by TLC), the catalyst will be filtered, and the methanol will be evaporated. The residue will be purified by silica gel chromatography to give (+)-sertralinetriflate (S41 or S42).

Synthesis of S43 or S44

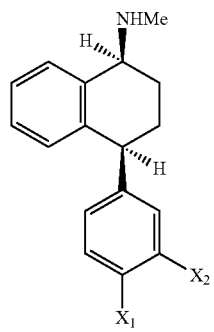

S41: X$_1$ = Cl, X$_2$ = OTf
S42: X$_1$ = OTf, X$_2$ = Cl

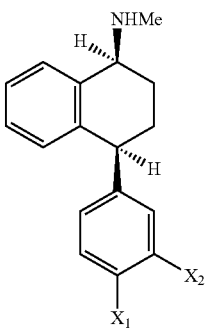

S43: X$_1$ = Cl, X$_2$ = SnBu$_3$
S44: X$_1$ = SnBu$_3$, X$_2$ = Cl

S41 or S42 (250 mg) will be dissolved in anhydrous dioxane (5 mL) and LiCl (119 mg, 2.8 mmol), Pd(PPh$_3$)$_4$ (32.4 mg, 0.028 mmol) and (Sn$^n$Bu$_3$)$_2$ (566 μl, 1.12 mmol) will be added. The mixture will be heated to 100° C. for 24 h. The reaction mixture will be concentrated under reduced pressure and subjected to column chromatography to give the title compound S43 or S44.

Synthesis of 21 or 22

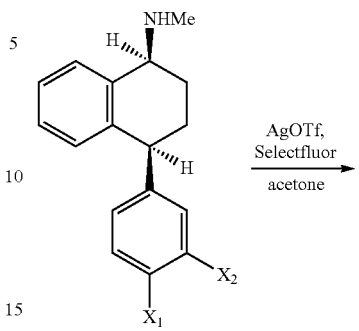

S43: X$_1$ = Cl, X$_2$ = SnBu$_3$
S44: X$_1$ = SnBu$_3$, X$_2$ = Cl

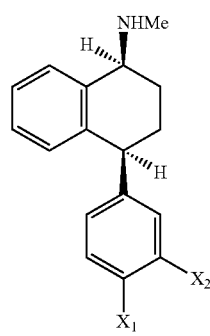

21: X$_1$ = Cl, X$_2$ = F
22: X$_1$ = F, X$_2$ = Cl

S43 or S44 (100 mg) will be dissolved in acetone (3.5 mL), and AgOTf (87.4 mg, 0.34 mmol) and Selectfluor (71 mg, 0.20 mmol, 1.2 eq.) will be added at room temperature. The mixture will be stirred for 20 min at room temperature and subsequently concentrated under reduced pressure. The concentrate will be subjected to column chromatography to afford the title compound 21 or 22.

Example 53

Fluorination of an Arylboronic Acid

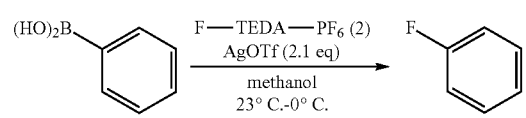

To an arylboronic acid (0.100 mmol, 1.00 equiv) in MeOH (1.0 mL) at 23° C. was added finely ground NaOH (0.0105 mmol, 1.05 equiv) and stirred for 1 hr. The reaction mixture was cooled to 0° C. and added to AgOTf (0.210 mmol, 2.10 equiv). After being stirred for 30 min at 0° C., the reaction mixture was concentrated in vacuo at 0° C., and was further concentrated with acetone (1.0 mL×2) at 0° C. to remove residual MeOH. To the residue was added MS3A (50 mg) and acetone (1.0 mL), and stirred for 20 min, after which time F-TEDA-BF$_4$ (0.105 mmol, 1.05 equiv) was added to the reaction mixture and stirred for 30 min before the product was isolated.

Example 54

(4-Fluorophenyl)silver (23)

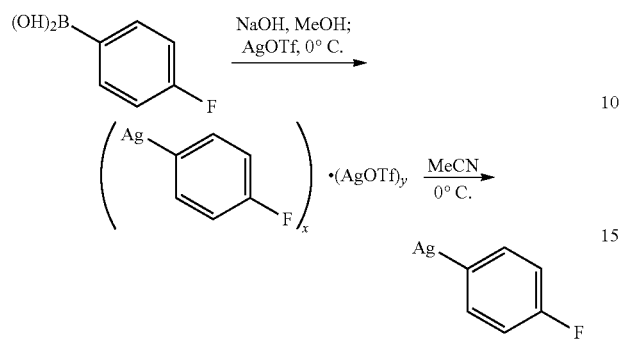

To NaOH (40.0 mg, 1.00 mmol, 1.00 equiv) in MeOH (1.0 mL) at 23° C. was added 4-fluorophenyl-boronic acid (140 mg, 1.00 mmol, 1.00 equiv). After stirring for 15 min at 23° C., the reaction mixture was cooled to 0° C. and was added to AgOTf (514 mg, 2.00 mmol, 2.00 equiv). After stirring for 30 min at 0° C., to the reaction mixture was added Et$_2$O (5 mL) and hexanes (10 mL) to precipitate an arylsilver complex. This precipitate contains various amount of AgOTf and the arylsilver to AgOTf ratio was irreproducible. Thus the precipitate was filtered off and washed with MeCN (2×2 mL) to remove AgOTf and subsequently washed with Et$_2$O (2×2 mL) at 0° C. to afford 101 mg of the title compound as a colorless solid (50% yield).

NMR Spectroscopy: $^1$H NMR (400 MHz, CDCl$_3$, −10° C., δ): 7.76 (dd, J=7.6 Hz, 7.6 Hz, 2H), 7.00 (dd, J=7.6 Hz, 7.6 Hz, 2H). $^{19}$F NMR (375 MHz, CDCl$_3$, −10° C., δ): −107.75 (s br). Due to the poor solubility and the thermal instability, the title compound was not amenable to further characterization.

Example 55

N-Boc-5-bromoindazole (S45)

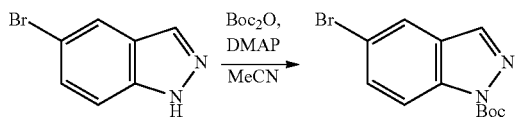 [SMILES: "MeCN" ; Brc1ccc2[nH]ncc2c1 ; CC(C)(C)OC(=O)n1ncc2cc(Br)ccc21]

To 5-bromoindazole (394 mg, 2.00 mmol, 1.00 equiv) in MeCN (4.0 mL) at 23° C. was added Boc$_2$O (436 mg, 2.00 mmol, 1.00 equiv) and 4-(dimethylamino)pyridine (24.4 mg, 0.200 mmol, 0.100 equiv). After stirring for 15 min at 23° C., the reaction mixture was concentrated in vacuo. The residue was filtered through a plug of silica gel eluting with hexanes/EtOAc 7:3 (v/v) to afford 588 mg of the title compound as a pale yellow oil (99% yield).

R$_f$=0.65 (hexanes/EtOAc 7:3 (v/v)). NMR Spectroscopy: $^1$H NMR (500 MHz, CDCl$_3$, 23° C., δ): 8.57 (s, 1H$_B$), 8.11 (s, 1H$_A$), 8.09 (d, J=9.0 Hz, 1H$_A$), 7.88 (s, 1H$_A$), 7.81 (s, 1H$_B$), 7.66-7.60 (m, 1H$_A$, 1H$_B$), 7.36 (d, J=9.0 Hz, 1H$_B$) 1.72 (s, 9H$_A$, 9H$_B$). (Note: NMR spectroscopy showed the product was a mixture of two rotamers around N-Boc moiety. The ratio of rotamers was 1 to 0.7. The peaks of major and minor isomer are shown with a subscript A and B respectively.) $^{13}$C NMR (125 MHz, CDCl$_3$, 23° C., δ): 148.96, 148.85, 147.80, 138.47, 138.35, 132.69, 131.88, 127.31, 123.67, 123.55, 123.04, 122.71, 120.89, 117.60, 116.79, 115.95, 87.11, 85.33, 28.09, 27.83. Mass Spectrometry: HRMS-FIA (m/z): Calcd for [M+Na]$^+$, 319.00526. Found, 319.00530.

Example 56

N-Boc-indazole-5-boronic acid, pinacol ester (S46)

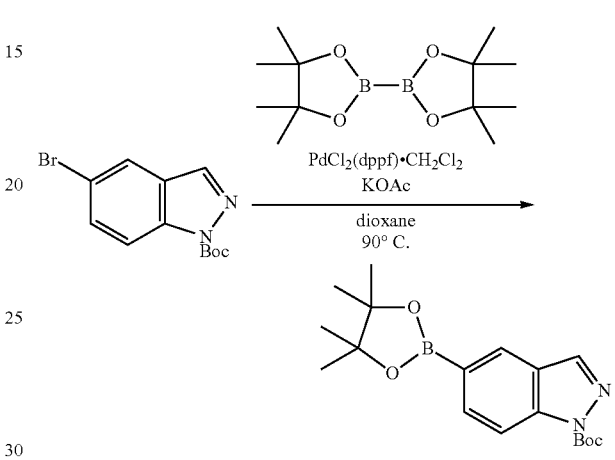

To N-Boc-5-bromoindazole (S45) (594 mg, 2.00 mmol, 1.00 equiv) in dioxane (10 mL) at 23° C. was added PdCl$_2$(dppf).CH$_2$Cl$_2$ (163 mg, 0.200 mmol, 0.100 equiv), bis(pinacolato)diborone (497 mg, 2.20 mmol, 1.10 equiv), and KOAc (392 mg, 4.00 mmol, 2.00 equiv). After stirring for 9.0 hr at 90° C., the reaction mixture was cooled to 23° C. and concentrated in vacuo. The residue was dissolved in CH$_2$Cl$_2$ and filtered through a plug of Celite. After the removal of CH$_2$Cl$_2$, the residue was purified by chromatography on silica gel eluting with hexanes/EtOAc 9:1 (v/v) to afford 500 mg of the title compound as a pale yellow oil (73% yield).

R$_f$=0.55 (hexanes/EtOAc 7:3 (v/v)). NMR Spectroscopy: $^1$H NMR (600 MHz, CDCl$_3$, 23° C., δ): 8.23 (s, 1H), 8.17 (d, J=8.4 Hz, 1H), 8.16 (s, 1H), 7.95 (d, J=8.4 Hz, 1H), 1.73 (s, 9H), 1.37 (s, 12H). $^{13}$C NMR (125 MHz, CDCl$_3$, 23° C., δ): 149.09, 141.27, 139.83, 134.67, 128.66, 125.56, 124.16 (br), 113.71, 84.80, 83.90, 28.07, 24.80. Mass Spectrometry: HRMS-FIA (m/z): Calcd for [M+Na]$^+$, 3677.17996. Found, 367.18018.

Example 57

N-Boc-indazole-5-boronic acid (S47)

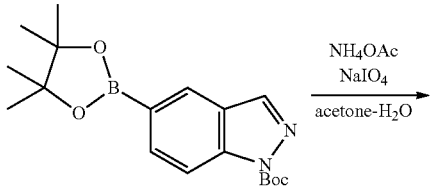

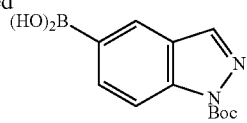

To N-Boc-indazole-5-boronic acid pinacol ester (S46) (390 mg, 1.13 mmol, 1.00 equiv) in acetone/H$_2$O (5.0 mL/5.0 mL) at 23° C. was added NH$_4$OAc (436 mg, 5.65 mmol, 5.00 equiv) and NaIO$_4$ (1.21 g, 5.65 mmol, 5.00 equiv). After stirring for 48 hr at 23° C., the reaction mixture was concentrated in vacuo to remove acetone. To the residual solution was added EtOAc (5 mL) and the phases were separated. The aqueous phase was extracted with EtOAc (2×5 mL). The combined organic phases are washed with brine (10 mL) and dried (Na$_2$SO$_4$). The filtrate was concentrated in vacuo and the residue was triturated with Et$_2$O to afford 200 mg of the title compound as a colorless solid (68% yield).

R$_f$=0.20 (hexanes/EtOAc 7:3 (v/v)). NMR Spectroscopy: $^1$H NMR (400 MHz, DMSO-d6, 23° C., δ): 8.42 (s, 1H), 8.29 (s, 1H), 8.18 (s, 2H), 8.03 (d, J=8.0 Hz, 1H), 7.98 (d, J=8.0 Hz, 1H), 1.64 (s, 9H). $^{13}$C NMR (100 MHz, DMSO-d6, 23° C., δ): 148.60, 140.28, 140.13, 134.57, 129.38 (br), 128.06, 125.45, 112.88, 84.38, 27.69. Mass Spectrometry: HRMS-FIA (m/z): Calcd for [M+Na]$^+$, 285.10171. Found, 285.10191.

Example 58

N-Boc-indole-5-boronic acid, neopentylglycol ester (S48)

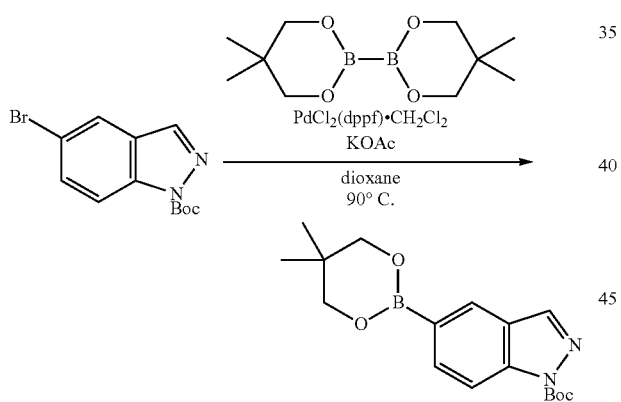

To N-Boc-5-bromoindole (592 mg, 2.00 mmol, 1.00 equiv) in dioxane (10 mL) at 23° C. was added PdCl$_2$(dppf).CH$_2$Cl$_2$ (163 mg, 0.200 mmol, 0.100 equiv), bis(neopentylglycolato)diborone (497 mg, 2.20 mmol, 1.10 equiv), and KOAc (392 mg, 4.00 mmol, 2.00 equiv). After stirring for 6.0 hr at 90° C., the reaction mixture was cooled to 23° C. and concentrated in vacuo. The residue was dissolved in CH$_2$Cl$_2$ and filtered through a plug of Celite. After the removal of CH$_2$Cl$_2$, the residue was purified by chromatography on silica gel eluting with hexanes/EtOAc 97:3 (v/v) to afford 609 mg of the title compound as a colorless solid (92% yield).

R$_f$=0.45 (hexanes/EtOAc 9:1 (v/v)). NMR Spectroscopy: $^1$H NMR (500 MHz, CDCl$_3$, 23° C., δ): 8.16 (d, J=7.5 Hz, 1H), 8.08 (s, 1H), 7.80 (d, J=8.5 Hz, 1H), 7.59 (d, J=3.5 Hz, 1H), 6.60 (d, J=3.5 Hz, 1H), 3.81 (s, 4H), 1.69 (s, 9H), 1.05 (s, 6H). $^{13}$C NMR (125 MHz, CDCl$_3$, 23° C., δ): 149.69, 136.96, 130.09, 129.72, 127.17, 126.10 (br), 125.61, 114.22, 107.59, 83.50, 72.25, 31.83, 28.11, 21.83. Mass Spectrometry: HRMS-FIA (m/z): Calcd for [M+H]$^+$, 330.18712. Found, 330.18650.

Example 59

N-Boc-indole-5-boronic acid (S49)

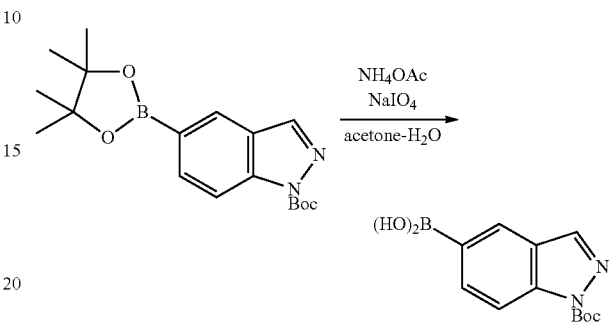

To N-Boc-indole-5-boronic acid pinacol ester (172 mg, 0.500 mmol, 1.00 equiv) in acetone/H$_2$O (5.0 mL/5.0 mL) at 23° C. was added NH$_4$OAc (193 mg, 2.50 mmol, 5.00 equiv) and NaIO$_4$ (535 mg, 2.00 mmol, 4.00 equiv). After stirring for 24 hr at 23° C., the reaction mixture was concentrated in vacuo to remove acetone. To the residual solution was added EtOAc (5 mL) and the phases were separated. The aqueous phase was extracted with EtOAc (2×5 mL). The combined organic phases are washed with brine (10 mL) and dried (Na$_2$SO$_4$). The filtrate was concentrated in vacuo and the residue was purified by chromatography on silica gel eluting with hexanes/EtOAc 1:1 (v/v) to afford 70.0 mg of the title compound as a colorless solid (54% yield).

R$_f$=0.50 (hexanes/EtOAc 1:1 (v/v)). NMR Spectroscopy: $^1$H NMR (500 MHz, CDCl$_3$, 23° C., δ): 8.56 (s, 1H), 8.31-8.23 (m, 2H), 7.67 (d, J=3.0 Hz, 1H), 6.75 (d, J=3.5 Hz, 1H), 1.72 (s, 9H). $^{13}$C NMR (125 MHz, CDCl$_3$, 23° C., δ): 149.71, 138.05, 131.31, 130.42, 129.41, 126.19, 124.31 (br), 114.69, 107.76, 83.91, 28.21. Mass Spectrometry: HRMS-FIA (m/z): Calcd for [M+Na]$^+$, 284.10646. Found, 284.10767.

Example 60

6-Quinoxaline boronic acid, pinacol ester (S50)

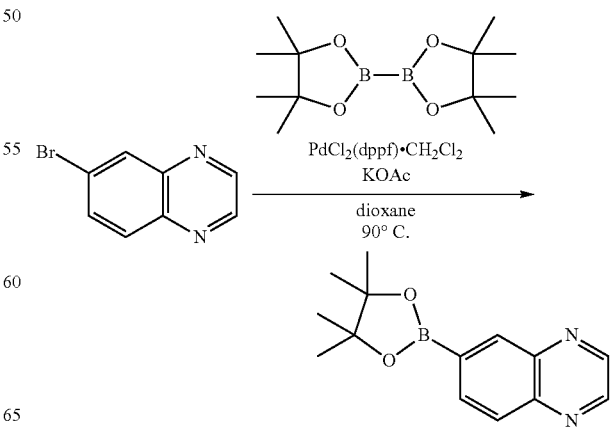

To 6-bromoquinoxaline (418 mg, 2.00 mmol, 1.00 equiv) in dioxane (10 mL) at 23° C. was added PdCl$_2$(dppf).CH$_2$Cl$_2$ (163 mg, 0.200 mmol, 0.100 equiv), bis(pinacolato)diborone (610 mg, 2.40 mmol, 1.20 equiv), and KOAc (392 mg, 4.00 mmol, 2.00 equiv). After stiffing for 1.5 hr at 90° C., the reaction mixture was cooled to 23° C. and concentrated in vacuo. The residue was dissolved in CH$_2$Cl$_2$ and filtered through a plug of Celite. After the removal of CH$_2$Cl$_2$, the residue was purified by chromatography on silica gel eluting with hexanes/EtOAc 4:1 (v/v) to afford 500 mg of the title compound as a colorless solid (98% yield).

R$_f$=0.45 (hexanes/EtOAc 1:1 (v/v)). NMR Spectroscopy: $^1$H NMR (500 MHz, CDCl$_3$, 23° C., δ): 8.86–8.82 (m, 2H), 8.59 (s, 1H), 8.12 (dd, J=8.0 Hz, 2.0 Hz, 1H), 8.06 (d, J=8.0 Hz, 1H), 1.37 (s, 12H). $^{13}$C NMR (125 MHz, CDCl$_3$, 23° C., δ): 145.53, 145.03, 144.37, 142.41, 137.31, 134.75, 131.90 (br), 128.44, 84.36, 24.86. Mass Spectrometry: HRMS-FIA (m/z): Calcd for [M+H]$^+$, 257.14558. Found, 257.14440.

Example 61

6-Quinoxaline boronic acid (S51)

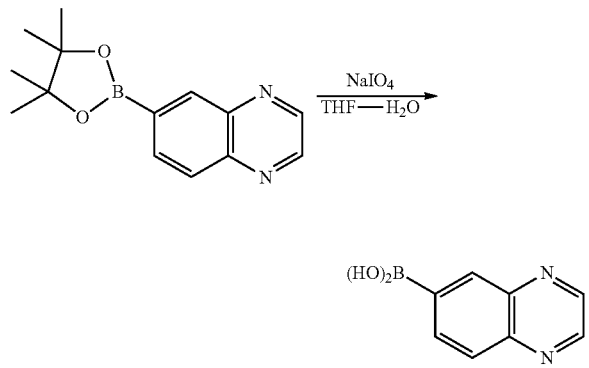

To 6-quinoxaline boronic acid pinacol ester (S50) (256 mg, 1.00 mmol, 1.00 equiv) in THF (2.0 mL) at 23° C. was added H$_2$O (8.0 mL) and NaIO$_4$ (321 mg, 1.50 mmol, 1.50 equiv). After stirring for 1.0 hr at 23° C., the reaction mixture was added to 1N HCl aq (20 mL) and was further stirred for 1.0 hr. To the reaction mixture was added EtOAc (20 mL) and the phases were separated. The aqueous phase was extracted with EtOAc (2×20 mL). The combined organic phases are washed with brine (20 mL) and dried (Na$_2$SO$_4$). The filtrate was concentrated in vacuo and the residue was triturated with Et$_2$O to afford 121 mg of the title compound as a colorless solid (70% yield).

R$_f$=0.10 (hexanes/EtOAc 1:1 (v/v)). NMR Spectroscopy: $^1$H NMR (500 MHz, DMSO-d6, 23° C., δ): 8.96–8.93 (m, 2H), 8.55 (s, 1H), 8.47 (s, 2H), 8.18 (d, J=8.0 Hz, 1H), 8.04 (d, J=8.0 Hz, 1H). $^{13}$C NMR (125 MHz, DMSO-d6, 23° C., δ): 146.08, 145.66, 143.21, 141.73, 136.61 (br), 135.82, 134.73, 127.77. Mass Spectrometry: HRMS-FIA (m/z): Calcd for [M+H]$^+$, 175.06733. Found, 176.06705.

Example 62

3-Methoxycarbonyl-5-methyinhenyl boronic acid (S52)

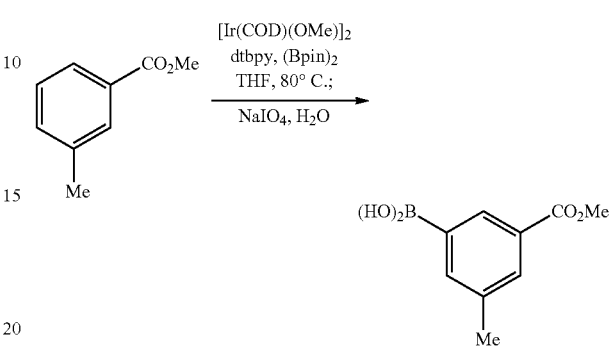

To m-toluic acid methyl ester (451 mg, 3.00 mmol, 1.00 equiv) in THF (6.0 mL) at 23° C. was added [Ir(COD) (OMe)]$_2$ (10 mg, 0.015 mmol, 0.50 mol %), dtbpy (8.0 mg, 0.030 mmol, 1.0 mol %) and bis(pinacolato)diborone (610 mg, 2.40 mmol, 0.800 equiv). After stirring for 24 hr at 80° C., the reaction mixture was added to H$_2$O (6.0 mL) and NaIO$_4$ (3.21 g, 15.0 mmol, 5.00 equiv). After stiffing for 8.0 hr at 23° C., the reaction mixture was added to 1N HCl aq (10 mL) and was further stirred for 1.0 hr. To the reaction mixture was added EtOAc (20 mL) and the phases were separated. The aqueous phase was extracted with EtOAc (2×20 mL). The combined organic phases are washed with brine (20 mL) and dried (Na$_2$SO$_4$). The filtrate was concentrated in vacuo and the residue was purified by chromatography on silica gel eluting with hexanes/EtOAc 7:3 (v/v) to afford 466 mg of the title compound as a colorless solid (80% yield).

R$_f$=0.15 (hexanes/EtOAc 7:3 (v/v)). NMR Spectroscopy: $^1$H NMR (500 MHz, DMSO-d6, 23° C., δ): 8.21 (s, 1H), 8.19 (s, 2H), 7.84 (s, 1H), 7.79 (s, 1H), 3.83 (s, 3H), 2.35 (s, 3H). $^{13}$C NMR (125 MHz, DMSO-d6, 23° C., δ): 166.71, 139.65, 136.97, 134.70 (br), 132.24, 131.14, 128.83, 51.99, 20.82.

Example 63

Large-scale fluorination of 4-biphenylboronic acid

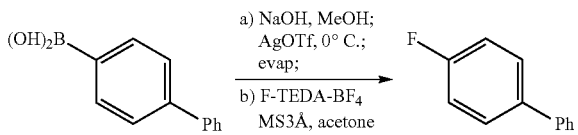

To NaOH (480 mg, 12.0 mmol, 1.20 equiv) in MeOH (20 mL) at 23° C. was added 4-biphenylboronic acid (1.98 g, 10.0 mmol, 1.00 equiv). After stirring for 15 min at 23° C., the reaction mixture was cooled to 0° C. and was added to AgOTf (7.71 g, 30.0 mmol, 3.00 equiv). After stirring for 30 min at 0° C., the solvent was removed under reduced pressure at 0° C. and the residual MeOH was completely removed by co-evaporation with acetone (20 mL×2). To the residue was added acetone (50 mL), MS3 Å (5.0 g), and 1-chloromethyl-4-fluoro-1,4-diazoniabicyclo[2.2.2]octane bis(trifluoroborate) (1) (3.72 g, 10.5 mmol, 1.05 equiv) and the reaction mixture was stirred for 30 min and concentrated in vacuo. The residue was dissolved in CH$_2$Cl$_2$ and filtered through a plug of Celite. After the removal of CH$_2$Cl$_2$, to the residue was added H$_2$O (30 mL) and Et$_2$O (30 mL) and the phases were separated. The aqueous phase was extracted with Et$_2$O (2×20 mL). The combined organic phases are washed with brine (30 mL) and dried (Na$_2$SO$_4$). The filtrate was concentrated in vacuo and the residue was purified by chromatography on silica gel eluting with hexanes to afford 1.62 g of 4-fluorobiphenyl as a colorless solid (94% yield).

Example 64

Fluorination with various amount of NaOH and AgOTf

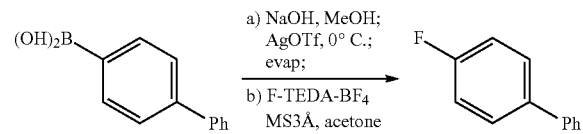

To NaOH (1.0-1.5 equiv) in MeOH (0.50 mL) at 23° C. was added a 4-biphenylboronic acid (19.8 mg, 0.100 mmol, 1.00 equiv). After stirring for 15 min at 23° C., the reaction mixture was cooled to 0° C. and was added to AgOTf (0-3.0 equiv). After stirring for 30 min at 0° C., the solvent was removed under reduced pressure at 0° C. and the residual MeOH was completely removed by co-evaporation with acetone (0.5 mL×2). To the residue was added acetone-d6 (0.5 mL), MS3 Å (50 mg), and 1-chloromethyl-4-fluoro-1,4-diazoniabicyclo[2.2.2]octane bis(trifluoroborate) (1) (37.2 mg, 0.105 mmol, 1.05 equiv) and the reaction mixture was stirred for 1.0 hr. The yields were determined by comparing the integration of the $^{19}$F NMR (375 MHz, acetone-d6, 23° C.) resonance of an arylfluoride and that of 3-nitrofluorobenzene (−112.0 ppm). The results are summarized in Table 6.

TABLE 6

Fluorination with various amounts of NaOH and AgOTf

| Entry | AgOTf (equiv) | NaOH (equiv) | Yield (%) |
|---|---|---|---|
| 1 | 0 | 1.0 | 0 |
| 2 | 1.0 | 1.0 | 43 |
| 3 | 2.0 | 1.0 | 82 |
| 4 | 2.0 | 1.2 | 78 |
| 5 | 2.0 | 1.5 | 63 |
| 6 | 3.0 | 1.0 | 90 |
| 7 | 3.0 | 1.2 | 95 |
| 8 | 3.0 | 1.5 | 83 |

Example 65

Comparison of Boronic Acid and Esters in Fluorination Yield

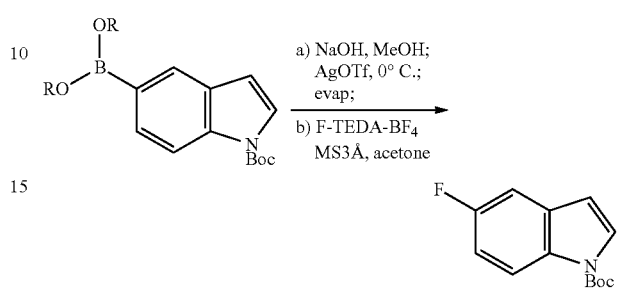

To NaOH (4.2 mg, 0.12 mmol, 1.2 equiv) in MeOH (0.50 mL) at 23° C. was added a boronic acid derivatives (0.100 mmol, 1.00 equiv). After stiffing for 15 min at 23° C., the reaction mixture was cooled to 0° C. and was added to AgOTf (77.1 mg, 0.300 mmol, 3.00 equiv). After stirring for 30 min at 0° C., the solvent was removed under reduced pressure at 0° C. and the residual MeOH was completely removed by co-evaporation with acetone (0.5 mL×2). To the residue was added acetone-d$_6$ (0.5 mL), MS3 Å (50 mg), and 1-chloromethyl-4-fluoro-1,4-diazoniabicyclo[2.2.2]octane bis(trifluoroborate) (1) (37.2 mg, 0.105 mmol, 1.05 equiv) and the reaction mixture was stirred for 1.0 hr. The yields were determined by comparing the integration of the $^{19}$F NMR (375 MHz, acetone-d6, 23° C.) resonance of an arylfluoride and that of 3-nitrofluorobenzene (−112.0 ppm). The results are summarized in Table 7.

TABLE 7

Comparison of boronic acid and esters in fluorination yield.

| Substrate | Yield (%) |
|---|---|
| (boronic acid, indole-Boc) | 97 |
| (neopentyl glycol boronate, indole-Boc) | 81 |
| (pinacol boronate, indole-Boc) | 70 |

Example 66

Fluorination of Aryl Boronic Acids—General Procedures

General procedure A: NMR yield with 2.0 equiv AgOTf

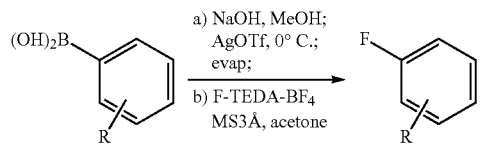

To NaOH (4.0 mg, 0.10 mmol, 1.0 equiv) in MeOH (0.50 mL) at 23° C. was added a boronic acid (0.100 mmol, 1.00 equiv). After stiffing for 15 min at 23° C., the reaction mixture was cooled to 0° C. and was added to AgOTf (51.4 mg, 0.200 mmol, 2.00 equiv). After stirring for 30 min at 0° C., the solvent was removed under reduced pressure at 0° C. and the residual MeOH was completely removed by co-evaporation with acetone (0.5 mL×2). To the residue was added acetone-d6 (0.5 mL), MS3 Å (50 mg), and 1-chloromethyl-4-fluoro-1,4-diazoniabicyclo[2.2.2]octane bis(trifluoroborate) (1) (37.2 mg, 0.105 mmol, 1.05 equiv) and the reaction mixture was stirred for 1.0 hr. The yields were determined by comparing the integration of the $^{19}$F NMR (375 MHz, acetone-d6, 23° C.) resonance of an arylfluoride and that of 3-nitrofluorobenzene (−112.0 ppm). The average yields of two runs are reported in Table 8.

General procedure B: NMR yields with 3.0 equiv AgOTf

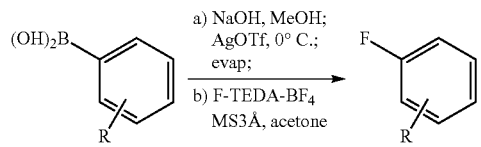

To NaOH (4.80 mg, 0.120 mmol, 1.20 equiv) in MeOH (1.0 mL) at 23° C. was added a boronic acid (0.100 mmol, 1.00 equiv). After stiffing for 15 min at 23° C., the reaction mixture was cooled to 0° C. and was added to AgOTf (77.1 mg, 0.300 mmol, 3.00 equiv). After stirring for 30 min at 0° C., the solvent was removed under reduced pressure at 0° C. and the residual MeOH was completely removed by co-evaporation with acetone (0.5 mL×2). To the residue was added acetone-d6 (0.5 mL), MS3 Å (50 mg), and 1-chloromethyl-4-fluoro-1,4-diazoniabicyclo[2.2.2]octane bis(trifluoroborate) (1) (37.2 mg, 0.105 mmol, 1.05 equiv) and the reaction mixture was stirred for 1.0 hr. The yields were determined by comparing the integration of the $^{19}$F NMR (375 MHz, acetone-d6, 23° C.) resonance of an arylfluoride and that of 3-nitrofluorobenzene (−112.0 ppm). The average yields of two runs are reported in Table 8. (Note: $^{19}$F NMR chemical shifts given in Table 8 correspond to those of authentic samples purchased from Aldrich, Alfa, or TCI, or those of data given in appropriate references.)

TABLE 8

NMR yields of fluorinations

| R | $^{19}$F chemical shift [ppm] in acetone-d$^6$ | NMR Yield [%] with 2.0 equiv AgOTf | NMR Yield [%] with 3.0 equiv AgOTf |
|---|---|---|---|
| H | −115.3 | 83 | 95 |
| 4-Ph | −118.1 | 82 | 95 |
| 4-OH | −128.2 | 58 | 70 |
| 4-$^t$Bu | −120.8 | 82 | 90 |
| 4-OMe | −126.8 | 84 | 98 |
| 2,4,6-Trimethyl | −129.7 | 73 | 73 |
| 4-F | −121.6 | 85 | 91 |
| 4-CO$_2$Me | −109.5 | 76 | 92 |
| 4-CN | −105.0 | 61 | 77 |
| 4-CHO | −105.9 | 71 | 71 |
| 4-Br | −117.4 | 73 | 93 |
| 4-NHAc | −114.4 | 79 | 89 |
| 4-CF$_3$ | −109.5 | 67 | 86 |
| 3,5-Dimethyl | −117.6 | 78 | 88 |
| 1-Naphthyl | −125.9 | 86 | 95 |
| N-Boc-5-Indazolyl | −120.0 | 74 | 95 |
| N-Boc-5-Indolyl | −123.2 | 81 | 97 |
| 6-Quinoxalinyl | −107.1 | 65 | 79 |
| 6-Quinolinyl | −113.8 | 63 | 80 |
| 3-Pyridyl | −125.6 | 59 | 72 |
| trans-2-Phenylvinyl | −132.2 | 74 | 90 |
| trans-1-Octen-1-yl | −132.4 | 85 | 92 |
| 1-Cyclohexyl | −102.5 | 65 | 83 |

General Procedure C: Isolated Yield with 2.0 equiv AgOTf

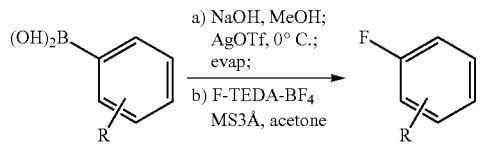

To NaOH (20.0 mg, 0.500 mmol, 1.00 equiv) in MeOH (2.5 mL) at 23° C. was added a boronic acid (0.500 mmol, 1.00 equiv). After stiffing for 15 min at 23° C., the reaction mixture was cooled to 0° C. and was added to AgOTf (257 mg, 1.00 mmol, 2.00 equiv). After stirring for 30 min at 0° C., the solvent was removed under reduced pressure at 0° C. and the residual MeOH was completely removed by co-evaporation with acetone (2.5 mL×2). To the residue was added acetone (5.0 mL), MS3 Å (250 mg), and 1-chloromethyl-4-fluoro-1,4-diazoniabicyclo[2.2.2]octane bis(trifluoroborate) (1) (186 mg, 0.525 mmol, 1.05 equiv). The reaction mixture was stirred for 1.0 hr and concentrated in vacuo. The residue was dissolved in CH$_2$Cl$_2$ and filtered through a plug of Celite. After the removal of CH$_2$Cl$_2$, the residue was added to H$_2$O (5 mL) and EtOAc (5 ml) and the phases were separated. The aqueous phase was extracted with EtOAc (2×3 mL). The combined organic phases are washed with brine (5 mL) and dried (Na$_2$SO$_4$). The filtrate was concentrated in vacuo and the residue was purified by chromatography on silica gel.

General Procedure D: Isolated Yield with 3.0 Equiv AgOTf

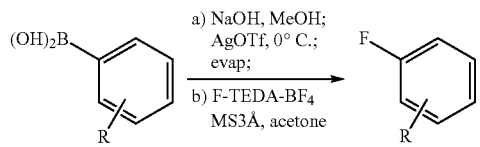

To NaOH (24.0 mg, 0.600 mmol, 1.20 equiv) in MeOH (2.5 mL) at 23° C. was added a boronic acid (0.500 mmol, 1.00 equiv). After stirring for 15 min at 23° C., the reaction mixture was cooled to 0° C. and was added to AgOTf (385 mg, 1.50 mmol, 3.00 equiv). After stiffing for 30 min at 0° C., the solvent was removed under reduced pressure at 0° C. and the residual MeOH was completely removed by co-evaporation with acetone (2.5 mL×2). To the residue was added acetone (5.0 mL), MS3 Å (250 mg), and 1-chloromethyl-4-fluoro-1,4-diazoniabicyclo[2.2.2]octane bis(trifluoroborate) (1) (186 mg, 0.525 mmol, 1.05 equiv). The reaction mixture was stirred for 1.0 hr and concentrated in vacuo. The residue was dissolved in CH$_2$Cl$_2$ and filtered through a plug of Celite. After the removal of CH$_2$Cl$_2$, the residue was added to H$_2$O (5 mL) and EtOAc (5 ml) and the phases were separated. The aqueous phase was extracted with EtOAc (2×3 mL). The combined organic phases are washed with brine (5 mL) and dried (Na$_2$SO$_4$). The filtrate was concentrated in vacuo and the residue was purified by chromatography on silica gel.

Example 67

Fluorination of Aryl Boronic Acids

4-Fluorobiphenyl (24)

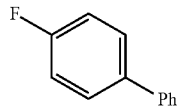

(General Procedure C) Yield: 70.6 mg (82%). $R_f$=0.60 (hexanes/EtOAc 19:1 (v/v)). NMR Spectroscopy: $^1$H NMR (500 MHz, CDCl$_3$, 23° C., δ): 7.60-7.54 (m, 4H), 7.47 (dd, J=7.5 Hz, 7.0 Hz, 2H), 7.36 (t, J=7.5 Hz, 1H), 7.14 (dd, J=8.0 Hz, 7.5 Hz, 2H). $^{13}$C NMR (125 MHz, CDCl$_3$, 23° C., δ): 162.44 (d, J=244 Hz), 140.24, 137.30, 129.0, 128.75 (d, J=8.5 Hz), 127.24, 127.00, 115.59 (d, J=21 Hz). $^{19}$F NMR (375 MHz, CDCl$_3$, 23° C., δ): −116.2.

4-Fluorophenol (25)

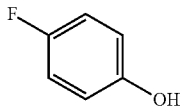

(General Procedure D) Yield: 39.0 mg (70%). $R_f$=0.58 (hexanes/EtOAc 7:3 (v/v)). NMR Spectroscopy: $^1$H NMR (500 MHz, CDCl$_3$, 23° C., δ): 6.95-6.95 (dd, J=8.0 Hz, 7.5 Hz, 2H), 6.80-6.76 (m, 2H), 5.41 (s, 1H). $^{13}$C NMR (125 MHz, CDCl$_3$, 23° C., δ): 157.32 (d, J=237 Hz), 151.17, 116.25 (d, J=8.0 Hz), 116.01 (d, J=21 Hz). $^{19}$F NMR (375 MHz, CDCl$_3$, 23° C., δ): −124.3.

Methyl 4-fluorobenzoate (26)

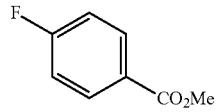

(General Procedure C) Yield: 58.6 mg (76%). $R_f$=0.85 (hexanes/EtOAc 7:3 (v/v)). NMR Spectroscopy: $^1$H NMR (400 MHz, CDCl$_3$, 23° C., δ): 8.05 (dd, J=8.8 Hz, 6.4 Hz, 2H), 7.11 (dd, J=8.8 Hz, 8.8 Hz, 2H), 3.91 (s, 3H). $^{13}$C NMR (125 MHz, CDCl$_3$, 23° C., δ): 166.13, 165.74 (d, J=253 Hz), 132.09 (d, J=9.1 Hz), 126.41, 115.49 (d, J=22 Hz), 52.2. $^{19}$F NMR (375 MHz, CDCl$_3$, 23° C., δ): −106.2.

4-Fluorobenzaldehyde (27)

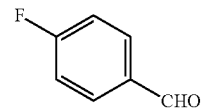

(General Procedure C) Yield: 37.8 mg (61%). $R_f$=0.77 (hexanes/EtOAc 7:3 (v/v)). NMR Spectroscopy: $^1$H NMR (500 MHz, CDCl$_3$, 23° C., δ): 9.95 (s, 1H), 7.92-7.88 (m, 2H), 7.22-7.18 (dd, J=8.0 Hz, 7.5 Hz, 2H). $^{13}$C NMR (125 MHz, CDCl$_3$, 23° C., δ): 190.43, 166.42 (d, J=255 Hz), 132.89, 132.14 (d, J=9.9 Hz), 116.25 (d, J=22 Hz). $^{19}$F NMR (375 MHz, CDCl$_3$, 23° C., δ): −102.9.

4-Fluoroacetanilide (28)

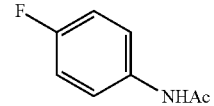

(General Procedure C) Yield: 59.0 mg (77%). $R_f$=0.25 (hexanes/EtOAc 1:1 (v/v)). NMR Spectroscopy: $^1$H NMR (500 MHz, CDCl$_3$, 23° C., δ): 7.51 (br s, 1H), 7.44 (dd, J=9.5 Hz, 5.0 Hz, 2H), 6.99 (dd, J=8.0 Hz, 7.5 Hz, 2H), 2.15 (s, 3H). $^{13}$C NMR (100 MHz, CDCl$_3$, 23° C., δ): 168.43, 159.34 (d, J=243 Hz), 133.84, 121.80 (d, J=7.3 Hz), 115.56 (d, J=23 Hz), 24.33. $^{19}$F NMR (375 MHz, CDCl$_3$, 23° C., δ): −118.4.

1-Fluoronaphthalene (29)

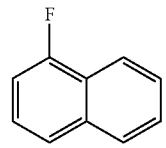 [SMILES: Fc1cccc2ccccc12]

(General Procedure C) Yield: 60.0 mg (82%). $R_f$=0.50 (hexanes). NMR Spectroscopy: $^1$H NMR (400 MHz, CDCl$_3$, 23° C., δ): 8.14-8.09 (m, 1H), 7.89-7.84 (m, 1H), 7.63 (d, J=8.0 Hz, 1H), 7.58-7.52 (m, 2H), 7.40 (ddd, J=8.8 Hz, 8.8

Hz, 4.8 Hz, 1H), 7.15 (dd, J=11.2 Hz. 8.0 Hz, 1H). $^{13}$C NMR (125 MHz, CDCl$_3$, 23° C., δ): 158.78 (d, J=250 Hz), 134.87, 127.51 (d, J=3.6 Hz), 126.81, 126.15, 125.58 (d, J=8.3 Hz), 123.68 (d, J=18 Hz), 123.64, 120.53 (d, J=5.5 Hz), 109.39 (d, J=20 Hz). $^{19}$F NMR (375 MHz, CDCl$_3$, 23° C., δ): −123.8.

N-Boc-5-fluoroindazole (30)

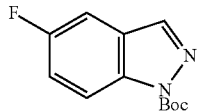

(General Procedure C) Yield: 88.6 mg (75%). R$_f$=0.60 (hexanes/EtOAc 7:3 (v/v)). NMR Spectroscopy: $^1$H NMR (400 MHz, CDCl$_3$, 23° C., δ): 8.15 (dd, J=8.8 Hz, 4.0 Hz, 1H), 8.12 (s, 1H), 7.35 (dd, J=8.4 Hz, 3.0 Hz, 1H), 7.27 (ddd, J=11.2 Hz, 8.8 Hz, 2.0 Hz, 1H), 1.72 (s, 9H). $^{13}$C NMR (100 MHz, CDCl$_3$, 23° C., δ): 159.20 (d, J=240 Hz), 148.96, 138.91, 136.44, 126.24 (d, J=10 Hz), 117.72 (d, J=26 Hz), 115.81 (d, J=9.1 Hz), 105.66 (d, J=24 Hz), 85.12, 28.10. $^{19}$F NMR (375 MHz, CDCl$_3$, 23° C., δ): −119.6. Mass Spectrometry: HRMS-FIA (m/z): Calcd for [M+Na]$^+$, 259.08533. Found, 259.08550.

N-Boc-5-fluoroindole (31)

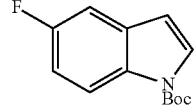

(General Procedure C) Yield: 88.2 mg (75%). R$_f$=0.75 (hexanes/EtOAc 7:3 (v/v)). NMR Spectroscopy: $^1$H NMR (500 MHz, CDCl$_3$, 23° C., δ): 8.08 (br, 1H), 7.62 (d, J=4.0 Hz, 1H), 7.20 (dd, J=6.5 Hz, 2.0 Hz, 1H), 7.03 (ddd, J=7.0 Hz, 6.5 Hz, 2.0 Hz, 1H), 6.52 (d, J=4.0 Hz, 1H), 1.68 (s, 9H). $^{13}$C NMR (125 MHz, CDCl$_3$, 23° C., δ): 159.27 (d, J=238 Hz), 149.51, 131.60, 131.38 (d, J=10 Hz), 127.51, 116.08 (d, J=9.1 Hz), 112.00 (d, J=24 Hz), 107.01, 106.27 (d, J=24 Hz), 83.9, 28.2. $^{19}$F NMR (375 MHz, CDCl$_3$, 23° C., δ): −121.7.

6-Fluoroquinoxaline (32)

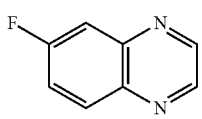

(General Procedure D) Yield: 52.6 mg (71%). NMR Spectroscopy: $^1$H NMR (400 MHz, CDCl$_3$, 23° C., δ): 8.84 (d, J=4.0 Hz, 1H), 8.81 (d, J=4.0 Hz, 1H), 8.11 (dd, J=9.2 Hz, 6.0 Hz, 1H), 7.72 (dd, J=9.2 Hz, 3.5 Hz, 1H), 7.56 (ddd, J=9.2 Hz, 6.0 Hz, 1H). $^{13}$C NMR (100 MHz, CDCl$_3$, 23° C., δ): 163.00 (d, J=249 Hz), 145.98, 145.25 (d, J=6.4 Hz), 144.57, 144.10 (d, J=14 Hz), 131.96 (d, J=10 Hz), 120.93 (d, J=26 Hz), 113.27 (d, J=21 Hz). $^{19}$F NMR (375 MHz, CDCl$_3$, 23° C., δ): −121.7.

6-Fluoroquinoline (33)

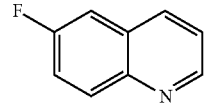

(General Procedure D) Yield: 55.2 mg (75%). R$_f$=0.47 (EtOAc). NMR Spectroscopy: $^1$H NMR (500 MHz, CDCl$_3$, 23° C., δ): 8.91 (dd, J=4.5 Hz, 1.5 Hz, 1H), 8.18 (d, J=8.0 Hz, 1H), 8.15 (dd, J=9.0 Hz, J=5.5 Hz, 1H), 7.53 (ddd, J=9.0 Hz, 8.5 Hz, 2.0 Hz, 1H), 7.50-7.45 (m, 2H). $^{13}$C NMR (100 MHz, CDCl$_3$, 23° C., δ): 160.43 (d, J=247 Hz), 149.56, 145.11, 135.70 (d, J=5.3 Hz), 131.80 (d, J=9.1 Hz), 128.86, 121.79, 119.94 (d, J=26 Hz), 110.74 (d, J=21 Hz). $^{19}$F NMR (375 MHz, CDCl$_3$, 23° C., δ): −113.0.

Methyl 3-fluoro-5-methylbenzoate (34)

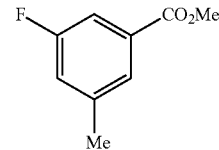 [SMILES: COC(=O)c1cc(C)cc(F)c1]

(General Procedure D) Yield: 60.5 mg (72%). R$_f$=0.70 (hexanes/EtOAc 7:3 (v/v)). NMR Spectroscopy: $^1$H NMR (400 MHz, CDCl$_3$, 23° C., δ): 7.65 (s, 1H), 7.51 (d, J=8.8 Hz, 1H), 7.07 (d, J=8.8 Hz, 1H), 3.91 (s, 3H), 2.39 (s, 3H). $^{13}$C NMR (100 MHz, CDCl$_3$, 23° C., δ): 166.14, 162.46 (d, J=245 Hz), 140.60 (d, J=7.3 Hz), 131.84 (d, J=8.0 Hz), 125.96 (d, J=2.9 Hz), 120.53 (d, J=21 Hz), 113.50 (d, J=23 Hz), 52.28, 21.19. $^{19}$F NMR (375 MHz, CDCl$_3$, 23° C., δ): −114.0. Mass Spectrometry: HRMS-FIA (m/z): Calcd for [M+H]$^+$, 169.06938. Found, 169.06993.

Example 68

One-Pot Hydrofluorination of Phenylacetylene

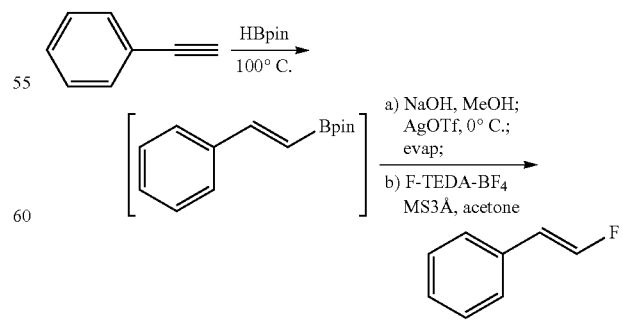

To phenylacetylene (35) (10.2 mg, 0.100 mmol, 1.00 equiv) at 23° C. was added pinacolborane (32.0 mg, 0.250 mmol, 2.50 equiv). The reaction mixture was heated to 100° C. and stirred for 36 hr before being cooled to 23° C. To the residue was added NaOH (4.8 mg, 0.12 mmol, 1.2 equiv) in MeOH (0.50 mL). After stirring for 15 min at 23° C., the reaction mixture was cooled to 0° C. and was added to AgOTf (77.1 mg, 0.300 mmol, 3.00 equiv). After stirring for 30 min at 0° C., the solvent was removed under reduced pressure at 0° C. and the residual MeOH was completely removed by co-evaporation with acetone (0.5 mL×2). To the residue was added acetone-d6 (0.5 mL), MS3 Å (50 mg), and 1-chloromethyl-4-fluoro-1,4-diazoniabicyclo[2.2.2]octane bis(trifluoroborate) (1) (37.2 mg, 0.105 mmol, 1.05 equiv) and the reaction mixture was stirred for 1.0 hr. The yields were determined to be 76% by comparing the integration of the $^{19}$F NMR (375 MHz, acetone-d6, 23° C.) resonance of an arylfluoride and that of 3-nitrofluorobenzene (−112.0 ppm).

Example 69

Identification of Optimal Silver(I) salt in Silane Reactions

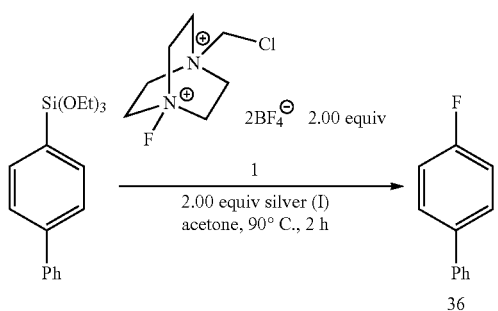

To 4-(biphenyl)triethoxysilane (6.32 mg, 0.0200 mmol, 1.00 equiv) in acetone (0.4 mL) at 23° C., a silver salt (0.0400 mmol, 2.00 equiv) and 1-chloromethyl-4-fluoro-1,4-diazoniabicyclo[2.2.2]octane bis(tetrafluoroborate) (1) (14.2 mg, 0.0400 mmol, 2.00 equiv) were added. The reaction mixture was stirred at 90° C. for 2 h in a sealed vial, then cooled to 23° C. To the reaction mixture was added 3-nitrofluorobenzene (2.00 μL, 0.0188 mmol). The yields were determined by comparing integration of the $^{19}$F NMR (375 MHz, acetone-d$_6$, 23° C.) resonance of 4-fluorobiphenyl (−118.1 ppm) and that of 3-nitrofluorobenzene (−112.0 ppm). Yields are reported in Table 9.

TABLE 9

Identification of optimal silver (I) salt in silane reactions

| Silver salt | Yield [%] ($^{19}$F NMR) |
|---|---|
| AgF | 21 |
| AgOAc | 12 |
| AgBF$_4$ | 11 |
| AgClO$_4$ | 5 |
| AgNO$_3$ | 0 |
| Ag$_2$CO$_3$ | 5 |
| AgCN | 0 |
| AgOCN | 0 |
| AgSCN | 0 |
| AgOTf | 6 |
| AgPF$_6$ | 10 |
| AgSbF$_6$ | 0 |

TABLE 9-continued

Identification of optimal silver (I) salt in silane reactions

| Silver salt | Yield [%] ($^{19}$F NMR) |
|---|---|
| Ag$_2$O | 69 |
| none | 0 |

Example 70

(4-Biphenyl)triethoxysilane (S53)

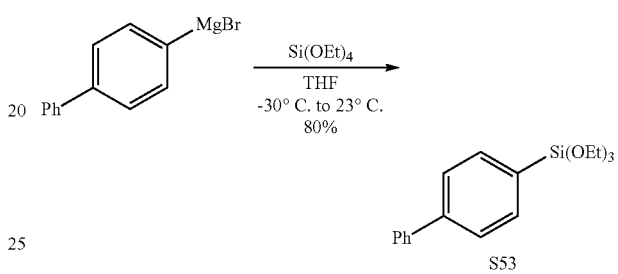

To tetraethyl orthosilicate (6.70 mL, 30.0 mmol, 3.00 equiv) in 20 mL of THF at −30° C. was added biphenylmagnesium bromide solution (0.50 M in THF, 20 mL, 10 mmol, 1.0 equiv) dropwise over 10 min. After stiffing at −30° C. for 1 h, the reaction mixture was warmed to 23° C. and was stirred for 12 h. The reaction mixture was poured into 100 mL of pentane, washed three times with water (3×20 mL), and dried over Na$_2$SO$_4$. After filtration, the solvent was removed under reduced pressure. Bulb-to-bulb distillation (125° C., 0.5 Torr) afforded 2.52 g of the title compound as a colorless oil (80% yield). R$_f$=0.50 (hexanes). NMR Spectroscopy: $^1$H NMR (500 MHz, CDCl$_3$, 23° C., δ): 7.75 (d, J=8.0 Hz, 2H), 7.62–7.60 (m, 4H), 7.45 (d, J=7.5 Hz, 2H), 7.36 (t, J=7.5 Hz, 1H), 3.90 (q, J=7.0 Hz, 6H), 1.27 (t, J=7.0 Hz, 9H). $^{13}$C NMR (125 MHz, CDCl$_3$, 23° C., δ): 142.96, 140.95, 135.28, 129.59, 128.76, 127.50, 127.17, 126.56, 58.76, 18.23.

Example 71

(4-Bromophenyl)triethoxysilane (S54)

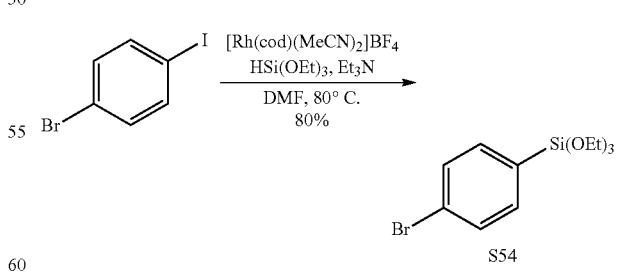

[Rh(cod)(MeCN)$_2$]BF$_4$ (22.0 mg, 0.0600 mmol, 0.0300 equiv) and 1-bromo-4-iodobenzene (563 mg, 2.00 mmol, 1.00 equiv) were charged in 20 mL vial capped with a rubber septum. The vial was evacuated and backfilled with nitrogen. To this vial, DMF (8 mL), triethylamine (0.830 mL, 6.00 mmol, 3.00 equiv) and triethoxysilane (0.730 mL, 4.00 mmol, 2.00 equiv) were added. The reaction mixture was stirred at 80° C. for 2 h, then cooled to 23° C. The mixture was diluted with ether (100 mL) and washed three times with water (3×40 mL), dried over Na$_2$SO$_4$, filtered and concentrated under reduced pressure. The residue was purified by Kugelrohr distillation to give 508 mg of the title compound as a colorless oil (80% yield). R$_f$=0.63 (hexanes). NMR Spectroscopy: $^1$H NMR (500 MHz, CDCl$_3$, 23° C., δ): 7.53–7.52 (m, 4H), 3.85 (q, J=7.0 Hz, 6H), 1.24 (t, J=7.0 Hz, 9H). $^{13}$C NMR (125 MHz, CDCl$_3$, 23° C., δ): 136.34, 131.04, 129.86, 125.33, 58.77, 18.16.

Example 72

(2,4,6-Trimethylphenyl)triethoxysilane (S55)

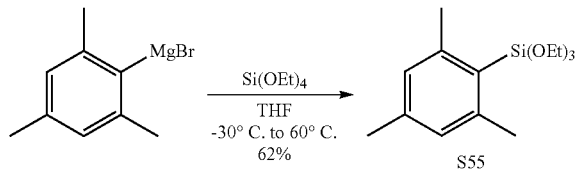

To tetraethyl orthosilicate (3.30 mL, 15.0 mmol, 3.00 equiv) in 10 mL of THF at −30° C. was added 2,4,6-trimethylphenylmagnesium bromide solution (1.0 M in THF, 5.0 mL, 5.0 mmol, 1.0 equiv) dropwise over 10 min. After stirring at −30° C. for 1 h, the reaction mixture was warmed to 23° C. and was further stirred for 12 h. The reaction mixture was poured into 100 mL of pentane, and was washed three times with water (3×20 mL) and dried over Na$_2$SO$_4$. After filtration, the solvent was removed under reduced pressure. Bulb-to-bulb distillation (125° C., 0.5 Torr) afforded 0.87 g of the title compound as a colorless oil (62% yield). R$_f$=0.14 (hexanes). NMR Spectroscopy: $^1$H NMR (500 MHz, CDCl$_3$, 23° C., δ): 6.80 (s, 2H), 3.83 (q, J=7.0 Hz, 6H), 2.51 (s, 6H), 2.26 (s, 3H), 1.24 (t, J=7.0 Hz, 9H). $^{13}$C NMR (125 MHz, CDCl$_3$, 23° C., δ): 145.92, 139.79, 128.81, 124.99, 58.10, 23.73, 21.08, 18.15.

Example 73

4-(Triethoxysilyl)phenylbenzoate (S56)

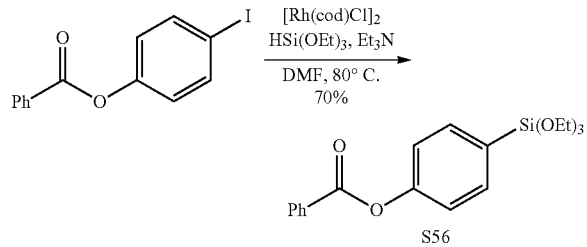

[Rh(cod)Cl]$_2$ (15.0 mg, 0.0300 mmol, 0.0300 equiv) and 4-iodophenyl benzoate (323 mg, 1.00 mmol, 1.00 equiv) were charged in 10 mL vial capped with a rubber septum. The vial was evacuated and backfilled with nitrogen. To this vial, DMF (4 mL), triethylamine (0.420 mL, 3.00 mmol, 3.00 equiv) and triethoxysilane (0.360 mL, 2.00 mmol, 2.00 equiv) were added. The reaction mixture was stirred at 80° C. for 2 h, then cooled to 23° C. The mixture was diluted with ether (50 mL) and washed three times with water (3×20 mL), dried over Na$_2$SO$_4$, filtered and concentrated under reduced pressure. The residue was purified by Kugelrohr distillation to give 252 mg of the title compound as a colorless oil (70% yield). R$_f$=0.30 (hexanes/EtOAc 1:1 (v/v)). NMR Spectroscopy: $^1$H NMR (500 MHz, CDCl$_3$, 23° C., δ): 8.24–8.21 (m, 2H), 7.78–7.75 (m, 2H), 7.68–7.64 (m, 1H), 7.56–7.52 (m, 2H), 7.28–7.25 (m, 2H), 3.90 (q, J=7.0 Hz, 6H), 1.27 (t, J=7.0 Hz, 9H). $^{13}$C NMR (125 MHz, CDCl$_3$, 23° C., δ): 164.93, 152.82, 136.25, 133.63, 130.19, 129.52, 128.63, 128.58, 121.22, 58.78, 18.22. Mass Spectrometry: HRMS-FIA (m/z): Calcd for [M+Na]$^+$, 378.17313. Found, 378.17314.

Example 74

4-(Triethoxysilyl)benzophenone (S57)

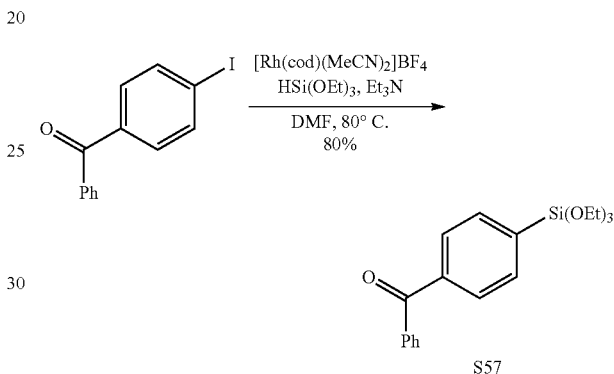

[Rh(cod)(MeCN)$_2$]BF$_4$ (11.0 mg, 0.0300 mmol, 0.0300 equiv) and 4-iodobenzophenone (307 mg, 1.00 mmol, 1.00 equiv) were charged in 10 mL vial capped with a rubber septum. The vial was evacuated and backfilled with nitrogen. To this vial, DMF (4 mL), triethylamine (0.420 mL, 3.00 mmol, 3.00 equiv) and triethoxysilane (0.360 mL, 2.00 mmol, 2.00 equiv) were added. The reaction mixture was stirred at 80° C. for 2 h, then cooled to 23° C. The mixture was diluted with ether (50 mL) and washed three times with water (3×20 mL), dried over Na$_2$SO$_4$, filtered and concentrated under reduced pressure. The residue was purified by Kugelrohr distillation to give 275 mg of the title compound as a colorless oil (80% yield). R$_f$=0.45 (hexanes/EtOAc 3:1 (v/v)). NMR Spectroscopy: $^1$H NMR (500 MHz, CDCl$_3$, 23° C., δ): 7.82–7.77 (m, 6H), 7.59 (t, J=7.5 Hz, 1H), 7.48 (dd, J=7.5 Hz, 7.5 Hz, 2H), 3.90 (q, J=7.0 Hz, 6H), 1.27 (t, J=7.0 Hz, 9H). $^{13}$C NMR (125 MHz, CDCl$_3$, 23° C., δ): 196.84, 139.05, 137.29, 136.34, 134.66, 132.54, 130.11, 129.00, 128.28, 58.91, 18.21. Mass Spectrometry: HRMS-FIA (m/z): Calcd for [M+Na]$^+$, 367.13361. Found, 367.13347.

Example 75

6-(Quinolinyl)triethoxysilane (S58)

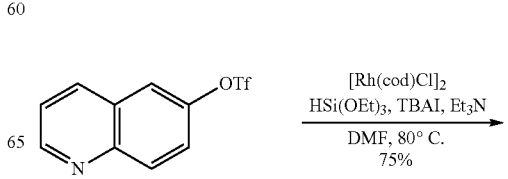

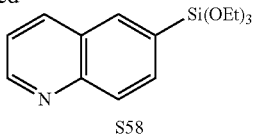

S58

[Rh(cod)Cl]$_2$ (15.0 mg, 0.0300 mmol, 0.0300 equiv), 6-(quinolinyl)trifluoromethanesulfonate (307 mg, 1.00 mmol, 1.00 equiv) and tetra-n-butylammonium iodide (369 mg, 1.00 mmol, 1.00 equiv) were charged in 10 mL vial capped with a rubber septum. The vial was evacuated and backfilled with nitrogen. To this vial, DMF (4 mL), triethylamine (0.420 mL, 3.00 mmol, 3.00 equiv) and triethoxysilane (0.360 mL, 2.00 mmol, 2.00 equiv) were added. The reaction mixture was stirred at 80° C. for 2 h, then cooled to 23° C. The mixture was diluted with ether (50 mL) and washed three times with water (3×20 mL), dried over Na$_2$SO$_4$, filtered and concentrated under reduced pressure. The residue was purified by Kugelrohr distillation to give 218 mg of the title compound as a colorless oil (75% yield). R$_f$=0.50 (hexanes/EtOAc 3:1 (v/v)). NMR Spectroscopy: $^1$H NMR (500 MHz, CDCl$_3$, 23° C., δ): 8.94 (dd, J=4.0, J=1.5 Hz, 1H), 8.19–8.18 (m, 2H), 8.10 (d, J=8.5 Hz, 1H), 7.95 (d, J=8.5 Hz, 1H), 7.41 (dd, J=8.5, 4.5 Hz, 1H), 3.92 (q, J=7.0 Hz, 6H), 1.27 (t, J=7.0 Hz, 9H). $^{13}$C NMR (125 MHz, CDCl$_3$, 23° C., δ): 151.26, 149.18, 136.46, 136.18, 134.11, 129.87, 128.67, 127.69, 121.21, 58.91. 18.23.

Example 76

4-(Triethoxysilyl)acetophenone (S59)

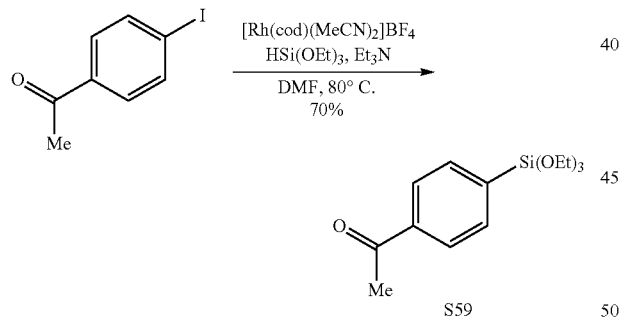

[Rh(cod)(MeCN)$_2$]BF$_4$ (11.0 mg, 0.0300 mmol, 0.0300 equiv) and 4-iodoacetonphenone (246 mg, 1.00 mmol, 1.00 equiv) were charged in 10 mL vial capped with a rubber septum. The vial was evacuated and backfilled with nitrogen. To this vial, DMF (4 mL), triethylamine (0.420 mL, 3.00 mmol, 3.00 equiv) and triethoxysilane (0.360 mL, 2.00 mmol, 2.00 equiv) were added. The reaction mixture was stirred at 80° C. for 2 h, then cooled to 23° C. The mixture was diluted with ether (50 mL) and washed three times with water (3×20 mL), dried over Na$_2$SO$_4$, filtered and concentrated under reduced pressure. The residue was purified by Kugelrohr distillation to give 197 mg of the title compound as a colorless oil (70% yield). R$_f$=0.56 (hexanes). NMR Spectroscopy: $^1$H NMR (500 MHz, CDCl$_3$, 23° C., δ): 7.93 (dd, J=6.5, J=1.5 Hz, 2H), 7.78 (dd, J=6.5, J=1.5 Hz, 2H), 3.88 (q, J=7.0 Hz, 6H), 2.61 (s, 3H), 1.25 (t, J=7.0 Hz, 9H). $^{13}$C NMR (125 MHz, CDCl$_3$, 23° C., δ): 198.37, 138.33, 137.32, 135.02, 127.28, 58.88, 26.68, 18.19.

Example 77

4-(Triethoxysilyl)acetanilide (S60)

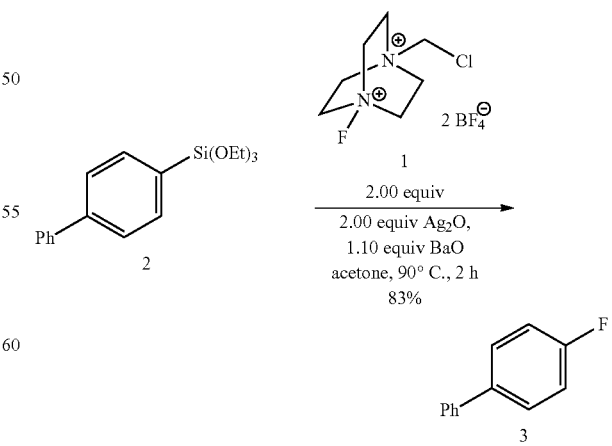

[Rh(cod)(MeCN)$_2$]BF$_4$ (11.0 mg, 0.0300 mmol, 0.0300 equiv) and 4-iodoacetanilide (260 mg, 1.00 mmol, 1.00 equiv) were charged in 10 mL vial capped with a rubber septum. The vial was evacuated and backfilled with nitrogen. To this vial, DMF (4 mL), triethylamine (0.420 mL, 3.00 mmol, 3.00 equiv) and triethoxysilane (0.360 mL, 2.00 mmol, 2.00 equiv) were added. The reaction mixture was stirred at 80° C. for 2 h, then cooled to 23° C. The mixture was diluted with ether (50 mL) and washed three times with water (3×20 mL), dried over Na$_2$SO$_4$, filtered and concentrated under reduced pressure. The residue was purified by Kugelrohr distillation to give 238 mg of the title compound as a colorless oil (80% yield). R$_f$=0.25 (hexanes/EtOAc 1:1 (v/v)). NMR Spectroscopy: $^1$H NMR (500 MHz, CDCl$_3$, 23° C., δ): 7.69 (d, J=8.0 Hz, 2H), 7.59 (d, J=8.5 Hz, 2H), 7.42 (br s, 1H), 3.85 (q, J=7.0 Hz, 6H), 2.17 (s, 3H), 1.23 (t, J=7.0 Hz, 9H). $^{13}$C NMR (125 MHz, CDCl$_3$, 23° C., δ): 168.39, 139.79, 135.77, 126.28, 118.89, 58.69, 24.66, 18.18.

Example 78

Fluorination of arylsilanes with F-TEDA-BF$_4$

To 4-(biphenyl)triethoxylsilane (2) (31.6 mg, 0.100 mmol, 1.00 equiv) in acetone (2.0 mL) at 23° C. was added silver oxide (46.4 mg, 0.200 mmol, 2.00 equiv), barium oxide (17.2 mg, 0.110 mmol, 1.10 equiv) and 1-chloromethyl-4-fluoro-1,4-diazoniabicyclo[2.2.2]octane bis(tetrafluoroborate) (1) (70.8 mg, 0.200 mmol, 2.00 equiv). The reaction mixture was stirred at 90° C. for 2 h in a sealed vial. The reaction mixture was cooled to 23° C. and concentrated under reduced pressure. To the residue was added $CH_2Cl_2$ (10 mL) and the mixture was filtered through a pad of Celite eluting with $CH_2Cl_2$. The filtrate was concentrated under reduced pressure and the residue was purified by chromatography on silica gel eluting with hexanes, to afford 14.3 mg of the title compound as a white solid (83% yield).

With 1.00 equivalent of $Ag_2O$

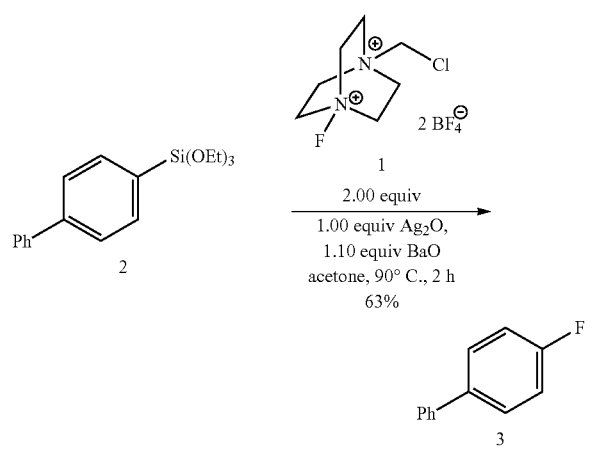

To 4-(biphenyl)triethoxylsilane (2) (31.6 mg, 0.100 mmol, 1.00 equiv) in acetone (2.0 mL) at 23° C. was added silver oxide (23.2 mg, 0.100 mmol, 1.00 equiv), barium oxide (17.2 mg, 0.110 mmol, 1.10 equiv) and 1-chloromethyl-4-fluoro-1,4-diazoniabicyclo[2.2.2]octane bis(tetrafluoroborate) (1) (70.8 mg, 0.200 mmol, 2.00 equiv). The reaction mixture was stirred at 90° C. for 2 h in a sealed vial, then cooled to 23° C. To the reaction mixture was added 3-nitrofluorobenzene (2.00 μL, 0.0188 mmol). The yield was determined to be 63% by comparing the integration of the $^{19}F$ NMR (375 MHz, acetone-$d_6$, 23° C.) resonance of 4-fluorobiphenyl (−118.1 ppm) and that of 3-nitrofluorobenzene (−112.0 ppm).

Background reaction without $Ag_2O$

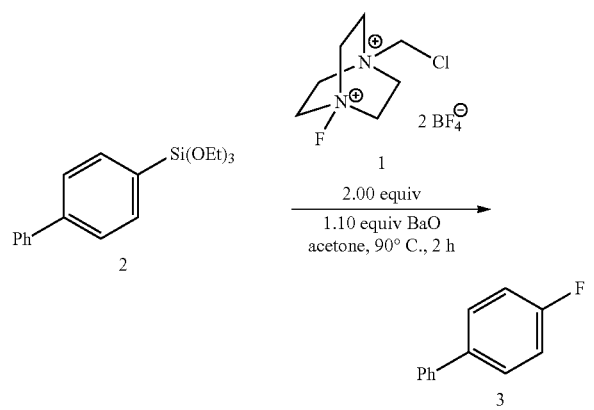

To 4-(biphenyl)triethoxylsilane (2) (6.32 mg, 0.0200 mmol, 1.00 equiv) in acetone (0.40 mL) at 23° C. was added barium oxide and 1-chloromethyl-4-fluoro-1,4-diazoniabicyclo[2.2.2]octane bis(tetrafluoroborate) (1) (14.2 mg, 0.0200 mmol, 2.00 equiv). The reaction mixture was stirred at 90° C. for 2 h in a sealed vial, then cooled to 23° C. To the reaction mixture was added 3-nitrofluorobenzene (2.00 μL, 0.0188 mmol). The yield was determined by comparing the integration of the $^{19}F$ NMR (375 MHz, acetone-$d_6$, 23° C.) resonance of 4-fluorobiphenyl (−118.1 ppm) and that of 3-nitrofluorobenzene (−112.0 ppm).

Yields are reported in Table 10.

TABLE 10

| | Background reaction without $Ag_2O$ |
|---|---|
| BaO | Yield [%] ($^{19}F$ NMR) |
| none | 0 |
| 1.1 equiv | 0 |

General Procedure a (for Volatile Compounds)

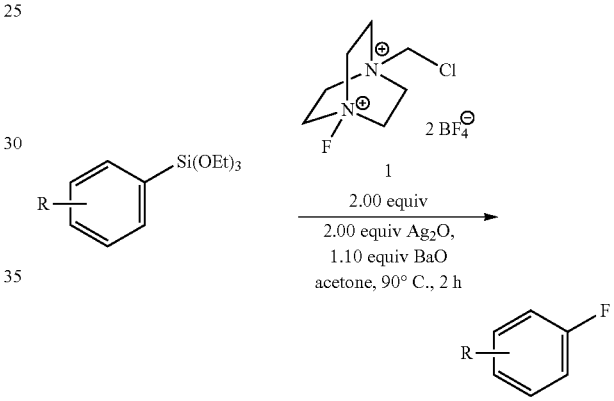

To arylsilane (0.100 mmol, 1.00 equiv) in acetone (2.0 mL) at 23° C. was added silver oxide (46.4 mg, 0.200 mmol, 2.00 equiv), barium oxide (15.6 mg, 0.100 mmol, 1.00 equiv) and 1-chloromethyl-4-fluoro-1,4-diazoniabicyclo[2.2.2]octane bis(tetrafluoroborate) (1) (70.8 mg, 0.200 mmol, 2.00 equiv). The reaction mixture was stirred for 2 h at 90° C. in a sealed vial, then cooled to 23° C. To the reaction mixture was added 3-nitrofluorobenzene (10.0 μL, 0.0939 mmol). The yields were determined by comparing the integration of the $^{19}F$ NMR (375 MHz, acetone-$d_6$, 23° C.) resonance of an arylfluoride and that of 3-nitrofluorobenzene (−112.0 ppm). Yields are reported in Table 11.

TABLE 11

| | Synthesis of volatile arylfluorides | |
|---|---|---|
| R | $^{19}F$ chemical shift | Yield [%] ($^{19}F$ NMR) |
| 4-Br (37) | −117.1 ppm | 85 |
| H (38) | −115.3 ppm | 90 |
| 2,4,6-Trimethyl (39) | −129.7 ppm | 73 |
| 3-(1,3-dioxolane) (40) | −115.1 ppm | 74 |
| 4-Me (41) | −120.5 ppm | 79 |
| 4-OMe (42) | −126.8 ppm | 76 |

General Procedure B (for Non-Volatile Compounds)

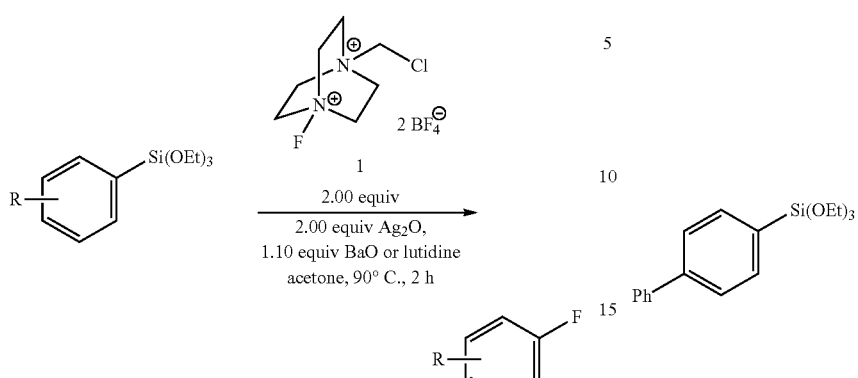

To arylsilane (0.100 mmol, 1.00 equiv) in acetone (2.0 mL) at 23° C. was added silver oxide (46.4 mg, 0.200 mmol, 2.00 equiv), barium oxide (17.2 mg, 0.110 mmol, 1.10 equiv) or 2,6-lutidine (12.8 µL, 0.110 mmol, 1.10 equiv) and 1-chloromethyl-4-fluoro-1,4-diazoniabicyclo[2.2.2]octane bis(tetrafluoroborate) (1) (70.8 mg, 0.200 mmol, 2.00 equiv). The reaction mixture was stirred for 2 h at 90° C. in a sealed vial. The reaction mixture was cooled to 23° C. and concentrated under reduced pressure. To the residue was added $CH_2Cl_2$ and the mixture was filtered through a pad of Celite eluting with $CH_2Cl_2$. The filtrate was concentrated under reduced pressure and the residue was purified by chromatography on silica gel or preparative TLC.

General Procedure C (for Heterocyclic Compounds)

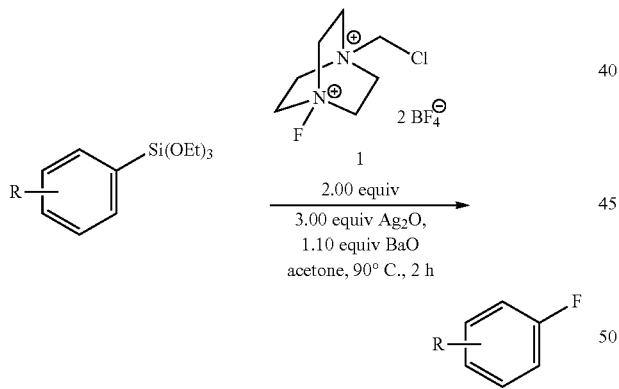

To arylsilane (0.100 mmol, 1.00 equiv) in acetone (2.0 mL) at 23° C. was added silver oxide (69.6 mg, 0.300 mmol, 3.00 equiv), barium oxide (17.2 mg, 0.110 mmol, 1.10 equiv) and 1-chloromethyl-4-fluoro-1,4-diazoniabicyclo-[2.2.2]octane bis(tetrafluoroborate) (1) (70.8 mg, 0.200 mmol, 2.00 equiv). The reaction mixture was stirred for 2 h at 90° C. in a sealed vial. The reaction mixture was cooled to 23° C., passed through a pad of Celite and concentrated under reduced pressure. To the residue was added $CH_2Cl_2$ (20 mL) and a saturated aqueous solution of $NaHCO_3$ (20 mL). The organic phase was separated, dried over $Na_2SO_4$, filtered and concentrated under reduced pressure. The residue was purified on preparative TLC.

5-mmol-Scale fluorination of 4-(biphenyl)triethoxysilane

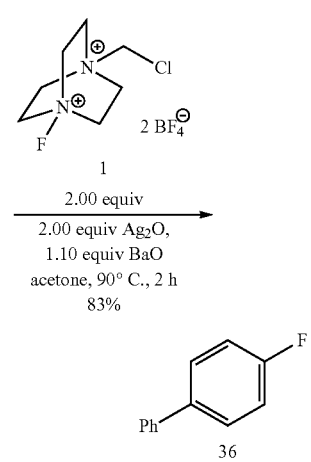

To 4-(biphenyl)triethoxylsilane (1.58 g, 5.00 mmol, 1.00 equiv) in acetone (100 mL) at 23° C. was added silver oxide (2.32 g, 10.0 mmol, 2.00 equiv), barium oxide (0.780 g, 5.00 mmol, 1.10 equiv) and 1-chloromethyl-4-fluoro-1,4-diazoniabicyclo[2.2.2]-octane bis(trifluoroborate) (1) (3.54 g, 10.0 mmol, 2.00 equiv). The reaction mixture was stirred at 90° C. for 2 h in a 350 mL sealed vessel. The reaction mixture was cooled to 23° C. and concentrated under reduced pressure. To the residue was added $CH_2Cl_2$ and the mixture was filtered through a pad of Celite eluting with $CH_2Cl_2$. The filtrate is concentrated under reduced pressure and the residue is purified by chromatography on silica gel eluting with hexane, to afford 714 mg of the title compound as a white solid (83% yield).

Example 79

Fluorination of arylsilanes with F-TEDA-BF$_4$

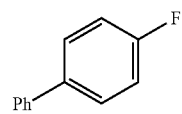

4-Fluorobiphenyl (36)

Yield: 14.3 mg (83%). $R_f$=0.60 (hexanes/EtOAc 19:1 (v/v)). NMR Spectroscopy: $^1$H NMR (500 MHz, CDCl$_3$, 23° C., δ): 7.60–7.54 (m, 4H), 7.47 (dd, J=7.5 Hz, 7.0 Hz, 2H), 7.36 (t, J=7.5 Hz, 1H), 7.14 (dd, J=8.0 Hz, 7.5 Hz, 2H). $^{13}$C NMR (125 MHz, CDCl$_3$, 23° C., δ): 162.44 (d, J=244 Hz), 140.25, 137.30, 128.80, 128.75 (d, J=8.5 Hz), 127.24, 127.00, 115.59 (d, J=21 Hz). $^{19}$F NMR (375 MHz, CDCl$_3$, 23° C., δ): −117.2. These spectroscopic data correspond to previously reported data.

101

1-Fluoronaphthalene (43)

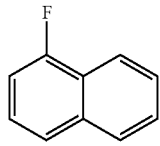

Yield: 10.9 mg (75%). $R_f$=0.40 (hexane/EtOAc 3:1 (v/v)). NMR Spectroscopy: $^1$H NMR (500 MHz, CDCl$_3$, 23° C., δ): 8.13–8.11 (m, 1H), 7.88–7.86 (m, 1H), 7.63 (d, J=8.5 Hz, 1H), 7.56–7.53 (m, 1H), 7.43–7.38 (m, 1H), 7.17–7.13 (m, 1H). $^{13}$C NMR (125 MHz, CDCl$_3$, 23° C., δ): 158.78 (d, J=250 Hz), 134.87 (d, J=4.5 Hz), 127.50 (d, J=3.6 Hz), 126.80, 126.15 (d, J=1.9 Hz), 125.58 (d, J=9.1 Hz), 123.76, 123.62 (d, J=3.6 Hz), 120.53 (d, J=5.5 Hz), 109.39 (d, J=20 Hz). $^{19}$F NMR (375 MHz, CDCl$_3$, 23° C., δ): −125.6. These spectroscopic data correspond to previously reported data.

4-Fluorophenyl benzoate (44)

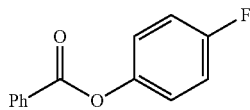

Yield: 16.9 mg (78%). $R_f$=0.20 (hexane/EtOAc 3:1 (v/v)). NMR Spectroscopy: $^1$H NMR (500 MHz, CDCl$_3$, 23° C., δ): 8.21–8.18 (m, 2H), 7.66–7.63 (m, 1H), 7.54–7.51 (m, 2H), 7.20–7.17 (m, 2H), 7.13–7.09 (m, 2H). $^{13}$C NMR (125 MHz, CDCl$_3$, 23° C., δ): 165.19, 160.30 (d, J=242 Hz), 146.75 (d, J=2.8 Hz), 133.71, 130.17, 129.29, 128.61, 123.10 (d, J=9.0 Hz), 116.14 (d, J=24 Hz). $^{19}$F NMR (375 MHz, CDCl$_3$, 23° C., δ): −119.2. These spectroscopic data correspond to previously reported data.

4-Fluorobenzophenone (45)

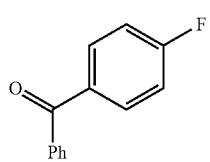 [SMILES: O=C(c1ccccc1)c1ccc(F)cc1]

Yield: 17.0 mg (85%). $R_f$=0.50 (hexane/EtOAc 3:1 (v/v)). NMR Spectroscopy: $^1$H NMR (500 MHz, CDCl$_3$, 23° C., δ): 7.86–7.84 (m, 2H), 7.78–7.76 (m, 2H), 7.61–7.58 (m, 1H), 7.51–7.48 (m, 2H), 7.18–7.15 (m, 2H). $^{13}$C NMR (125 MHz, CDCl$_3$, 23° C., δ): 195.27, 165.39 (d, J=252 Hz), 137.51, 133.79, 132.66 (d, J=9.1 Hz), 132.45, 129.87, 128.35, 115.45 (d, J=22 Hz). $^{19}$F NMR (375 MHz, CDCl$_3$, 23° C., δ): −108.7. These spectroscopic data correspond to previously reported data.

102

6-Fluoroquinoline (46)

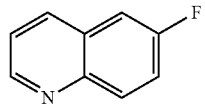 [SMILES: Fc1ccc2ncccc2c1]

Yield: 8.8 mg (60%). $R_f$=0.47 (EtOAc). NMR Spectroscopy: $^1$H NMR (500 MHz, CDCl$_3$, 23° C., δ): 8.91 (dd, J=4.5 Hz, 1.5 Hz, 1H), 8.18 (d, J=8.0 Hz, 1H), 8.15 (dd, J=9.0 Hz, J=5.5 Hz, 1H), 7.53 (ddd, J=9.0 Hz, 8.5 Hz, 2.0 Hz, 1H), 7.50-7.45 (m, 2H). $^{13}$C NMR (125 MHz, CDCl$_3$, 23° C., δ): 160.43 (d, J=247 Hz), 149.56, 145.11, 135.70 (d, J=5.3 Hz), 131.80 (d, J=9.1 Hz), 128.86, 121.79, 119.94 (d, J=26 Hz), 110.74 (d, J=21 Hz). $^{19}$F NMR (375 MHz, CDCl$_3$, 23° C., δ): −113.0. These spectroscopic data correspond to previously reported data.

Ethyl 4-fluorobenzoate (47)

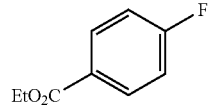

Yield: 14.3 mg (85%). $R_f$=0.30 (hexane/EtOAc 3:1 (v/v)). NMR Spectroscopy: $^1$H NMR (500 MHz, CDCl$_3$, 23° C., δ): 8.06 (dd, J=9.0 Hz, J=5.5 Hz, 2H), 7.10 (dd, J=9.0 Hz, J=8.5 Hz, 2H), 4.37 (q, J=7.0 Hz, 2H), 1.39 (t, J=9.0 Hz, 3H). $^{13}$C NMR (125 MHz, CDCl$_3$, 23° C., δ): 165.68 (d, J=252 Hz), 165.65, 132.04 (d, J=10 Hz), 126.72, 115.42 (d, J=22 Hz), 61.07, 14.30. $^{19}$F NMR (375 MHz, CDCl$_3$, 23° C., δ): −108.4. These spectroscopic data correspond to previously reported data.

4-Fluoroacetophenone (48)

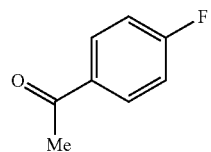

Yield: 11.3 mg (82%). $R_f$=0.30 (hexane/EtOAc 3:1 (v/v)). NMR Spectroscopy: $^1$H NMR (500 MHz, CDCl$_3$, 23° C., δ): 7.99–7.96 (m, 2H), 7.14–7.11 (m, 2H), 2.58 (s, 3H). $^{13}$C NMR (125 MHz, CDCl$_3$, 23° C., δ): 196.68, 165.99 (d, J=253 Hz), 133.84, 131.16 (d, J=9.1 Hz), 115.88 (d, J=22 Hz), 26.75. $^{19}$F NMR (375 MHz, CDCl$_3$, 23° C., δ): −108.4. These spectroscopic data correspond to previously reported data.

4-Fluoroacetophenone (49)

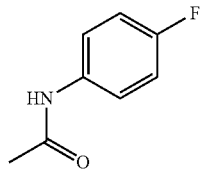

Yield: 10.7 mg (70%). $R_f$=0.30 (hexane/EtOAc 3:1 (v/v)). NMR Spectroscopy: $^1$H NMR (500 MHz, CDCl$_3$, 23° C., δ): 7.99–7.96 (m, 2H), 7.14–7.11 (m, 2H), 2.58 (s, 3H). $^{13}$C NMR (125 MHz, CDCl$_3$, 23° C., δ): 168.43, 159.35 (d, J=242 Hz), 133.83, 121.81 (d, J=7.3 Hz), 115.56 (d, J=23 Hz), 24.32. $^{19}$F NMR (375 MHz, CDCl$_3$, 23° C., δ): –121.4. These spectroscopic data correspond to previously reported data.

Example 80

Regeneration of Ag$_2$O

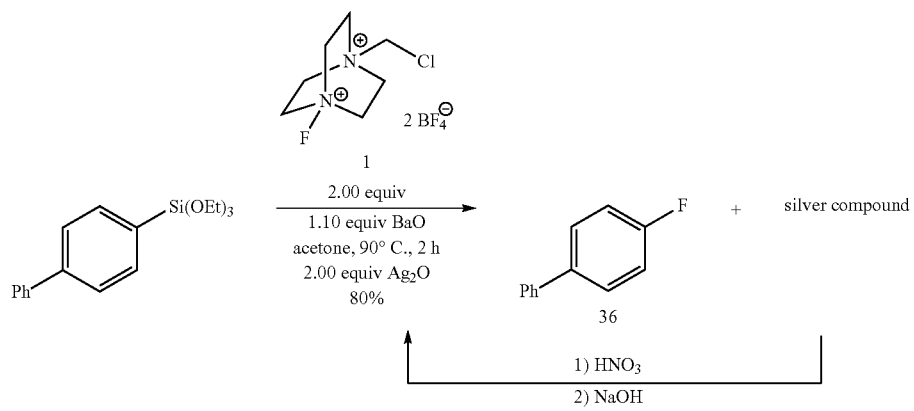

To 4-(biphenyl)triethoxysilane (158 mg, 0.500 mmol, 1.00 equiv) in acetone (10.0 mL) at 23° C. was added silver oxide (232 mg, 1.00 mmol, 2.00 equiv), barium oxide (86.0 mg, 0.550 mmol, 1.10 equiv) and 1-chloromethyl-4-fluoro-1,4-diazoniabicyclo[2.2.2]-octane bis(tetrafluoroborate) (1) (354 mg, 0.200 mmol, 2.00 equiv). The reaction mixture was stirred at 90° C. for 2 hr in a sealed vial. The reaction mixture was cooled to 23° C. and concentrated under reduced pressure. The residue was washed with CH$_2$Cl$_2$ (3×20 mL) and the solid was dissolved in 50 mL HNO$_3$ (10%, v/v in H$_2$O). After stiffing for 30 min at 23° C., the reaction mixture was filtered. To the filtrate was added NaOH (10%, v/v in H$_2$O, 50 mL). The suspention was filtered and the solid residue washed with water (3×20 mL) to afford 188 mg Ag$_2$O (81%) as a brown powder.

To 4-(biphenyl)triethoxylsilane (31.6 g, 0.100 mmol, 1.00 equiv) in acetone (2.0 mL) at 23° C. was added the regenerated silver oxide (46.4 mg, 0.200 mmol, 2.00 equiv), barium oxide (17.2 mg, 0.110 mmol, 1.10 equiv) and 1-chloromethyl-4-fluoro-1,4-diazoniabicyclo[2.2.2]-octane bis(tetrafluoroborate) (1) (70.8 mg, 0.200 mmol, 2.00 equiv). The reaction mixture was stirred at 90° C. for 2 h in a sealed vial, then cooled to 23° C. To the reaction mixture was added 3-nitrofluorobenzene (2.00 µL, 0.0188 mmol). The yield was determined to be 80% by comparing the integration of the $^{19}$F NMR (375 MHz, acetone-d$_6$, 23° C.) resonance of 4-fluorobiphenyl (–118.1 ppm) and that of 3-nitrofluorobenzene (–112.0 ppm).

Example 81

Effect of the Bases in the Ag-Catalyzed Fluorination Reaction with Arylstannanes

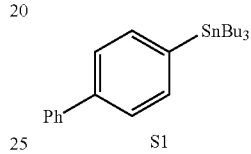
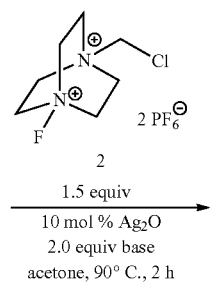
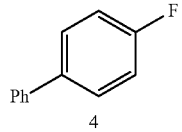

To 4-(biphenyl)tributylstannane (S1) (8.9 mg, 0.020 mmol, 1.0 equiv) in acetone (0.4 mL) at 23° C., silver oxide (0.46 mg, 0.002 mmol, 0.10 equiv), 1-chloromethyl-4-fluoro-1,4-diazoniabicyclo[2.2.2]octane bis(hexafluorophosphate) (2) (14.1 mg, 0.0300 mmol, 1.50 equiv) and base (0.040 mmol, 2.0 equiv) were added. The reaction mixture was stirred at 90° C. for 2 h in a sealed vial, then cooled to 23° C. To the reaction mixture was added 3-nitrofluorobenzene (2.00 µL, 0.0188 mmol). The yields were determined by comparing integration of the $^{19}$F NMR (375 MHz, acetone-d$_6$, 23° C.) resonance of 4-fluorobiphenyl (–118.1 ppm) and that of 3-nitrofluorobenzene (–112.0 ppm). Yields are reported in Table 12.

TABLE 12

Effect of the Bases in the Ag-catalyzed Fluorination Reaction

| Base | Yield [%] ($^{19}$F NMR) |
|---|---|
| None | 38 |
| NaHCO$_3$ | 85 |
| KHCO$_3$ | 17 |
| NaOH | 0 |
| KOH | 21 |
| Ba(OH)$_2$ | 48 |
| Na$_2$CO$_3$ | 5 |
| K$_2$CO$_3$ | 0 |
| Cs$_2$CO$_3$ | 0 |
| K$_3$PO$_4$ | 0 |

Background reaction without Ag$_2$O

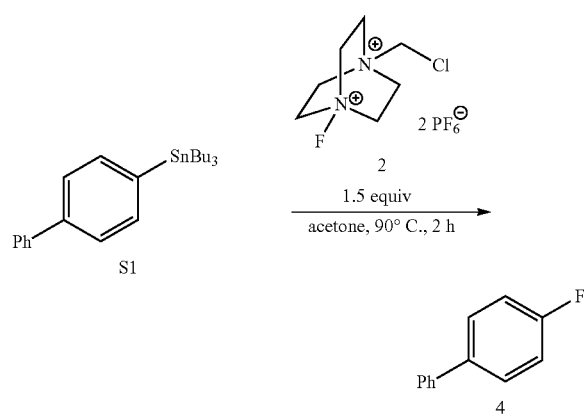

To 4-(biphenyl)tributylstannane (S1) (8.9 mg, 0.020 mmol, 1.0 equiv) in acetone (0.4 mL) at 23° C., 1-chloromethyl-4-fluoro-1,4-diazoniabicyclo[2.2.2]octane bis(hexafluorophosphate) (2) (14.1 mg, 0.0300 mmol, 1.50 equiv) were added. The reaction mixture was stirred at 90° C. for 2 h in a sealed vial, then cooled to 23° C. To the reaction mixture was added 3-nitrofluorobenzene (2.00 μL, 0.0188 mmol). The yields were determined by comparing integration of the $^{19}$F NMR (375 MHz, acetone-d$_6$, 23° C.) resonance of 4-fluorobiphenyl (−118.1 ppm) and that of 3-nitrofluorobenzene (−112.0 ppm). Yields are reported in Table 13.

TABLE 13

Background reaction without Ag$_2$O

| NaHCO$_3$ | Yield [%] ($^{19}$F NMR) |
|---|---|
| None | 1 |
| 2.0 equiv | 4 |

Example 82

Effect of NaHCO$_3$

To 4-(biphenyl)tributylstannane (S1) (8.9 mg, 0.020 mmol, 1.0 equiv) in acetone (0.4 mL) at 23° C., silver oxide (0.23 mg, 0.0010 mmol, 0.050 equiv), 1-chloromethyl-4-fluoro-1,4-diazoniabicyclo[2.2.2]octane bis(hexafluorophosphate) (2) (14.1 mg, 0.0300 mmol, 1.50 equiv) and sodium bicarbonate were added. The reaction mixture was stirred at 90° C. for 2 h in a sealed vial, then cooled to 23° C. To the reaction mixture was added 3-nitrofluorobenzene (2.00 μL, 0.0188 mmol). The yields were determined by comparing integration of the $^{19}$F NMR (375 MHz, acetone-d$_6$, 23° C.) resonance of 4-fluorobiphenyl (−118.1 ppm) and that of 3-nitrofluorobenzene (−112.0 ppm). Yields are reported in Table 14.

TABLE 14

Effect of NaHCO$_3$

| NaHCO$_3$ | Yield [%] ($^{19}$F NMR) |
|---|---|
| 0.5 equiv | 59 |
| 1.0 equiv | 70 |
| 2.0 equiv (from Merck) | 85 |
| 2.0 equiv (from Mallinckrodt) | 86 |
| 2.0 equiv (washed with acetone) | 86 |
| 5.0 equiv | 85 |

TABLE 15

Impurities of NaHCO$_3$ from different companies

| Maximum impurities and specifications | Merck | Mallinckrodt |
|---|---|---|
| Assay (NaHCO$_3$) | 99.7-100.3% | 100.0% |
| Insoluble matter | 0.015% | <0.003% |
| Chloride | 0.003% | <0.003% |
| Phosphate | 0.001% | <0.001% |
| Sulfur compounds (as SO$_4$) | 0.003% | <0.003% |
| Heavy Metals (as Pb) | 5 ppm | <0.0005% |

TABLE 15-continued

Impurities of NaHCO₃ from different companies

| Maximum impurities and specifications | Merck | Mallinckrodt |
|---|---|---|
| Ammounium | 5 ppm | <0.0005% |
| Calcium | 0.02% | <0.02% |
| Iron | 0.001% | <0.001% |
| Potassium | 0.005% | <0.005% |

Example 83

Effect of the Additives in the Ag-Catalyzed Fluorination Reaction with Arylstannanes

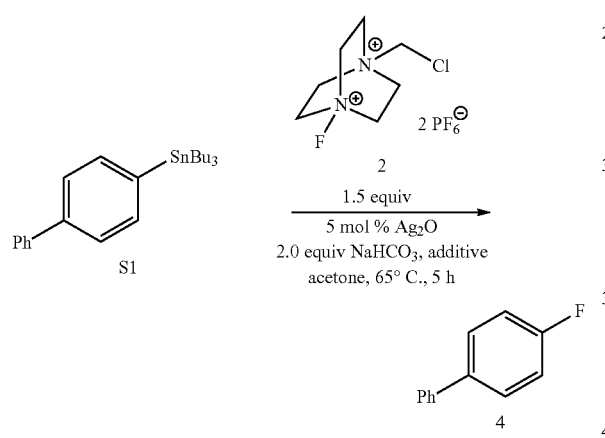

To 4-(biphenyl)tributylstannane (S1) (8.9 mg, 0.020 mmol, 1.0 equiv) in acetone (0.4 mL) at 23° C., silver oxide (0.23 mg, 0.001 mmol, 0.050 equiv), 1-chloromethyl-4-fluoro-1,4-diazoniabicyclo[2.2.2]octane bis(hexafluorophosphate) (2) (14.1 mg, 0.0300 mmol, 1.50 equiv), sodium bicarbonate (3.36 mg, 0.0400 mmol, 2.00 equiv) and additive were added. The reaction mixture was stirred at 65° C. for 5 h in a sealed vial, then cooled to 23° C. To the reaction mixture was added 3-nitrofluorobenzene (2.00 □L, 0.0188 mmol). The yields were determined by comparing integration of the $^{19}$F NMR (375 MHz, acetone-d₆, 23° C.) resonance of 4-fluorobiphenyl (−118.1 ppm) and that of 3-nitrofluorobenzene (−112.0 ppm). Yields are reported in Table 16.

TABLE 16

Effect of the additives in the Ag-catalyzed Fluorination Reaction

| Additive (1 equiv) | Yield [%] ($^{19}$F NMR) | Additive | Yield [%] ($^{19}$F NMR) |
|---|---|---|---|
| None | 76 | 3 Å MS | 15 |
| lutidine | 44 | NaOTf (0.5 equiv) | 81 |
| LiCl | 0 | NaOTf (1.0 equiv) | 89 |
| BaO | 78 | NaOTf (2.0 equiv) | 86 |

Example 84

Effect of Catalyst Loading on the Ag-catalyzed Fluorination Reaction

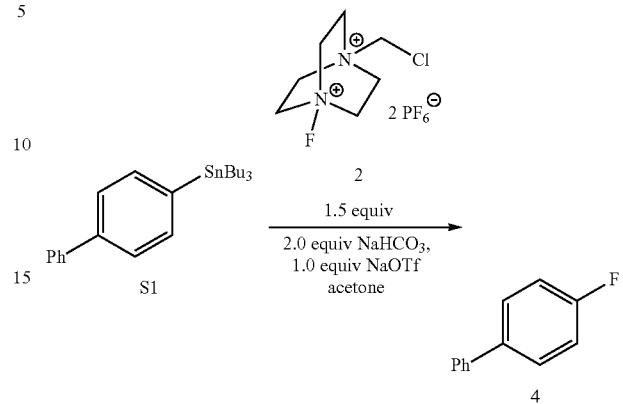

To 4-(biphenyl)tributylstannane (S1) (8.9 mg, 0.020 mmol, 1.0 equiv) in acetone (0.4 mL) at 23° C., silver salt, 1-chloromethyl-4-fluoro-1,4-diazoniabicyclo[2.2.2]octane bis(hexafluorophosphate) (2) (14.1 mg, 0.0300 mmol, 1.50 equiv) and sodium bicarbonate (3.4 mg, 0.040 mmol, 2.0 equiv) were added. The reaction mixture was stirred in a sealed vial, then cooled to 23° C. To the reaction mixture was added 3-nitrofluorobenzene (2.00 □L, 0.0188 mmol). The yields were determined by comparing integration of the $^{19}$F NMR (375 MHz, acetone-d₆, 23° C.) resonance of 4-fluorobiphenyl (−118.1 ppm) and that of 3-nitrofluorobenzene (−112.0 ppm). Yields are reported in Table 17.

TABLE 17

Effect of Catalyst Loading on the Ag-catalyzed Fluorination Reaction

| Ag (mol %) | Temperature | Time (h) | Yield [%] ($^{19}$F NMR) |
|---|---|---|---|
| Ag₂O (5 mol %) | 65 | 5 | 85 |
| Ag₂O (2 mol %) | 65 | 12 | 80 |
| Ag₂O (1 mol %) | 65 | 12 | 70 |
| Ag₂O (1 mol %) | 90 | 12 | 85 |

Example 85

Fluorination of Arylstannanes in the presence of Ag₂O

General Procedure A (for Volatile Compounds)

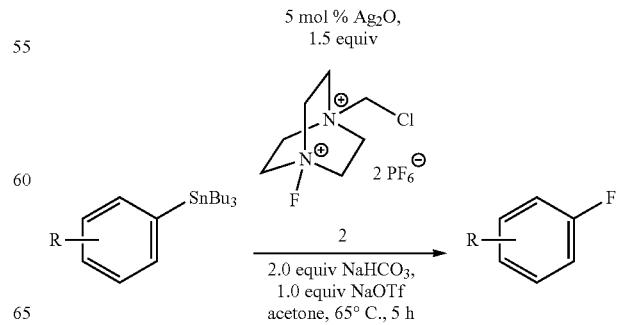

To arylstannane (0.100 mmol, 1.00 equiv) in acetone (2.0 mL) at 23° C. was added silver oxide (1.16 mg, 0.00500 mmol, 0.05 equiv), sodium bicarbonate (16.8 mg, 0.200 mmol, 2.00 equiv), sodium trifluoromethanesulfonate (17.2 mg, 0.100 mmol, 1.00 equiv) and 1-chloromethyl-4-fluoro-1,4-diazoniabicyclo[2.2.2]octane bis(hexafluorophosphate) (1) (70.5 mg, 0.150 mmol, 1.50 equiv). The reaction mixture was stirred for 5 h at 65° C. in a sealed vial, then cooled to 23° C. To the reaction mixture was added 3-nitrofluorobenzene (10.0 □L, 0.0939 mmol). The yields were determined by comparing the integration of the $^{19}$F NMR (375 MHz, acetone-$d_6$, 23° C.) resonance of an arylfluoride and that of 3-nitrofluorobenzene (−112.0 ppm). Yields are reported in Table 18.

TABLE 18

Synthesis of volatile arylfluorides

| R | $^{19}$F chemical shift | Yield [%] ($^{19}$F NMR) |
|---|---|---|
| 4-CN (50) | −105.0 ppm | 86 |
| 4-Br (51) | −117.1 ppm | 72 |
| 2,4,6-Trimethyl (52) | −129.7 ppm | 76 |
| 4-OMe (53) | −126.8 ppm | 73 |

4-Fluorobiphenyl (2)

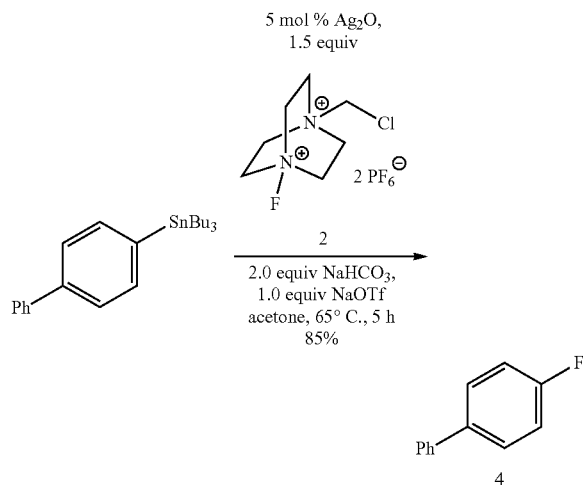

To (4-Biphenyl)tributylstannane (44.4 mg, 0.100 mmol, 1.00 equiv) in acetone (2.0 mL) at 23° C. was added silver oxide (1.16 mg, 0.00500 mmol, 0.05 equiv), sodium bicarbonate (16.8 mg, 0.200 mmol, 2.00 equiv), sodium trifluoromethanesulfonate (17.2 mg, 0.100 mmol, 1.00 equiv) and 1-chloromethyl-4-fluoro-1,4-diazoniabicyclo[2.2.2]octane bis(hexafluorophosphate) (2) (70.5 mg, 0.150 mmol, 1.50 equiv). The reaction mixture was stirred for 5 h at 65° C. in a sealed vial, then cooled to 23° C. and concentrated in vacuo. The residue was purified by preparative TLC with hexane/EtOAc 19:1 (v/v) to afford 14.6 mg of the title compound as a white solid (85% yield).

$R_f$=0.60 (hexanes/EtOAc 19:1 (v/v)). NMR Spectroscopy: $^1$H NMR (500 MHz, CDCl$_3$, 23° C., □): 7.60-7.54 (m, 4H), 7.47 (dd, J=7.5 Hz, 7.0 Hz, 2H), 7.36 (t, J=7.5 Hz, 1H), 7.14 (dd, J=8.0 Hz, 7.5 Hz, 2H). $^{13}$C NMR (125 MHz, CDCl$_3$, 23° C., δ): 162.44 (d, J=244 Hz), 140.25, 137.30, 128.80, 128.75 (d, J=8.5 Hz), 127.24, 127.00, 115.59 (d, J=21 Hz). $^{19}$F NMR (375 MHz, CDCl$_3$, 23° C., δ): −117.2. These spectroscopic data correspond to previously reported data.

Ethyl 4-fluorobenzoate (47)

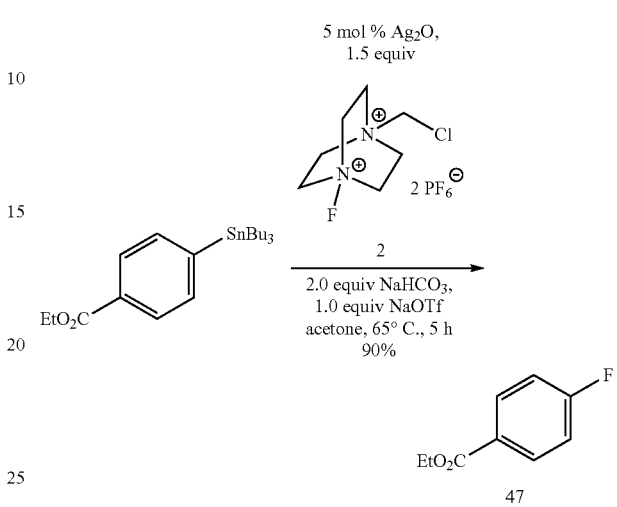

To ethyl 4-(tributylstannane)benzoate (44.0 mg, 0.100 mmol, 1.00 equiv) in acetone (2.0 mL) at 23° C. was added silver oxide (1.16 mg, 0.00500 mmol, 0.05 equiv), sodium bicarbonate (16.8 mg, 0.200 mmol, 2.00 equiv), sodium trifluoromethanesulfonate (17.2 mg, 0.100 mmol, 1.00 equiv) and 1-chloromethyl-4-fluoro-1,4-diazoniabicyclo[2.2.2]octane bis(hexafluorophosphate) (2) (70.5 mg, 0.150 mmol, 1.50 equiv). The reaction mixture was stirred for 5 h at 65° C. in a sealed vial, then cooled to 23° C. and concentrated in vacuo. The residue was purified by preparative TLC with hexane/EtOAc 3:1 (v/v) to afford 15.1 mg of the title compound as a white solid (90% yield).

$R_f$=0.30 (hexane/EtOAc 3:1 (v/v)). NMR Spectroscopy: $^1$H NMR (500 MHz, CDCl$_3$, 23° C., δ): 8.06 (dd, J=9.0 Hz, 5.5 Hz, 2H), 7.10 (dd, J=9.0 Hz, 8.5 Hz, 2H), 4.37 (q, J=7.0 Hz, 2H), 1.39 (t, J=9.0 Hz, 3H). $^{13}$C NMR (125 MHz, CDCl$_3$, 23° C., δ): 165.68 (d, J=252 Hz), 165.65, 132.04 (d, J=10 Hz), 126.72, 115.42 (d, J=22 Hz), 61.07, 14.30. $^{19}$F NMR (375 MHz, CDCl$_3$, 23° C., δ): −108.4. These spectroscopic data correspond to previously reported data.

3-Deoxy-3-fluoroestrone (15)

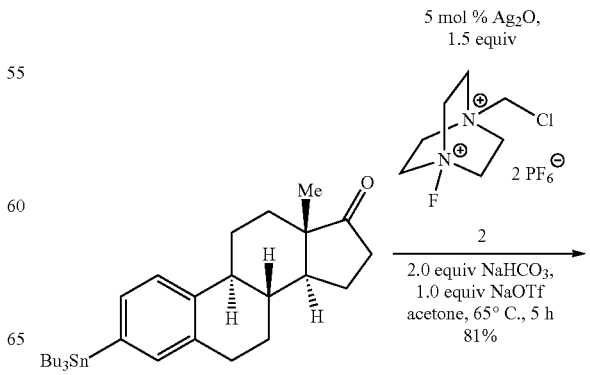

-continued

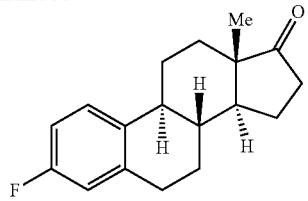

To 3-deoxy-3-(tributylstannyl)estrone (54.4 mg, 0.100 mmol, 1.00 equiv) in acetone (2.0 mL) at 23° C. was added silver oxide (1.16 mg, 0.00500 mmol, 0.05 equiv), sodium bicarbonate (16.8 mg, 0.200 mmol, 2.00 equiv), sodium trifluoromethanesulfonate (17.2 mg, 0.100 mmol, 1.00 equiv) and 1-chloromethyl-4-fluoro-1,4-diazoniabicyclo[2.2.2]octane bis(hexafluorophosphate) (2) (70.5 mg, 0.150 mmol, 1.50 equiv). The reaction mixture was stirred for 5 h at 65° C. in a sealed vial, then cooled to 23° C. and concentrated in vacuo. The residue was purified by preparative TLC with hexane/EtOAc 9:1 (v/v) to afford 22.0 mg of the title compound as a white solid (81% yield).

$R_f$=0.33 (hexane/EtOAc 9:1 (v/v)). NMR Spectroscopy: $^1$H NMR (500 MHz, CDCl$_3$, 23° C., δ): 7.23 (dd, J=8.0 Hz, 6.0 Hz, 1H), 6.85–6.77 (m, 2H), 2.92–2.88 (m, 2H), 2.51 (dd, J=19.0 Hz, 9.0 Hz, 1H), 2.42–2.38 (m, 1H), 2.29–2.23 (m, 1H), 2.18–1.94 (m, 4H), 1.67–1.41 (m, 6H,), 0.91 (s, 3H). $^{13}$C NMR (125 MHz, CDCl$_3$, 23° C., □): 220.69, 160.99 (d, J=242 Hz), 138.65 (d, J=7.3 Hz), 135.31, 126.76 (d, J=7.3 Hz), 115.10 (d, J=20 Hz), 112.48 (d, J=20 Hz), 50.38, 47.92, 43.98, 38.10, 35.82, 31.52, 29.45, 26.30, 25.88, 21.56, 13.81. $^{19}$F NMR (375 MHz, CDCl$_3$, 23° C., δ): –118.5. These spectroscopic data correspond to previously reported data.

N-Boc-4-(fluoro)-L-phenylalanine Methyl Ester (50)

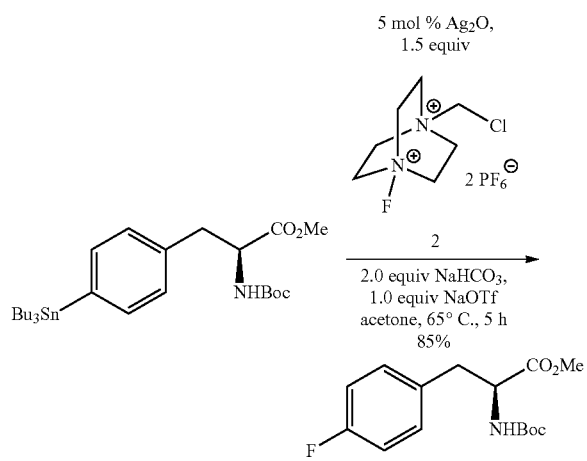

To N-Boc-4-(Tributylstannyl)-L-phenylalanine Methyl Ester (56.9 mg, 0.100 mmol, 1.00 equiv) in acetone (2.0 mL) at 23° C. was added silver oxide (1.16 mg, 0.00500 mmol, 0.05 equiv), sodium bicarbonate (16.8 mg, 0.200 mmol, 2.00 equiv), sodium trifluoromethanesulfonate (17.2 mg, 0.100 mmol, 1.00 equiv) and 1-chloromethyl-4-fluoro-1,4-diazoniabicyclo[2.2.2]octane bis(hexafluorophosphate) (2) (70.5 mg, 0.150 mmol, 1.50 equiv). The reaction mixture was stirred for 5 h at 65° C. in a sealed vial, then cooled to 23° C. and concentrated in vacuo. The residue was purified by preparative TLC with hexane/EtOAc 5:1 (v/v) to afford 25.2 mg of the title compound as a white solid (85% yield).

$R_f$=0.30 (hexane/EtOAc 5:1 (v/v)). NMR Spectroscopy: $^1$H NMR (500 MHz, CDCl$_3$, 23° C., δ): 7.08 (dd, J=8.5 Hz, 5.5 Hz, 2H), 6.98–6.96 (m, 2H), 4.98 (d, J=7.5 Hz, 1H), 4.57–4.54 (m, 1H), 3.70 (s, 3H), 3.09 (dd, J=14.0 Hz, 5.5 Hz, 1H), 3.00 (dd, J=14.0 Hz, 5.5 Hz, 1H), 1.41 (s, 9H). $^{13}$C NMR (125 MHz, CDCl$_3$, 23° C., δ): 172.16, 161.97 (d, J=243 Hz), 154.99, 131.75, 130.75 (d, J=8.1 Hz), 115.35 (d, J=21 Hz), 80.00, 54.40, 52.23, 37.61, 28.25. $^{19}$F NMR (375 MHz, CDCl$_3$, 23° C., δ): –118.5. These spectroscopic data correspond to previously reported data.

4'-(Fluoro)flavanone (51)

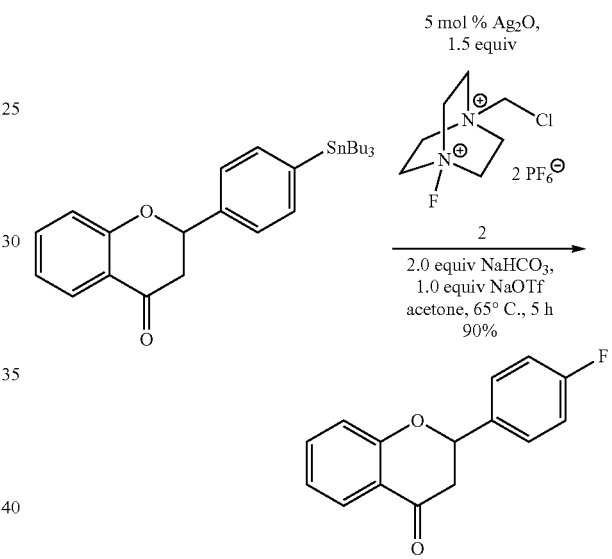

To 4'-(Trifluoromethanesulfonyl)flavanone (51.4 mg, 0.100 mmol, 1.00 equiv) in acetone (2.0 mL) at 23° C. was added silver oxide (1.16 mg, 0.00500 mmol, 0.05 equiv), sodium bicarbonate (16.8 mg, 0.200 mmol, 2.00 equiv), sodium trifluoromethanesulfonate (17.2 mg, 0.100 mmol, 1.00 equiv) and 1-chloromethyl-4-fluoro-1,4-diazoniabicyclo[2.2.2]octane bis(hexafluorophosphate) (2) (70.5 mg, 0.150 mmol, 1.50 equiv). The reaction mixture was stirred for 5 h at 65° C. in a sealed vial, then cooled to 23° C. and concentrated in vacuo. The residue was purified by preparative TLC with hexane/EtOAc 5:1 (v/v) to afford 21.8 mg of the title compound as a white solid (90% yield).

$R_f$=0.50 (hexane/EtOAc 5:1 (v/v)). NMR Spectroscopy: $^1$H NMR (500 MHz, CDCl$_3$, 23° C., δ): 7.93 (dd, J=8.0 Hz, 1.5 Hz, 1H), 7.53–7.46 (m, 3H), 7.14–7.04 (m, 4H), 5.87 (dd, J=13.0 Hz, 2.5 Hz, 1H), 3.06 (dd, J=16.5 Hz, 2.5 Hz, 1H), 2.88 (dd, J=16.5 Hz, 3.5 Hz, 1H). $^{13}$C NMR (125 MHz, CDCl$_3$, 23° C., δ): 191.68, 162.79 (d, J=247 Hz), 161.37, 136.25, 134.57 (d, J=3.6 Hz) 128.01 (d, J=9.1 Hz), 127.06, 121.74, 120.87, 118.06, 115.78 (d, J=22 Hz), 78.90, 44.64. $^{19}$F NMR (375 MHz, CDCl$_3$, 23° C., δ): –115.5. These spectroscopic data correspond to previously reported data.

4-(Fluoro)maculosin (52)

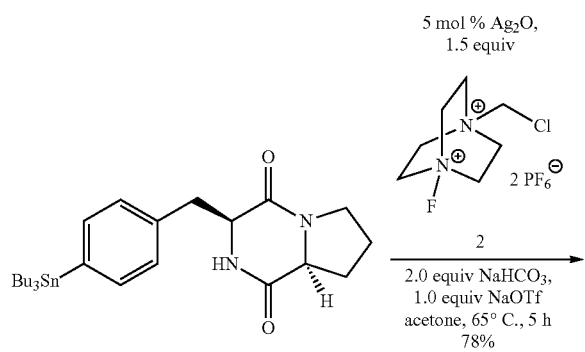

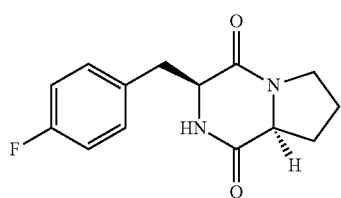

To 4-(Tributylstannyl)maculosin (37.3 mg, 0.0698 mmol, 1.00 equiv) in acetone (1.4 mL) at 23° C. was added silver oxide (0.81 mg, 0.0035 mmol, 0.050 equiv), sodium bicarbonate (11.8 mg, 0.140 mmol, 2.00 equiv), sodium trifluoromethanesulfonate (11.9 mg, 0.0698 mmol, 1.00 equiv) and 1-chloromethyl-4-fluoro-1,4-diazoniabicyclo[2.2.2]octane bis(hexafluorophosphate) (2) (49.3 mg, 0.105 mmol, 1.50 equiv). The reaction mixture was stirred for 5 h at 65° C. in a sealed vial, then cooled to 23° C. and concentrated in vacuo. The residue was purified by preparative TLC with DCM/MeOH 10:1 (v/v) to afford 14.3 mg of the title compound as a colorless oil (78% yield).

$R_f$=0.30 (DCM/MeOH 10:1 (v/v)). NMR Spectroscopy: $^1$H NMR (500 MHz, CDCl$_3$, 23° C., δ): 7.18 (dd, J=8.0 Hz, 5.5 Hz, 1H), 7.01 (t, J=9.0 Hz, 2H), 6.18 (m, 1H), 4.21–4.18 (m, 1H), 3.67–3.61 (m, 1H), 3.42–3.37 (m, 1H), 3.14–3.02 (m, 3H), 2.25–2.20 (m, 1H), 1.98–1.92 (m, 1H), 1.86–1.69 (m, 2H). $^{13}$C NMR (125 MHz, CDCl$_3$, 23° C., δ): 168.93, 164.55, 162.31 (d, J=246 Hz), 131.38 (d, J=8.3 Hz) 130.94 (d, J=3.6 Hz), 115.74 (d, J=22 Hz), 59.03, 57.82, 45.23, 39.70, 28.78, 21.66. $^{19}$F NMR (375 MHz, CDCl$_3$, 23° C., δ): −117.5. These spectroscopic data correspond to previously reported data.

3-(Fluoro)-β-estradiol-β-hepta-benzoyl-lactose (53)

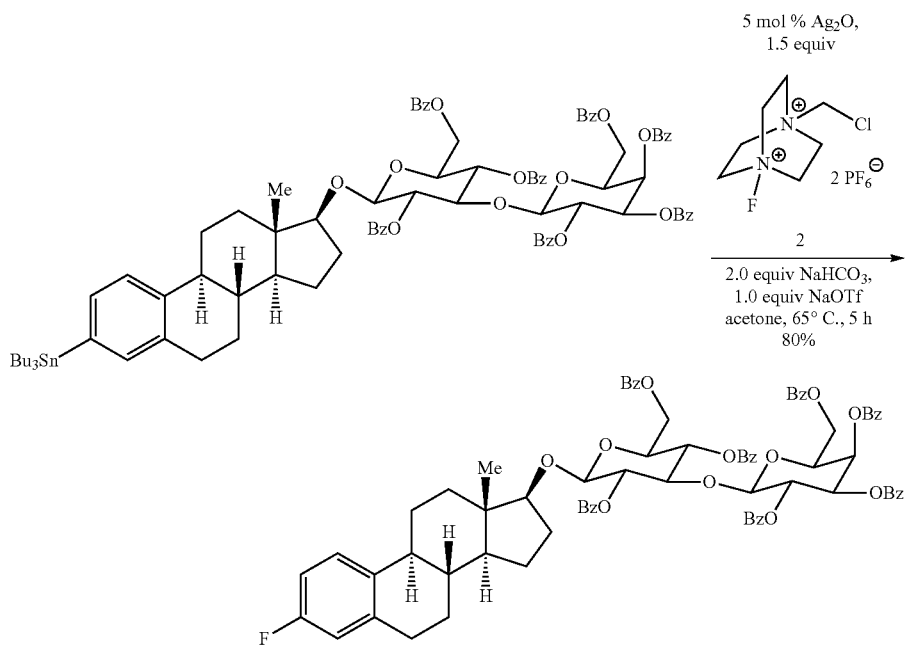

To 3-(tributylstannyl)-β-estradiol-β-hepta-benzoyl-lactose (53.3 mg, 0.0333 mmol, 1.00 equiv) in acetone (0.66 mL) at 23° C. was added silver oxide (0.38 mg, 0.0017 mmol, 0.050 equiv), sodium bicarbonate (5.54 mg, 0.0666 mmol, 2.00 equiv), sodium trifluoromethanesulfonate (5.67 mg, 0.0333 mmol, 1.00 equiv) and 1-chloromethyl-4-fluoro-1,4-diazoniabicyclo[2.2.2]octane bis(hexafluorophosphate) (2) (23.5 mg, 0.0500 mmol, 1.50 equiv). The reaction mixture was stirred for 5 h at 65° C. in a sealed vial, then cooled to 23° C. and concentrated in vacuo. The residue was purified by preparative TLC with hexane/EtOAc 3:1 (v/v) to afford 35.0 mg of the title compound as a colorless oil (80% yield).

$R_f$=0.3 (hexane/EtOAc 3:1 (v/v)). NMR Spectroscopy: $^1$H NMR (500 MHz, CDCl$_3$, 23° C., δ): 8.02–7.96 (m, 10H), 7.91 (dd, J=8.0 Hz, 1.0 Hz, 2H), 7.73 (dd, J=8.0 Hz, 1.0 Hz, 2H), 7.65–7.30 (m, 18H), 7.22 (dd, J=8.5 Hz, 7.5 Hz, 2H), 7.16–7.11 (m, 3H), 6.80–6.78 (m, 1H), 6.72 (dd, J=10.0 Hz, 2.5 Hz, 1H), 5.81 (dd, J=9.5 Hz, 9.0 Hz, 1H), 5.75–5.71 (m, 2H), 5.47 (dd, J=10.0 Hz, 8.5 Hz, 1H), 5.38 (dd, J=10.0 Hz, 3.5 Hz, 1H), 4.88 (d, J=8.0 Hz, 1H), 4.76 (d, J=8.0 Hz, 1H), 4.62-4.60 (m, 1H), 4.50 (dd, J=11.5 Hz, 5.0 Hz, 1H), 4.23 (dd, J=10.0 Hz, 9.0 Hz, 1H), 3.91 (dd, J=6.5 Hz, 6.5 Hz, 1H), 3.84-3.82 (m, 1H), 3.75 (dd, J=11.5 Hz, 7.0 Hz, 1H), 3.69 (dd, J=11.5 Hz, 7.0 Hz, 1H), 3.58 (dd, J=9.0 Hz, 8.0 Hz, 1H), 2.79-2.77 (m, 2H), 2.06-2.03 (m, 2H), 1.98-1.92 (m, 1H), 1.83-1.78 (m, 1H), 1.68-1.54 (m, 4H), 1.30-1.22 (m, 4H), 1.15-1.01 (m, 2H), 0.57 (s, 3H). $^{13}$C NMR (125 MHz, CDCl$_3$, 23° C., δ): 165.82, 165.57, 165.43, 165.39, 165.20, 165.12, 164.79, 160.84 (d, J=242 Hz), 138.78 (d, J=7.3 Hz), 135.71, 133.52, 133.37, 133.34, 133.29, 133.23, 133.14, 133.09, 129.99, 129.74, 129.73, 129.71, 129.66, 129.63, 129.59, 129.49, 129.40, 128.84, 128.69, 128.62, 128.56, 128.49, 128.29, 128.22, 126.68 (d, J=8.1 Hz), 114.98 (d, J=20 Hz), 112.20 (d, J=21 Hz), 101.81, 100.98, 90.02, 76.32, 72.98, 72.96, 71.94, 71.74, 71.39, 69.92, 67.54, 62.57, 61.13, 49.60, 43.79, 43.11, 38.15, 37.16, 29.50, 28.67, 26.85, 25.99, 22.96, 11.33. $^{19}$F NMR (375 MHz, CDCl$_3$, 23° C., δ): -120.5. Mass Spectrometry: HRMS-FIA (m/z): Calcd for [M+NH$_4$], 1344.4963. Found, 1344.4962.

N-Boc-4-(Fluoro)-L-phenylalanyl-L-phenylalanine Methyl Ester (54)

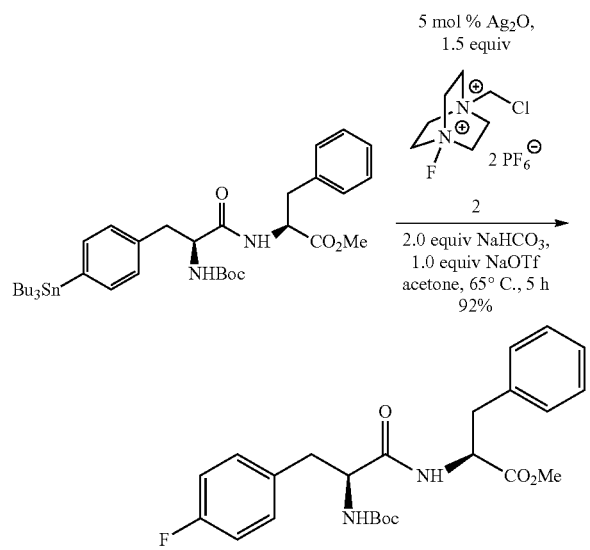

To N-Boc-4-(Tributylstannyl)-L-phenylalanyl-L-phenylalanine methyl ester (1.43 g, 2.00 mmol, 1.00 equiv) in acetone (40 mL) at 23° C. was added silver oxide (23.2 mg, 0.100 mmol, 0.050 equiv), sodium bicarbonate (336 mg, 4.00 mmol, 2.00 equiv), sodium trifluoromethanesulfonate (342 mg, 1.00 mmol, 1.00 equiv) and 1-chloromethyl-4-fluoro-1,4-diazoniabicyclo[2.2.2]octane bis(hexafluorophosphate) (2) (1.41 g, 3.00 mmol, 1.50 equiv).

The reaction mixture was stirred for 5 h at 65° C. in a sealed vial, then cooled to 23° C. and concentrated in vacuo. The residue was purified by preparative TLC with hexane/EtOAc 2:1 (v/v) to afford 817 mg of the title compound as a white solid (92% yield).

R$_f$=0.30 (hexane/EtOAc 2:1 (v/v)). NMR Spectroscopy: $^1$H NMR (500 MHz, CDCl$_3$, 23° C., δ): 7.28-7.22 (m, 3H), 7.16-7.13 (m, 2H), 7.03-7.93 (m, 4H), 6.38 (d, J=6.5 Hz, 1H), 5.06 (br s, 1H), 4.78 (br s, 1H), 4.32 (br s, 1H), 3.68 (s, 3H), 3.09-2.99 (m, 4H), 1.41 (s, 9H). $^{13}$C NMR (125 MHz, CDCl$_3$, 23° C., δ): 171.32, 170.61, 161.82 (d, J=244 Hz), 155.17, 135.52, 132.19, 130.79 (d, J=7.3 Hz), 129.12, 128.49, 127.08, 115.59 (d, J=21 Hz), 80.13, 55.60, 53.17, 52.22, 37.85, 37.48, 28.17. $^{19}$F NMR (375 MHz, CDCl$_3$, 23° C., δ): -118.8.

6-Demethoxy-6-fluoroquinine (55)

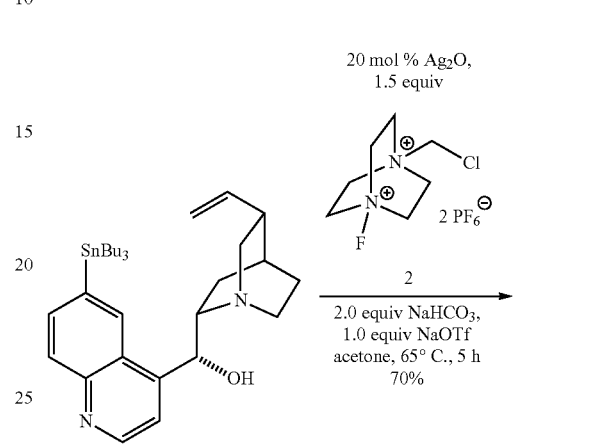

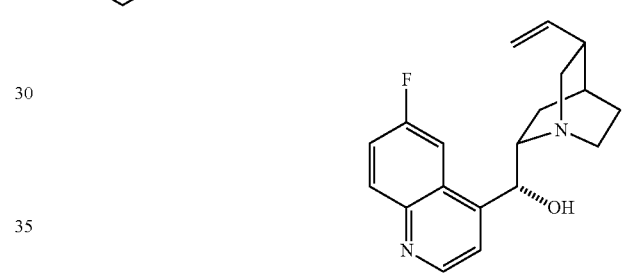

To 6-Demethoxy-6-(tributylstannyl)quinine (29.2 mg, 0.0500 mmol, 1.00 equiv) in acetone (1 mL) at 23° C. was added silver oxide (2.32 mg, 0.0100 mmol, 0.200 equiv), sodium bicarbonate (8.4 mg, 1.0 mmol, 2.0 equiv), sodium trifluoromethanesulfonate (8.5 mg, 1.0 mmol, 1.0 equiv) and 1-chloromethyl-4-fluoro-1,4-diazoniabicyclo[2.2.2]octane bis(hexafluorophosphate) (2) (35.3 mg, 0.075 mmol, 1.50 equiv). The reaction mixture was stirred for 5 h at 65° C. in a sealed vial, then cooled to 23° C. and concentrated in vacuo. The residue was purified by preparative TLC with CH$_2$Cl$_2$/MeOH 9:1 (v/v) to afford 10.9 mg of the title compound as a white solid (70% yield).

R$_f$=0.40 (CH$_2$Cl$_2$/MeOH 9:1 (v/v)). NMR Spectroscopy: $^1$H NMR (500 MHz, CD$_3$CN, 23° C., δ): 8.85 (d, J=4.2 Hz, 1H), 8.10 (dd, J=9.0 Hz, 5.4 Hz, 1H), 7.97 (dd, J=9.0 Hz, 3.0 Hz, 1H,), 7.65 (d, J=4.2 Hz, 1H), 7.54 (ddd, J=9.0 Hz, 9.0 Hz, 3.0 Hz, 1H), 5.83 (d, J=3.0 Hz, 1H), 5.78-5.72 (m, 1H), 5.06 (d, J=17.4 Hz, 1H), 4.99 (d, J=10.2 Hz, 1H), 3.92-3.86 (m, 1H), 3.48-3.43 (m, 1H), 3.35 (dd, J=13.2 Hz, 7.2 Hz, 1H), 3.06-3.00 (m, 2H), 2.68 (s br, 1H), 2.05-1.99 (m, 3H), 1.84-1.78 (m, 1H), 1.65-1.58 (m, 1H). $^{13}$C NMR (125 MHz, CD$_3$CN, 23° C., δ): 161.48 d, J=244 Hz), 150.63, 146.83 (d, J=6.1 Hz), 146.45, 139.78, 133.81 (d, J=9.9 Hz), 126.76 (d, J=9.9 Hz), 120.78, 120.18 (d, J=26 Hz), 116.68, 108.25 (d, J=24 Hz), 68.99, 61.30, 55.61, 4.78, 38.38, 27.87, 25.32, 20.44. $^{19}$F NMR (375 MHz, CD$_3$CN, 23° C., δ): -113.6.

4-(Fluoro)-leu-enkephalin (56)

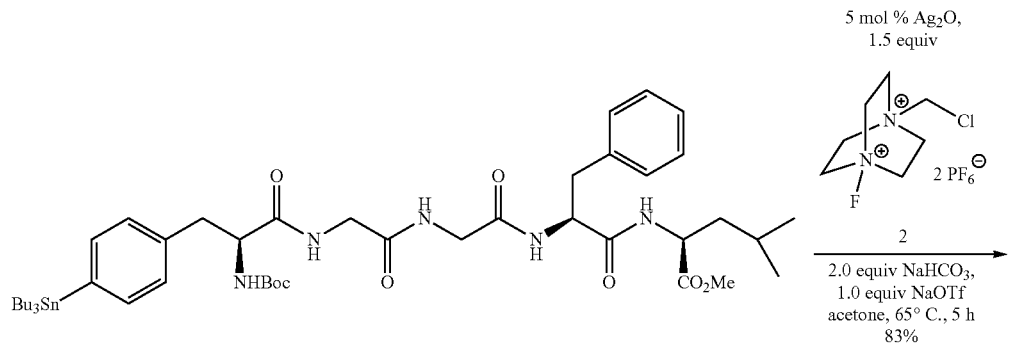

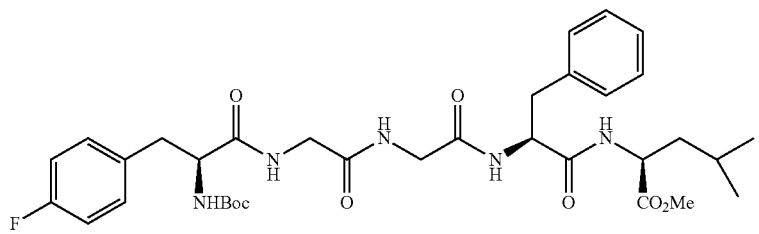

To N-Boc-4-(tributylstannyl)-L-phenylalanyl-glycylglycyl-L-phenylalanyl-L-leucine Methyl Ester (18.9 mg, 0.0200 mmol, 1.00 equiv) in acetone (0.40 mL) at 23° C. was added silver oxide (0.23 mg, 0.0010 mmol, 0.050 equiv), sodium bicarbonate (3.36 mg, 0.0400 mmol, 2.00 equiv), sodium trifluoromethanesulfonate (3.42 mg, 0.0200 mmol, 1.00 equiv) and 1-chloromethyl-4-fluoro-1,4-diazoniabicyclo[2.2.2]octane bis(hexafluorophosphate) (2) (14.1 mg, 0.0300 mmol, 1.50 equiv). The reaction mixture was stirred for 5 h at 65° C. in a sealed vial, then cooled to 23° C. and concentrated in vacuo. The residue was purified by preparative TLC with DCM/MeOH 10:1 (v/v) to afford 11.2 mg of the title compound as a white solid (83% yield).

$R_f$=0.40 (DCM/MeOH 10:1 (v/v)). NMR Spectroscopy: $^1$H NMR (500 MHz, CDCl$_3$, 23° C., δ): 7.86 (br s, 1H), 7.60 (br s, 1H), 7.50 (br s, 1H), 7.23–7.15 (m, 5H), 7.07–7.04 (m, 2H), 6.92–6.88 (m, 2H), 5.77 (br s, 1H), 5.07 (br s, 1H), 4.63–4.58 (m, 2H), 4.18–4.00 (m, 4H), 3.70 (s, 3H), 3.14–3.10 (m, 1H), 3.03–2.99 (m, 2H), 2.92–2.88 (m, 1H), 1.58–1.51 (m, 3H), 1.40 (s, 9H), 0.88 (d, J=6.0 Hz, 6H). $^{13}$C NMR (125 MHz, CDCl$_3$, 23° C., δ): 173.02, 171.99, 170.72, 168.79, 168.28, 161.82 (d, J=243 Hz), 155.76, 136.49, 132.33, 130.82 (d, J=8.1 Hz), 129.52, 128.34, 126.78, 115.22 (d, J=21 Hz), 80.05, 55.50, 54.16, 52.18, 50.81, 43.07, 41.18, 39.0, 38.13, 29.68, 28.33, 24.77, 22.71, 22.03. $^{19}$F NMR (375 MHz, CDCl$_3$, 23° C., δ): –118.5. Mass Spectrometry: HRMS-FIA (m/z): Calcd for [M+H]$^+$, 672.3403. Found, 672.3397.

(14-Fluoro)ezetimibe (57)

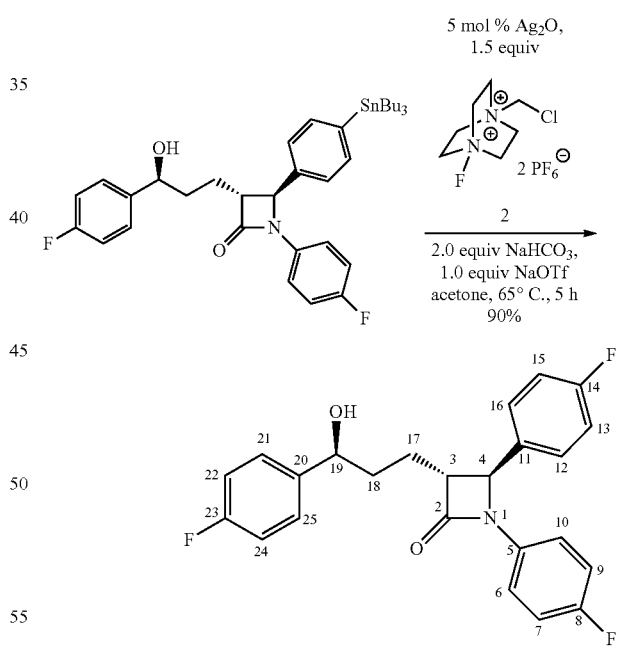

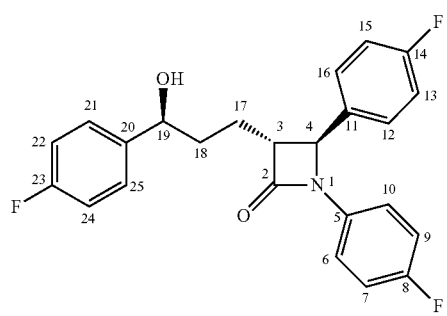

To (Tributylstannyl)ezetimibe (19.8 mg, 0.0290 mmol, 1.00 equiv) in acetone (0.6 mL) at 23° C. was added silver oxide (0.34 mg, 0.0015 mmol, 0.050 equiv), sodium bicarbonate (4.87 mg, 0.0580 mmol, 2.00 equiv), sodium trifluoromethanesulfonate (4.96 mg, 0.0290 mmol, 1.00 equiv) and 1-chloromethyl-4-fluoro-1,4-diazoniabicyclo[2.2.2]octane bis(hexafluorophosphate) (2) (20.5 mg, 0.0436 mmol, 1.50 equiv). The reaction mixture was stirred for 5 h at 65° C. in a sealed vial, then cooled to 23° C. and concentrated in vacuo.

The residue was purified by preparative TLC with hexane/EtOAc 2:1 (v/v) to afford 10.7 mg of the title compound as a white solid (90% yield).

$R_f$=0.3 (hexane/EtOAc 2:1 (v/v)). NMR Spectroscopy: $^1$H NMR (500 MHz, CDCl$_3$, 23° C., δ): 7.31–7.28 (m, 4H, H-12, H-16, H-21, H-25), 7.22–7.20 (m, 2H, H-6, H-10), 7.08–7.00 (m, 4H, H-13, H-15, H-22, H-24), 6.95–6.92 (m, 2H, H-7, H-9), 4.72 (m, 1H, H-19), 4.61 (d, J=2.0 Hz, 1H, H-2), 3.07–3.05 (m, 1H, H-3), 2.17 (br s, 1H, OH), 2.03–1.89 (m, 4H, H-17, H-18). $^{13}$C NMR (125 MHz, CDCl$_3$, 23° C., δ): 167.25 (C-4), 162.75 (d, J=246 Hz, C-23), 162.23 (d, J=244 Hz, C-14), 159.04 (d, J=241 Hz, C-8), 139.97 (C-11), 133.66 (C-5), 133.30 (C-20), 127.55 (d, J=8.7 Hz, C-12, C-16), 127.36 (d, J=7.4 Hz, C-21, C-25), 118.32 (d, J=7.4 Hz, C-6, C-10), 116.32 (d, J=22 Hz, C-22, C-24), 115.89 (d, J=23 Hz, C-7, C-9), 115.38 (d, J=21 Hz, C-13, C-15), 73.16 (C-19), 60.77 (C-2), 60.48 (C-3), 36.56 (C-18), 25.07 (C-17). $^{19}$F NMR (375 MHz, CDCl$_3$, 23° C., δ): −115.71, −118.20, −120.62. Mass Spectrometry: HRMS-FIA (m/z): Calcd for [M+Na]$^+$, 434.1338. Found, 434.1344.

(5-Fluoro)DOPA (58)

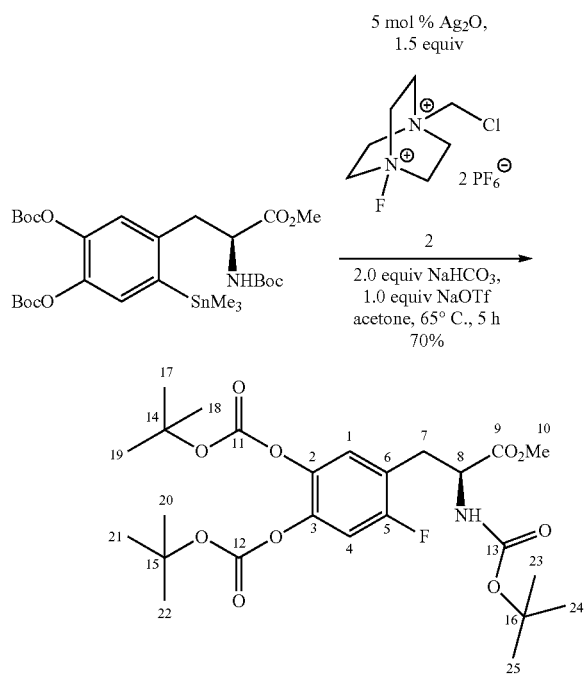

To (Tributylstannyl)DOPA (54 mg, 0.0800 mmol, 1.00 equiv) in acetone (1.6 mL) at 23° C. was added silver oxide (0.93 mg, 0.0040 mmol, 0.050 equiv), sodium bicarbonate (13.4 mg, 0.160 mmol, 2.00 equiv), sodium trifluoromethanesulfonate (13.7 mg, 0.0800 mmol, 1.00 equiv) and 1-chloromethyl-4-fluoro-1,4-diazoniabicyclo[2.2.2]octane bis(hexafluorophosphate) (2) (56.4 mg, 0.120 mmol, 1.50 equiv). The reaction mixture was stirred for 5 h at 65° C. in a sealed vial, then cooled to 23° C. and concentrated in vacuo. The residue was purified by preparative TLC with hexane/EtOAc 2:1 (v/v) to afford 29.7 mg of the title compound as a white solid (70% yield).

$R_f$=0.3 (hexane/EtOAc 2:1 (v/v)). NMR Spectroscopy: $^1$H NMR (500 MHz, CDCl$_3$, 23° C., δ): 7.05 (d, J=7.0 Hz, 1H, H-1), 7.01 (d, J=9.5 Hz, 1H, H-4), 5.08 (d, J=7.5 Hz, 1H, NH), 4.56–4.55 (m, 1H, H-8), 3.71 (s, 3H, H-10), 3.15–3.06 (m, 2H, H-7), 1.54 (s, 18H, H-17, H-18, H-19, H-20, H-21, H-22), 1.41 (s, 9H, H-23, H24, H-25). $^{13}$C NMR (125 MHz, CDCl$_3$, 23° C., δ): 171.85 (C-9), 158.05 (d, J=244 Hz, C-5), 154.97 (C-13), 150.62 (C-11), 150.21 (C-12), 141.94 (C-3), 138.48 (C-2), 125.18 (C-1), 121.31 (d, J=17 Hz, C-6), 110.66 (d, J=27 Hz, C-4), 84.20 (C-14), 83.91 (C-15), 80.04 (C-16), 53.38 (C-8), 52.43 (C-10), 31.48 (C-7), 28.22 (C-23, C-24, C-25), 27.57 (C-17, C-18, C-19, C-20, C-21, C-22). $^{19}$F NMR (375 MHz, CDCl$_3$, 23° C., δ): −120.11. Mass Spectrometry: HRMS-FIA (m/z): Calcd for [M+Na]$^+$, 552.2216. Found, 552.2215.

Rifamycin S derivative (59)

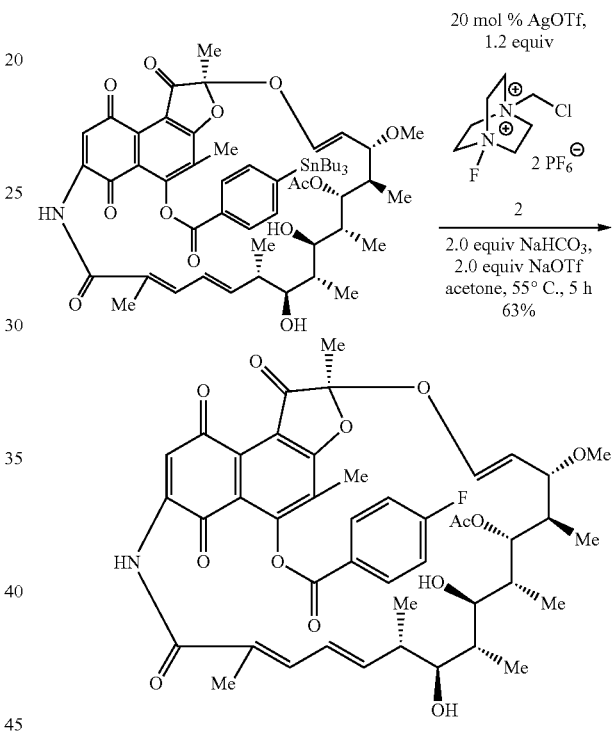

To Rifamycin S derivative (32.7 mg, 0.0300 mmol, 1.00 equiv) in acetone (0.6 mL) at 23° C. was added silver triflate (1.54 mg, 0.00600 mmol, 0.200 equiv), sodium bicarbonate (5.04 mg, 0.0600 mmol, 2.00 equiv), sodium trifluoromethanesulfonate (10.3 mg, 0.0600 mmol, 2.00 equiv) and 1-chloromethyl-4-fluoro-1,4-diazoniabicyclo[2.2.2]octane bis(hexafluorophosphate) (2) (16.9 mg, 0.0360 mmol, 1.20 equiv). The reaction mixture was stirred for 5 h at 55° C. in a sealed vial, then cooled to 23° C. and concentrated in vacuo. The residue was purified by preparative TLC with hexane/EtOAc 2:1 (v/v) to afford 15.4 mg of the title compound as a yellow solid (63% yield).

$R_f$=0.20 (hexane/EtOAc 2:1 (v/v)). NMR Spectroscopy: $^1$H NMR (500 MHz, CDCl$_3$, 23° C., δ): 8.31 (dd, J=8.5 Hz, 5.0 Hz, 2H), 8.23 (s, 1H), 7.80 (s, 1H), 7.26–7.22 (m, 2H), 6.25–6.17 (m, 3H), 5.89 (dd, J=15.5 Hz, 6.5 Hz, 1H), 5.13 (dd, J=12.5 Hz, 7.5 Hz, 1H), 4.64 (d, J=10.5 Hz, 1H), 3.70 (d, J=4.5 Hz, 1H), 3.59 (d, J=10.0 Hz, 1H), 3.38–3.37 (m, 2H), 3.12 (s, 3H), 3.05–3.02 (m, 1H), 2.34 (s, 3H), 2.32–2.29 (m, 1H), 2.04 (s, 3H), 1.97 (s, 3H), 1.81–1.80 (m, 1H), 1.77 (s, 3H), 1.69–1.67 (m, 1H), 1.08 (d, J=7.0 Hz, 3H), 0.84 (d, J=7.0

Hz, 3H), 0.68 (d, J=7.0 Hz, 3H), 0.18 (d, J=7.0 Hz, 3H). $^{13}$C NMR (125 MHz, CDCl$_3$, 23° C., δ): 192.37, 182.00, 177.77, 173.28, 173.11, 168.47 (d, J=229 Hz), 165.52, 163.22, 155.61, 144.76, 141.89, 139.94, 133.51 (d, J=9.1 Hz), 132.22, 130.78, 124.67, 124.12, 124.01, 118.47, 116.14, 115.88 (d, J=20 Hz), 114.81, 108.83, 81.53, 73.48, 73.14, 60.37, 56.89, 39.02, 37.38, 37.27, 32.76, 22.03, 21.06, 21.02, 19.99, 16.93, 14.18, 11.75, 11.18, 8.84, 8.79. $^{19}$F NMR (375 MHz, CDCl$_3$, 23° C., δ): −106.55. Mass Spectrometry: HRMS-FIA (m/z): Calcd for [M+H]$^+$, 818.3183. Found, 818.3164.

What is claimed is:

1. A method of fluorinating an organic compound, the method comprising providing an organic compound selected from the group consisting of aryl and heteroaryl tin species; vinyl, aryl, and heteroaryl boron species; and vinyl, aryl, and heteroaryl silicon species; a silver salt; and an organic, electrophilic fluorinating agent selected from the group consisting of N-fluoropyridinium triflate, N-fluoro-2,4,6-trimethylpyridinium triflate, N-fluoro-2,4,6-trimethylpyridinium tetrafluoroborate, N-fluoro-2,6-dichloropyridinium tetrafluoroborate, N-fluoro-2,6-dichloropyridinium triflate, N-fluoropylidinium pyridine heptafluorodiborate, N-fluoropyridinium tetrafluoroborate, N-fluoropyridinium triflate, an N-fluoroarylsulfonimide, N-chloromethyl-N'-fluorotriethylenediammonium bis(tetrafluoroborate), and N-chloromethyl-N'-fluorotriethylenediammonium bis(hexafluorophosphate), under conditions sufficient to fluorinate the organic compound, thereby providing a fluorinated organic compound.

2. The method of claim 1, wherein the tin species comprises an organostannane, wherein the organostannane comprises a trialkyltin moiety.

3. The method of claim 1, wherein the boron comprises a boron substituent of the formulae:

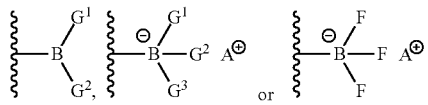

wherein G$^1$, G$^2$ and G$^3$ are, independently, —OH, —OR, or —R;

each R is, independently, optionally substituted aliphatic, optionally substituted heteroaliphatic, optionally substituted aryl, or optionally substituted heteroaryl;

or G$^1$ and G$^2$ are joined to form an optionally substituted 5- to 8-membered ring having at least one O atom directly attached to B, wherein the ring is comprised of carbon atoms and optionally one or more additional heteroatoms independently selected from the group consisting of N, S, and O; and wherein A$^⊕$ is a metal cation or ammonium.

4. The method of claim 1, wherein the silicon species is a trialkoxysilane.

5. The method claim 1, wherein the silver salt is selected from the group consisting of silver(I) fluoride, silver(I) acetate, silver(I) tetrafluoroborate, silver(I) perchlorate, silver(I) nitrate, silver(I) carbonate, silver(I) cyanide, silver(I) benzoate, silver(I) triflate, silver(I) hexafluorophosphate, silver(I) hexafluoroantimonate, silver(I) oxide, silver(I) nitrite and silver(I) phosphate.

6. The method of claim 1, wherein the method comprises a catalytic amount of the silver salt relative to the organic compound.

7. The method of claim 1, wherein the fluorinating agent comprises $^{18}$F or $^{19}$F.

8. The method of claim 1, wherein the method further comprises a base selected from NaOH, KOH, BaO, MgO, NaHCO$_3$, KHCO$_3$, Na$_2$CO$_3$ and Ba(OH)$_2$.

9. The method of claim 1, wherein the method further comprises a triflate salt in addition to the silver salt.

10. The method of claim 9, wherein the salt is sodium triflate.

11. The method of claim 1, wherein the organic compound is immobilized on a solid support.

12. The method of claim 1, wherein the silver salt and the fluorinating agent are added to the organic compound.

13. The method of claim 8, wherein the silver salt and the base are added to the organic compound, resulting in an intermediate product and wherein the intermediate product is isolated and the fluorinating agent and the silver-containing compound are added thereto, resulting in formation of the fluorinated organic compound.

14. A method of fluorinating an aryl or heteroaryl tin species, the method comprising combining silver(I) triflate, an aryl or heteroaryl tin species, a base, and N-chloromethyl-N'-fluorotriethylenediammonium bis(hexafluorophosphate), under conditions sufficient to fluorinate the aryl or heteroaryl tin species, thereby providing a fluorinated aryl or heteroaryl compound.

15. A method of fluorinating a vinyl, aryl, or heteroaryl boron species, the method comprising combining silver(I) triflate, a vinyl, aryl, or heteroaryl boron species, a base, and N-chloromethyl-N'-fluorotriethylenediammonium bis(tetrafluoroborate), under conditions sufficient to fluorinate the vinyl, aryl, or heteroaryl boron species, thereby providing a fluorinated vinyl, aryl, or heteroaryl compound.

16. A method of fluorinating a vinyl, aryl, or heteroaryl silicon species, the method comprising combining silver(I) oxide, a vinyl, aryl, or heteroaryl silicon species, a base and N-chloromethyl-N'-fluorotriethylenediammonium bis(tetrafluoroborate), under conditions sufficient to fluorinate the vinyl, aryl, or heteroaryl silicon species, thereby providing a fluorinated vinyl, aryl, or heteroaryl organic compound.

* * * * *